US012492255B2

(12) United States Patent
Hoofd et al.

(10) Patent No.: US 12,492,255 B2
(45) Date of Patent: Dec. 9, 2025

(54) ANTI-TREM2 ANTIBODIES AND METHODS OF USE

(71) Applicant: iTeos Belgium SA, Gosselies (BE)

(72) Inventors: Catherine Hoofd, Gosselies (BE); Thibaut Janss, Gosselies (BE); Romain Pirson, Gosselies (BE); Virginie Rabolli, Gosselies (BE); Yvonne McGrath, Gosselies (BE); Reece Marillier, Gosselies (BE); Quentin Dubray, Gosselies (BE); Clotilde Hoyos, Gosselies (BE); Julie Chesné, Gosselies (BE); Chiara Martinoli, Milan (IT); Stefan Loverix, Ternat (BE); Laura Saerens, Gosselies (BE)

(73) Assignee: iTeos Belgium SA, Gosselies (BE)

( * ) Notice: Subject to any disclaimer, the term of this patent is extended or adjusted under 35 U.S.C. 154(b) by 0 days.

(21) Appl. No.: 19/217,020

(22) Filed: May 23, 2025

(65) Prior Publication Data

US 2025/0282868 A1 Sep. 11, 2025

Related U.S. Application Data

(63) Continuation of application No. 18/821,530, filed on Aug. 30, 2024, now abandoned.

(60) Provisional application No. 63/640,439, filed on Apr. 30, 2024, provisional application No. 63/580,184, filed on Sep. 1, 2023.

(51) Int. Cl.

| | |
|---|---|
| ***C07K 16/28*** | (2006.01) |
| ***A61K 39/00*** | (2006.01) |
| ***A61P 35/00*** | (2006.01) |
| ***A61P 37/04*** | (2006.01) |

(52) U.S. Cl.

CPC .......... *C07K 16/2803* (2013.01); *A61P 35/00* (2018.01); *A61P 37/04* (2018.01); *A61K 2039/505* (2013.01); *C07K 2317/52* (2013.01); *C07K 2317/565* (2013.01); *C07K 2317/76* (2013.01)

(58) Field of Classification Search

CPC ............ C07K 16/2803; C07K 2317/52; C07K 2317/565; C07K 2317/76; A61P 35/00; A61P 37/04; A61K 2039/505

See application file for complete search history.

(56) References Cited

U.S. PATENT DOCUMENTS

| | | | | |
|---|---|---|---|---|
| 9,221,902 | B2 * | 12/2015 | Smider | C40B 40/08 |
| 10,428,143 | B2 | 10/2019 | Krummel et al. | |
| 11,325,973 | B2 | 5/2022 | Krummel et al. | |
| 2017/0334977 | A1 | 11/2017 | Butovsky et al. | |
| 2019/0330335 | A1 | 10/2019 | Schwabe et al. | |
| 2020/0277373 | A1 | 9/2020 | Chen et al. | |
| 2025/0101101 | A1 | 3/2025 | Hoofd et al. | |

FOREIGN PATENT DOCUMENTS

| | | | |
|---|---|---|---|
| WO | WO-2018015573 | A2 | 1/2018 |
| WO | WO-2018195506 | A1 | 10/2018 |
| WO | WO-2019028292 | A1 | 2/2019 |
| WO | WO-2019055841 | A1 | 3/2019 |
| WO | WO-2019118513 | A1 | 6/2019 |
| WO | WO-2020079580 | A1 | 4/2020 |
| WO | WO-2020112889 | A2 | 6/2020 |
| WO | WO-2020121195 | A1 | 6/2020 |
| WO | WO-2020123664 | A1 | 6/2020 |
| WO | WO-2020172450 | A1 | 8/2020 |
| WO | WO-2020172457 | A1 | 8/2020 |
| WO | WO-2020194317 | A1 | 10/2020 |
| WO | WO-2021113655 | A1 | 6/2021 |
| WO | WO-2021173565 | A1 | 9/2021 |
| WO | WO-2021174003 | A2 | 9/2021 |
| WO | WO-2021203030 | A2 | 10/2021 |
| WO | WO-2022040246 | A1 | 2/2022 |
| WO | WO-2022187092 | A1 | 9/2022 |
| WO | WO-2023039612 | A1 | 3/2023 |
| WO | WO-2023097327 | A1 | 6/2023 |
| WO | WO-2023172643 | A1 | 9/2023 |
| WO | WO-2024015560 | A1 | 1/2024 |
| WO | WO-2025046298 | A2 | 3/2025 |

OTHER PUBLICATIONS

Kabat (The Journal of Biological Chemistry (1977) 252(19): 6609-6616) (Year: 1977).*
Chothia (Journal of Molecular Biology (1987) 196: 901-917) (Year: 1987).*
MacCallum (Journal of Molecular Biology (1996) 262: 732-745) (Year: 1996).*
Lefranc (The Immunologist (1999) 7: 132-136) (Year: 1999).*
Dondelinger (Frontiers in Immunology (2018) 9: Article 2278) (Year: 2018).*
PCT International Search Report and Written Opinion from PCT/IB2024/000473, dated Mar. 13, 2025.
Deczkowska et al., "The Physiology, Pathology, and Potential Therapeutic Applications of the TREM2 Signaling Pathway," Cell. 2020; 181(6):1207-1217.
Dujardin et al., "Fighting fire with fire: The immune system might be key in our fight against Alzheimer's disease," Drug Discovery Today. 2022; 27(5):1261-1283.
Beckermann et al., "A phase 1b open-label study to evaluate the safety, tolerability, pharmacokinetics, and pharmacodynamics of py314 in combination with pembrolizumab in patients with advanced renal cell carcinoma," Investigational New Drugs. 2024; 42:179-184.

(Continued)

*Primary Examiner* — Julie Wu
*Assistant Examiner* — Elizabeth A Shupe
(74) *Attorney, Agent, or Firm* — Dechert LLP; Andrew T. Wilkins; Sharla F. Flohr

(57) ABSTRACT

Provided herein are anti-TREM2 antibodies. Polynucleotides, vectors, host cells, and methods of production are also provided herein. Methods of treating a disease or disorder, such as cancer with an anti-TREM2 antibody are further provided.

25 Claims, 37 Drawing Sheets

Specification includes a Sequence Listing.

(56) References Cited

OTHER PUBLICATIONS

Binnewies et al., "Targeting TREM2 on tumor-associated macrophages enhances immunotherapy," Cell Reports. 2021; 37(3):109844.
Cassetta and Pollard, "A timeline of tumour-associated macrophage biology," Nature Reviews Cancer. 2023; 23:238-257.
Colonna, "The biology of TREM receptors," Nature Reviews Immunology. 2023; 23(9):580-594.
Guerreiro et al., "TREM2 Variants in Alzheimer's Disease," New England Journal of Medicine. 2013; 368(2):117-127.
Hou et al., "TREM2 sustains macrophage-hepatocyte metabolic coordination in nonalcoholic fatty liver disease and sepsis," Journal of Clinical Investigation. 2021; 131(4):e135197.
Jaitin et al, "Lipid-Associated Macrophages Control Metabolic Homeostasis in a Trem2-Dependent Manner," Cell. 2019; 178(3):686-698.e14.
Katzenelenbogen et al., "Coupled scRNA-Seq and Intracellular Protein Activity Reveal an Immunosuppressive Role of TREM2 in Cancer," Cell. 2020; 182(4):872-885.e19.
Lopez-Yrigoyen et al, "Macrophage targeting in cancer," Annals of New York Academy of Sciences. 2021; 1499(1):18-41.
Molgora et al, "TREM2 Modulation Remodels the Tumor Myeloid Landscape Enhancing Anti-PD-1 Immunotherapy," Cell. 2020; 182(4):886-900.e17.
Obradovic et al, "Single-cell protein activity analysis identifies recurrence-associated renal tumor macrophages," Cell. 2021; 184(11):P2988-3005.E16.
Park et al, "TREM2 macrophages drive NK cell paucity and dysfunction in lung cancer," Nature Immunology. 2023; 24:792-801.
Patnaik et al "A phase 1a dose-escalation study of PY314, a TREM2 (Triggering Receptor Expressed on Macrophages 2) targeting monoclonal antibody," Journal of Clinical Oncology. 2022; 40 (Suppl 16):2648.
Piollet et al, "TREM2 protects from atherosclerosis by limiting necrotic core formation," Nature Cardiovascular Research. 2024; 3(3):269-282.
Schlepckow et al, "Stimulation of TREM2 with agonistic antibodies—an emerging therapeutic option for Alzheimer's disease," The Lancet Neurology. 2023; 22(11):1048-1060.
Sun et al, "TREM2 inhibition triggers antitumor cell activity of myeloid cells in glioblastoma," Science Advances. 2023; 9(19):eade3559.
Wang et al, "Anti-human TREM2 induces microglia proliferation and reduces pathology in an Alzheimer's disease model," Journal of Experimental Medicine. 2020; 217(9):e20200785.
Wang et al, "Prolonged hypernutrition impairs TREM2-dependent efferocytosis to license chronic liver inflammation and NASH development," Immunity. 2023; 56(1):58-77.e11.
Xiong et al, "A gene expression signature of TREM2hi macrophages and γδ T cells predicts immunotherapy response," Nature Communications. 2020; 11(1):5084.
Yofe et al, Spatial and temporal mapping of breast cancer lung metastases identify TREM2 macrophages as regulators of the metastatic boundary, Cancer Discovery. 2023; 13(12):2610-2631.
Yu et al, "TREM2 is associated with tumor immunity and implies poor prognosis in glioma," Frontiers in Immunology. 2023; 13:1089266.
Zhang et al, "Immunosuppressive TREM2(+) macrophages are associated with undesirable prognosis and responses to anti-PD-1 immunotherapy in non-small cell lung cancer," Cancer Immunology, Immunotherapy. 2022; 71:2511-2522.
Zhang et al, "Neuregulin 4 suppresses NASH-HCC development by restraining tumor-prone liver microenvironment," Cell Metabolism. 2022; 34(9):1359-1376.e7.
Zhang et al, "High TREM2 expression correlates with poor prognosis in gastric cancer," Human Pathology. 2018; 72:91-99.
Zhang et al, "Single-cell analyses reveal key immune cell subsets associated with response to PD-L1 blockade in triple-negative breast cancer," Cancer Cell. 2021; 39(12):1578-1593.e8.

* cited by examiner

EOS006164

EOS006163

EOS006162

PN-37012

PN-37012

EOS006338

EOS006337

EOS004284

EOS006215

EOS004282

EOS004281

EOS006342

EOS006341

ANTI-TREM2 ANTIBODIES AND METHODS OF USE

CROSS REFERENCE TO RELATED APPLICATIONS

This application is a continuation of U.S. application Ser. No. 18/821,530, filed Aug. 30, 2024, which claims the benefit of and priority to U.S. Provisional Application No. 63/580,184, filed Sep. 1, 2023, and U.S. Provisional Application No. 63/640,439, filed Apr. 30, 2024; the entire contents of which are hereby incorporated by reference in their entireties.

SUBMISSION OF SEQUENCE LISTING XML

The content of the following submission on Sequence Listing XML is incorporated herein by reference in its entirety: a computer readable form (CRF) of the Sequence Listing (file name: 404541-ITW-005WO_SL.xml, date created Aug. 27, 2024, size 178,198 bytes).

FIELD

The present disclosure relates to anti-TREM2 antibodies and methods of using the same.

BACKGROUND

In normal tissues, myeloid cells are essential for proper functioning of both innate and adaptive immunity and notably for tissue damage repair and resolution of inflammation. However, in the setting of cancer, a significant excess of macrophages and dysfunctional or skewed populations of these and other cell types are commonly described. When considered as an aggregate population defined by single markers, such as CD68 or CD163, "macrophage" infiltration is correlated with worse outcomes in subjects across multiple tumor types (de Visser, Cancer Immunol Immunother, 2008; 57:1531-9; Hanada et al., Int J Urol 2000; 7:263-9; Yao et al., Clin Cancer Res, 520, 2001; 7:4021-6); (Ruffell et al., PNAS, 523 2012; 109:2796-801).

Triggering receptors expressed on myeloid cells or "TREMs" are a group of transmembrane glycoproteins that are expressed on different types of myeloid cells, such as macrophage, dendritic cell, osteoclast, microglia, mast cells, monocytes, lung epithelial cells, Langerhans cells of skin, Kupffer cells, and neutrophils (Takaki, R. et al., Immunol. Rev., 2006; 214:118-29). TREMs have an immunoglobulin (Ig)-type fold in their extracellular domain and thus belong to the immunoglobulin superfamily (IgSF). TREM receptors contain a short intracellular domain, but lack docking motifs for signaling mediators and require adaptor proteins, such as DAP 12 (DNAX-activating protein of 12 kDa) for cell activation. Two members of TREMs have been reported: TREM1 and TREM2, both of which play an important role in immune and inflammatory responses.

TREM2 can be activated by lipopolysaccharides (LPS), heat shock protein 60, neuritic debris, bacteria, apolipoprotein E and a broad array of anionic and zwitterionic lipids, e.g., phosphatidic acid (PA), phosphatidylglycerol (PG), phosphatidylserine (PS), phosphatidylinositol (PI), phosphatidylcholine (PC), cardiolipin and sphingomyelin. Activation of the TREM2 program is mainly restricted to pathologies associated with tissue damage and inflammation such as neurodegenerative diseases, atherosclerosis, obesity but also cancer. TREM2 activation increases phagocytic capacity of microglia and macrophages, reduces the release of proinflammatory cytokines, and limits TLR signaling.

Accordingly, there is a need in the art for improved agents that modulate TREM2, for use in the treatment of cancer and other TREM2-mediated disorders.

SUMMARY

The present disclosure provides anti-TREM2 antibodies and polypeptides. Nucleic acids encoding such anti-TREM2 antibodies, vectors, host cells, methods of manufacture, and methods for their use are also provided herein. The anti-TREM2 antibodies disclosed herein are particularly useful because they reduce TREM2-mediated efferocytosis and can be used to treat cancer in a subject.

In an aspect, provided herein is an antibody that specifically binds to human TREM2, comprising a VH comprising CDRH1, CDRH2, and CDRH3, and a VL comprising CDRL1, CDRL2, and CDRL3, wherein the CDRH1, CDRH2, and CDRH3 comprise the CDRH1, CDRH2, and CDRH3 amino acid sequences of a VH amino acid sequence set forth in any one of SEQ ID NOs: 87-109; and the CDRL1, CDRL2, and CDRL3 comprise the CDRL1, CDRL2, CDRL3 amino acid sequences of a VL amino acid sequence set forth in any one of SEQ ID NOS: 110-125.

In some embodiments, the VH amino acid sequence and the VL amino acid sequence are as set forth in: SEQ ID NOs: 87 and 110; 88 and 111; 89 and 112; 90 and 113; 91 and 114; 92 and 115; 93 and 116; 94 and 117; 95 and 118; 96 and 119; 97 and 120; 98 and 121; 99 and 119; 100 and 122; 101 and 110; 102 and 123; 103 and 115; 104 and 118; 105 and 124; 106 and 125; 107 and 110; 108 and 111; or 109 and 121, respectively.

In some embodiments, the CDRH1 comprises an amino acid sequence selected from the group consisting of SEQ ID NOs: 19-31. In some embodiments, the CDRH1 comprises an amino acid sequence selected from the group consisting of SEQ ID NO: 20, SEQ ID NO: 29, and SEQ ID NO: 19.

In some embodiments, the CDRH2 comprises an amino acid sequence selected from the group consisting of SEQ ID NOs: 32-41. In some embodiments, the CDRH2 comprises an amino acid sequence selected from the group consisting of SEQ ID NO: 33, SEQ ID NO: 40, and SEQ ID NO: 32.

In some embodiments, the CDRH3 comprises an amino acid sequence selected from the group consisting of SEQ ID NOs: 42-59. In some embodiments, the CDRH3 comprises an amino acid sequence selected from the group consisting of SEQ ID NO: 43, SEQ ID NO: 53, and SEQ ID NO: 55.

In some embodiments, the CDRL1 comprises an amino acid sequence selected from the group consisting of SEQ ID NOs: 60-65. In some embodiments, the CDRL1 comprises an amino acid sequence selected from the group consisting of SEQ ID NO: 60 and SEQ ID NO: 65.

In some embodiments, the CDRL2 comprises an amino acid sequence selected from the group consisting of SEQ ID NOs: 66-70. In some embodiments, the CDRL2 comprises an amino acid sequence selected from the group consisting of SEQ ID NO: 66 and SEQ ID NO: 70.

In some embodiments, the CDRL3 comprises an amino acid sequence selected from the group consisting of SEQ ID NOs: 71-86. In some embodiments, the CDRL3 comprises an amino acid sequence selected from the group consisting of SEQ ID NO: 72, SEQ ID NO: 82, and SEQ ID NO: 71.

In some embodiments, the CDRH1, CDRH2, and CDRH3 each comprise the amino acid sequence of the CDRH1, CDRH2, and CDRH3 selected from the group consisting of: (a) the CDRH1 sequence set forth in SEQ ID NO: 19, the CDRH2 sequence set forth in SEQ ID NO: 32, and the CDRH3 sequence set forth in SEQ ID NO: 42; (b) the CDRH1 sequence set forth in SEQ ID NO: 20, the CDRH2 sequence set forth in SEQ ID NO: 33, and the CDRH3 sequence set forth in SEQ ID NO: 43; (c) the CDRH1 sequence set forth in SEQ ID NO: 21, the CDRH2 sequence set forth in SEQ ID NO: 34, and the CDRH3 sequence set forth in SEQ ID NO: 44; (d) the CDRH1 sequence set forth in SEQ ID NO: 22, the CDRH2 sequence set forth in SEQ ID NO: 34, and the CDRH3 sequence set forth in SEQ ID NO: 45; (e) the CDRH1 sequence set forth in SEQ ID NO: 23, the CDRH2 sequence set forth in SEQ ID NO: 35, and the CDRH3 sequence set forth in SEQ ID NO: 46; (f) the CDRH1 sequence set forth in SEQ ID NO: 24, the CDRH2 sequence set forth in SEQ ID NO: 36, and the CDRH3 sequence set forth in SEQ ID NO: 47; (g) the CDRH1 sequence set forth in SEQ ID NO: 21, the CDRH2 sequence set forth in SEQ ID NO: 34, and the CDRH3 sequence set forth in SEQ ID NO: 48; (h) the CDRH1 sequence set forth in SEQ ID NO: 25, the CDRH2 sequence set forth in SEQ ID NO: 37, and the CDRH3 sequence set forth in SEQ ID NO: 49; (i) the CDRH1 sequence set forth in SEQ ID NO: 26, the CDRH2 sequence set forth in SEQ ID NO: 37, and the CDRH3 sequence set forth in SEQ ID NO: 50; (j) the CDRH1 sequence set forth in SEQ ID NO: 27, the CDRH2 sequence set forth in SEQ ID NO: 38, and the CDRH3 sequence set forth in SEQ ID NO: 51; (k) the CDRH1 sequence set forth in SEQ ID NO: 28, the CDRH2 sequence set forth in SEQ ID NO: 39, and the CDRH3 sequence set forth in SEQ ID NO: 52; (l) the CDRH1 sequence set forth in SEQ ID NO: 29, the CDRH2 sequence set forth in SEQ ID NO: 40, and the CDRH3 sequence set forth in SEQ ID NO: 53; (m) the CDRH1 sequence set forth in SEQ ID NO: 30, the CDRH2 sequence set forth in SEQ ID NO: 38, and the CDRH3 sequence set forth in SEQ ID NO: 53; (n) the CDRH1 sequence set forth in SEQ ID NO: 19, the CDRH2 sequence set forth in SEQ ID NO: 32, and the CDRH3 sequence set forth in SEQ ID NO: 54; (o) the CDRH1 sequence set forth in SEQ ID NO: 19, the CDRH2 sequence set forth in SEQ ID NO: 32, and the CDRH3 sequence set forth in SEQ ID NO: 55; (p) the CDRH1 sequence set forth in SEQ ID NO: 22, the CDRH2 sequence set forth in SEQ ID NO: 34, and the CDRH3 sequence set forth in SEQ ID NO: 56; (q) the CDRH1 sequence set forth in SEQ ID NO: 23, the CDRH2 sequence set forth in SEQ ID NO: 35, and the CDRH3 sequence set forth in SEQ ID NO: 47; (r) the CDRH1 sequence set forth in SEQ ID NO: 21, the CDRH2 sequence set forth in SEQ ID NO: 34, and the CDRH3 sequence set forth in SEQ ID NO: 57; (s) the CDRH1 sequence set forth in SEQ ID NO: 27, the CDRH2 sequence set forth in SEQ ID NO: 38, and the CDRH3 sequence set forth in SEQ ID NO: 58; and (t) the CDRH1 sequence set forth in SEQ ID NO: 31, the CDRH2 sequence set forth in SEQ ID NO: 41, and the CDRH3 sequence set forth in SEQ ID NO: 59.

In some embodiments, the CDRH1, CDRH2, and CDRH3 each comprise the amino acid sequence of the CDRH1, CDRH2, and CDRH3 selected from the group consisting of: (a) the CDRH1 sequence set forth in SEQ ID NO: 19, the CDRH2 sequence set forth in SEQ ID NO: 32, and the CDRH3 sequence set forth in SEQ ID NO: 55; (b) the CDRH1 sequence set forth in SEQ ID NO: 20, the CDRH2 sequence set forth in SEQ ID NO: 33, and the CDRH3 sequence set forth in SEQ ID NO: 43; and (c) the CDRH1 sequence set forth in SEQ ID NO: 29, the CDRH2 sequence set forth in SEQ ID NO: 40, and the CDRH3 sequence set forth in SEQ ID NO: 53.

In some embodiments, the VH comprises an amino acid sequence at least 80%, at least 85%, at least 90%, at least 95%, at least 96%, at least 97%, at least 98%, or at least 99% identical to the amino acid sequence set forth in any one of SEQ ID NOs: 87-109. In some embodiments, the VH comprises an amino acid sequence set forth in any one of SEQ ID NOs: 87-109.

In some embodiments, the CDRL1, CDRL2, and CDRL3 each comprise the amino acid sequence of the CDRL1, CDRL2, and CDRL3 selected from the group consisting of: (a) the CDRL1 sequence set forth in SEQ ID NO: 60, the CDRL2 sequence set forth in SEQ ID NO: 66, and the CDRL3 sequence set forth in SEQ ID NO: 71; (b) the CDRL1 sequence set forth in SEQ ID NO: 60, the CDRL2 sequence set forth in SEQ ID NO: 66, and the CDRL3 sequence set forth in SEQ ID NO: 72; (c) the CDRL1 sequence set forth in SEQ ID NO: 61, the CDRL2 sequence set forth in SEQ ID NO: 67, and the CDRL3 sequence set forth in SEQ ID NO: 73; (d) the CDRL1 sequence set forth in SEQ ID NO: 62, the CDRL2 sequence set forth in SEQ ID NO: 67, and the CDRL3 sequence set forth in SEQ ID NO: 74; (e) the CDRL1 sequence set forth in SEQ ID NO: 63, the CDRL2 sequence set forth in SEQ ID NO: 68, and the CDRL3 sequence set forth in SEQ ID NO: 75; (f) the CDRL1 sequence set forth in SEQ ID NO: 63, the CDRL2 sequence set forth in SEQ ID NO: 68, and the CDRL3 sequence set forth in SEQ ID NO: 76; (g) the CDRL1 sequence set forth in SEQ ID NO: 64, the CDRL2 sequence set forth in SEQ ID NO: 69, and the CDRL3 sequence set forth in SEQ ID NO: 77; (h) the CDRL1 sequence set forth in SEQ ID NO: 64, the CDRL2 sequence set forth in SEQ ID NO: 69, and the CDRL3 sequence set forth in SEQ ID NO: 78; (i) the CDRL1 sequence set forth in SEQ ID NO: 64, the CDRL2 sequence set forth in SEQ ID NO: 69, and the CDRL3 sequence set forth in SEQ ID NO: 79; (j) the CDRL1 sequence set forth in SEQ ID NO: 65, the CDRL2 sequence set forth in SEQ ID NO: 70, and the CDRL3 sequence set forth in SEQ ID NO: 80; (k) the CDRL1 sequence set forth in SEQ ID NO: 65, the CDRL2 sequence set forth in SEQ ID NO: 70, and the CDRL3 sequence set forth in SEQ ID NO: 81; (l) the CDRL1 sequence set forth in SEQ ID NO: 65, the CDRL2 sequence set forth in SEQ ID NO: 70, and the CDRL3 sequence set forth in SEQ ID NO: 82; (m) the CDRL1 sequence set forth in SEQ ID NO: 60, the CDRL2 sequence set forth in SEQ ID NO: 66, and the CDRL3 sequence set forth in SEQ ID NO: 83; (n) the CDRL1 sequence set forth in SEQ ID NO: 62, the CDRL2 sequence set forth in SEQ ID NO: 67, and the CDRL3 sequence set forth in SEQ ID NO: 84; (0) the CDRL1 sequence set forth in SEQ ID NO: 63, the CDRL2 sequence set forth in SEQ ID NO: 68, and the CDRL3 sequence set forth in SEQ ID NO: 74; (p) the CDRL1 sequence set forth in SEQ ID NO: 64, the CDRL2 sequence set forth in SEQ ID NO: 69, and the CDRL3 sequence set forth in SEQ ID NO: 79; (q) the CDRL1 sequence set forth in SEQ ID NO: 65, the CDRL2 sequence set forth in SEQ ID NO: 70, and the CDRL3 sequence set forth in SEQ ID NO: 85; and (r) the CDRL1 sequence set forth in SEQ ID NO: 60, the CDRL2 sequence set forth in SEQ ID NO: 66, and the CDRL3 sequence set forth in SEQ ID NO: 86.

In some embodiments, the CDRL1, CDRL2, and CDRL3 each comprise the amino acid sequence of the CDRL1, CDRL2, and CDRL3 selected from the group consisting of: (a) the CDRL1 sequence set forth in SEQ ID NO: 60, the CDRL2 sequence set forth in SEQ ID NO: 66, and the CDRL3 sequence set forth in SEQ ID NO: 71; (b) the CDRL1 sequence set forth in SEQ ID NO: 60, the CDRL2 sequence set forth in SEQ ID NO: 66, and the CDRL3 sequence set forth in SEQ ID NO: 72; and (c) the CDRL1 sequence set forth in SEQ ID NO: 65, the CDRL2 sequence set forth in SEQ ID NO: 70, and the CDRL3 sequence set forth in SEQ ID NO: 82.

In some embodiments, the VL comprises an amino acid sequence at least 80%, at least 85%, at least 90%, at least 95%, at least 96%, at least 97%, at least 98%, or at least 99% identical to the amino acid sequence set forth in any one of SEQ ID NOs: 110-125. In some embodiments, the VL comprises an amino acid sequence set forth in any one of SEQ ID NOs: 110-125.

In an aspect, provided herein is an antibody that specifically binds to human TREM2, comprising: (a) a VH comprising a CDRH1 comprising the amino acid sequence set forth in SEQ ID NO: 20, a CDRH2 comprising the amino acid sequence set forth in SEQ ID NO: 33, and a CDRH3 comprising the amino acid sequence set forth in SEQ ID NO: 43; and (b) a VL comprising a CDRL1 comprising the amino acid sequence set forth in SEQ ID NO: 60, a CDRL2 comprising the amino acid sequence set forth in SEQ ID NO: 66, and a CDRL3 comprising the amino acid sequence set forth in SEQ ID NO: 72.

In an aspect, provided herein is an antibody that specifically binds to human TREM2, comprising: (a) a VH comprising a CDRH1 comprising the amino acid sequence set forth in SEQ ID NO: 29, a CDRH2 comprising the amino acid sequence set forth in SEQ ID NO: 40, and a CDRH3 comprising the amino acid sequence set forth in SEQ ID NO: 53; and (b) a VL comprising a CDRL1 comprising the amino acid sequence set forth in SEQ ID NO: 65, a CDRL2 comprising the amino acid sequence set forth in SEQ ID NO: 70, and a CDRL3 comprising the amino acid sequence set forth in SEQ ID NO: 82.

In an aspect, provided herein is an antibody that specifically binds to human TREM2, comprising: (a) a VH comprising a CDRH1 comprising the amino acid sequence set forth in SEQ ID NO: 19, a CDRH2 comprising the amino acid sequence set forth in SEQ ID NO: 32, and a CDRH3 comprising the amino acid sequence set forth in SEQ ID NO: 55; and (b) a VL comprising a CDRL1 comprising the amino acid sequence set forth in SEQ ID NO: 60, a CDRL2 comprising the amino acid sequence set forth in SEQ ID NO: 66, and a CDRL3 comprising the amino acid sequence set forth in SEQ ID NO: 71.

In an aspect, provided herein is an antibody that specifically binds to TREM2, comprising a VH and a VL, wherein:
(i) the VH comprises:
(a) a CDRH1 comprising the amino acid sequence GTF$X_1X_2$YAIS (SEQ ID NO: 8), wherein:
$X_1$ is S or A;
$X_2$ is S or Q; and/or
(b) a CDRH2 comprising the amino acid sequence $X_1$IIP$X_2$SGTANYAQKFQG (SEQ ID NO: 9), wherein:
$X_1$ is G or V;
$X_2$ is I or D; and/or
(c) a CDRH3 comprising the amino acid sequence ARTQE$X_1$T$X_2$FD$X_3$ (SEQ ID NO: 10), wherein:
$X_1$ is Y or N;
$X_2$ is A, I, or L;
$X_3$ is I or S; and
(ii) the VL comprises:
(a) a CDRL1 comprising the amino acid sequence RASQSVSSYLA (SEQ ID NO: 60); and/or
(b) a CDRL2 comprising the amino acid sequence DASNRAT (SEQ ID NO: 66); and/or
(c) a CDRL3 comprising the amino acid sequence QQD$X_1X_2$WPIT (SEQ ID NO: 17), wherein:
$X_1$ is Y or F;
$X_2$ is H or E.

In an aspect, provided herein is an antibody that specifically binds to TREM2, comprising a VH and a VL, wherein:
(i) the VH comprises:
(a) a CDRH1 comprising the amino acid sequence FTF$X_1X_2X_3X_4$MS (SEQ ID NO: 11), wherein:
$X_1$ is G or D;
$X_2$ is D or E;
$X_3$ is Y or H;
$X_4$ is A or T; and/or
(b) a CDRH2 comprising the amino acid sequence FIGSKAY$X_1X_2$TTEYTASVKG (SEQ ID NO: 12), wherein:
$X_1$ is G or V;
$X_2$ is I or D; and/or
(c) a CDRH3 comprising the amino acid sequence ARGKR$X_1X_2$Y$X_3X_4$W$X_5$PAFDV (SEQ ID NO: 13), wherein:
$X_1$ is Y or R;
$X_2$ is S or D;
$X_3$ is G or T;
$X_4$ is Y or G;
$X_5$ is H, T, or V; and
(ii) the VL comprises:
(a) a CDRL1 comprising the amino acid sequence QASQDITNYLN (SEQ ID NO: 65); and/or
(b) a CDRL2 comprising the amino acid sequence DASNLET (SEQ ID NO: 70); and/or
(c) a CDRL3 comprising the amino acid sequence Q$X_1$YD$X_2$Y$X_3X_4$ (SEQ ID NO: 18), wherein:
$X_1$ is Q or E;
$X_2$ is S or Q;
$X_3$ is L or I;
$X_4$ is T or A.

In some embodiments, the antibody further comprises heavy and/or light chain constant regions. In some embodiments, the heavy chain constant region is selected from the group consisting of human IgG1, IgG2, IgG3, IgG4, IgA1, and IgA2. In some embodiments, the IgG1 is non-fucosylated IgG1. In some embodiments, the amino acid sequence of IgG1 comprises a N297A mutation. In some embodiments, the heavy chain constant region comprises an amino acid sequence set forth in SEQ ID NO: 159 or SEQ ID NO: 160. In some embodiments, the light chain constant region is selected from the group consisting of human lambda and kappa. In some embodiments, the light chain constant region comprises an amino acid sequence set forth in SEQ ID NO: 157 or SEQ ID NO: 158.

In some embodiments, the antibody comprises: (a) a heavy chain comprising an amino acid sequence set forth in SEQ ID NO: 164 or SEQ ID NO: 165, and a light chain comprising an amino acid sequence set forth in SEQ ID NO: 161; (b) a heavy chain comprising an amino acid sequence set forth in SEQ ID NO: 166 or SEQ ID NO: 167, and a light chain comprising an amino acid sequence set forth in SEQ ID NO: 162; or (c) a heavy chain comprising an amino acid sequence set forth in SEQ ID NO: 168 or SEQ ID NO: 169, and a light chain comprising an amino acid sequence set forth in SEQ ID NO: 163.

Also provided is an antibody that competes for binding to TREM2 with, or binds to the same epitope as, any antibody described herein.

In an aspect, provided herein is a polypeptide comprising a VH comprising the CDRH1, CDRH2, and CDRH3 amino acid sequences of an VH amino acid sequence set forth in any one of SEQ ID NOs: 87-109. In some embodiments, the VH comprises the CDRH1, CDRH2, and CDRH3 amino acid sequences set forth in SEQ ID NOs: 19, 32, and 42; 20, 33, and 43; 21, 34, and 44; 22, 34, and 46; 23, 35, and 46; 24, 36, and 47; 21, 34, and 48; 25, 37, and 49; 26, 37, and 50; 27, 38, and 51; 28, 39, and 52; 29, 40, and 53; 30, 38, and 53; 19, 32, and 54; 19, 32, and 55; 22, 34, and 56; 23, 35, and 47; 21, 34, and 57; 27, 38, and 58; or 31, 41, and 59, respectively.

In an aspect, provided herein is a polypeptide comprising a VL comprising the CDRL1, CDRL2, and CDRL3 amino acid sequences of a VL amino acid sequence set forth in any one of SEQ ID NOs: 110-125. In some embodiments, the VL comprises the CDRL1, CDRL2, and CDRL3 amino acid sequences set forth in SEQ ID NOs: 60, 66, and 71; 60, 66, and 72; 61, 67, and 73; 62, 67, and 74; 63, 68, and 75; 63, 68, and 76; 64, 69, and 77; 64, 69, and 78; 64, 69, and 79; 65, 70, and 80; 65, 70, and 81; 65, 70, and 82; 60, 66, and 83; 62, 67, and 84; 63, 68, and 74; 64, 69, and 79; 65, 70, and 85; or 60, 66, and 86, respectively.

In an aspect, provided herein is a polypeptide comprising an amino acid sequence set forth in any one of SEQ ID NOs: 87-125 and 161-169.

In some embodiments, the anti-TREM2 antibody described herein is an antagonist or a reverse agonist.

In some embodiments, the antibody or polypeptide described herein is conjugated to a cytotoxic agent, cytostatic agent, toxin, radionuclide, or detectable label.

Also provided is a polynucleotide or polynucleotides encoding a VH and/or a VL, or a heavy chain and/or a light chain of any antibody or polypeptide described herein.

Also provided is an expression vector comprising any polynucleotide or polynucleotides described herein.

Also provided is a host cell comprising: (a) any polynucleotide or polynucleotides described herein; (b) any expression vector described herein; (c) a first polynucleotide encoding a heavy chain variable region or a heavy chain of any antibody described herein and a second polynucleotide encoding a light chain variable region or a light chain of any antibody described herein; and/or (d) a first expression vector comprising a first polynucleotide encoding a heavy chain variable region or a heavy chain of any antibody described herein and a second expression vector comprising a second polynucleotide encoding a light chain variable region or a light chain of any antibody described herein.

Also provided is a method for producing an antibody that binds to human TREM2, comprising culturing any host cell described herein under conditions which permit expression of the antibody.

Also provided is a pharmaceutical composition comprising any antibody or polypeptide described herein, and at least one pharmaceutically acceptable carrier.

Also provided is any antibody, polypeptide, or pharmaceutical composition described herein for use as a medicament.

Also provided is a method of reducing binding of low-density lipoprotein (LDL) to TREM2 in a subject, wherein the method comprises administering to the subject an effective amount of any antibody, polypeptide, or pharmaceutical composition described herein.

Also provided is a method of reducing efferocytosis in a subject, wherein the method comprises administering to the subject an effective amount of any antibody, polypeptide, or pharmaceutical composition described herein.

Also provided is a method of treating a disease or disorder in a subject, wherein the method comprises administering to the subject an effective amount of any antibody, polypeptide, or pharmaceutical composition described herein. In some embodiments, the disease or disorder is cancer. In some embodiments, the cancer is selected from the group consisting of: lung cancer, liver cancer, ovarian cancer, kidney cancer, prostate cancer, testicular cancer, uterine cancer, gallbladder cancer, sarcoma, Ewing sarcoma, thyroid cancer, melanoma, skin cancer, pancreatic cancer, gastric cancer, gastrointestinal/stomach (GIST) cancer, lymphoma, head and neck cancer, glioma or brain cancer, colon cancer, rectal cancer, colorectal cancer, breast cancer, renal cell carcinoma, or kidney cancer. In some embodiments, the glioma or brain cancer is glioblastoma multiforme (GBM). In some embodiments, the liver cancer is hepatocellular carcinoma (HCC). In some embodiments, the uterine cancer is uterine corpus endometrial carcinoma (UCEC). In some embodiments, the antibody is administered to the subject simultaneously or sequentially in combination with an additional therapeutic agent.

Also provided is the use of any antibody, polypeptide, or pharmaceutical composition described herein, for the manufacture of a medicament for reducing binding of LDL to TREM2, reducing efferocytosis, or treating cancer, in a subject.

Also provided is an antibody, a polypeptide, or a pharmaceutical composition, for use in reducing binding of LDL to TREM2, reducing efferocytosis, or treating cancer, in a subject.

BRIEF DESCRIPTION OF THE DRAWINGS

FIGS. 1A and 1C depict the side view (parallel with cell membrane) and FIGS. 1B and 1D depict the top view (looking down onto the cell membrane).

FIGS. 4A-4E show representative results with a dose-response dependency of the anti-TREM2 antibodies and the ratio pSYK/totSYK. Exemplary antibodies have been normalized against benchmark antibody 6E7.

FIGS. 5A-5D show a dose-dependent decrease of LDL-Alexafluor-488 binding when CHO over-expressing human TREM2/DAP12 were incubated with selected anti-TREM2 antibodies. Exemplary antibodies have been normalized against benchmark antibody MOR044746.

FIG. 8A shows the level of CXCL10 released by M2a-like monocyte derived macrophages when anti-TREM2 antibody is applied since the monocytic state. Quantity of CXCL10 was measured by Meso Scale Discovery assay and is normalized against the control isotype. Dashed line represents the level of CXCL10 released when cells are exposed to control isotype. Each type of symbol represents a healthy donor (7 donors, in triplicates or quadruplicates). FIG. 8B shows the level of CCL17 released by M2a-like when anti-TREM2 antibody is applied since the monocytic state. Quantity of CCL17 was measured by Meso Scale Discovery assay and is normalized against the control isotype. Dashed line represents the level of CCL17 released when cells are exposed to control isotype. Each type of symbol represents a healthy donor (3 donors, in quadruplicates).

FIGS. 9A-9C show the levels of CCL22 (FIG. 9A), M-CSF (FIG. 9B), and CXCL9 (FIG. 9C) released by M2a-like monocyte derived macrophages stimulated with LPS when EOS006215 antibody is applied over a range of doses, starting at 10 μg/mL (66.6 nM) followed by a 3-fold dilution series (9 points) since the monocytic state. Quantities of CCL22, M-CSF, and CXCL9 were measured by Meso Scale Discovery assay. Each data point represents a quadruplicate (mean+−SD). Representative data from 1 healthy donor.

FIGS. 15A-15F shows tumor growth curves from MC38 tumor bearing mice under treatment. Median (FIG. 15A) and individual growth curves from mice treated with vehicle (FIG. 15B), anti-PD-1 antibody (FIG. 15C), EOS006215 (FIG. 15D) and the combination of EOS006215 and anti-PD-1 antibody in concurrent (FIG. 15E) or sequential (FIG. 15F) treatment are shown. * represents a statistical significance of $p<0.05$.

FIG. 17A shows mean in vivo bioluminescence intensity (BLI) over time. FIG. 17B shows the percentage of mice without metastasis, confirmed by ex-vivo BLI measurement, at study end.

DETAILED DESCRIPTION

Figure 1A:
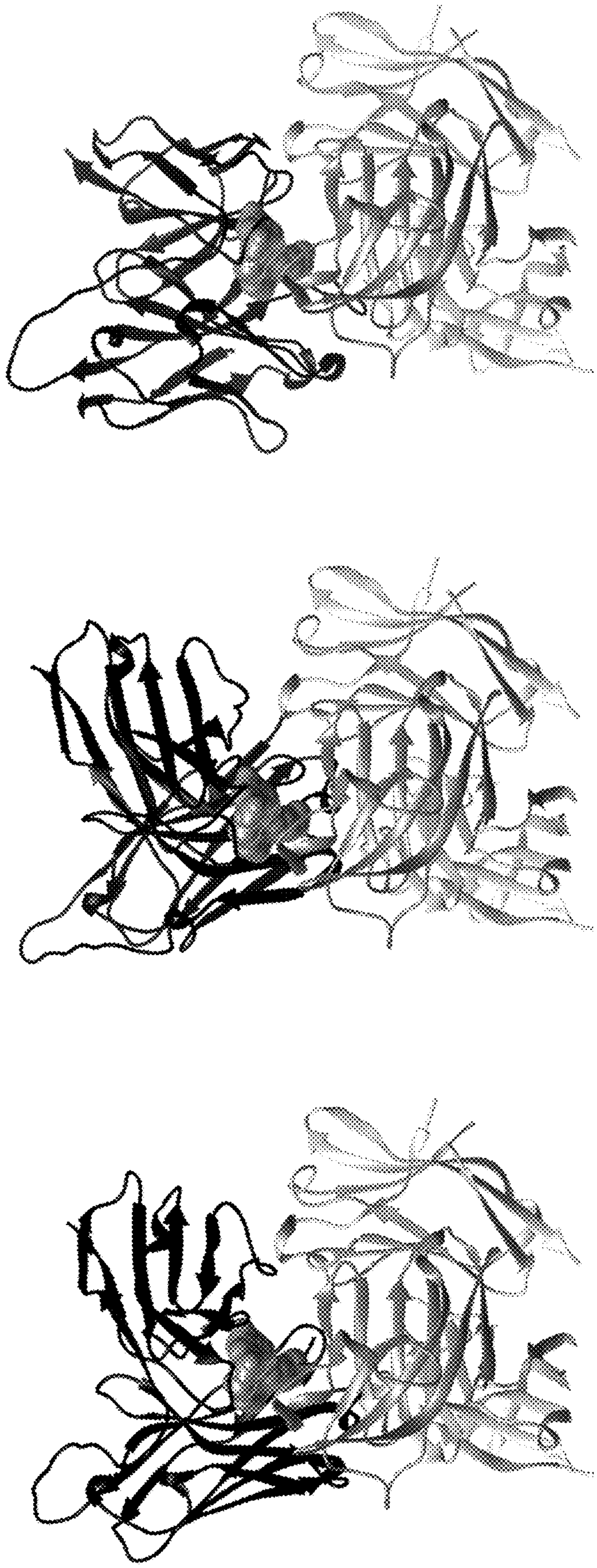
FIGS. 1A-1D show the expected impact of anti-TREM2 antibodies on the oligomerization of TREM2 extracellular domain occurring in presence of phosphatidylserine (PS). Models were built using AlphaFold Multimer algorithm. Each antibody is seen as an scFv in black, the TREM2 molecule with which it is in complex is in dark grey, and the other two TREM2 molecules as found in the crystallographic trimer are in white. All proteins are in ribbon representation, and PS is rendered in atomic surface representation. Trimer formation is prohibited for EOS006162, EOS006163, EOS006164 (FIGS. 1A and 1B) in contrast to benchmark PN-37012 (FIGS. 1C and 1D).

The present disclosure provides anti-TREM2 antibodies and polypeptides. Nucleic acids encoding such anti-TREM2 antibodies, vectors, host cells, methods of manufacture, and methods for their use are also provided herein. The anti-TREM2 antibodies disclosed herein are particularly useful for treating cancer in a subject.

Definitions

As used herein, the terms "antibody" and "antibodies" include full-length antibodies, antigen-binding fragments of full-length antibodies, and molecules comprising antibody CDRs, VH regions, and/or VL regions. Examples of antibodies include, without limitation, monoclonal antibodies, recombinantly produced antibodies, monospecific antibodies, multi-specific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single-domain antibodies (sdAb), monovalent antibodies, single chain antibodies or single-chain Fvs (scFv), camelized antibodies, affibody molecules, VHH fragments, Fab fragments, F(ab')2 fragments, disulfide-linked Fvs (sdFv), anti-idiotypic (anti-Id) antibodies (including, e.g., anti-anti-Id antibodies), and antigen-binding fragments of any of the above. Antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), any subclass (e.g., $IgG_{2a}$ or $IgG_{2b}$), or species (e.g., mouse $IgG_{2a}$ or $IgG_{2b}$) of immunoglobulin molecule. In certain embodiments, an antibody described herein is an $IgG_1$ antibody.

As used herein, the terms "antigen-binding domain," "antigen-binding region," "antigen-binding fragment" and similar terms refers to any polypeptide that specifically binds to an antigen. Examples of antigen-binding domains include polypeptides derived from antibodies, such as Fab fragments, $F(ab')_2$ fragments, disulfide-linked Fvs (sdFv), single-chain Fvs (scFv), CDRs, VH domains, VL domains, single-domain antibodies (sdAb), VHH fragments, camelid antibodies, and antigen-binding fragments of any of the above. The term also encompasses synthetic antigen-binding proteins or antibody mimetic proteins such as, for example, anticalins and DARPins.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). For example, in general, there are three CDRs in each heavy chain variable region (e.g., HCDR1, HCDR2, and HCDR3) and three CDRs in each light chain variable region (LCDR1, LCDR2, and LCDR3). Without wishing to be bound by any particular mechanism or theory, it is believed that the CDRs of the light and heavy chains are primarily responsible for the interaction and specificity of the antibody with antigen. In certain embodiments, the variable region is a human variable region.

The terms "VL" and "VL domain" are used interchangeably to refer to the light chain variable region of an antibody.

The terms "VH" and "VH domain" are used interchangeably to refer to the heavy chain variable region of an antibody.

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen, but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., IgG1, IgG2, IgG3, and IgG4. In specific embodiments, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

As used herein, the term "Fc region" refers to the portion of an immunoglobulin formed by the Fc domains of its two heavy chains. The Fc region can be a wild-type Fc region (native Fc region) or a variant Fc region. A native Fc region is homodimeric. The Fc region can be derived from any native immunoglobulin. In some embodiments, the Fc region is formed from an IgA, IgD, IgE, or IgG heavy chain constant region. In some embodiments, the Fc region is formed from an IgG heavy chain constant region. In some embodiments, the IgG heavy chain is an IgG1, IgG2, IgG3, or IgG4 heavy chain constant region. In some embodiments, the Fc region is formed from an IgG1 heavy chain constant region.

As used herein, the term "variant Fc region" refers to a variant of an Fc region with one or more alteration(s) relative to a native Fc region. Alterations can include amino acid substitutions, additions and/or deletions, linkage of additional moieties, and/or alteration of the native glycans. The term encompasses heterodimeric Fc regions where each of the constituent Fc domains is different. The term also encompasses single chain Fc regions where the constituent Fc domains are linked together by a linker moiety.

As used herein, the term "Fc domain" refers to the portion of a single immunoglobulin heavy chain comprising both the CH2 and CH3 domains of the antibody. In some embodiments, the Fc domain comprises at least a portion of a hinge (e.g., upper, middle, and/or lower hinge region) region, a CH2 domain, and a CH3 domain.

As used herein, the term "hinge region" refers to the portion of a heavy chain molecule that joins the CH1 domain to the CH2 domain. This hinge region comprises approximately 25 amino acid residues and is flexible, thus allowing the two N-terminal antigen binding regions to move independently. Hinge regions can be subdivided into three distinct domains: upper, middle, and lower hinge domains.

As used herein, the term "EU position" refers to the amino acid position in the EU numbering convention for the Fc region described in Edelman, G M et al., Proc. Natl. Acad. USA, 63, 78-85 (1969) and Kabat et al., in "Sequences of Proteins of Immunological Interest," U.S. Dept. Health and Human Services, 5th edition, 1991.

As used herein, the term "affinity" or "binding affinity" refers to the strength of the binding interaction between two molecules, e.g., between an antibody and an antigen. Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$, and $k_{off}$ can be determined by techniques known to one of ordinary skill in the art, such as BIAcore® or KinExA.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50 (Pt 4): 339-350; McPherson A (1990) Eur J Biochem 189:1-23; Chayen N E (1997) Structure 5:1269-1274; McPherson A (1976) J Biol Chem 251:6300-6303). Antibody: antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds. Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed. Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270:1388-1394 and Cunningham B C & Wells J A (1989) Science 244:1081-1085 for a description of mutagenesis techniques, including alanine scanning mutagenesis techniques. In a specific embodiment, the epitope of an antibody is predicted using AlphaFold-multimer algorithm.

As used herein, the term "specifically binds" refers to the specificity of a binding molecule (e.g., an antibody) for an antigen, as is understood by one skilled in the art. Binding molecules that specifically bind to an antigen typically bind to the antigen with an equilibrium dissociation constant ($K_D$) of less than $1\times10^{-6}$ M, as measured by, e.g., ELISA assay, surface plasmon resonance, or other suitable assays known in the art. The skilled worker will appreciate that, in certain embodiments, a binding molecule can specifically bind to different antigens, e.g., different antigens that share a common epitope that is recognized by the binding molecule.

As used herein, the term "TREM2" (also known as "triggering receptor expressed on myeloid cells 2," TREM2a, TREM2b, or TREM2c) refers to a transmembrane glycoprotein that belongs to the immunoglobulin superfamily (IgSF). The entire TREM2 protein (SEQ ID NO: 1) consists of a leading signal peptide (amino acids 1-18), a single V-type IgSF extracellular region (amino acids 19-132), a stalk region (amino acids 133-172), a positively-charged transmembrane domain (amino acids 173-197), and a cytosolic tail (amino acids 198-230) (Feuerbach et al., Neurosci. Lett. 660 (2017): 109-114). The genomic sequence of human TREM2 gene can be found in GenBank (Gene ID: 54209). Due to alternative splicing, three TREM2 isoforms are present in the human (protein sequences available in ENSEMBL under IDs ENSP00000362205, ENSP00000342651, and ENSP00000362214). The term "TREM2" is used to refer collectively to all isoforms of TREM2. Exemplary protein and mRNA sequences for the longest human TREM2 isoform are: Triggering receptor expressed on myeloid cells 2 precursor isoform 1 precursor [*Homo sapiens*] (NP_061838.1)

```
                                         (SEQ ID NO: 1)
MEPLRLLILLFVTELSGAHNTTVFQGVAGQSLQVSCPYDSMKHWGRRKAW

CRQLGEKGPCQRVVSTHNLWLLSFLRRWNGSTAITDDTLGGTLTITLRNL

QPHDAGLYQCQSLHGSEADTLRKVLVEVLADPLDHRDAGDLWFPGESESF

EDAHVEHSISRSLLEGEIPFPPTSILLLLACIFLIKILAASALWAAAWHG

QKPGTHPPSELDCGHDPGYQLQTLPGLRDT
```

*Homo sapiens* triggering receptor expressed on myeloid cells 2 (TREM2), transcript variant 1, mRNA (NCBI Reference Sequence: NM_018965.4)

```
                                         (SEQ ID NO: 4)
actctgcttc tgcccttggc tggggaaggg tggcatggag

cctctccggc tgctcatctt actctttgtc acagagctgt

ccggagccca caacaccaca gtgttccagg gcgtggcggg

ccagtccctg caggtgtctt gcccctatga ctccatgaag

cactggggga ggcgcaaggc ctggtgccgc cagctgggag

agaagggccc atgccagcgt gtggtcagca cgcacaactt

gtggctgctg tccttcctga ggaggtggaa tgggagcaca

gccatcacag acgataccct gggtggcact ctcaccatta

cgctgcggaa tctacaaccc catgatgcgg gtctctacca

gtgccagagc ctccatggca gtgaggctga caccctcagg

aaggtcctgg tggaggtgct ggcagacccc ctggatcacc
```

-continued

```
gggatgctgg agatctctgg ttccccgggg agtctgagag

cttcgaggat gcccatgtgg agcacagcat ctccaggagc

ctcttggaag gagaaatccc cttcccaccc acttccatcc

ttctcctcct ggcctgcatc tttctcatca agattctagc

agccagcgcc ctctgggctg cagcctggca tggacagaag

ccagggacac atccacccag tgaactggac tgtggccatg

acccagggta tcagctccaa actctgccag ggctgagaga

cacgtgaagg aagatgatgg gaggaaaagc ccaggagaag

tcccaccagg gaccagccca gcctgcatac ttgccacttg

gccaccagga ctccttgttc tgctctggca agagactact

ctgcctgaac actgcttctc ctggaccctg gaagcaggga

ctggttgagg gagtggggag gtggtaagaa cacctgacaa

cttctgaata ttggacattt taaacactta caaataaatc

caagactgtc atatttagct gga
```

An exemplary amino acid sequence of human TREM2 isoform 2 is: Triggering receptor expressed on myeloid cells 2 precursor isoform 2 precursor [*Homo sapiens*] (NP_001258750.1)

```
                                   (SEQ ID NO: 2)
MEPLRLLILLFVTELSGAHNTTVFQGVAGQSLQVSCPYDSMKHWGRRKAW

CRQLGEKGPCQRVVSTHNLWLLSFLRRWNGSTAITDDTLGGTLTITLRNL

QPHDAGLYQCQSLHGSEADTLRKVLVEVLADPLDHRDAGDLWFPGESESF

EDAHVEHSISRAERHVKEDDGRKSPGEVPPGTSPACILATWPPGLLVLLW

QETTLPEHCESWTLEAGTG
```

An exemplary amino acid sequence of human TREM2 isoform 3 is:

```
                                   (SEQ ID NO: 3)
MEPLRLLILLFVTELSGAHNTTVFQGVAGQSLQVSCPYDSMKHWGRRKAW

CRQLGEKGPCQRVVSTHNLWLLSFLRRWNGSTAITDDTLGGTLTITLRNL

QPHDAGLYQCQSLHGSEADTLRKVLVEVLADPLDHRDAGDLWFPGESESF

EDAHVEHSISRPSQGSHLPSCLSKEPLGRRNPLPTHFHPSPPGLHLSHQD

SSSQRPLGCSLAWTEARDTSTQ
```

As used herein, human TREM2 protein also encompasses proteins that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with any of SEQ ID NO: 1, 2, or 3, wherein such proteins still have the ligand binding, intracellular signaling, facilitating phagocytosis and degradation of phagocytic material, and/or other regulatory function of TREM2. The sequences of murine, cynomolgus, and other TREM2 proteins are known in the art.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F, (1990) PNAS 87:2264-2268, modified as in Karlin S & Altschul S F, (1993) PNAS 90:5873-5877, each of which is herein incorporated by reference in its entirety. Such an algorithm is incorporated into the NBLAST and XBLAST programs of Altschul S F et al., (1990) J Mol Biol 215:403, which is herein incorporated by reference in its entirety. BLAST nucleotide searches can be performed with the NBLAST nucleotide program parameters set, e.g., at score=100, wordlength=12 to obtain nucleotide sequences homologous to a nucleic acid molecule described herein. BLAST protein searches can be performed with the XBLAST program parameters set, e.g., at score=50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25:3389-3402, which is herein incorporated by reference in its entirety. Alternatively, PSI BLAST can be used to perform an iterated search which detects distant relationships between molecules. Id. When utilizing BLAST, Gapped BLAST, and PSI BLAST programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, (1988) *CABIOS* 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein with respect to an antibody or polynucleotide, the term "isolated" refers to an antibody or polynucleotide that is separated from one or more contaminants (e.g., polypeptides, polynucleotides, lipids, or carbohydrates, etc.) which are present in a natural source of the antibody or polynucleotide. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

As used herein, the term "treat," "treating," and "treatment" refer to therapeutic or preventative measures described herein. The methods of "treatment" employ administration of a polypeptide to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In an embodiment, the subject is a human or non-human mammal. In an embodiment, the subject is a human.

As used herein, the term "about" or "approximately" when referring to a measurable value, such as a dosage, encompasses variations of ±20%, ±15%, ±10%, ±5%, ±1%, or ±0.1% of a given value or range, as are appropriate to perform the methods disclosed herein.

Anti-TREM2 Antibodies

In an aspect, an antibody described herein which specifically binds to TREM2 (e.g., human TREM2), comprises a heavy chain variable region (VH) comprising:

(a) a CDRH1 comprising, consisting of, or consisting essentially of the amino acid sequence $X_1TFX_2X_3X_4X_5X_6$ (SEQ ID NO: 5), wherein:

$X_1$ is G or F;
$X_2$ is S, A, G, or D;
$X_3$ is S, Q, N, D, T, or E;
$X_4$ is A, G, T, or Y;
$X_5$ is I or M;
$X_6$ is S, G, or T; and/or (b) a CDRH2 comprising, consisting of, or consisting essentially of the amino acid sequence $X_1IX_2X_3X_4X_5X_6X_7X_8X_9X_{10}X_{11}X_{12}X_{13}X_{14}X_{15}$ (SEQ ID NO: 6), wherein:

$X_1$ is G, V, A, E, F, or Y;
$X_2$ is I, S, Y, or G;
$X_3$ is P, G, H, A, or S;
$X_4$ is I, D, S, N, or K;
$X_5$ is S, G, or A;
$X_6$ is G, S, D, or Y;
$X_7$ is T, S, K, G, or A;
$X_8$ is A, T, N, G, or I;
$X_9$ is N, Y, or T;
$X_{10}$ is Y, N, or T;
$X_{11}$ is A, P, or E;
$X_{12}$ is Q, D, S, or Y;
$X_{13}$ is K, S, L, or T;
$X_{14}$ is F, V, K, or A;
$X_{15}$ is Q, K, or S; and/or (c) a CDRH3 comprising, consisting of, or consisting essentially of the amino acid sequence $AX_1X_2X_3X_4X_5X_6X_7X_8X_9X_{10}$ (SEQ ID NO: 7), wherein:

$X_1$ is R, K, or S;
$X_2$ is T, H, S, D, L, G, or H;
$X_3$ is Q, Y, P, T, R, K, or G;
$X_4$ is E, D, A, K, G, or R;
$X_5$ is Y, N, R, G, or V;
$X_6$ is T, G, F, Q, W, Y, S, or D;
$X_7$ is A, I, Y, G, V, T, F, or L;
$X_8$ is F, A, Y, G, V, T, or L;
$X_9$ is D, F, G, M, or Y;
$X_{10}$ is I, D, E, P, W, or S.

In specific embodiments, the antibody comprises one, two, or all three of the CDRHs above.

In certain embodiments, the antibody comprises a VH comprising:

(a) a CDRH1 comprising, consisting of, or consisting essentially of the amino acid sequence $X_1TFX_2X_3X_4X_5X_6$ (SEQ ID NO: 5), wherein:

$X_1$ is G or F;
$X_2$ is S, A, or D;
$X_3$ is S, Q, or D;
$X_4$ is Y;
$X_5$ is I or M;
$X_6$ is S; and/or (b) a CDRH2 comprising, consisting of, or consisting essentially of the amino acid sequence $X_1IX_2X_3X_4X_5X_6X_7X_8X_9X_{10}X_{11}X_{12}X_{13}X_{14}X_{15}$ (SEQ ID NO: 6), wherein:

$X_1$ is G, V, or F;
$X_2$ is I or G;
$X_3$ is P or S;
$X_4$ is I, D, or K;
$X_5$ is S or A;
$X_6$ is G or Y;
$X_7$ is T or S;
$X_8$ is A;
$X_9$ is N or T;
$X_{10}$ is Y or T;
$X_{11}$ is A or E;
$X_{12}$ is Q or Y;
$X_{13}$ is K or T;
$X_{14}$ is F or A;
$X_{15}$ is Q or S; and/or (c) a CDRH3 comprising, consisting of, or consisting essentially of the amino acid sequence $AX_1X_2X_3X_4X_5X_6X_7X_8X_9X_{10}$ (SEQ ID NO: 7), wherein:

$X_1$ is R;
$X_2$ is T or G;
$X_3$ is Q or K;
$X_4$ is E or R;
$X_5$ is Y or N;
$X_6$ is T or S;
$X_7$ is I, Y, or L;
$X_8$ is F or T;
$X_9$ is D or Y;
$X_{10}$ is I, W, or S.

In specific embodiments, the antibody comprises one, two, or all three of the CDRHs above.

In certain embodiments, the antibody comprises a VH comprising:

(a) a CDRH1 comprising, consisting of, or consisting essentially of the amino acid sequence $GTFX_1X_2YAIS$ (SEQ ID NO: 8), wherein:

$X_1$ is S or A;
$X_2$ is S or Q; and/or (b) a CDRH2 comprising, consisting of, or consisting essentially of the amino acid sequence $X_1IIPX_2SGTANYAQKFQG$ (SEQ ID NO: 9), wherein:

$X_1$ is G or V;
$X_2$ is I or D; and/or (c) a CDRH3 comprising, consisting of, or consisting essentially of the amino acid sequence $ARTQEXITX_2FDX_3$ (SEQ ID NO: 10), wherein:

$X_1$ is Y or N;
$X_2$ is A, I, or L;
$X_3$ is I or S.

In specific embodiments, the antibody comprises one, two, or all three of the CDRHs above.

In certain embodiments, the antibody comprises a VH comprising:

(a) a CDRH1 comprising, consisting of, or consisting essentially of the amino acid sequence $FTFX_1X_2X_3X_4MS$ (SEQ ID NO: 11), wherein:

$X_1$ is G or D;
$X_2$ is D or E;

$X_3$ is Y or H;

$X_4$ is A or T; and/or (b) a CDRH2 comprising, consisting of, or consisting essentially of the amino acid sequence FIGSKAY$X_1X_2$TTEYTASVKG (SEQ ID NO: 12), wherein:

$X_1$ is G or V;

$X_2$ is I or D; and/or (c) a CDRH3 comprising, consisting of, or consisting essentially of the amino acid sequence ARGKR$X_1X_2$Y$X_3X_4$W$X_5$PAFDV (SEQ ID NO: 13), wherein:

$X_1$ is Y or R;

$X_2$ is S or D;

$X_3$ is G or T;

$X_4$ is Y or G;

$X_5$ is H, T, or V.

In specific embodiments, the antibody comprises one, two, or all three of the CDRHs above.

In certain embodiments, the antibody comprises the CDRH1 of one of the antibodies in Table 1. In some embodiments, the antibody comprises the CDRH2 of one of the antibodies in Table 1. In certain embodiments, the antibody comprises the CDRH3 of one of the antibodies in Table 1. In certain embodiments, the antibody comprises one, two, or all three of the CDRHs of one of the antibodies in Table 1 (e.g., the CDRHs in one row of Table 1, for example, all of the CDRHs are from antibody EOS006164). In some embodiments, the antibody comprises the VH framework regions described herein. In specific embodiments, the antibody comprises the VH framework regions (FRs) of an antibody set forth in Table 4 (e.g., one, two, three, or four of the framework regions in one row of Table 4).

In another aspect, an antibody described herein which specifically binds to TREM2 (e.g., human TREM2), comprises a light chain variable region (VL) comprising:

(a) a CDRL1 comprising, consisting of, or consisting essentially of the amino acid sequence $X_1X_2$SQ$X_3X_4X_5X_6X_7X_8X_9$ (SEQ ID NO: 14), wherein:

$X_1$ is R, Q, or K;

$X_2$ is A or S;

$X_3$ is S or D;

$X_4$ is V or I;

$X_5$ is S, L, or T;

$X_6$ is S, N, or Y;

$X_7$ is Y or S;

$X_8$ is L, Y, F, or S;

$X_9$ is A, L, or N; and/or (b) a CDRL2 comprising, consisting of, or consisting essentially of the amino acid sequence $X_1$AS$X_2X_3X_4X_5$ (SEQ ID NO: 15), wherein:

$X_1$ is D, G, or W;

$X_2$ is N, S, or T;

$X_3$ is R or L;

$X_4$ is A or E;

$X_5$ is T or S; and/or (c) a CDRL3 comprising, consisting of, or consisting essentially of the amino acid sequence Q$X_1X_2X_3X_4X_5X_6X_7$ (SEQ ID NO: 16), wherein:

$X_1$ is Q or E;

$X_2$ is D, Y, or H;

$X_3$ is Y, D, V, F, or S;

$X_4$ is H, E, D, S, V, L, I, G, Q, or A;

$X_5$ is W, V, P, F, A, T, Y, or L;

$X_6$ is P, L, or I;

$X_7$ is I, Y, T, A, or F.

In specific embodiments, the antibody comprises one, two, or all three of the CDRLs above.

In certain embodiments, the antibody comprises a VL comprising:

(a) a CDRL1 comprising, consisting of, or consisting essentially of the amino acid sequence $X_1X_2$SQ$X_3X_4X_5X_6X_7X_8X_9$ (SEQ ID NO: 14), wherein:

$X_1$ is R or Q;

$X_2$ is A;

$X_3$ is S or D;

$X_4$ is V or I;

$X_5$ is S or T;

$X_6$ is S or N;

$X_7$ is Y;

$X_8$ is L;

$X_9$ is A or N; and/or (b) a CDRL2 comprising, consisting of, or consisting essentially of the amino acid sequence $X_1$AS$X_2X_3X_4X_5$ (SEQ ID NO: 15), wherein:

$X_1$ is D;

$X_2$ is N;

$X_3$ is R or L;

$X_4$ is A or E;

$X_5$ is T; and/or (c) a CDRL3 comprising, consisting of, or consisting essentially of the amino acid sequence Q$X_1X_2X_3X_4X_5X_6X_7$ (SEQ ID NO: 16), wherein:

$X_1$ is Q or E;

$X_2$ is D or Y;

$X_3$ is Y or D;

$X_4$ is H, E, or S;

$X_5$ is W or Y;

$X_6$ is P or I;

$X_7$ is I or T.

In specific embodiments, the antibody comprises one, two, or all three of the CDRLs above.

In certain embodiments, the antibody comprises a VL comprising:

(a) a CDRL1 comprising, consisting of, or consisting essentially of the amino acid sequence RASQSVSSYLA (SEQ ID NO: 60); and/or (b) a CDRL2 comprising, consisting of, or consisting essentially of the amino acid sequence DASNRAT (SEQ ID NO: 66); and/or (c) a CDRL3 comprising, consisting of, or consisting essentially of the amino acid sequence QQD$X_1X_2$WPIT (SEQ ID NO: 17), wherein:

$X_1$ is Y or F;

$X_2$ is H or E.

In specific embodiments, the antibody comprises one, two, or all three of the CDRLs above.

In certain embodiments, the antibody comprises a VL comprising:

(a) a CDRL1 comprising, consisting of, or consisting essentially of the amino acid sequence QASQDITNYLN (SEQ ID NO: 65); and/or (b) a CDRL2 comprising, consisting of, or consisting essentially of the amino acid sequence DASNLET (SEQ ID NO: 70); and/or (c) a CDRL3 comprising, consisting of, or consisting essentially of the amino acid sequence Q$X_1$YD$X_2$Y$X_3X_4$ (SEQ ID NO: 18), wherein:

$X_1$ is Q or E;

$X_2$ is S or Q;

$X_3$ is L or I;

$X_4$ is T or A.

In specific embodiments, the antibody comprises one, two, or all three of the CDRLs above.

In certain embodiments, the antibody comprises the CDRL1 of one of the antibodies in Table 2. In some embodiments, the antibody comprises the CDRL2 of one of the antibodies in Table 2. In certain embodiments, the antibody comprises the CDRL3 of one of the antibodies in Table 2. In certain embodiments, the antibody comprises one, two, or all three of the CDRLs of one of the antibodies in Table 2 (e.g., the CDRLs in one row of Table 2, for example, all of the CDRLs are from antibody EOS006164). In some embodiments, the antibody comprises the VL framework regions described herein. In specific embodiments, the antibody comprises the VL framework regions (FRs) of an antibody set forth in Table 5 (e.g., one, two, three, or four of the framework regions in one row of Table 5).

TABLE 1

| VH CDR sequences | | | |
|---|---|---|---|
| Antibody | CDRH1 (SEQ ID NO) | CDRH2 (SEQ ID NO) | CDRH3 (SEQ ID NO) |
| EOS006165 | GTFSSYAIS (19) | GIIPISGTANYAQKFQG (32) | ARTQEYTAFDI (42) |
| EOS006163 | GTFAQYAIS (20) | VIIPDSGTANYAQKFQG (33) | ARTQENTIFDI (43) |
| EOS006167 | FTFSNYAMS (21) | AISGSGGSTYYADSVKG (34) | AKHYDRGRAFDI (44) |
| EOS006168 | FTFSSYAMS (22) | AISGSGGSTYYADSVKG (34) | AKSPAYFGYGET (45) |
| EOS006170 | GSISSSNWWS (23) | EIYHSGSTNYNPSLKS (35) | ARDTKYQAGMDV (46) |
| EOS006177 | GSISDSAWWS (24) | EIYHDADTNYNPSLKS (36) | ARDTKYWGGMDV (47) |
| EOS006169 | FTFSNYAMS (21) | AISGSGGSTYYADSVKG (34) | AKDRGGYEVGPTFDP (48) |
| EOS006178 | FTFSNYGMG (25) | AISANAGKTYYADSVKG (37) | ASLRGGYEVGPTFDP (49) |
| EOS006176 | FTFSTHAMT (26) | AISANAGKTYYADSVKG (37) | ASLRGGYEVGPTFDS (50) |
| EOS006166 | FTFGDYAMS (27) | FIGSKAYGGTTEYTASVKG (38) | ARGKRYSYGYWHPAFDV (51) |
| EOS006174 | FTFGEYTMS (28) | FIGSKAYAGTTEYTASVKG (39) | ARGKRYSYGGWVPAFDV (52) |
| EOS006164 | FTFDDYTMS (29) | FIGSKAYSATTEYTASVKG (40) | ARGKRYSYTYWTPAFDV (53) |
| EOS006181 | FTFDDHAMS (30) | FIGSKAYGGTTEYTASVKG (38) | ARGKRYSYTYWTPAFDV (53) |
| EOS006172 | GTFSSYAIS (19) | GIIPISGTANYAQKFQG (32) | ARTQEYTLFDI (54) |
| EOS006162 | GTFSSYAIS (19) | GIIPISGTANYAQKFQG (32) | ARTQEYTLFDS (55) |
| EOS006180 | FTFSSYAMS (22) | AISGSGGSTYYADSVKG (34) | AKHPAVFGYGET (56) |
| EOS006175 | GSISSSNWWS (23) | EIYHSGSTNYNPSLKS (35) | ARDTKYWGGMDV (47) |
| EOS006179 | FTFSNYAMS (21) | AISGSGGSTYYADSVKG (34) | AKLRGGYEVGPTFDP (57) |
| EOS006173 | FTFGDYAMS (27) | FIGSKAYGGTTEYTASVKG (38) | ARGKRRDYGYWHPAFDV (58) |
| EOS006171 | FTFSDYYMS (31) | YISSSGSTIYYADSVKG (41) | ARLGGYYSLGPMDV (59) |
| EOS004281 | GTFSSYAIS (19) | GIIPISGTANYAQKFQG (32) | ARTQEYTLFDS (55) |

TABLE 1-continued

| VH CDR sequences | | | |
|---|---|---|---|
| Antibody | CDRH1 (SEQ ID NO) | CDRH2 (SEQ ID NO) | CDRH3 (SEQ ID NO) |
| EOS004282 | GTFSSYAIS (19) | GIIPISGTANYAQKFQG (32) | ARTQEYTLFDS (55) |
| EOS004283 | GTFAQYAIS (20) | VIIPDSGTANYAQKFQG (33) | ARTQENTIFDI (43) |
| EOS006233 | GTFAQYAIS (20) | VIIPDSGTANYAQKFQG (33) | ARTQENTIFDI (43) |
| EOS004284 | FTFDDYTMS (29) | FIGSKAYSATTEYTASVKG (40) | ARGKRYSYTYWTPAFDV (53) |
| EOS006215 | FTFDDYTMS (29) | FIGSKAYSATTEYTASVKG (40) | ARGKRYSYTYWTPAFDV (53) |

TABLE 2

| VL CDR sequences | | | |
|---|---|---|---|
| Antibody | CDRL1 (SEQ ID NO) | CDRL2 (SEQ ID NO) | CDRL3 (SEQ ID NO) |
| EOS006165 | RASQSVSSYLA (60) | DASNRAT (66) | QQDYHWPIT (71) |
| EOS006163 | RASQSVSSYLA (60) | DASNRAT (66) | QQDYEWPIT (72) |
| EOS006167 | RASQSVSSSYLA (61) | GASSRAT (67) | QQYDDVPYT (73) |
| EOS006168 | RASQSVSSSFLA (62) | GASSRAT (67) | QQYYSPPIT (74) |
| EOS006170 | QASQDISNYLN (63) | DASNLAT (68) | QQYVVFPT (75) |
| EOS006177 | QASQDISNYLN (63) | DASNLAT (68) | QQYVEAPT (76) |
| EOS006169 | KSSQSVLYSSNNKNYLA (64) | WASTRES (69) | QQHYLTPIT (77) |
| EOS006178 | KSSQSVLYSSNNKNYLA (64) | WASTRES (69) | QQHYLWPIS (78) |
| EOS006176 | KSSQSVLYSSNNKNYLA (64) | WASTRES (69) | QQHYIWPIT (79) |
| EOS006166 | QASQDITNYLN (65) | DASNLET (70) | QQYDSYLT (80) |
| EOS006174 | QASQDITNYLN (65) | DASNLET (70) | QEYDSYLA (81) |
| EOS006164 | QASQDITNYLN (65) | DASNLET (70) | QEYDSYIT (82) |
| EOS006181 | QASQDITNYLN (65) | DASNLET (70) | QQYDSYLT (80) |
| EOS006172 | RASQSVSSYLA (60) | DASNRAT (66) | QQDFHWPIT (83) |
| EOS006162 | RASQSVSSYLA (60) | DASNRAT (66) | QQDYHWPIT (71) |
| EOS006180 | RASQSVSSSFLA (62) | GASSRAT (67) | QQYYGLPIT (84) |

TABLE 2-continued

| VL CDR sequences | | | |
|---|---|---|---|
| Antibody | CDRL1 (SEQ ID NO) | CDRL2 (SEQ ID NO) | CDRL3 (SEQ ID NO) |
| EOS006175 | QASQDISNYLN (63) | DASNLAT (68) | QQYVEAPT (76) |
| EOS006179 | KSSQSVLYSSNNKNYLA (64) | WASTRES (69) | QQHYIWPIT (79) |
| EOS006173 | QASQDITNYLN (65) | DASNLET (70) | QEYDQYLT (85) |
| EOS006171 | RASQSVSSYLA (60) | DASNRAT (66) | QQDSAFPFT (86) |
| EOS004281 | RASQSVSSYLA (60) | DASNRAT (66) | QQDYHWPIT (71) |
| EOS004282 | RASQSVSSYLA (60) | DASNRAT (66) | QQDYHWPIT (71) |
| EOS004283 | RASQSVSSYLA (60) | DASNRAT (66) | QQDYEWPIT (72) |
| EOS006233 | RASQSVSSYLA (60) | DASNRAT (66) | QQDYEWPIT (72) |
| EOS004284 | QASQDITNYLN (65) | DASNLET (70) | QEYDSYIT (82) |
| EOS006215 | QASQDITNYLN (65) | DASNLET (70) | QEYDSYIT (82) |

In specific embodiments, the antibody comprises one, two, three, four, five, or all six of the CDRs above; i.e., one, two, three, four, five, or all six of CDRH1, CDRH2, CDRH3, CDRL1, CDRL2, and/or CDRL3 in Tables 1 and 2). In certain embodiments, the antibody comprises the CDRH1 of one of the antibodies in Table 1. In some embodiments, the antibody comprises the CDRH2 of one of the antibodies in Table 1. In certain embodiments, the antibody comprises the CDRH3 of one of the antibodies in Table 1. In some embodiments, the antibody comprises the CDRL1 of one of the antibodies in Table 2. In some embodiments, the antibody comprises the CDRL2 of one of the antibodies in Table 2. In certain embodiments, the antibody comprises the CDRL3 of one of the antibodies in Table 2. In some embodiments, the antibody comprises one, two, or all three of the VH CDRs of one of the antibodies in Table 1 (e.g., the VH CDRs in one row of Table 1, for example, all of the VH CDRs are from the antibody EOS004281). In certain embodiments, the antibody comprises one, two, or all three of the VL CDRs of one of the antibodies in Table 2 (e.g., the VL CDRs in one row of Table 2, for example, all of the VL CDRs are from the antibody EOS004281).

In some embodiments, an antibody described herein which specifically bind to TREM2 (e.g., human TREM2), comprises a VH and a VL, wherein:

(i) the VH comprises:

(a) a CDRH1 comprising, consisting of, or consisting essentially of the amino acid sequence $X_1TFX_2X_3X_4X_5X_6$ (SEQ ID NO: 5), wherein:

$X_1$ is G or F;

$X_2$ is S, A, G, or D;

$X_3$ is S, Q, N, D, T, or E;

$X_4$ is A, G, T, or Y;

$X_5$ is I or M;

$X_6$ is S, G, or T; and/or (b) a CDRH2 comprising, consisting of, or consisting essentially of the amino acid sequence $X_1IX_2X_3X_4X_5X_6X_7X_8X_9X_{10}X_{11}X_{12}X_{13}X_{14}X_{15}$ (SEQ ID NO: 6), wherein:

$X_1$ is G, V, A, E, F, or Y;

$X_2$ is I, S, Y, or G;

$X_3$ is P, G, H, A, or S;

$X_4$ is I, D, S, N, or K;

$X_5$ is S, G, or A;

$X_6$ is G, S, D, or Y;

$X_7$ is T, S, K, G, or A;

$X_8$ is A, T, N, G, or I;

$X_9$ is N, Y, or T;

$X_{10}$ is Y, N, or T;

$X_{11}$ is A, P, or E;

$X_{12}$ is Q, D, S, or Y;

$X_{13}$ is K, S, L, or T;

$X_{14}$ is F, V, K, or A;

$X_{15}$ is Q, K, or S; and/or (c) a CDRH3 comprising, consisting of, or consisting essentially of the amino acid sequence $AX_1X_2X_3X_4X_5X_6X_7X_8X_9X_{10}$ (SEQ ID NO: 7), wherein:

$X_1$ is R, K, or S;

$X_2$ is T, H, S, D, L, G, or H;

$X_3$ is Q, Y, P, T, R, K, or G;

$X_4$ is E, D, A, K, G, or R;

$X_5$ is Y, N, R, G, or V;

$X_6$ is T, G, F, Q, W, Y, S, or D;

$X_7$ is A, I, Y, G, V, T, F, or L;

$X_8$ is F, A, Y, G, V, T, or L;

$X_9$ is D, F, G, M, or Y;

$X_{10}$ is I, D, E, P, W, or S; and (ii) the VL comprises:

(a) a CDRL1 comprising, consisting of, or consisting essentially of the amino acid sequence $X_1X_2SQX_3X_4X_5X_6X_7X_8X_9$ (SEQ ID NO: 14), wherein:

$X_1$ is R, Q, or K;

$X_2$ is A or S;

$X_3$ is S or D;

$X_4$ is V or I;

$X_5$ is S, L, or T;

$X_6$ is S, N, or Y;

$X_7$ is Y or S;

$X_8$ is L, Y, F, or S;

$X_9$ is A, L, or N; and/or (b) a CDRL2 comprising, consisting of, or consisting essentially of the amino acid sequence $X_1ASX_2X_3X_4X_5$ (SEQ ID NO: 15), wherein:

$X_1$ is D, G, or W;

$X_2$ is N, S, or T;

$X_3$ is R or L;

$X_4$ is A or E;

$X_5$ is T or S; and/or (c) a CDRL3 comprising, consisting of, or consisting essentially of the amino acid sequence $QX_1X_2X_3X_4X_5X_6X_7$ (SEQ ID NO: 16), wherein:

$X_1$ is Q or E;

$X_2$ is D, Y, or H;

$X_3$ is Y, D, V, F, or S;

$X_4$ is H, E, D, S, V, L, I, G, Q, or A;

$X_5$ is W, V, P, F, A, T, Y, or L;

$X_6$ is P, L, or I;

$X_7$ is I, Y, T, A, or F.

In some embodiments, an antibody described herein which specifically bind to TREM2 (e.g., human TREM2), comprises a VH and a VL, wherein:

(i) the VH comprises:

(a) a CDRH1 comprising, consisting of, or consisting essentially of the amino acid sequence $X_1TFX_2X_3X_4X_5X_6$ (SEQ ID NO: 5), wherein:

$X_1$ is G or F;

$X_2$ is S, A, or D;

$X_3$ is S, Q, or D;

$X_4$ is Y;

$X_5$ is I or M;

$X_6$ is S; and/or (b) a CDRH2 comprising, consisting of, or consisting essentially of the amino acid sequence $X_1IX_2X_3X_4X_5X_6X_7X_8X_9X_{10}X_{11}X_{12}X_{13}X_{14}X_{15}$ (SEQ ID NO: 6), wherein:

$X_1$ is G, V, or F;

$X_2$ is I or G;

$X_3$ is P or S;

$X_4$ is I, D, or K;

$X_5$ is S or A;

$X_6$ is G or Y;

$X_7$ is T or S;

$X_8$ is A;

$X_9$ is N or T;

$X_{10}$ is Y or T;

$X_{11}$ is A or E;

$X_{12}$ is Q or Y;

$X_{13}$ is K or T;

$X_{14}$ is F or A;

$X_{15}$ is Q or S; and/or (c) a CDRH3 comprising, consisting of, or consisting essentially of the amino acid sequence $AX_1X_2X_3X_4X_5X_6X_7X_8X_9X_{10}$ (SEQ ID NO: 7), wherein:

$X_1$ is R;

$X_2$ is T or G;

$X_3$ is Q or K;

$X_4$ is E or R;

$X_5$ is Y or N;

$X_6$ is T or S;

$X_7$ is I, Y, or L;

$X_8$ is F or T;

$X_9$ is D or Y;

$X_{10}$ is I, W, or S; and (ii) the VL comprises:

(a) a CDRL1 comprising, consisting of, or consisting essentially of the amino acid sequence $X_1X_2SQX_3X_4X_5X_6X_7X_8X_9$ (SEQ ID NO: 14), wherein:

$X_1$ is R or Q;

$X_2$ is A;

$X_3$ is S or D;

$X_4$ is V or I;

$X_5$ is S or T;

$X_6$ is S or N;

$X_7$ is Y;

$X_8$ is L;

$X_9$ is A or N; and/or (b) a CDRL2 comprising, consisting of, or consisting essentially of the amino acid sequence $X_1ASX_2X_3X_4X_5$ (SEQ ID NO: 15), wherein:

$X_1$ is D;

$X_2$ is N;

$X_3$ is R or L;

$X_4$ is A or E;

$X_5$ is T; and/or (c) a CDRL3 comprising, consisting of, or consisting essentially of the amino acid sequence $QX_1X_2X_3X_4X_5X_6X_7$ (SEQ ID NO: 16), wherein:

$X_1$ is Q or E;

$X_2$ is D or Y;

$X_3$ is Y or D;

$X_4$ is H, E, or S;

$X_5$ is W or Y;

$X_6$ is P or I;

$X_7$ is I or T.

In some embodiments, an antibody described herein which specifically bind to TREM2 (e.g., human TREM2), comprises a VH and a VL, wherein:

(i) the VH comprises:

(a) a CDRH1 comprising, consisting of, or consisting essentially of the amino acid sequence $GTFX_1X_2YAIS$ (SEQ ID NO: 8), wherein:

$X_1$ is S or A;

$X_2$ is S or Q; and/or (b) a CDRH2 comprising, consisting of, or consisting essentially of the amino acid sequence $X_1IIPX_2SGTANYAQKFQG$ (SEQ ID NO: 9), wherein:

$X_1$ is G or V;

$X_2$ is I or D; and/or (c) a CDRH3 comprising, consisting of, or consisting essentially of the amino acid sequence $ARTQEX_1TX_2FDX_3$ (SEQ ID NO: 10), wherein:

$X_1$ is Y or N;

$X_2$ is A, I, or L;

$X_3$ is I or S; and (ii) the VL comprises:

(a) a CDRL1 comprising, consisting of, or consisting essentially of the amino acid sequence RASQSVSSYLA (SEQ ID NO: 60); and/or (b) a CDRL2 comprising, consisting of, or consisting essentially of the amino acid sequence DASNRAT (SEQ ID NO: 66); and/or (c) a CDRL3 comprising, consisting of, or consisting essentially of the amino acid sequence $QQDX_1X_2WPIT$ (SEQ ID NO: 17), wherein:

$X_1$ is Y or F;

$X_2$ is H or E.

In some embodiments, an antibody described herein which specifically bind to TREM2 (e.g., human TREM2), comprises a VH and a VL, wherein:

(i) the VH comprises:

(a) a CDRH1 comprising, consisting of, or consisting essentially of the amino acid sequence $FTFX_1X_2X_3X_4MS$ (SEQ ID NO: 11), wherein:

$X_1$ is G or D;

$X_2$ is D or E;

$X_3$ is Y or H;

$X_4$ is A or T; and/or (b) a CDRH2 comprising, consisting of, or consisting essentially of the amino acid sequence $FIGSKAYX_1X_2TTEYTASVKG$ (SEQ ID NO: 12), wherein:

$X_1$ is G or V;

$X_2$ is I or D; and/or (c) a CDRH3 comprising, consisting of, or consisting essentially of the amino acid sequence $ARGKRX_1X_2YX_3X_4WX_5PAFDV$ (SEQ ID NO: 13), wherein:

$X_1$ is Y or R;

$X_2$ is S or D;

$X_3$ is G or T;

$X_4$ is Y or G;

$X_5$ is H, T, or V; and (ii) the VL comprises:

(a) a CDRL1 comprising, consisting of, or consisting essentially of the amino acid sequence QASQDITNYLN (SEQ ID NO: 65); and/or (b) a CDRL2 comprising, consisting of, or consisting essentially of the amino acid sequence DASNLET (SEQ ID NO: 70); and/or (c) a CDRL3 comprising, consisting of, or consisting essentially of the amino acid sequence $QX_1YDX_2YX_3X_4$ (SEQ ID NO: 18), wherein:

$X_1$ is Q or E;

$X_2$ is S or Q;

$X_3$ is L or I;

$X_4$ is T or A.

In specific embodiments, the VH comprises two or all three of the VH CDRs above and/or the VL comprises two or all three of the VL CDRs above. In certain embodiments, the antibody comprises the CDRH1 of one of the antibodies in Table 1. In some embodiments, the antibody comprises the CDRH2 of one of the antibodies in Table 1. In certain embodiments, the antibody comprises the CDRH3 of one of the antibodies in Table 1. In some embodiments, the antibody comprises the CDRL1 of one of the antibodies in Table 2. In some embodiments, the antibody comprises the CDRL2 of one of the antibodies in Table 2. In certain embodiments, the antibody comprises the CDRL3 of one of the antibodies in Table 2. In some embodiments, the antibody comprises one, two, or all three of the VH CDRs of one of the antibodies in Table 1 (e.g., the VH CDRs in one row of Table 1). In certain embodiments, the antibody comprises one, two, or all three of the VL CDRs of one of the antibodies in Table 2 (e.g., the VL CDRs in one row in Table 2).

In certain embodiments, provided herein is an antibody which specifically binds to TREM2 (e.g., human TREM2) and comprises a VH comprising one, two, or all three of the VH CDRs of an antibody in Table 1 (e.g., the VH CDRs in one row of Table 1). In some embodiments, the antibody comprises one, two, three, or all four of the VH framework regions described herein. In specific embodiments, the antibody comprises one, two, three, or all four of the VH framework regions (FRs) set forth in Table 4 (e.g., one, two, three, or four of the framework regions in one row in Table 4).

In certain embodiments, provided herein is an antibody which specifically binds to TREM2 (e.g., human TREM2) and comprises a VL comprising one, two, or all three of the VL CDRs of an antibody in Table 2 (e.g., the VL CDRs in one row of Table 2). In some embodiments, the antibody comprises one, two, three, or all four of the VL framework regions described herein. In specific embodiments, the antibody comprises one, two, three, or all four of the VL framework regions (FRs) set forth in Table 5 (e.g., one, two, three, or four of the framework regions in one row in Table 5).

In certain embodiments, provided herein is an antibody which specifically binds to TREM2 (e.g., human TREM2) and comprises VH CDRs and VL CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215, for example as set forth in Tables 1 and 2 (e.g., the VH CDRs and VL CDRs in the same row are all from the same antibody as designated by the name of the antibody in the first column of Tables 1 and 2, for example, the VH CDRs and VL CDRs in the first row of Tables 1 and 2, respectively, are all from antibody EOS004281). In some embodiments, the antibody comprises the VH framework regions and VL framework regions described herein. In specific embodiments, the antibody comprises VH framework regions (FRs) and VL framework regions (FRs) set forth in Tables 4 and 5 (e.g., the VH FRs and VL FRs are all from the same antibody).

In a particular embodiment, an antibody described herein which specifically binds to TREM2 (e.g., human TREM2), comprises a VH comprising CDRH1, CDRH2, and CDRH3 as set forth in Table 1, for example, CDRH1, CDRH2, and CDRH3 of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215, (e.g., the VH CDRs are in one row of Table 1). In some embodiments, the antibody comprises VH framework regions of an antibody set forth in Table 4 (e.g., one, two, three, or four of the framework regions in one row in Table 4). In certain embodiments, the antibody comprises a VH comprising one, two, three, or four of the framework regions of the VH amino acid sequence set forth in any one of SEQ ID NOs: 87-109. In some embodiments, the antibody comprises one, two, three, or four of the framework regions of a VH amino acid sequence which is at least 75%, 80%, 85%, 90%, 95%, or 100% identical to one, two, three, or four of the framework regions of a VH amino acid sequence set forth in any one of SEQ ID NOs: 87-109. In some embodiments, the antibody comprises a VH comprising one, two, three, or four of the framework regions of the VH amino acid sequence set forth in any one of SEQ ID NOs: 87-109 comprising 1, 2, 3, 4, 5, 6, 7, 8, 9, or 10 amino acid substitutions, deletions, and/or insertions, preferably 1, 2, 3, 4, 5, 6, 7, 8, 9, or 10 amino acid substitutions.

In a particular embodiment, an antibody described herein, which specifically binds to TREM2 (e.g., human TREM2), comprises the CDRH1, CDRH2, and CDRH3 of EOS006165, for example, the CDRH1, CDRH2, and CDRH3 of EOS006165 as set forth in Table 1 (SEQ ID NOs: 19, 32, and 42, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006165).

In a particular embodiment, an antibody described herein, which specifically binds to TREM2 (e.g., human TREM2), comprises the CDRH1, CDRH2, and CDRH3 of EOS006163, EOS004283, or EOS006233, for example, the CDRH1, CDRH2, and CDRH3 of EOS006163, EOS004283, or EOS006233 as set forth in Table 1 (SEQ ID NOs: 20, 33, and 43, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006163, EOS004283, or EOS006233).

In a particular embodiment, an antibody described herein, which specifically binds to TREM2 (e.g., human TREM2), comprises the CDRH1, CDRH2, and CDRH3 of EOS006167, for example, the CDRH1, CDRH2, and CDRH3 of EOS006167 as set forth in Table 1 (SEQ ID NOs: 21, 34, and 44, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006167).

In a particular embodiment, an antibody described herein, which specifically binds to TREM2 (e.g., human TREM2), comprises the CDRH1, CDRH2, and CDRH3 of EOS006168, for example, the CDRH1, CDRH2, and CDRH3 of EOS006168 as set forth in Table 1 (SEQ ID NOs: 22, 34, and 45, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006168).

In a particular embodiment, an antibody described herein, which specifically binds to TREM2 (e.g., human TREM2), comprises the CDRH1, CDRH2, and CDRH3 of EOS006170, for example, the CDRH1, CDRH2, and CDRH3 of EOS006170 as set forth in Table 1 (SEQ ID NOs: 23, 35, and 46, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006170).

In a particular embodiment, an antibody described herein, which specifically binds to TREM2 (e.g., human TREM2), comprises the CDRH1, CDRH2, and CDRH3 of EOS006177, for example, the CDRH1, CDRH2, and CDRH3 of EOS006177 as set forth in Table 1 (SEQ ID NOs: 24, 36, and 47, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006177).

In a particular embodiment, an antibody described herein, which specifically binds to TREM2 (e.g., human TREM2), comprises the CDRH1, CDRH2, and CDRH3 of EOS006169, for example, the CDRH1, CDRH2, and CDRH3 of EOS006169 as set forth in Table 1 (SEQ ID NOs: 21, 34, and 48, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006169).

In a particular embodiment, an antibody described herein, which specifically binds to TREM2 (e.g., human TREM2), comprises the CDRH1, CDRH2, and CDRH3 of EOS006178, for example, the CDRH1, CDRH2, and CDRH3 of EOS006178 as set forth in Table 1 (SEQ ID NOs: 25, 37, and 49, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006178).

In a particular embodiment, an antibody described herein, which specifically binds to TREM2 (e.g., human TREM2), comprises the CDRH1, CDRH2, and CDRH3 of EOS006176, for example, the CDRH1, CDRH2, and CDRH3 of EOS006176 as set forth in Table 1 (SEQ ID NOs: 26, 37, and 50, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006176).

In a particular embodiment, an antibody described herein, which specifically binds to TREM2 (e.g., human TREM2), comprises the CDRH1, CDRH2, and CDRH3 of EOS006166, for example, the CDRH1, CDRH2, and CDRH3 of EOS006166 as set forth in Table 1 (SEQ ID NOs: 27, 38, and 51, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006166).

In a particular embodiment, an antibody described herein, which specifically binds to TREM2 (e.g., human TREM2), comprises the CDRH1, CDRH2, and CDRH3 of EOS006174, for example, the CDRH1, CDRH2, and CDRH3 of EOS006174 as set forth in Table 1 (SEQ ID NOs: 28, 39, and 52, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006174).

In a particular embodiment, an antibody described herein, which specifically binds to TREM2 (e.g., human TREM2), comprises the CDRH1, CDRH2, and CDRH3 of EOS006164, EOS004284, or EOS006215, for example, the CDRH1, CDRH2, and CDRH3 of EOS006164, EOS004284, or EOS006215 as set forth in Table 1 (SEQ ID NOs: 29, 40, and 53, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006164, EOS004284, or EOS006215).

In a particular embodiment, an antibody described herein, which specifically binds to TREM2 (e.g., human TREM2), comprises the CDRH1, CDRH2, and CDRH3 of EOS006181, for example, the CDRH1, CDRH2, and CDRH3 of EOS006181 as set forth in Table 1 (SEQ ID NOs: 30, 38, and 53, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006181).

In a particular embodiment, an antibody described herein, which specifically binds to TREM2 (e.g., human TREM2), comprises the CDRH1, CDRH2, and CDRH3 of EOS006172, for example, the CDRH1, CDRH2, and CDRH3 of EOS006172 as set forth in Table 1 (SEQ ID NOs: 19, 32, and 54, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006172).

In a particular embodiment, an antibody described herein, which specifically binds to TREM2 (e.g., human TREM2), comprises the CDRH1, CDRH2, and CDRH3 of EOS006162, EOS004281, or EOS004282, for example, the CDRH1, CDRH2, and CDRH3 of EOS006162, EOS004281, or EOS004282 as set forth in Table 1 (SEQ ID NOs: 19, 32, and 55, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006162, EOS004281, or EOS004282).

In a particular embodiment, an antibody described herein, which specifically binds to TREM2 (e.g., human TREM2), comprises the CDRH1, CDRH2, and CDRH3 of EOS006180, for example, the CDRH1, CDRH2, and CDRH3 of EOS006180 as set forth in Table 1 (SEQ ID NOs: 22, 34, and 56, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006180).

In a particular embodiment, an antibody described herein, which specifically binds to TREM2 (e.g., human TREM2), comprises the CDRH1, CDRH2, and CDRH3 of EOS006175, for example, the CDRH1, CDRH2, and CDRH3 of EOS006175 as set forth in Table 1 (SEQ ID NOs: 23, 35, and 47, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006175).

In a particular embodiment, an antibody described herein, which specifically binds to TREM2 (e.g., human TREM2), comprises the CDRH1, CDRH2, and CDRH3 of EOS006179, for example, the CDRH1, CDRH2, and CDRH3 of EOS006179 as set forth in Table 1 (SEQ ID NOs: 21, 34, and 57, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006179).

In a particular embodiment, an antibody described herein, which specifically binds to TREM2 (e.g., human TREM2), comprises the CDRH1, CDRH2, and CDRH3 of EOS006173, for example, the CDRH1, CDRH2, and CDRH3 of EOS006173 as set forth in Table 1 (SEQ ID NOs: 27, 38, and 58, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006173).

In a particular embodiment, an antibody described herein, which specifically binds to TREM2 (e.g., human TREM2), comprises the CDRH1, CDRH2, and CDRH3 of EOS006171, for example, the CDRH1, CDRH2, and CDRH3 of EOS006171 as set forth in Table 1 (SEQ ID NOs: 31, 41, and 59, respectively). In certain embodiments, the antibody further comprises one, two, three, or all four VH framework regions derived from the VH of a human or primate antibody. In some embodiments, the antibody comprises VH framework regions of an antibody set forth in Table 4 (e.g., the framework regions of EOS006171).

In a particular embodiment, an antibody described herein which specifically binds to TREM2 (e.g., human TREM2), comprises a VL comprising CDRL1, CDRL2, and CDRL3 as set forth in Table 2, for example, CDRL1, CDRL2, and CDRL3 of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215, (e.g., the VL CDRs are in one row of Table 2). In some embodiments, the antibody comprises VL framework regions of an antibody set forth in Table 5 (e.g., one, two, three, or four of the framework regions in one row in Table 5). In certain embodiments, the antibody comprises a VL comprising one, two, three, or four of the framework regions of the VL amino acid sequence set forth in any one of SEQ ID NOs: 110-125. In some embodiments, the antibody comprises one, two, three, or four of the framework regions of a VL amino acid sequence which is at least 75%, 80%, 85%, 90%, 95%, or 100% identical to one, two, three, or four of the framework regions of a VL amino acid sequence set forth in any one of SEQ ID NOs: 110-125. In some embodiments, the antibody comprises a VL comprising one, two, three, or four of the framework regions of the VL amino acid sequence set forth in any one of SEQ ID NOs: 110-125 comprising 1, 2, 3, 4, 5, 6, 7, 8, 9, or 10 amino acid substitutions, deletions, and/or insertions, preferably 1, 2, 3, 4, 5, 6, 7, 8, 9, or 10 amino acid substitutions.

In a particular embodiment, an antibody described herein, which specifically binds to TREM2 (e.g., human TREM2), comprises the CDRL1, CDRL2, and CDRL3 of EOS006165, for example, the CDRL1, CDRL2, and CDRL3 of EOS006165 as set forth in Table 2 (SEQ ID NOs: 60, 66, and 71, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006165).

In a particular embodiment, an antibody described herein, which specifically binds to TREM2 (e.g., human TREM2), comprises the CDRL1, CDRL2, and CDRL3 of EOS006163, EOS004283, or EOS006233, for example, the CDRL1, CDRL2, and CDRL3 of EOS006163, EOS004283, or EOS006233 as set forth in Table 2 (SEQ ID NOs: 60, 66, and 72, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006163, EOS004283, or EOS006233).

In a particular embodiment, an antibody described herein, which specifically binds to TREM2 (e.g., human TREM2), comprises the CDRL1, CDRL2, and CDRL3 of EOS006167, for example, the CDRL1, CDRL2, and CDRL3 of EOS006167 as set forth in Table 2 (SEQ ID NOs: 61, 67, and 73, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006167).

In a particular embodiment, an antibody described herein, which specifically binds to TREM2 (e.g., human TREM2), comprises the CDRL1, CDRL2, and CDRL3 of EOS006168, for example, the CDRL1, CDRL2, and CDRL3 of EOS006168 as set forth in Table 2 (SEQ ID NOs: 62, 67, and 74, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006168).

In a particular embodiment, an antibody described herein, which specifically binds to TREM2 (e.g., human TREM2), comprises the CDRL1, CDRL2, and CDRL3 of EOS006170, for example, the CDRL1, CDRL2, and CDRL3 of EOS006170 as set forth in Table 2 (SEQ ID NOs: 63, 68, and 75, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006170).

In a particular embodiment, an antibody described herein, which specifically binds to TREM2 (e.g., human TREM2), comprises the CDRL1, CDRL2, and CDRL3 of EOS006177, for example, the CDRL1, CDRL2, and CDRL3 of EOS006177 as set forth in Table 2 (SEQ ID NOs: 63, 68, and 76, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006177).

In a particular embodiment, an antibody described herein, which specifically binds to TREM2 (e.g., human TREM2), comprises the CDRL1, CDRL2, and CDRL3 of EOS006169, for example, the CDRL1, CDRL2, and CDRL3 of EOS006169 as set forth in Table 2 (SEQ ID NOs: 64, 69, and 77, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006169).

In a particular embodiment, an antibody described herein, which specifically binds to TREM2 (e.g., human TREM2), comprises the CDRL1, CDRL2, and CDRL3 of EOS006178, for example, the CDRL1, CDRL2, and CDRL3 of EOS006178 as set forth in Table 2 (SEQ ID NOs: 64, 69, and 78, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006178).

In a particular embodiment, an antibody described herein, which specifically binds to TREM2 (e.g., human TREM2), comprises the CDRL1, CDRL2, and CDRL3 of EOS006176, for example, the CDRL1, CDRL2, and CDRL3 of EOS006176 as set forth in Table 2 (SEQ ID NOs: 64, 69, and 79, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006176).

In a particular embodiment, an antibody described herein, which specifically binds to TREM2 (e.g., human TREM2), comprises the CDRL1, CDRL2, and CDRL3 of EOS006166, for example, the CDRL1, CDRL2, and CDRL3 of EOS006166 as set forth in Table 2 (SEQ ID NOs: 65, 70, and 80, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006166).

In a particular embodiment, an antibody described herein, which specifically binds to TREM2 (e.g., human TREM2), comprises the CDRL1, CDRL2, and CDRL3 of EOS006174, for example, the CDRL1, CDRL2, and CDRL3 of EOS006174 as set forth in Table 2 (SEQ ID NOs: 65, 70, and 81, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006174).

In a particular embodiment, an antibody described herein, which specifically binds to TREM2 (e.g., human TREM2), comprises the CDRL1, CDRL2, and CDRL3 of EOS006164, EOS004284, or EOS006215, for example, the CDRL1, CDRL2, and CDRL3 of EOS006164, EOS004284, or EOS006215 as set forth in Table 2 (SEQ ID NOs: 65, 70, and 82, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006164, EOS004284, or EOS006215).

In a particular embodiment, an antibody described herein, which specifically binds to TREM2 (e.g., human TREM2), comprises the CDRL1, CDRL2, and CDRL3 of EOS006181, for example, the CDRL1, CDRL2, and CDRL3 of EOS006181 as set forth in Table 2 (SEQ ID NOs: 65, 70, and 80, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006181).

In a particular embodiment, an antibody described herein, which specifically binds to TREM2 (e.g., human TREM2), comprises the CDRL1, CDRL2, and CDRL3 of EOS006172, for example, the CDRL1, CDRL2, and CDRL3 of EOS006172 as set forth in Table 2 (SEQ ID NOs: 60, 66, and 83, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006172).

In a particular embodiment, an antibody described herein, which specifically binds to TREM2 (e.g., human TREM2), comprises the CDRL1, CDRL2, and CDRL3 of EOS006162, EOS004281, or EOS004282, for example, the CDRL1, CDRL2, and CDRL3 of EOS006162, EOS004281, or EOS004282 as set forth in Table 2 (SEQ ID NOs: 60, 66, and 71, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006162, EOS004281, or EOS004282).

In a particular embodiment, an antibody described herein, which specifically binds to TREM2 (e.g., human TREM2), comprises the CDRL1, CDRL2, and CDRL3 of EOS006180, for example, the CDRL1, CDRL2, and CDRL3 of EOS006180 as set forth in Table 2 (SEQ ID NOs: 62, 67, and 84, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006180).

In a particular embodiment, an antibody described herein, which specifically binds to TREM2 (e.g., human TREM2), comprises the CDRL1, CDRL2, and CDRL3 of EOS006175, for example, the CDRL1, CDRL2, and CDRL3 of EOS006175 as set forth in Table 2 (SEQ ID NOs: 63, 68, and 76, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006175).

In a particular embodiment, an antibody described herein, which specifically binds to TREM2 (e.g., human TREM2), comprises the CDRL1, CDRL2, and CDRL3 of EOS006179, for example, the CDRL1, CDRL2, and CDRL3 of EOS006179 as set forth in Table 2 (SEQ ID NOs: 64, 69, and 79, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006179).

In a particular embodiment, an antibody described herein, which specifically binds to TREM2 (e.g., human TREM2), comprises the CDRL1, CDRL2, and CDRL3 of EOS006173, for example, the CDRL1, CDRL2, and CDRL3 of EOS006173 as set forth in Table 2 (SEQ ID NOs: 65, 70, and 85, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006173).

In a particular embodiment, an antibody described herein, which specifically binds to TREM2 (e.g., human TREM2), comprises the CDRL1, CDRL2, and CDRL3 of EOS006171, for example, the CDRL1, CDRL2, and CDRL3 of EOS006171 as set forth in Table 2 (SEQ ID NOs: 60, 66, and 86, respectively). In certain embodiments, the antibody further comprises one, two, three, or all four VL framework regions derived from the VL of a human or primate antibody. In some embodiments, the antibody comprises VL framework regions of an antibody set forth in Table 5 (e.g., the framework regions of EOS006171).

In a particular embodiment, an antibody described herein, which specifically binds to TREM2 (e.g., human TREM2), comprises (i) a VH comprising CDRH1, CDRH2, and CDRH3 as set forth in Table 1, for example, CDRH1, CDRH2, and CDRH3 of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215, (e.g. the VH CDRs in one row in Table 1), and (ii) a VL comprising CDRL1, CDRL2, and CDRL3 as set forth in Table 2, for example, CDRL1, CDRL2, and CDRL3 of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215, (e.g., the VL CDRs in one row in Table 2). In some embodiments, the antibody comprises VH framework regions and VL framework regions of an antibody set forth in Tables 4 and 5, respectively (e.g., the framework regions of a single antibody as designated by its name, for example, all of the FRs are from EOS004281).

In a particular embodiment, an antibody described herein, which specifically binds to TREM2 (e.g., human TREM2), comprises the CDRH1, CDRH2, CDRH3, CDRL1, CDRL2, and CDRL3 of EOS006165, for example, the CDRH1, CDRH2, CDRH3, CDRL1, CDRL2, and CDRL3 of EOS006165 as set forth in Tables 1 and 2 (SEQ ID NOs: 19, 32, 42, 60, 66, and 71, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006165).

In a particular embodiment, an antibody described herein, which specifically binds to TREM2 (e.g., human TREM2), comprises the CDRH1, CDRH2, CDRH3, CDRL1, CDRL2, and CDRL3 of EOS006163, EOS004283, or EOS006233, for example, the CDRH1, CDRH2, CDRH3, CDRL1, CDRL2, and CDRL3 of EOS006163, EOS004283, or EOS006233 as set forth in Tables 1 and 2 (SEQ ID NOs: 20, 33, 43, 60, 66, and 72, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006163, EOS004283, or EOS006233).

In a particular embodiment, an antibody described herein, which specifically binds to TREM2 (e.g., human TREM2), comprises the CDRH1, CDRH2, CDRH3, CDRL1, CDRL2, and CDRL3 of EOS006167, for example, the CDRH1, CDRH2, CDRH3, CDRL1, CDRL2, and CDRL3 of EOS006167 as set forth in Tables 1 and 2 (SEQ ID NOs: 21, 34, 44, 61, 67, and 73, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006167).

In a particular embodiment, an antibody described herein, which specifically binds to TREM2 (e.g., human TREM2), comprises the CDRH1, CDRH2, CDRH3, CDRL1, CDRL2, and CDRL3 of EOS006168, for example, the CDRH1, CDRH2, CDRH3, CDRL1, CDRL2, and CDRL3 of EOS006168 as set forth in Tables 1 and 2 (SEQ ID NOs: 22, 34, 45, 62, 67, and 74, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006168).

In a particular embodiment, an antibody described herein, which specifically binds to TREM2 (e.g., human TREM2), comprises the CDRH1, CDRH2, CDRH3, CDRL1, CDRL2, and CDRL3 of EOS006170, for example, the CDRH1, CDRH2, CDRH3, CDRL1, CDRL2, and CDRL3 of EOS006170 as set forth in Tables 1 and 2 (SEQ ID NOs: 23, 35, 46, 63, 68, and 75, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006170).

In a particular embodiment, an antibody described herein, which specifically binds to TREM2 (e.g., human TREM2), comprises the CDRH1, CDRH2, CDRH3, CDRL1, CDRL2, and CDRL3 of EOS006177, for example, the CDRH1, CDRH2, CDRH3, CDRL1, CDRL2, and CDRL3 of EOS006177 as set forth in Tables 1 and 2 (SEQ ID NOs: 24, 36, 47, 63, 68, and 76, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006177).

In a particular embodiment, an antibody described herein, which specifically binds to TREM2 (e.g., human TREM2), comprises the CDRH1, CDRH2, CDRH3, CDRL1, CDRL2, and CDRL3 of EOS006169, for example, the CDRH1, CDRH2, CDRH3, CDRL1, CDRL2, and CDRL3 of EOS006169 as set forth in Tables 1 and 2 (SEQ ID NOs: 21, 34, 48, 64, 69, and 77, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006169).

In a particular embodiment, an antibody described herein, which specifically binds to TREM2 (e.g., human TREM2), comprises the CDRH1, CDRH2, CDRH3, CDRL1, CDRL2, and CDRL3 of EOS006178, for example, the CDRH1, CDRH2, CDRH3, CDRL1, CDRL2, and CDRL3 of EOS006178 as set forth in Tables 1 and 2 (SEQ ID NOs: 25, 37, 49, 64, 69, and 78, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006178).

In a particular embodiment, an antibody described herein, which specifically binds to TREM2 (e.g., human TREM2), comprises the CDRH1, CDRH2, CDRH3, CDRL1, CDRL2, and CDRL3 of EOS006176, for example, the CDRH1, CDRH2, CDRH3, CDRL1, CDRL2, and CDRL3 of EOS006176 as set forth in Tables 1 and 2 (SEQ ID NOs: 26, 37, 50, 64, 69, and 79, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006176).

In a particular embodiment, an antibody described herein, which specifically binds to TREM2 (e.g., human TREM2), comprises the CDRH1, CDRH2, CDRH3, CDRL1, CDRL2, and CDRL3 of EOS006166, for example, the CDRH1, CDRH2, CDRH3, CDRL1, CDRL2, and CDRL3 of EOS006166 as set forth in Tables 1 and 2 (SEQ ID NOs: 27, 38, 51, 65, 70, and 80, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006166).

In a particular embodiment, an antibody described herein, which specifically binds to TREM2 (e.g., human TREM2), comprises the CDRH1, CDRH2, CDRH3, CDRL1, CDRL2, and CDRL3 of EOS006174, for example, the CDRH1, CDRH2, CDRH3, CDRL1, CDRL2, and CDRL3 of EOS006174 as set forth in Tables 1 and 2 (SEQ ID NOs: 28, 39, 52, 65, 70, and 81, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006174).

In a particular embodiment, an antibody described herein, which specifically binds to TREM2 (e.g., human TREM2), comprises the CDRH1, CDRH2, CDRH3, CDRL1, CDRL2, and CDRL3 of EOS006164, EOS004284, or EOS006215, for example, the CDRH1, CDRH2, CDRH3, CDRL1, CDRL2, and CDRL3 of EOS006164, EOS004284, or EOS006215 as set forth in Tables 1 and 2 (SEQ ID NOs: 29, 40, 53, 65, 70, and 82, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006164, EOS004284, or EOS006215).

In a particular embodiment, an antibody described herein, which specifically binds to TREM2 (e.g., human TREM2), comprises the CDRH1, CDRH2, CDRH3, CDRL1, CDRL2, and CDRL3 of EOS006181, for example, the CDRH1, CDRH2, CDRH3, CDRL1, CDRL2, and CDRL3 of EOS006181 as set forth in Tables 1 and 2 (SEQ ID NOs: 30, 38, 53, 65, 70, and 80, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006181).

In a particular embodiment, an antibody described herein, which specifically binds to TREM2 (e.g., human TREM2), comprises the CDRH1, CDRH2, CDRH3, CDRL1, CDRL2, and CDRL3 of EOS006172, for example, the CDRH1, CDRH2, CDRH3, CDRL1, CDRL2, and CDRL3 of EOS006172 as set forth in Tables 1 and 2 (SEQ ID NOs: 19, 32, 54, 60, 66, and 83, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006172).

In a particular embodiment, an antibody described herein, which specifically binds to TREM2 (e.g., human TREM2), comprises the CDRH1, CDRH2, CDRH3, CDRL1, CDRL2, and CDRL3 of EOS006162, EOS004281, or EOS004282, for example, the CDRH1, CDRH2, CDRH3, CDRL1, CDRL2, and CDRL3 of EOS006162, EOS004281, or EOS004282 as set forth in Tables 1 and 2 (SEQ ID NOs: 19, 32, 55, 60, 66, and 71, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006162, EOS004281, or EOS004282).

In a particular embodiment, an antibody described herein, which specifically binds to TREM2 (e.g., human TREM2), comprises the CDRH1, CDRH2, CDRH3, CDRL1, CDRL2, and CDRL3 of EOS006180, for example, the CDRH1, CDRH2, CDRH3, CDRL1, CDRL2, and CDRL3 of EOS006180 as set forth in Tables 1 and 2 (SEQ ID NOs: 22, 34, 56, 62, 67, and 84, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006180).

In a particular embodiment, an antibody described herein, which specifically binds to TREM2 (e.g., human TREM2), comprises the CDRH1, CDRH2, CDRH3, CDRL1, CDRL2, and CDRL3 of EOS006175, for example, the CDRH1, CDRH2, CDRH3, CDRL1, CDRL2, and CDRL3 of EOS006175 as set forth in Tables 1 and 2 (SEQ ID NOs: 23, 35, 47, 63, 68, and 76, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006175).

In a particular embodiment, an antibody described herein, which specifically binds to TREM2 (e.g., human TREM2), comprises the CDRH1, CDRH2, CDRH3, CDRL1, CDRL2, and CDRL3 of EOS006179, for example, the CDRH1, CDRH2, CDRH3, CDRL1, CDRL2, and CDRL3 of EOS006179 as set forth in Tables 1 and 2 (SEQ ID NOs: 21, 34, 57, 64, 69, and 79, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006179).

In a particular embodiment, an antibody described herein, which specifically binds to TREM2 (e.g., human TREM2), comprises the CDRH1, CDRH2, CDRH3, CDRL1, CDRL2, and CDRL3 of EOS006173, for example, the CDRH1, CDRH2, CDRH3, CDRL1, CDRL2, and CDRL3 of EOS006173 as set forth in Tables 1 and 2 (SEQ ID NOs: 27, 38, 58, 65, 70, and 85, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006173).

In a particular embodiment, an antibody described herein, which specifically binds to TREM2 (e.g., human TREM2), comprises the CDRH1, CDRH2, CDRH3, CDRL1, CDRL2, and CDRL3 of EOS006171, for example, the CDRH1, CDRH2, CDRH3, CDRL1, CDRL2, and CDRL3 of EOS006171 as set forth in Tables 1 and 2 (SEQ ID NOs: 31, 41, 59, 60, 66, and 86, respectively). In certain embodiments, the antibody further comprises one, two, three, or all four VH framework regions derived from the VH of a human or primate antibody and one, two, three, or all four VL framework regions derived from the VL of a human or primate antibody. In some embodiments, the antibody comprises VH framework regions and VL framework regions of an antibody set forth in Tables 4 and 5, respectively (e.g., the framework regions of EOS006171).

TABLE 3

VH and VL sequences

| Antibody | VH (SEQ ID NO) | VL (SEQ ID NO) |
|---|---|---|
| EOS006165 | QVQLVQSGAEVKKPGSSVKVSCKASG GTFSSYAISWVRQAPGQGLEWMGGII PISGTANYAQKFQGRVTITADESTST AYMELSSLRSEDTAVYYCARTQEYTA FDIWGQGTMVTVSS (87) | EIVLTQSPATLSLSPGERATLSCRASQSVS SYLAWFQQKPGQAPRLLIYDASNRATGIPA RFSGSGSGTDFTLTISSLEPEDFAVYYCQQ DYHWPITFGGGTKVEIK (110) |
| EOS006163 | QVQLVQSGAEVKKPGSSVKVSCKASG GTFAQYAISWVRQAPGQGLEWMGVII PDSGTANYAQKFQGRVTITADESTST AYMELSSLRSEDTAVYYCARTQENTI FDIWGQGTMVTVSS (88) | EIVLTQSPATLSLSPGERATLSCRASQSVS SYLAWFQQKPGQAPRLLIYDASNRATGIPA RFSGSGSGTDFTLTISSLEPEDFAVYYCQQ DYEWPITFGGGTKVEIK (111) |
| EOS006167 | EVQLLESGGGLVQPGGSLRLSCAASG FTFSNYAMSWVRQAPGKGLEWVSAIS GSGGSTYYADSVKGRFTISRDNSKNT LYLQMNSLRAEDTAVYYCAKHYDRGR AFDIWGQGTMVTVSS (89) | EIVLTQSPGTLSLSPGERATLSCRASQSVS SSYLAWYQQKPGQAPRLLIYGASSRATGIP DRFSGSGSGTDFTLTISRLEPEDFAVYYCQ QYDDVPYTFGGGTKVEIK (112) |
| EOS006168 | EVQLLESGGGLVQPGGSLRLSCAASG FTFSSYAMSWVRQAPGKGLEWVSAIS GSGGSTYYADSVKGRFTISRDNSKNT LYLQMNSLRAEDTAVYYCAKSPAYFG YGETWGQGTLVTVSS (90) | EIVLTQSPGTLSLSPGERATLSCRASQSVS SSFLAWYQQKPGQAPRLLIYGASSRATGIP DRFSGSGSGTDFTLTISRLEPEDFAVYYCQ QYYSPPITFGGGTKVEIK (113) |

TABLE 3-continued

VH and VL sequences

| Antibody | VH (SEQ ID NO) | VL (SEQ ID NO) |
|---|---|---|
| EOS006170 | QVQLQESGPGLVKPSGTLSLTCAVSG GSISSSNWWSWVRQPPGKGLEWIGEI YHSGSTNYNPSLKSRVTISVDKSKNQ FSLKLSSVTAADTAVYYCARDTKYQA GMDVWGQGTTVTVSS (91) | DIQMTQSPSSLSASVGDRVTITCQASQDIS NYLNWYQQKPGKAPKLLIYDASNLATGVPS RFSGSGSGTDFTFTISSLQPEDIATYYCQQ YVVFPTFGGGTKVEIK (114) |
| EOS006177 | QVQLQESGPGLVKPSGTLSLTCAVSG GSISDSAWWSWVRQPPGKGLEWIGEI YHDADTNYNPSLKSRVTISVDKSKNQ FSLKLSSVTAADTAVYYCARDTKYWG GMDVWGQGTTVTVSS (92) | DIQMTQSPSSLSASVGDRVTITCQASQDIS NYLNWYQQKPGKAPKLLIYDASNLATGVPS RFSGSGSGTDFTFTISSLQPEDIATYYCQQ YVEAPTFGGGTKVEIK (115) |
| EOS006169 | EVQLLESGGGLVQPGGSLRLSCAASG FTFSNYAMSWVRQAPGKGLEWVSAIS GSGGSTYYADSVKGRFTISRDNSKNT LYLQMNSLRAEDTAVYYCAKDRGGYE VGPTFDPWGQGTLVTVSS (93) | DIVMTQSPDSLAVSLGERATINCKSSQSVL YSSNNKNYLAWYQQKPGQPPKLLIYWASTR ESGVPDRFSGSGSGTDFTLTISSLQAEDVA VYYCQQHYLTPITFGGGTKVEIK (116) |
| EOS006178 | EVQLLESGGGLVQPGGSLRLSCAASG FTFSNYGMGWVRQAPGKGLEWVSAIS ANAGKTYYADSVKGRFTISRDNSKNT LYLQMNSLRAEDTAVYYCASLRGGYE VGPTFDPWGQGTLVTVSS (94) | DIVMTQSPDSLAVSLGERATINCKSSQSVL YSSNNKNYLAWYQQKPGQPPKLLIYWASTR ESGVPDRFSGSGSGTDFTLTISSLQAEDVA VYYCQQHYLWPISFGGGTKVEIK (117) |
| EOS006176 | EVQLLESGGGLVQPGGSLRLSCAASG FTFSTHAMTWVRQAPGKGLEWVSAIS ANAGKTYYADSVKGRFTISRDNSKNT LYLQMNSLRAEDTAVYYCASLRGGYE VGPTFDSWGQGTLVTVSS (95) | DIVMTQSPDSLAVSLGERATINCKSSQSVL YSSNNKNYLAWYQQKPGQPPKLLIYWASTR ESGVPDRFSGSGSGTDFTLTISSLQAEDVA VYYCQQHYIWPITFGGGTKVEIK (118) |
| EOS006166 | EVQLVESGGGLVQPGRSLRLSCTASG FTFGDYAMSWFRQAPGKGLEWVGFIG SKAYGGTTEYTASVKGRFTISRDGSK SIAYLQMNSLKTEDTAVYYCARGKRY SYGYWHPAFDVWGQGTMVTVSS (96) | DIQMTQSPSSLSASVGDRVTITCQASQDIT NYLNWYQQKPGKAPKLLIYDASNLETGVPS RFSGSGSGTDFTFTISSLQPEDIATYYCQQ YDSYLTFGGGTKVEIK (119) |
| EOS006174 | EVQLVESGGGLVQPGRSLRLSCTASG FTFGEYTMSWFRQAPGKGLEWVGFIG SKAYAGTTEYTASVKGRFTISRDGSK SIAYLQMNSLKTEDTAVYYCARGKRY SYGGWVPAFDVWGQGTMVTVSS (97) | DIQMTQSPSSLSASVGDRVTITCQASQDIT NYLNWYQQKPGKAPKLLIYDASNLETGVPS RFSGSGSGTDFTFTISSLQPEDIATYYCQE YDSYLAFGGGTKVEIK (120) |
| EOS006164 | EVQLVESGGGLVQPGRSLRLSCTASG FTFDDYTMSWFRQAPGKGLEWVGFIG SKAYSATTEYTASVKGRFTISRDGSK SIAYLQMNSLKTEDTAVYYCARGKRY SYTYWTPAFDVWGQGTMVTVSS (98) | DIQMTQSPSSLSASVGDRVTITCQASQDIT NYLNWYQQKPGKAPKLLIYDASNLETGVPS RFSGSGSGTDFTFTISSLQPEDIATYYCQE YDSYITFGGGTKVEIK (121) |
| EOS006181 | EVQLVESGGGLVQPGRSLRLSCTASG FTFDDHAMSWFRQAPGKGLEWVGFIG SKAYGGTTEYTASVKGRFTISRDGSK SIAYLQMNSLKTEDTAVYYCARGKRY SYTYWTPAFDVWGQGTMVTVSS (99) | DIQMTQSPSSLSASVGDRVTITCQASQDIT NYLNWYQQKPGKAPKLLIYDASNLETGVPS RFSGSGSGTDFTFTISSLQPEDIATYYCQQ YDSYLTFGGGTKVEIK (119) |
| EOS006172 | QVQLVQSGAEVKKPGSSVKVSCKASG GTFSSYAISWVRQAPGQGLEWMGGII PISGTANYAQKFQGRVTITADESTST AYMELSSLRSEDTAVYYCARTQEYTL FDIWGQGTMVTVSS (100) | EIVLTQSPATLSLSPGERATLSCRASQSVS SYLAWFQQKPGQAPRLLIYDASNRATGIPA RFSGSGSGTDFTLTISSLEPEDFAVYYCQQ DFHWPITFGGGTKVEIK (122) |
| EOS006162 | QVQLVQSGAEVKKPGSSVKVSCKASG GTFSSYAISWVRQAPGQGLEWMGGII PISGTANYAQKFQGRVTITADESTST AYMELSSLRSEDTAVYYCARTQEYTL FDSWGQGTMVTVSS (101) | EIVLTQSPATLSLSPGERATLSCRASQSVS SYLAWFQQKPGQAPRLLIYDASNRATGIPA RFSGSGSGTDFTLTISSLEPEDFAVYYCQQ DYHWPITFGGGTKVEIK (110) |
| EOS006180 | EVQLLESGGGLVQPGGSLRLSCAASG FTFSSYAMSWVRQAPGKGLEWVSAIS GSGGSTYYADSVKGRFTISRDNSKNT LYLQMNSLRAEDTAVYYCAKHPAVFG YGETWGQGTLVTVSS (102) | EIVLTQSPGTLSLSPGERATLSCRASQSVS SSFLAWYQQKPGQAPRLLIYGASSRATGIP DRFSGSGSGTDFTLTISRLEPEDFAVYYCQ QYYGLPITFGGGTKVEIK (123) |

TABLE 3-continued

VH and VL sequences

| Antibody | VH (SEQ ID NO) | VL (SEQ ID NO) |
|---|---|---|
| EOS006175 | QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCARDTKYWGGMDVWGQGTTVTVSS (103) | DIQMTQSPSSLSASVGDRVTITCQASQDISNYLNWYQQKPGKAPKLLIYDASNLATGVPSRFSGSGSGTDFTFTISSLQPEDIATYYCQQYVEAPTFGGGTKVEIK (115) |
| EOS006179 | EVQLLESGGGLVQPGGSLRLSCAASGFTFSNYAMSWVRQAPGKGLEWVSAISGSGGSTYYADSVKGRFTISRDNSKNTLYLQMNSLRAEDTAVYYCAKLRGGYEVGPTFDPWGQGTLVTVSS (104) | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQHYIWPITFGGGTKVEIK (118) |
| EOS006173 | EVQLVESGGGLVQPGRSLRLSCTASGFTFGDYAMSWFRQAPGKGLEWVGFIGSKAYGGTTEYTASVKGRFTISRDGSKSIAYLQMNSLKTEDTAVYYCARGKRRDYGYWHPAFDVWGQGTMVTVSS (105) | DIQMTQSPSSLSASVGDRVTITCQASQDITNYLNWYQQKPGKAPKLLIYDASNLETGVPSRFSGSGSGTDFTFTISSLQPEDIATYYCQEYDQYLTFGGGTKVEIK (124) |
| EOS006171 | QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARLGGYYSLGPMDVWGQGTTVTVSS (106) | EIVLTQSPATLSLSPGERATLSCRASQSVSSYLAWYQQKPGQAPRLLIYDASNRATGIPARFSGSGSGTDFTLTISSLEPEDFAVYYCQQDSAFPFTFGGGTKVEIK (125) |
| EOS004281 | QVQLVQSGAEVKKPGSSVKVSCKASGGTFSSYAISWVRQAPGQGLEWMGGIIPISGTANYAQKFQGRVTITADESTSTAYMELSSLRSEDTAVYYCARTQEYTLFDSWGQGTLVTVSS (107) | EIVLTQSPATLSLSPGERATLSCRASQSVSSYLAWFQQKPGQAPRLLIYDASNRATGIPARFSGSGSGTDFTLTISSLEPEDFAVYYCQQDYHWPITFGGGTKVEIK (110) |
| EOS004282 | QVQLVQSGAEVKKPGSSVKVSCKASGGTFSSYAISWVRQAPGQGLEWMGGIIPISGTANYAQKFQGRVTITADESTSTAYMELSSLRSEDTAVYYCARTQEYTLFDSWGQGTLVTVSS (107) | ETVLTQSPATLSLSPGERATLSCRASQSVSSYLAWFQQKPGQAPRLLIYDASNRATGIPARFSGSGSGTDFTLTISSLEPEDFAVYYCQQDYHWPITFGGGTKVEIK (110) |
| EOS004283 | QVQLVQSGAEVKKPGSSVKVSCKASGGTFAQYAISWVRQAPGQGLEWMGVIIPDSGTANYAQKFQGRVTITADESTSTAYMELSSLRSEDTAVYYCARTQENTIFDIWGQGTLVTVSS (108) | EIVLTQSPATLSLSPGERATLSCRASQSVSSYLAWFQQKPGQAPRLLIYDASNRATGIPARFSGSGSGTDFTLTISSLEPEDFAVYYCQQDYEWPITFGGGTKVEIK (111) |
| EOS006233 | QVQLVQSGAEVKKPGSSVKVSCKASGGTFAQYAISWVRQAPGQGLEWMGVIIPDSGTANYAQKFQGRVTITADESTSTAYMELSSLRSEDTAVYYCARTQENTIFDIWGQGTLVTVSS (108) | EIVLTQSPATLSLSPGERATLSCRASQSVSSYLAWFQQKPGQAPRLLIYDASNRATGIPARFSGSGSGTDFTLTISSLEPEDFAVYYCQQDYEWPITFGGGTKVEIK (111) |
| EOS004284 | EVQLVESGGGLVQPGRSLRLSCTASGFTFDDYTMSWFRQAPGKGLEWVGFIGSKAYSATTEYTASVKGRFTISRDGSKSIAYLQMNSLKTEDTAVYYCARGKRYSYTYWTPAFDVWGQGTLVTVSS (109) | DIQMTQSPSSLSASVGDRVTITCQASQDITNYLNWYQQKPGKAPKLLIYDASNLETGVPSRFSGSGSGTDFTFTISSLQPEDIATYYCQEYDSYITFGGGTKVEIK (121) |
| EOS006215 | EVQLVESGGGLVQPGRSLRLSCTASGFTFDDYTMSWFRQAPGKGLEWVGFIGSKAYSATTEYTASVKGRFTISRDGSKSIAYLQMNSLKTEDTAVYYCARGKRYSYTYWTPAFDVWGQGTLVTVSS (109) | DIQMTQSPSSLSASVGDRVTITCQASQDITNYLNWYQQKPGKAPKLLIYDASNLETGVPSRFSGSGSGTDFTFTISSLQPEDIATYYCQEYDSYITFGGGTKVEIK (121) |

TABLE 4

| VH framework sequences | | | | |
|---|---|---|---|---|
| Antibody | VH FR1 (SEQ ID NO) | VH FR2 (SEQ ID NO) | VH FR3 (SEQ ID NO) | VH FR4 (SEQ ID NO) |
| EOS006165 | QVQLVQSGAEVKKPGSSVKVSCKASG (126) | WVRQAPGQGLEWMG (131) | RVTITADESTSTAYMELSSLRSEDTAVYYC (136) | WGQGTMVTVSS (141) |
| EOS006163 | QVQLVQSGAEVKKPGSSVKVSCKASG (126) | WVRQAPGQGLEWMG (131) | RVTITADESTSTAYMELSSLRSEDTAVYYC (136) | WGQGTMVTVSS (141) |
| EOS006167 | EVQLLESGGGLVQPGGSLRLSCAASG (127) | WVRQAPGKGLEWVS (132) | RFTISRDNSKNTLYLQMNSLRAEDTAVYYC (137) | WGQGTMVTVSS (141) |
| EOS006168 | EVQLLESGGGLVQPGGSLRLSCAASG (127) | WVRQAPGKGLEWVS (132) | RFTISRDNSKNTLYLQMNSLRAEDTAVYYC (137) | WGQGTLVTVSS (142) |
| EOS006170 | QVQLQESGPGLVKPSGTLSLTCAVSG (128) | WVRQPPGKGLEWIG (133) | RVTISVDKSKNQFSLKLSSVTAADTAVYYC (138) | WGQGTTVTVSS (143) |
| EOS006177 | QVQLQESGPGLVKPSGTLSLTCAVSG (128) | WVRQPPGKGLEWIG (133) | RVTISVDKSKNQFSLKLSSVTAADTAVYYC (138) | WGQGTTVTVSS (143) |
| EOS006169 | EVQLLESGGGLVQPGGSLRLSCAASG (127) | WVRQAPGKGLEWVS (132) | RFTISRDNSKNTLYLQMNSLRAEDTAVYYC (137) | WGQGTLVTVSS (142) |
| EOS006178 | EVQLLESGGGLVQPGGSLRLSCAASG (127) | WVRQAPGKGLEWVS (132) | RFTISRDNSKNTLYLQMNSLRAEDTAVYYC (137) | WGQGTLVTVSS (142) |
| EOS006176 | EVQLLESGGGLVQPGGSLRLSCAASG (127) | WVRQAPGKGLEWVS (132) | RFTISRDNSKNTLYLQMNSLRAEDTAVYYC (137) | WGQGTLVTVSS (142) |
| EOS006166 | EVQLVESGGGLVQPGRSLRLSCTASG (129) | WFRQAPGKGLEWVG (134) | RFTISRDGSKSIAYLQMNSLKTEDTAVYYC (139) | WGQGTMVTVSS (141) |
| EOS006174 | EVQLVESGGGLVQPGRSLRLSCTASG (129) | WFRQAPGKGLEWVG (134) | RFTISRDGSKSIAYLQMNSLKTEDTAVYYC (139) | WGQGTMVTVSS (141) |
| EOS006164 | EVQLVESGGGLVQPGRSLRLSCTASG (129) | WFRQAPGKGLEWVG (134) | RFTISRDGSKSIAYLQMNSLKTEDTAVYYC (139) | WGQGTMVTVSS (141) |
| EOS006181 | EVQLVESGGGLVQPGRSLRLSCTASG (129) | WFRQAPGKGLEWVG (134) | RFTISRDGSKSIAYLQMNSLKTEDTAVYYC (139) | WGQGTMVTVSS (141) |
| EOS006172 | QVQLVQSGAEVKKPGSSVKVSCKASG (126) | WVRQAPGQGLEWMG (131) | RVTITADESTSTAYMELSSLRSEDTAVYYC (136) | WGQGTMVTVSS (141) |
| EOS006162 | QVQLVQSGAEVKKPGSSVKVSCKASG (126) | WVRQAPGQGLEWMG (131) | RVTITADESTSTAYMELSSLRSEDTAVYYC (136) | WGQGTMVTVSS (141) |
| EOS006180 | EVQLLESGGGLVQPGGSLRLSCAASG (127) | WVRQAPGKGLEWVS (132) | RFTISRDNSKNTLYLQMNSLRAEDTAVYYC (137) | WGQGTLVTVSS (142) |
| EOS006175 | QVQLQESGPGLVKPSGTLSLTCAVSG (128) | WVRQPPGKGLEWIG (133) | RVTISVDKSKNQFSLKLSSVTAADTAVYYC (138) | WGQGTTVTVSS (143) |

TABLE 4-continued

| VH framework sequences | | | | |
|---|---|---|---|---|
| Antibody | VH FR1 (SEQ ID NO) | VH FR2 (SEQ ID NO) | VH FR3 (SEQ ID NO) | VH FR4 (SEQ ID NO) |
| EOS006179 | EVQLLESGGGLVQPGGSL RLSCAASG (127) | WVRQAPGKG LEWVS (132) | RFTISRDNSKNTLYLQMNSL RAEDTAVYYC (137) | WGQGTLV TVSS (142) |
| EOS006173 | EVQLVESGGGLVQPGRSL RLSCTASG (129) | WFRQAPGKG LEWVG (134) | RFTISRDGSKSIAYLQMNSL KTEDTAVYYC (139) | WGQGTMV TVSS (141) |
| EOS006171 | QVQLVESGGGLVKPGGSL RLSCAASG (130) | WIRQAPGKG LEWVS (135) | RFTISRDNAKNSLYLQMNSL RAEDTAVYYC (140) | WGQGTTV TVSS (143) |
| EOS004281 | QVQLVQSGAEVKKPGSSV KVSCKASG (126) | WVRQAPGQG LEWMG (131) | RVTITADESTSTAYMELSSL RSEDTAVYYC (136) | WGQGTLV TVSS (142) |
| EOS004282 | QVQLVQSGAEVKKPGSSV KVSCKASG (126) | WVRQAPGQG LEWMG (131) | RVTITADESTSTAYMELSSL RSEDTAVYYC (136) | WGQGTLV TVSS (142) |
| EOS004283 | QVQLVQSGAEVKKPGSSV KVSCKASG (126) | WVRQAPGQG LEWMG (131) | RVTITADESTSTAYMELSSL RSEDTAVYYC (136) | WGQGTLV TVSS (142) |
| EOS006233 | QVQLVQSGAEVKKPGSSV KVSCKASG (126) | WVRQAPGQG LEWMG (131) | RVTITADESTSTAYMELSSL RSEDTAVYYC (136) | WGQGTLV TVSS (142) |
| EOS004284 | EVQLVESGGGLVQPGRSL RLSCTASG (129) | WFRQAPGKG LEWVG (134) | RFTISRDGSKSIAYLQMNSL KTEDTAVYYC (139) | WGQGTLV TVSS (142) |
| EOS006215 | EVQLVESGGGLVQPGRSL RLSCTASG (129) | WFRQAPGKG LEWVG (134) | RFTISRDGSKSIAYLQMNSL KTEDTAVYYC (139) | WGQGTLV TVSS (142) |

The VH framework regions described in Table 4 are determined based upon the boundaries of the VH CDRs. In other words, the VH CDRs are determined by a combination of CDR numbering systems, and the framework regions are the amino acid residues surrounding the CDRs in the variable region in the format FR1, CDR1, FR2, CDR2, FR3, CDR3, and FR4. In some embodiments, methionine is replaced with leucine at amino acid position 6 in VH FR4.

TABLE 5

| VL framework sequences | | | | |
|---|---|---|---|---|
| Antibody | VL FR1 (SEQ ID NO) | VL FR2 (SEQ ID NO) | VL FR3 (SEQ ID NO) | VL FR4 (SEQ ID NO) |
| EOS006165 | EIVLTQSPATLSLSPG ERATLSC (144) | WFQQKPGQAP RLLIY (148) | GIPARFSGSGSGTDFTLTISS LEPEDFAVYYC (152) | FGGGTKV EIK (156) |
| EOS006163 | EIVLTQSPATLSLSPG ERATLSC (144) | WFQQKPGQAP RLLIY (148) | GIPARFSGSGSGTDFTLTISS LEPEDFAVYYC (152) | FGGGTKV EIK (156) |
| EOS006167 | EIVLTQSPGTLSLSPG ERATLSC (145) | WYQQKPGQAP RLLIY (149) | GIPDRFSGSGSGTDFTLTISR LEPEDFAVYYC (153) | FGGGTKV EIK (156) |
| EOS006168 | EIVLTQSPGTLSLSPG ERATLSC (145) | WYQQKPGQAP RLLIY (149) | GIPDRFSGSGSGTDFTLTISR LEPEDFAVYYC (153) | FGGGTKV EIK (156) |
| EOS006170 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |

TABLE 5-continued

VL framework sequences

| Antibody | VL FR1 (SEQ ID NO) | VL FR2 (SEQ ID NO) | VL FR3 (SEQ ID NO) | VL FR4 (SEQ ID NO) |
|---|---|---|---|---|
| EOS006177 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |
| EOS006169 | DIVMTQSPDSLAVSLG ERATINC (147) | WYQQKPGQPP KLLIY (151) | GVPDRFSGSGSGTDFTLTISS LQAEDVAVYYC (155) | FGGGTKV EIK (156) |
| EOS006178 | DIVMTQSPDSLAVSLG ERATINC (147) | WYQQKPGQPP KLLIY (151) | GVPDRFSGSGSGTDFTLTISS LQAEDVAVYYC (155) | FGGGTKV EIK (156) |
| EOS006176 | DIVMTQSPDSLAVSLG ERATINC (147) | WYQQKPGQPP KLLIY (151) | GVPDRFSGSGSGTDFTLTISS LQAEDVAVYYC (155) | FGGGTKV EIK (156) |
| EOS006166 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |
| EOS006174 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |
| EOS006164 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |
| EOS006181 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |
| EOS006172 | EIVLTQSPATLSLSPG ERATLSC (144) | WFQQKPGQAP RLLIY (148) | GIPARFSGSGSGTDFTLTISS LEPEDFAVYYC (152) | FGGGTKV EIK (156) |
| EOS006162 | EIVLTQSPATLSLSPG ERATLSC (144) | WFQQKPGQAP RLLIY (148) | GIPARFSGSGSGTDFTLTISS LEPEDFAVYYC (152) | FGGGTKV EIK (156) |
| EOS006180 | EIVLTQSPGTLSLSPG ERATLSC (145) | WYQQKPGQAP RLLIY (149) | GIPDRFSGSGSGTDFTLTISR LEPEDFAVYYC (153) | FGGGTKV EIK (156) |
| EOS006175 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |
| EOS006179 | DIVMTQSPDSLAVSLG ERATINC (147) | WYQQKPGQPP KLLIY (151) | GVPDRFSGSGSGTDFTLTISS LQAEDVAVYYC (155) | FGGGTKV EIK (156) |
| EOS006173 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |
| EOS006171 | EIVLTQSPATLSLSPG ERATLSC (144) | WYQQKPGQAP RLLIY (149) | GIPARFSGSGSGTDFTLTISS LEPEDFAVYYC (152) | FGGGTKV EIK (156) |
| EOS004281 | EIVLTQSPATLSLSPG ERATLSC (144) | WFQQKPGQAP RLLIY (148) | GIPARFSGSGSGTDFTLTISS LEPEDFAVYYC (152) | FGGGTKV EIK (156) |
| EOS004282 | EIVLTQSPATLSLSPG ERATLSC (144) | WFQQKPGQAP RLLIY (148) | GIPARFSGSGSGTDFTLTISS ELPEDFAVYYC (152) | FGGGTKV EIK (156) |
| EOS004283 | EIVLTQSPATLSLSPG ERATLSC (144) | WFQQKPGQAP RLLIY (148) | GIPARFSGSGSGTDFTLTISS LEPEDFAVYYC (152) | FGGGTKV EIK (156) |

TABLE 5-continued

| VL framework sequences | | | | |
|---|---|---|---|---|
| Antibody | VL FR1 (SEQ ID NO) | VL FR2 (SEQ ID NO) | VL FR3 (SEQ ID NO) | VL FR4 (SEQ ID NO) |
| EOS006233 | EIVLTQSPATLSLSPG ERATLSC (144) | WFQQKPGQAP RLLIY (148) | GIPARFSGSGSGTDFTLTISS LEPEDFAVYYC (152) | FGGGTKV EIK (156) |
| EOS004284 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |
| EOS006215 | DIQMTQSPSSLSASVG DRVTITC (146) | WYQQKPGKAP KLLIY (150) | GVPSRFSGSGSGTDFTFTISS LQPEDIATYYC (154) | FGGGTKV EIK (156) |

The VL framework regions described in Table 5 are determined based upon the boundaries of the Kabat numbering system for CDRs. In other words, the VL CDRs are determined by Kabat, and the framework regions are the amino acid residues surrounding the CDRs in the variable region in the format FR1, CDR1, FR2, CDR2, FR3, CDR3, and FR4.

In certain embodiments, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence of a VH domain of an antibody listed in Table 3 (e.g., the VH domain in one row in Table 3). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 87 (e.g., antibody EOS006165). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 88 (e.g., antibody EOS006163). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 89 (e.g., antibody EOS006167). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 90 (e.g., antibody EOS006168). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 91 (e.g., antibody EOS006170). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 92 (e.g., antibody EOS006177). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 93 (e.g., antibody EOS006169). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 94 (e.g., antibody EOS006178). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 95 (e.g., antibody EOS006176). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 96 (e.g., antibody EOS006166). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 97 (e.g., antibody EOS006174). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 98 (e.g., antibody EOS006164). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 99 (e.g., antibody EOS006181). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 100 (e.g., antibody EOS006172). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 101 (e.g., antibody EOS006162). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 102 (e.g., antibody EOS006180). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 103 (e.g., antibody EOS006175). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 104 (e.g., antibody EOS006179). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 105 (e.g., antibody EOS006173). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 106 (e.g., antibody EOS006171). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 107 (e.g., antibody EOS004281 or EOS004282). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 108 (e.g., antibody EOS004283 or EOS006233). In a specific embodiment, an antibody that specifically binds to TREM2 (e.g., human TREM2) comprises a VH domain comprising an amino acid sequence at least 80%, at least 85%, at least 90%, at least 95%, at least 96%, at least 97%, at least 98%, or at least 99% identical to the amino acid sequence set forth in SEQ ID NO: 109 (e.g., antibody EOS004284 or EOS006215).

In certain embodiments, an antibody that specifically binds to TREM2 (e.g., human TREM2) comprises a VH domain comprising an amino acid sequence of a VH domain of an antibody listed in Table 3 (e.g., the VH domain in one row in Table 3). In a specific embodiment, an antibody that specifically binds to TREM2 (e.g., human TREM2) comprises a VH domain comprising an amino acid sequence set forth in SEQ ID NO: 87 (e.g., antibody EOS006165). In a specific embodiment, an antibody that specifically binds to TREM2 (e.g., human TREM2) comprises a VH domain comprising an amino acid sequence set forth in SEQ ID NO: 88 (e.g., antibody EOS006163). In a specific embodiment, an antibody that specifically binds to TREM2 (e.g., human TREM2) comprises a VH domain comprising an amino acid sequence set forth in SEQ ID NO: 89 (e.g., antibody EOS006167). In a specific embodiment, an antibody that specifically binds to TREM2 (e.g., human TREM2) comprises a VH domain comprising an amino acid sequence set forth in SEQ ID NO: 90 (e.g., antibody EOS006168). In a specific embodiment, an antibody that specifically binds to TREM2 (e.g., human TREM2) comprises a VH domain comprising an amino acid sequence set forth in SEQ ID NO: 91 (e.g., antibody EOS006170). In a specific embodiment, an antibody that specifically binds to TREM2 (e.g., human TREM2) comprises a VH domain comprising an amino acid sequence set forth in SEQ ID NO: 92 (e.g., antibody EOS006177). In a specific embodiment, an antibody that specifically binds to TREM2 (e.g., human TREM2) comprises a VH domain comprising an amino acid sequence set forth in SEQ ID NO: 93 (e.g., antibody EOS006169). In a specific embodiment, an antibody that specifically binds to TREM2 (e.g., human TREM2) comprises a VH domain comprising an amino acid sequence set forth in SEQ ID NO: 94 (e.g., antibody EOS006178). In a specific embodiment, an antibody that specifically binds to TREM2 (e.g., human TREM2) comprises a VH domain comprising an amino acid sequence set forth in SEQ ID NO: 95 (e.g., antibody EOS006176). In a specific embodiment, an antibody that specifically binds to TREM2 (e.g., human TREM2) comprises a VH domain comprising an amino acid sequence set forth in SEQ ID NO: 96 (e.g., antibody EOS006166). In a specific embodiment, an antibody that specifically binds to TREM2 (e.g., human TREM2) comprises a VH domain comprising an amino acid sequence set forth in SEQ ID NO: 97 (e.g., antibody EOS006174). In a specific embodiment, an antibody that specifically binds to TREM2 (e.g., human TREM2) comprises a VH domain comprising an amino acid sequence set forth in SEQ ID NO: 98 (e.g., antibody EOS006164). In a specific embodiment, an antibody that specifically binds to TREM2 (e.g., human TREM2) comprises a VH domain comprising an amino acid sequence set forth in SEQ ID NO: 99 (e.g., antibody EOS006181). In a specific embodiment, an antibody that specifically binds to TREM2 (e.g., human TREM2) comprises a VH domain comprising an amino acid sequence set forth in SEQ ID NO: 100 (e.g., antibody EOS006172). In a specific embodiment, an antibody that specifically binds to TREM2 (e.g., human TREM2) comprises a VH domain comprising an amino acid sequence set forth in SEQ ID NO: 101 (e.g., antibody EOS006162). In a specific embodiment, an antibody that specifically binds to TREM2 (e.g., human TREM2) comprises a VH domain comprising an amino acid sequence set forth in SEQ ID NO: 102 (e.g., antibody EOS006180). In a specific embodiment, an antibody that specifically binds to TREM2 (e.g., human TREM2) comprises a VH domain comprising an amino acid sequence set forth in SEQ ID NO: 103 (e.g., antibody EOS006175). In a specific embodiment, an antibody that specifically binds to TREM2 (e.g., human TREM2) comprises a VH domain comprising an amino acid sequence set forth in SEQ ID NO: 104 (e.g., antibody EOS006179). In a specific embodiment, an antibody that specifically binds to TREM2 (e.g., human TREM2) comprises a VH domain comprising an amino acid sequence set forth in SEQ ID NO: 105 (e.g., antibody EOS006173). In a specific embodiment, an antibody that specifically binds to TREM2 (e.g., human TREM2) comprises a VH domain comprising an amino acid sequence set forth in SEQ ID NO: 106 (e.g., antibody EOS006171). In a specific embodiment, an antibody that specifically binds to TREM2 (e.g., human TREM2) comprises a VH domain comprising an amino acid sequence set forth in SEQ ID NO: 107 (e.g., antibody EOS004281 or EOS004282). In a specific embodiment, an antibody that specifically binds to TREM2 (e.g., human TREM2) comprises a VH domain comprising an amino acid sequence set forth in SEQ ID NO: 108 (e.g., antibody EOS004283 or EOS006233). In a specific embodiment, an antibody that specifically binds to TREM2 (e.g., human TREM2) comprises a VH domain comprising an amino acid sequence set forth in SEQ ID NO: 109 (e.g., antibody EOS004284 or EOS006215).

In certain embodiments, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence of a VH domain of an antibody listed in Table 3 (e.g., the VH domain in one row in Table 3). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 87 (e.g., antibody EOS006165). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 88 (e.g., antibody EOS006163). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 89 (e.g., antibody EOS006167). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 90 (e.g., antibody EOS006168). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 91 (e.g., antibody EOS006170). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 92 (e.g., antibody EOS006177). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 93 (e.g., antibody EOS006169). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 94 (e.g., antibody EOS006178). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 95 (e.g., antibody EOS006176). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 96 (e.g., antibody EOS006166). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 97 (e.g., antibody EOS006174). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 98 (e.g., antibody EOS006164). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 99 (e.g., antibody EOS006181). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 100 (e.g., antibody EOS006172). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 101 (e.g., antibody EOS006162). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 102 (e.g., antibody EOS006180). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 103 (e.g., antibody EOS006175). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 104 (e.g., antibody EOS006179). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 105 (e.g., antibody EOS006173). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 106 (e.g., antibody EOS006171). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 107 (e.g., antibody EOS004281 or EOS004282). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 108 (e.g., antibody EOS004283 or EOS006233). In a specific embodiment, an antibody that specifically binds to TREM2 (e.g., human TREM2) comprises a VH domain consisting of an amino acid sequence at least 80%, at least 85%, at least 90%, at least 95%, at least 96%, at least 97%, at least 98%, or at least 99% identical to the amino acid sequence set forth in SEQ ID NO: 109 (e.g., antibody EOS004284 or EOS006215).

In certain embodiments, an antibody that specifically binds to TREM2 (e.g., human TREM2) comprises a VH domain consisting of an amino acid sequence of a VH domain of an antibody listed in Table 3 (e.g., the VH domain in one row in Table 3). In a specific embodiment, an antibody that specifically binds to TREM2 (e.g., human TREM2) comprises a VH domain consisting of an amino acid sequence set forth in SEQ ID NO: 87 (e.g., antibody EOS006165). In a specific embodiment, an antibody that specifically binds to TREM2 (e.g., human TREM2) consisting of a VH domain comprising an amino acid sequence set forth in SEQ ID NO: 88 (e.g., antibody EOS006163). In a specific embodiment, an antibody that specifically binds to TREM2 (e.g., human TREM2) comprises a VH domain consisting of an amino acid sequence set forth in SEQ ID NO: 89 (e.g., antibody EOS006167). In a specific embodiment, an antibody that specifically binds to TREM2 (e.g., human TREM2) comprises a VH domain consisting of an amino acid sequence set forth in SEQ ID NO: 90 (e.g., antibody EOS006168). In a specific embodiment, an antibody that specifically binds to TREM2 (e.g., human TREM2) comprises a VH domain consisting of an amino acid sequence set forth in SEQ ID NO: 91 (e.g., antibody EOS006170). In a specific embodiment, an antibody that specifically binds to TREM2 (e.g., human TREM2) comprises a VH domain consisting of an amino acid sequence set forth in SEQ ID NO: 92 (e.g., antibody EOS006177). In a specific embodiment, an antibody that specifically binds to TREM2 (e.g., human TREM2) comprises a VH domain consisting of an amino acid sequence set forth in SEQ ID NO: 93 (e.g., antibody EOS006169). In a specific embodiment, an antibody that specifically binds to TREM2 (e.g., human TREM2) comprises a VH domain consisting of an amino acid sequence set forth in SEQ ID NO: 94 (e.g., antibody EOS006178). In a specific embodiment, an antibody that specifically binds to TREM2 (e.g., human TREM2) comprises a VH domain consisting of an amino acid sequence set forth in SEQ ID NO: 95 (e.g., antibody EOS006176). In a specific embodiment, an antibody that specifically binds to TREM2 (e.g., human TREM2) comprises a VH domain consisting of an amino acid sequence set forth in SEQ ID NO: 96 (e.g., antibody EOS006166). In a specific embodiment, an antibody that specifically binds to TREM2 (e.g., human TREM2) comprises a VH domain consisting of an amino acid sequence set forth in SEQ ID NO: 97 (e.g., antibody EOS006174). In a specific embodiment, an antibody that specifically binds to TREM2 (e.g., human TREM2) comprises a VH domain consisting of an amino acid sequence set forth in SEQ ID NO: 98 (e.g., antibody EOS006164). In a specific embodiment, an antibody that specifically binds to TREM2 (e.g., human TREM2) comprises a VH domain consisting of an amino acid sequence set forth in SEQ ID NO: 99 (e.g., antibody EOS006181). In a specific embodiment, an antibody that specifically binds to TREM2 (e.g., human TREM2) comprises a VH domain consisting of an amino acid sequence set forth in SEQ ID NO: 100 (e.g., antibody EOS006172). In a specific embodiment, an antibody that specifically binds to TREM2 (e.g., human TREM2) comprises a VH domain consisting of an amino acid sequence set forth in SEQ ID NO: 101 (e.g., antibody EOS006162). In a specific embodiment, an antibody that specifically binds to TREM2 (e.g., human TREM2) comprises a VH domain consisting of an amino acid sequence set forth in SEQ ID NO: 102 (e.g., antibody EOS006180). In a specific embodiment, an antibody that specifically binds to TREM2 (e.g., human TREM2) comprises a VH domain consisting of an amino acid sequence set forth in SEQ ID NO: 103 (e.g., antibody EOS006175). In a specific embodiment, an antibody that specifically binds to TREM2 (e.g., human TREM2) comprises a VH domain consisting of an amino acid sequence set forth in SEQ ID NO: 104 (e.g., antibody EOS006179). In a specific embodiment, an antibody that specifically binds to TREM2 (e.g., human TREM2) comprises a VH domain consisting of an amino acid sequence set forth in SEQ ID NO: 105 (e.g., antibody EOS006173). In a specific embodiment, an antibody that specifically binds to TREM2 (e.g., human TREM2) comprises a VH domain consisting of an amino acid sequence set forth in SEQ ID NO: 106 (e.g., antibody EOS006171). In a specific embodiment, an antibody that specifically binds to TREM2 (e.g., human TREM2) comprises a VH domain consisting of an amino acid sequence set forth in SEQ ID NO: 107 (e.g., antibody EOS004281 or EOS004282). In a specific embodiment, an antibody that specifically binds to TREM2 (e.g., human TREM2) comprises a VH domain consisting of an amino acid sequence set forth in SEQ ID NO: 108 (e.g., antibody EOS004283 or EOS06233). In a specific embodiment, an antibody that specifically binds to TREM2 (e.g., human TREM2) comprises a VH domain consisting of an amino acid sequence set forth in SEQ ID NO: 109 (e.g., antibody EOS004284 or EOS006215).

In certain embodiments, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence of a VL domain of an antibody listed in Table 3 (e.g., the VL domain in one row in Table 3). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 110 (e.g., antibody EOS006165, EOS006162, EOS004281, or EOS004282). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 111 (e.g., antibody EOS006163, EOS004283, or EOS006233). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 112 (e.g., antibody EOS006167). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 113 (e.g., antibody EOS006168). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 114 (e.g., antibody EOS006170). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 115 (e.g., antibody EOS006177 or EOS006175). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 116 (e.g., antibody EOS006169). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 117 (e.g., antibody EOS006178). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 118 (e.g., antibody EOS006176 or EOS006179). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 119 (e.g., antibody EOS006166 or EOS006181). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 120 (e.g., antibody EOS006174). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 121 (e.g., antibody EOS006164, EOS004284, or EOS006215). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 122 (e.g., antibody EOS006172). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 123 (e.g., antibody EOS006180). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 124 (e.g., antibody EOS006173). In a specific embodiment, an antibody that specifically binds to TREM2 (e.g., human TREM2) comprises a VL domain comprising an amino acid sequence at least 80%, at least 85%, at least 90%, at least 95%, at least 96%, at least 97%, at least 98%, or at least 99% identical to the amino acid sequence set forth in SEQ ID NO: 125 (e.g., antibody EOS006171).

In certain embodiments, an antibody that specifically binds to TREM2 (e.g., human TREM2) comprises a VL domain comprising an amino acid sequence of a VL domain of an antibody listed in Table 3 (e.g., the VL domain in one row in Table 3). In a specific embodiment, an antibody that specifically binds to TREM2 (e.g., human TREM2) comprises a VL domain comprising an amino acid sequence set forth in SEQ ID NO: 110 (e.g., antibody EOS006165, EOS006162, EOS004281, EOS004282). In a specific embodiment, an antibody that specifically binds to TREM2 (e.g., human TREM2) comprises a VL domain comprising an amino acid sequence set forth in SEQ ID NO: 111 (e.g., antibody EOS006163, EOS004283, or EOS006233). In a specific embodiment, an antibody that specifically binds to TREM2 (e.g., human TREM2) comprises a VL domain comprising an amino acid sequence set forth in SEQ ID NO: 112 (e.g., antibody EOS006167). In a specific embodiment, an antibody that specifically binds to TREM2 (e.g., human TREM2) comprises a VL domain comprising an amino acid sequence set forth in SEQ ID NO: 113 (e.g., antibody EOS006168). In a specific embodiment, an antibody that specifically binds to TREM2 (e.g., human TREM2) comprises a VL domain comprising an amino acid sequence set forth in SEQ ID NO: 114 (e.g., antibody EOS006170). In a specific embodiment, an antibody that specifically binds to TREM2 (e.g., human TREM2) comprises a VL domain comprising an amino acid sequence set forth in SEQ ID NO: 115 (e.g., antibody EOS006177 or EOS006175). In a specific embodiment, an antibody that specifically binds to TREM2 (e.g., human TREM2) comprises a VL domain comprising an amino acid sequence set forth in SEQ ID NO: 116 (e.g., antibody EOS006169). In a specific embodiment, an antibody that specifically binds to TREM2 (e.g., human TREM2) comprises a VL domain comprising an amino acid sequence set forth in SEQ ID NO: 117 (e.g., antibody EOS006178). In a specific embodiment, an antibody that specifically binds to TREM2 (e.g., human TREM2) comprises a VL domain comprising an amino acid sequence set forth in SEQ ID NO: 118 (e.g., antibody EOS006176 or EOS006179). In a specific embodiment, an antibody that specifically binds to TREM2 (e.g., human TREM2) comprises a VL domain comprising an amino acid sequence set forth in SEQ ID NO: 119 (e.g., antibody EOS006166 or EOS006181). In a specific embodiment, an antibody that specifically binds to TREM2 (e.g., human TREM2) comprises a VL domain comprising an amino acid sequence set forth in SEQ ID NO: 120 (e.g., antibody EOS006174). In a specific embodiment, an antibody that specifically binds to TREM2 (e.g., human TREM2) comprises a VL domain comprising an amino acid sequence set forth in SEQ ID NO: 121 (e.g., antibody EOS006164, EOS004284, or EOS006215). In a specific embodiment, an antibody that specifically binds to TREM2 (e.g., human TREM2) comprises a VL domain comprising an amino acid sequence set forth in SEQ ID NO: 122 (e.g., antibody EOS006172). In a specific embodiment, an antibody that specifically binds to TREM2 (e.g., human TREM2) comprises a VL domain comprising an amino acid sequence set forth in SEQ ID NO: 123 (e.g., antibody EOS006180). In a specific embodiment, an antibody that specifically binds to TREM2 (e.g., human TREM2) comprises a VL domain comprising an amino acid sequence set forth in SEQ ID NO: 124 (e.g., antibody EOS006173). In a specific embodiment, an antibody that specifically binds to TREM2 (e.g., human TREM2) comprises a VL domain comprising an amino acid sequence set forth in SEQ ID NO: 125 (e.g., antibody EOS006171).

In certain embodiments, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence of a VL domain of an antibody listed in Table 3 (e.g., the VL domain in one row in Table 3). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 110 (e.g., antibody EOS006165, EOS006162, EOS004281, or EOS004282). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 111 (e.g., antibody EOS006163, EOS004283, or EOS006233). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 112 (e.g., antibody EOS006167). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 113 (e.g., antibody EOS006168). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 114 (e.g., antibody EOS006170). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 115 (e.g., antibody EOS006177 or EOS006175). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 116 (e.g., antibody EOS006169). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 117 (e.g., antibody EOS006178). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 118 (e.g., antibody EOS006176 or EOS006179). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 119 (e.g., antibody EOS006166 or EOS006181). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 120 (e.g., antibody EOS006174). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 121 (e.g., antibody EOS006164, EOS004284, or EOS006215). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 122 (e.g., antibody EOS006172). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 123 (e.g., antibody EOS006180). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 124 (e.g., antibody EOS006173). In a specific embodiment, an antibody that specifically binds to TREM2 (e.g., human TREM2) comprises a VL domain consisting of an amino acid sequence at least 80%, at least 85%, at least 90%, at least 95%, at least 96%, at least 97%, at least 98%, or at least 99% identical to the amino acid sequence set forth in SEQ ID NO: 125 (e.g., antibody EOS006171).

In certain embodiments, an antibody that specifically binds to TREM2 (e.g., human TREM2) comprises a VL domain consisting of an amino acid sequence of a VL domain of an antibody listed in Table 3 (e.g., the VL domain in one row in Table 3). In a specific embodiment, an antibody that specifically binds to TREM2 (e.g., human TREM2) comprises a VL domain consisting of an amino acid sequence set forth in SEQ ID NO: 110 (e.g., antibody EOS006165, EOS006162, EOS004281, or EOS004282). In a specific embodiment, an antibody that specifically binds to TREM2 (e.g., human TREM2) comprises a VL domain consisting of an amino acid sequence set forth in SEQ ID NO: 111 (e.g., antibody EOS006163, EOS004283, or EOS006233). In a specific embodiment, an antibody that specifically binds to TREM2 (e.g., human TREM2) comprises a VL domain consisting of an amino acid sequence set forth in SEQ ID NO: 112 (e.g., antibody EOS006167). In a specific embodiment, an antibody that specifically binds to TREM2 (e.g., human TREM2) comprises a VL domain consisting of an amino acid sequence set forth in SEQ ID NO: 113 (e.g., antibody EOS006168). In a specific embodiment, an antibody that specifically binds to TREM2 (e.g., human TREM2) comprises a VL domain consisting of an amino acid sequence set forth in SEQ ID NO: 114 (e.g., antibody EOS006170). In a specific embodiment, an antibody that specifically binds to TREM2 (e.g., human TREM2) comprises a VL domain consisting of an amino acid sequence set forth in SEQ ID NO: 115 (e.g., antibody EOS006177 or EOS006175). In a specific embodiment, an antibody that specifically binds to TREM2 (e.g., human TREM2) comprises a VL domain consisting of an amino acid sequence set forth in SEQ ID NO: 116 (e.g., antibody EOS006169). In a specific embodiment, an antibody that specifically binds to TREM2 (e.g., human TREM2) comprises a VL domain consisting of an amino acid sequence set forth in SEQ ID NO: 117 (e.g., antibody EOS006178). In a specific embodiment, an antibody that specifically binds to TREM2 (e.g., human TREM2) comprises a VL domain consisting of an amino acid sequence set forth in SEQ ID NO: 118 (e.g., antibody EOS006176 or EOS006179). In a specific embodiment, an antibody that specifically binds to TREM2 (e.g., human TREM2) comprises a VL domain consisting of an amino acid sequence set forth in SEQ ID NO: 119 (e.g., antibody EOS006166 or EOS006181). In a specific embodiment, an antibody that specifically binds to TREM2 (e.g., human TREM2) comprises a VL domain consisting of an amino acid sequence set forth in SEQ ID NO: 120 (e.g., antibody EOS006174). In a specific embodiment, an antibody that specifically binds to TREM2 (e.g., human TREM2) comprises a VL domain consisting of an amino acid sequence set forth in SEQ ID NO: 121 (e.g., antibody EOS006164, EOS004284, or EOS006215). In a specific embodiment, an antibody that specifically binds to TREM2 (e.g., human TREM2) comprises a VL domain consisting of an amino acid sequence set forth in SEQ ID NO: 122 (e.g., antibody EOS006172). In a specific embodiment, an antibody that specifically binds to TREM2 (e.g., human TREM2) comprises a VL domain consisting of an amino acid sequence set forth in SEQ ID NO: 123 (e.g., antibody EOS006180). In a specific embodiment, an antibody that specifically binds to TREM2 (e.g., human TREM2) comprises a VL domain consisting of an amino acid sequence set forth in SEQ ID NO: 124 (e.g., antibody EOS006173). In a specific embodiment, an antibody that specifically binds to TREM2 (e.g., human TREM2) comprises a VL domain consisting of an amino acid sequence set forth in SEQ ID NO: 125 (e.g., antibody EOS006171).

In certain embodiments, an antibody that specifically binds to TREM2 (e.g., human TREM2) comprises a VH domain and a VL domain, wherein the VH domain and the VL domain comprise the amino acid sequence of a VH domain and a VL domain of an antibody listed in Table 3 or an amino acid sequence at least 80%, 85%, 90%, 95%, 96%, 97%, 98%, or 99% identical thereto (e.g., the VH domain and VL domain in one row of Table 3). In a specific embodiment, an antibody that specifically binds to TREM2 (e.g., human TREM2) comprises a VH domain comprising the amino acid sequence set forth in SEQ ID NO: 87 or an amino acid sequence at least 80%, 85%, 90%, 95%, 96%, 97%, 98%, or 99% identical thereto, and a VL domain comprising the amino acid sequence set forth in SEQ ID NO: 110 or an amino acid sequence at least 80%, 85%, 90%, 95%, 96%, 97%, 98%, or 99% identical thereto (e.g., antibody EOS006165). In a specific embodiment, an antibody that specifically binds to TREM2 (e.g., human TREM2) comprises a VH domain comprising the amino acid sequence set forth in SEQ ID NO: 88 or an amino acid sequence at least 80%, 85%, 90%, 95%, 96%, 97%, 98%, or 99% identical thereto, and a VL domain comprising the amino acid sequence set forth in SEQ ID NO: 111 or an amino acid sequence at least 80%, 85%, 90%, 95%, 96%, 97%, 98%, or 99% identical thereto (e.g., antibody EOS006163). In a specific embodiment, an antibody that specifically binds to TREM2 (e.g., human TREM2) comprises a VH domain comprising the amino acid sequence set forth in SEQ ID NO: 89 or an amino acid sequence at least 80%, 85%, 90%, 95%, 96%, 97%, 98%, or 99% identical thereto, and a VL domain comprising the amino acid sequence set forth in SEQ ID NO: 112 or an amino acid sequence at least 80%, 85%, 90%, 95%, 96%, 97%, 98%, or 99% identical thereto (e.g., antibody EOS006167). In a specific embodiment, an antibody that specifically binds to TREM2 (e.g., human TREM2) comprises a VH domain comprising the amino acid sequence set forth in SEQ ID NO: 90 or an amino acid sequence at least 80%, 85%, 90%, 95%, 96%, 97%, 98%, or 99% identical thereto, and a VL domain comprising the amino acid sequence set forth in SEQ ID NO:113 or an amino acid sequence at least 80%, 85%, 90%, 95%, 96%, 97%, 98%, or 99% identical thereto (e.g., antibody EOS006168). In a specific embodiment, an antibody that specifically binds to TREM2 (e.g., human TREM2) comprises a VH domain comprising the amino acid sequence set forth in SEQ ID NO: 91 or an amino acid sequence at least 80%, 85%, 90%, 95%, 96%, 97%, 98%, or 99% identical thereto, and a VL domain comprising the amino acid sequence set forth in SEQ ID NO: 114 or an amino acid sequence at least 80%, 85%, 90%, 95%, 96%, 97%, 98%, or 99% identical thereto (e.g., antibody EOS006170). In a specific embodiment, an antibody that specifically binds to TREM2 (e.g., human TREM2) comprises a VH domain comprising the amino acid sequence set forth in SEQ ID NO: 92 or an amino acid sequence at least 80%, 85%, 90%, 95%, 96%, 97%, 98%, or 99% identical thereto, and a VL domain comprising the amino acid sequence set forth in SEQ ID NO: 115 or an amino acid sequence at least 80%, 85%, 90%, 95%, 96%, 97%, 98%, or 99% identical thereto (e.g., antibody EOS006177). In a specific embodiment, an antibody that specifically binds to TREM2 (e.g., human TREM2) comprises a VH domain comprising the amino acid sequence set forth in SEQ ID NO: 93 or an amino acid sequence at least 80%, 85%, 90%, 95%, 96%, 97%, 98%, or 99% identical thereto, and a VL domain comprising the amino acid sequence set forth in SEQ ID NO: 116 or an amino acid sequence at least 80%, 85%, 90%, 95%, 96%, 97%, 98%, or 99% identical thereto (e.g., antibody EOS006169). In a specific embodiment, an antibody that specifically binds to TREM2 (e.g., human TREM2) comprises a VH domain comprising the amino acid sequence set forth in SEQ ID NO: 94 or an amino acid sequence at least 80%, 85%, 90%, 95%, 96%, 97%, 98%, or 99% identical thereto, and a VL domain comprising the amino acid sequence set forth in SEQ ID NO: 117 or an amino acid sequence at least 80%, 85%, 90%, 95%, 96%, 97%, 98%, or 99% identical thereto (e.g., antibody EOS006178). In a specific embodiment, an antibody that specifically binds to TREM2 (e.g., human TREM2) comprises a VH domain comprising the amino acid sequence set forth in SEQ ID NO: 95 or an amino acid sequence at least 80%, 85%, 90%, 95%, 96%, 97%, 98%, or 99% identical thereto, and a VL domain comprising the amino acid sequence set forth in SEQ ID NO: 118 or an amino acid sequence at least 80%, 85%, 90%, 95%, 96%, 97%, 98%, or 99% identical thereto (e.g., antibody EOS006176). In a specific embodiment, an antibody that specifically binds to TREM2 (e.g., human TREM2) comprises a VH domain comprising the amino acid sequence set forth in SEQ ID NO: 96 or an amino acid sequence at least 80%, 85%, 90%, 95%, 96%, 97%, 98%, or 99% identical thereto, and a VL domain comprising the amino acid sequence set forth in SEQ ID NO: 119 or an amino acid sequence at least 80%, 85%, 90%, 95%, 96%, 97%, 98%, or 99% identical thereto (e.g., antibody EOS006166). In a specific embodiment, an antibody that specifically binds to TREM2 (e.g., human TREM2) comprises a VH domain comprising the amino acid sequence set forth in SEQ ID NO: 97 or an amino acid sequence at least 80%, 85%, 90%, 95%, 96%, 97%, 98%, or 99% identical thereto, and a VL domain comprising the amino acid sequence set forth in SEQ ID NO: 120 or an amino acid sequence at least 80%, 85%, 90%, 95%, 96%, 97%, 98%, or 99% identical thereto (e.g., antibody EOS006174). In a specific embodiment, an antibody that specifically binds to TREM2 (e.g., human TREM2) comprises a VH domain comprising the amino acid sequence set forth in SEQ ID NO: 98 or an amino acid sequence at least 80%, 85%, 90%, 95%, 96%, 97%, 98%, or 99% identical thereto, and a VL domain comprising the amino acid sequence set forth in SEQ ID NO: 121 or an amino acid sequence at least 80%, 85%, 90%, 95%, 96%, 97%, 98%, or 99% identical thereto (e.g., antibody EOS006164). In a specific embodiment, an antibody that specifically binds to TREM2 (e.g., human TREM2) comprises a VH domain comprising the amino acid sequence set forth in SEQ ID NO: 99 or an amino acid sequence at least 80%, 85%, 90%, 95%, 96%, 97%, 98%, or 99% identical thereto, and a VL domain comprising the amino acid sequence set forth in SEQ ID NO: 119 or an amino acid sequence at least 80%, 85%, 90%, 95%, 96%, 97%, 98%, or 99% identical thereto (e.g., antibody EOS006181). In a specific embodiment, an antibody that specifically binds to TREM2 (e.g., human TREM2) comprises a VH domain comprising the amino acid sequence set forth in SEQ ID NO: 100 or an amino acid sequence at least 80%, 85%, 90%, 95%, 96%, 97%, 98%, or 99% identical thereto, and a VL domain comprising the amino acid sequence set forth in SEQ ID NO: 122 or an amino acid sequence at least 80%, 85%, 90%, 95%, 96%, 97%, 98%, or 99% identical thereto (e.g., antibody EOS006172). In a specific embodiment, an antibody that specifically binds to TREM2 (e.g., human TREM2) comprises a VH domain comprising the amino acid sequence set forth in SEQ ID NO: 101 or an amino acid sequence at least 80%, 85%, 90%, 95%, 96%, 97%, 98%, or 99% identical thereto, and a VL domain comprising the amino acid sequence set forth in SEQ ID NO: 110 or an amino acid sequence at least 80%, 85%, 90%, 95%, 96%, 97%, 98%, or 99% identical thereto (e.g., antibody EOS006162). In a specific embodiment, an antibody that specifically binds to TREM2 (e.g., human TREM2) comprises a VH domain comprising the amino acid sequence set forth in SEQ ID NO: 102 or an amino acid sequence at least 80%, 85%, 90%, 95%, 96%, 97%, 98%, or 99% identical thereto, and a VL domain comprising the amino acid sequence set forth in SEQ ID NO: 123 or an amino acid sequence at least 80%, 85%, 90%, 95%, 96%, 97%, 98%, or 99% identical thereto (e.g., antibody EOS006180). In a specific embodiment, an antibody that specifically binds to TREM2 (e.g., human TREM2) comprises a VH domain comprising the amino acid sequence set forth in SEQ ID NO: 103 or an amino acid sequence at least 80%, 85%, 90%, 95%, 96%, 97%, 98%, or 99% identical thereto, and a VL domain comprising the amino acid sequence set forth in SEQ ID NO: 115 or an amino acid sequence at least 80%, 85%, 90%, 95%, 96%, 97%, 98%, or 99% identical thereto (e.g., antibody EOS006175). In a specific embodiment, an antibody that specifically binds to TREM2 (e.g., human TREM2) comprises a VH domain comprising the amino acid sequence set forth in SEQ ID NO: 104 or an amino acid sequence at least 80%, 85%, 90%, 95%, 96%, 97%, 98%, or 99% identical thereto, and a VL domain comprising the amino acid sequence set forth in SEQ ID NO: 118 or an amino acid sequence at least 80%, 85%, 90%, 95%, 96%, 97%, 98%, or 99% identical thereto (e.g., antibody EOS006179). In a specific embodiment, an antibody that specifically binds to TREM2 (e.g., human TREM2) comprises a VH domain comprising the amino acid sequence set forth in SEQ ID NO: 105 or an amino acid sequence at least 80%, 85%, 90%, 95%, 96%, 97%, 98%, or 99% identical thereto, and a VL domain comprising the amino acid sequence set forth in SEQ ID NO: 124 or an amino acid sequence at least 80%, 85%, 90%, 95%, 96%, 97%, 98%, or 99% identical thereto (e.g., antibody EOS006173). In a specific embodiment, an antibody that specifically binds to TREM2 (e.g., human TREM2) comprises a VH domain comprising the amino acid sequence set forth in SEQ ID NO: 106 or an amino acid sequence at least 80%, 85%, 90%, 95%, 96%, 97%, 98%, or 99% identical thereto, and a VL domain comprising the amino acid sequence set forth in SEQ ID NO: 125 or an amino acid sequence at least 80%, 85%, 90%, 95%, 96%, 97%, 98%, or 99% identical thereto (e.g., antibody EOS006171). In a specific embodiment, an antibody that specifically binds to TREM2 (e.g., human TREM2) comprises a VH domain comprising the amino acid sequence set forth in SEQ ID NO: 107 or an amino acid sequence at least 80%, 85%, 90%, 95%, 96%, 97%, 98%, or 99% identical thereto, and a VL domain comprising the amino acid sequence set forth in SEQ ID NO: 110 or an amino acid sequence at least 80%, 85%, 90%, 95%, 96%, 97%, 98%, or 99% identical thereto (e.g., antibody EOS004281 or EOS004282). In a specific embodiment, an antibody that specifically binds to TREM2 (e.g., human TREM2) comprises a VH domain comprising the amino acid sequence set forth in SEQ ID NO: 108 or an amino acid sequence at least 80%, 85%, 90%, 95%, 96%, 97%, 98%, or 99% identical thereto, and a VL domain comprising the amino acid sequence set forth in SEQ ID NO: 111 or an amino acid sequence at least 80%, 85%, 90%, 95%, 96%, 97%, 98%, or 99% identical thereto (e.g., antibody EOS004283 or EOS006233). In a specific embodiment, an antibody that specifically binds to TREM2 (e.g., human TREM2) comprises a VH domain comprising the amino acid sequence set forth in SEQ ID NO: 109 or an amino acid sequence at least 80%, 85%, 90%, 95%, 96%, 97%, 98%, or 99% identical thereto, and a VL domain comprising the amino acid sequence set forth in SEQ ID NO: 121 or an amino acid sequence at least 80%, 85%, 90%, 95%, 96%, 97%, 98%, or 99% identical thereto (e.g., antibody EOS004284 or EOS006215).

In certain embodiments, an antibody that specifically binds to TREM2 (e.g., human TREM2) comprises a VH domain and a VL domain, wherein the VH domain and the VL domain consist of the amino acid sequence of a VH domain and a VL domain of an antibody listed in Table 3 or an amino acid sequence at least 80%, 85%, 90%, 95%, 96%, 97%, 98%, or 99% identical thereto (e.g., the VH domain and VL domain in one row of Table 3). In a specific embodiment, an antibody that specifically binds to TREM2 (e.g., human TREM2) comprises a VH domain consisting of the amino acid sequence set forth in SEQ ID NO: 87 or an amino acid sequence at least 80%, 85%, 90%, 95%, 96%, 97%, 98%, or 99% identical thereto, and a VL domain consisting of the amino acid sequence set forth in SEQ ID NO: 110 or an amino acid sequence at least 80%, 85%, 90%, 95%, 96%, 97%, 98%, or 99% identical thereto (e.g., antibody EOS006165). In a specific embodiment, an antibody that specifically binds to TREM2 (e.g., human TREM2) comprises a VH domain consisting of the amino acid sequence set forth in SEQ ID NO: 88 or an amino acid sequence at least 80%, 85%, 90%, 95%, 96%, 97%, 98%, or 99% identical thereto, and a VL domain consisting of the amino acid sequence set forth in SEQ ID NO: 111 or an amino acid sequence at least 80%, 85%, 90%, 95%, 96%, 97%, 98%, or 99% identical thereto (e.g., antibody EOS006163). In a specific embodiment, an antibody that specifically binds to TREM2 (e.g., human TREM2) comprises a VH domain consisting of the amino acid sequence set forth in SEQ ID NO: 89 or an amino acid sequence at least 80%, 85%, 90%, 95%, 96%, 97%, 98%, or 99% identical thereto, and a VL domain consisting of the amino acid sequence set forth in SEQ ID NO: 112 or an amino acid sequence at least 80%, 85%, 90%, 95%, 96%, 97%, 98%, or 99% identical thereto (e.g., antibody EOS006167). In a specific embodiment, an antibody that specifically binds to TREM2 (e.g., human TREM2) comprises a VH domain consisting of the amino acid sequence set forth in SEQ ID NO: 90 or an amino acid sequence at least 80%, 85%, 90%, 95%, 96%, 97%, 98%, or 99% identical thereto, and a VL domain consisting of the amino acid sequence set forth in SEQ ID NO: 113 or an amino acid sequence at least 80%, 85%, 90%, 95%, 96%, 97%, 98%, or 99% identical thereto (e.g., antibody EOS006168). In a specific embodiment, an antibody that specifically binds to TREM2 (e.g., human TREM2) comprises a VH domain consisting of the amino acid sequence set forth in SEQ ID NO: 91 or an amino acid sequence at least 80%, 85%, 90%, 95%, 96%, 97%, 98%, or 99% identical thereto, and a VL domain consisting of the amino acid sequence set forth in SEQ ID NO: 114 or an amino acid sequence at least 80%, 85%, 90%, 95%, 96%, 97%, 98%, or 99% identical thereto (e.g., antibody EOS006170). In a specific embodiment, an antibody that specifically binds to TREM2 (e.g., human TREM2) comprises a VH domain consisting of the amino acid sequence set forth in SEQ ID NO: 92 or an amino acid sequence at least 80%, 85%, 90%, 95%, 96%, 97%, 98%, or 99% identical thereto, and a VL domain consisting of the amino acid sequence set forth in SEQ ID NO: 115 or an amino acid sequence at least 80%, 85%, 90%, 95%, 96%, 97%, 98%, or 99% identical thereto (e.g., antibody EOS006177). In a specific embodiment, an antibody that specifically binds to TREM2 (e.g., human TREM2) comprises a VH domain consisting of the amino acid sequence set forth in SEQ ID NO: 93 or an amino acid sequence at least 80%, 85%, 90%, 95%, 96%, 97%, 98%, or 99% identical thereto, and a VL domain consisting of the amino acid sequence set forth in SEQ ID NO: 116 or an amino acid sequence at least 80%, 85%, 90%, 95%, 96%, 97%, 98%, or 99% identical thereto (e.g., antibody EOS006169). In a specific embodiment, an antibody that specifically binds to TREM2 (e.g., human TREM2) comprises a VH domain consisting of the amino acid sequence set forth in SEQ ID NO: 94 or an amino acid sequence at least 80%, 85%, 90%, 95%, 96%, 97%, 98%, or 99% identical thereto, and a VL domain consisting of the amino acid sequence set forth in SEQ ID NO: 117 or an amino acid sequence at least 80%, 85%, 90%, 95%, 96%, 97%, 98%, or 99% identical thereto (e.g., antibody EOS006178). In a specific embodiment, an antibody that specifically binds to TREM2 (e.g., human TREM2) comprises a VH domain consisting of the amino acid sequence set forth in SEQ ID NO: 95 or an amino acid sequence at least 80%, 85%, 90%, 95%, 96%, 97%, 98%, or 99% identical thereto, and a VL domain consisting of the amino acid sequence set forth in SEQ ID NO: 118 or an amino acid sequence at least 80%, 85%, 90%, 95%, 96%, 97%, 98%, or 99% identical thereto (e.g., antibody EOS006176). In a specific embodiment, an antibody that specifically binds to TREM2 (e.g., human TREM2) comprises a VH domain consisting of the amino acid sequence set forth in SEQ ID NO: 96 or an amino acid sequence at least 80%, 85%, 90%, 95%, 96%, 97%, 98%, or 99% identical thereto, and a VL domain consisting of the amino acid sequence set forth in SEQ ID NO: 119 or an amino acid sequence at least 80%, 85%, 90%, 95%, 96%, 97%, 98%, or 99% identical thereto (e.g., antibody EOS006166). In a specific embodiment, an antibody that specifically binds to TREM2 (e.g., human TREM2) comprises a VH domain consisting of the amino acid sequence set forth in SEQ ID NO: 97 or an amino acid sequence at least 80%, 85%, 90%, 95%, 96%, 97%, 98%, or 99% identical thereto, and a VL domain consisting of the amino acid sequence set forth in SEQ ID NO: 120 or an amino acid sequence at least 80%, 85%, 90%, 95%, 96%, 97%, 98%, or 99% identical thereto (e.g., antibody EOS006174). In a specific embodiment, an antibody that specifically binds to TREM2 (e.g., human TREM2) comprises a VH domain consisting of the amino acid sequence set forth in SEQ ID NO: 98 or an amino acid sequence at least 80%, 85%, 90%, 95%, 96%, 97%, 98%, or 99% identical thereto, and a VL domain consisting of the amino acid sequence set forth in SEQ ID NO: 121 or an amino acid sequence at least 80%, 85%, 90%, 95%, 96%, 97%, 98%, or 99% identical thereto (e.g., antibody EOS006164). In a specific embodiment, an antibody that specifically binds to TREM2 (e.g., human TREM2) comprises a VH domain consisting of the amino acid sequence set forth in SEQ ID NO: 99 or an amino acid sequence at least 80%, 85%, 90%, 95%, 96%, 97%, 98%, or 99% identical thereto, and a VL domain consisting of the amino acid sequence set forth in SEQ ID NO: 119 or an amino acid sequence at least 80%, 85%, 90%, 95%, 96%, 97%, 98%, or 99% identical thereto (e.g., antibody EOS006181). In a specific embodiment, an antibody that specifically binds to TREM2 (e.g., human TREM2) comprises a VH domain consisting of the amino acid sequence set forth in SEQ ID NO: 100 or an amino acid sequence at least 80%, 85%, 90%, 95%, 96%, 97%, 98%, or 99% identical thereto, and a VL domain consisting of the amino acid sequence set forth in SEQ ID NO: 122 or an amino acid sequence at least 80%, 85%, 90%, 95%, 96%, 97%, 98%, or 99% identical thereto (e.g., antibody EOS006172). In a specific embodiment, an antibody that specifically binds to TREM2 (e.g., human TREM2) comprises a VH domain consisting of the amino acid sequence set forth in SEQ ID NO: 101 or an amino acid sequence at least 80%, 85%, 90%, 95%, 96%, 97%, 98%, or 99% identical thereto, and a VL domain consisting of the amino acid sequence set forth in SEQ ID NO: 110 or an amino acid sequence at least 80%, 85%, 90%, 95%, 96%, 97%, 98%, or 99% identical thereto (e.g., antibody EOS006162). In a specific embodiment, an antibody that specifically binds to TREM2 (e.g., human TREM2) comprises a VH domain consisting of the amino acid sequence set forth in SEQ ID NO: 102 or an amino acid sequence at least 80%, 85%, 90%, 95%, 96%, 97%, 98%, or 99% identical thereto, and a VL domain consisting of the amino acid sequence set forth in SEQ ID NO: 123 or an amino acid sequence at least 80%, 85%, 90%, 95%, 96%, 97%, 98%, or 99% identical thereto (e.g., antibody EOS006180). In a specific embodiment, an antibody that specifically binds to TREM2 (e.g., human TREM2) comprises a VH domain consisting of the amino acid sequence set forth in SEQ ID NO: 103 or an amino acid sequence at least 80%, 85%, 90%, 95%, 96%, 97%, 98%, or 99% identical thereto, and a VL domain consisting of the amino acid sequence set forth in SEQ ID NO: 115 or an amino acid sequence at least 80%, 85%, 90%, 95%, 96%, 97%, 98%, or 99% identical thereto (e.g., antibody EOS006175). In a specific embodiment, an antibody that specifically binds to TREM2 (e.g., human TREM2) comprises a VH domain consisting of the amino acid sequence set forth in SEQ ID NO: 104 or an amino acid sequence at least 80%, 85%, 90%, 95%, 96%, 97%, 98%, or 99% identical thereto, and a VL domain consisting of the amino acid sequence set forth in SEQ ID NO: 118 or an amino acid sequence at least 80%, 85%, 90%, 95%, 96%, 97%, 98%, or 99% identical thereto (e.g., antibody EOS006179). In a specific embodiment, an antibody that specifically binds to TREM2 (e.g., human TREM2) comprises a VH domain consisting of the amino acid sequence set forth in SEQ ID NO: 105 or an amino acid sequence at least 80%, 85%, 90%, 95%, 96%, 97%, 98%, or 99% identical thereto, and a VL domain consisting of the amino acid sequence set forth in SEQ ID NO: 124 or an amino acid sequence at least 80%, 85%, 90%, 95%, 96%, 97%, 98%, or 99% identical thereto (e.g., antibody EOS006173). In a specific embodiment, an antibody that specifically binds to TREM2 (e.g., human TREM2) comprises a VH domain consisting of the amino acid sequence set forth in SEQ ID NO: 106 or an amino acid sequence at least 80%, 85%, 90%, 95%, 96%, 97%, 98%, or 99% identical thereto, and a VL domain consisting of the amino acid sequence set forth in SEQ ID NO: 125 or an amino acid sequence at least 80%, 85%, 90%, 95%, 96%, 97%, 98%, or 99% identical thereto (e.g., antibody EOS006171). In a specific embodiment, an antibody that specifically binds to TREM2 (e.g., human TREM2) comprises a VH domain consisting of the amino acid sequence set forth in SEQ ID NO: 107 or an amino acid sequence at least 80%, 85%, 90%, 95%, 96%, 97%, 98%, or 99% identical thereto, and a VL domain consisting of the amino acid sequence set forth in SEQ ID NO: 110 or an amino acid sequence at least 80%, 85%, 90%, 95%, 96%, 97%, 98%, or 99% identical thereto (e.g., antibody EOS004281 or EOS004282). In a specific embodiment, an antibody that specifically binds to TREM2 (e.g., human TREM2) comprises a VH domain consisting of the amino acid sequence set forth in SEQ ID NO: 108 or an amino acid sequence at least 80%, 85%, 90%, 95%, 96%, 97%, 98%, or 99% identical thereto, and a VL domain consisting of the amino acid sequence set forth in SEQ ID NO: 111 or an amino acid sequence at least 80%, 85%, 90%, 95%, 96%, 97%, 98%, or 99% identical thereto (e.g., antibody EOS004283 or EOS006233). In a specific embodiment, an antibody that specifically binds to TREM2 (e.g., human TREM2) comprises a VH domain consisting of the amino acid sequence set forth in SEQ ID NO: 109 or an amino acid sequence at least 80%, 85%, 90%, 95%, 96%, 97%, 98%, or 99% identical thereto, and a VL domain consisting of the amino acid sequence set forth in SEQ ID NO: 121 or an amino acid sequence at least 80%, 85%, 90%, 95%, 96%, 97%, 98%, or 99% identical thereto (e.g., antibody EOS004284 or EOS006215).

In certain aspects, an antibody described herein may be described by its VL domain alone, or its VH domain alone, or by its 3 VL CDRs alone, or its 3 VH CDRs alone. See, for example, Rader C et al., (1998) PNAS 95:8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also, Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also, Kim S J & Hong H J, (2007) J Microbiol 45:572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

The individual CDRs of an antibody disclosed herein can be determined according to any CDR numbering scheme known in the art.

In certain embodiments, one or more of the CDRs of an antibody disclosed herein can be determined according to Kabat et al., J. Biol. Chem. 252, 6609-6616 (1977) and Kabat et al., Sequences of protein of immunological interest (1991), each of which is herein incorporated by reference in its entirety.

In some embodiments, an antibody provided herein comprises the CDRH1, CDRH2, and/or CDRH3 of a VH amino acid sequence set forth in any of SEQ ID NOs: 87-109 as determined by the Kabat numbering scheme. In some embodiments, an antibody provided herein comprises the CDRL1, CDRL2, and/or CDRL3 of a VL amino acid sequence set forth in any of SEQ ID NOs: 110-125 as determined by the Kabat numbering scheme.

In certain embodiments, one or more of the CDRs of an antibody disclosed herein can be determined according to the Chothia numbering scheme, which refers to the location of immunoglobulin structural loops (see, e.g., Chothia C & Lesk A M, (1987), J Mol Biol 196:901-917; Al-Lazikani B et al., (1997) J Mol Biol 273:927-948; Chothia C et al., (1992) J Mol Biol 227:799-817; Tramontano A et al., (1990)

J Mol Biol 215(1): 175-82; and U.S. Pat. No. 7,709,226, all of which are herein incorporated by reference in their entireties).

In some embodiments, an antibody provided herein comprises the CDRH1, CDRH2, and/or CDRH3 of a VH amino acid sequence set forth in any of SEQ ID NOs: 87-109 as determined by the Chothia numbering system. In some embodiments, an antibody provided herein comprises the CDRL1, CDRL2, and/or CDRL3 of a VL amino acid sequence set forth in any of SEQ ID NOs: 110-125 as determined by the Chothia numbering system.

In certain embodiments, one or more of the CDRs of an antibody disclosed herein can be determined according to MacCallum R M et al., (1996) J Mol Biol 262:732-745, herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), herein incorporated by reference in its entirety.

In some embodiments, an antibody provided herein comprises the CDRH1, CDRH2, and/or CDRH3 of a VH amino acid sequence set forth in any of SEQ ID NOs: 87-109 as determined by the MacCallum numbering system. In some embodiments, an antibody provided herein comprises the CDRL1, CDRL2, and/or CDRL3 of a VL amino acid sequence set forth in any of SEQ ID NOs: 110-125 as determined by the MacCallum numbering system.

In certain embodiments, the CDRs of an antibody disclosed herein can be determined according to the IMGT numbering system as described in: Lefranc M-P, (1999) The Immunologist 7:132-136; Lefranc M-P et al., (1999) Nucleic Acids Res 27:209-212, and Lefranc M-P et al., (2009) Nucleic Acids Res 37: D1006-D1012, each of which is herein incorporated by reference in its entirety.

In some embodiments, an antibody provided herein comprises the CDRH1, CDRH2, and/or CDRH3 of a VH amino acid sequence set forth in any of SEQ ID NOs: 87-109 as determined by the IMGT numbering system. In some embodiments, an antibody provided herein comprises the CDRL1, CDRL2, and/or CDRL3 of a VL amino acid sequence set forth in any of SEQ ID NOs: 110-125 as determined by the IMGT numbering system.

In certain embodiments, the CDRs of an antibody disclosed herein can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety.

In some embodiments, an antibody provided herein comprises the CDRH1, CDRH2, and/or CDRH3 of a VH amino acid sequence set forth in any of SEQ ID NOs: 87-109 as determined by the AbM numbering scheme. In some embodiments, an antibody provided herein comprises the CDRL1, CDRL2, and/or CDRL3 of a VL amino acid sequence set forth in any of SEQ ID NOs: 110-125 as determined by the AbM numbering scheme.

In certain embodiments, the CDRs of an antibody disclosed herein can be determined according to the AHo numbering system, as described in Honegger and Plückthun, A., J. Mol. Biol. 309:657-670 (2001), herein incorporated by reference in its entirety.

In some embodiments, an antibody provided herein comprises the CDRH1, CDRH2, and/or CDRH3 of a VH amino acid sequence set forth in any of SEQ ID NOs: 87-109 as determined by the AHo numbering system. In some embodiments, an antibody provided herein comprises the CDRL1, CDRL2, and/or CDRL3 of a VL amino acid sequence set forth in any of SEQ ID NOs: 110-125 as determined by the AHo numbering system.

In certain embodiments, the individual CDRs of an antibody disclosed herein are each independently determined according to one of the Kabat, Chothia, MacCallum, IMGT, AHo, or AbM numbering schemes, or by structural analysis of the antibody, wherein the structural analysis identifies residues in the variable region(s) predicted to make contact with an epitope region of TREM2.

In certain embodiments, the instant disclosure provides an antibody that specifically binds TREM2 (e.g., human TREM2) comprising a VH comprising the CDRH1, CDRH2, and CDRH3 amino acid sequences of a VH amino acid sequence set forth in any one of SEQ ID NOs: 87-109, and a VL comprising the CDRL1, CDRL2, and CDRL3 amino acid sequences of a VL amino acid sequence set forth in any one of SEQ ID NOs: 110-125, wherein each CDR is independently determined according to one of the Kabat, Chothia, MacCallum, IMGT, AHo, or AbM numbering schemes, or by structural analysis of the antibody, wherein the structural analysis identifies residues in the variable region(s) predicted to make contact with an epitope region of TREM2 (e.g., human TREM2).

In certain embodiments, the instant disclosure provides an antibody that specifically binds TREM2 (e.g., human TREM2) comprising a VH comprising the CDRH1, CDRH2, and CDRH3 amino acid sequences of a VH amino acid sequence set forth in any one of SEQ ID NOs: 87-109, and a VL comprising the CDRL1, CDRL2, and CDRL3 amino acid sequences of a VL amino acid sequence set forth in any one of SEQ ID NOs: 110-125, wherein the VH amino acid sequence and the VL amino acid sequence are from the same antibody (i.e., as shown in Table 3), and wherein each CDR is independently determined according to one of the Kabat, Chothia, MacCallum, IMGT, AHo, or AbM numbering schemes, or by structural analysis of the antibody, wherein the structural analysis identifies residues in the variable region(s) predicted to make contact with an epitope region of TREM2 (e.g., human TREM2).

In some embodiments, the instant disclosure provides an antibody that specifically binds to TREM2 (e.g., human TREM2), wherein the antibody comprises the CDRH1, CDRH2, CDRH3, CDRL1, CDRL2, and CDRL3 amino acid sequences of the VH and VL amino acid sequences set forth in SEQ ID NOs: 87 and 110; SEQ ID NOs: 88 and 111; SEQ ID NOs: 89 and 112; SEQ ID NOs: 90 and 113; SEQ ID NOs: 91 and 114; SEQ ID NOs: 92 and 115; SEQ ID NOs: 93 and 116; SEQ ID NOs: 94 and 117; SEQ ID NOs: 95 and 118; SEQ ID NOs: 96 and 119; SEQ ID NOs: 97 and 120; SEQ ID NOs: 98 and 121; SEQ ID NOs: 99 and 119; SEQ ID NOs: 100 and 122; SEQ ID NOs: 101 and 110; SEQ ID NOs: 102 and 123; SEQ ID NOs: 103 and 115; SEQ ID NOs: 104 and 118; SEQ ID NOs: 105 and 124; SEQ ID NOs: 106 and 125; SEQ ID NOS: 107 and 110; SEQ ID NOs: 108 and 111; or SEQ ID NOs: 109 and 121, respectively.

In a specific embodiment, the position of one or more CDRs along the VH (e.g., CDR1, CDR2, or CDR3) and/or VL (e.g., CDR1, CDR2, or CDR3) region of an antibody described herein may vary by one, two, three, four, five, or six amino acid positions so long as specific binding to TREM2 (e.g., human TREM2) is maintained (e.g., substantially maintained, for example, at least 50%, at least 60%, at least 70%, at least 80%, at least 90%, at least 95%). For example, in one embodiment, the position defining a CDR of any of antibody described herein (e.g., EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215) may vary by shifting the N-terminal and/or C-terminal boundary of the CDR by one, two, three, four, five, or six amino acids, relative to the CDR position of any one of the antibodies described herein (e.g., EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215, identified in, e.g., Table 1 or 2), so long as specific binding to TREM2 (e.g., human TREM2) is maintained (e.g., substantially maintained, for example, at least 50%, at least 60%, at least 70%, at least 80%, at least 90%, at least 95%). In another embodiment, the length of one or more CDRs along the VH (e.g., CDR1, CDR2, or CDR3) and/or VL (e.g., CDR1, CDR2, or CDR3) region of an antibody described herein may vary (e.g., be shorter or longer) by one, two, three, four, five, or more amino acids, so long as specific binding to TREM2 (e.g., human TREM2) is maintained (e.g., substantially maintained, for example, at least 50%, at least 60%, at least 70%, at least 80%, at least 90%, at least 95%).

In one embodiment, a CDRH1, CDRH2, CDRH3, CDRL1, CDRL2, and/or CDRL3 described herein may be one, two, three, four, five, or more amino acids shorter than one or more of the CDRs described herein (e.g., SEQ ID NOs: 19-86) so long as specific binding to TREM2 (e.g., human TREM2) is maintained (e.g., substantially maintained, for example, at least 50%, at least 60%, at least 70%, at least 80%, at least 90%, at least 95%). In another embodiment, a CDRH1, CDRH2, CDRH3, CDRL1, CDRL2, and/or CDRL3 described herein may be one, two, three, four, five, or more amino acids longer than one or more of the CDRs described herein (e.g., SEQ ID NOs: 19-86) so long as specific binding to TREM2 (e.g., human TREM2) is maintained (e.g., substantially maintained, for example, at least 50%, at least 60%, at least 70%, at least 80%, at least 90%, at least 95%). In another embodiment, the amino terminus of a CDRH1, CDRH2, CDRH3, CDRL1, CDRL2, and/or CDRL3 described herein may be extended by one, two, three, four, five, or more amino acids compared to one or more of the CDRs described herein (e.g., SEQ ID NOs: 19-86) so long as specific binding to TREM2 (e.g., human TREM2) is maintained (e.g., substantially maintained, for example, at least 50%, at least 60%, at least 70%, at least 80%, at least 90%, at least 95%). In another embodiment, the carboxy terminus of a CDRH1, CDRH2, CDRH3, CDRL1, CDRL2, and/or CDRL3 described herein may be extended by one, two, three, four, five, or more amino acids compared to one or more of the CDRs described herein (e.g., SEQ ID NOs: 19-86) so long as specific binding to TREM2 (e.g., human TREM2) is maintained (e.g., substantially maintained, for example, at least 50%, at least 60%, at least 70%, at least 80%, at least 90%, at least 95%). In another embodiment, the amino terminus of a CDRH1, CDRH2, CDRH3, CDRL1, CDRL2, and/or CDRL3 described herein may be shortened by one, two, three, four, five, or more amino acids compared to one or more of the CDRs described herein (e.g., SEQ ID NOs: 19-86) so long as specific binding to TREM2 (e.g., human TREM2) is maintained (e.g., substantially maintained, for example, at least 50%, at least 60%, at least 70%, at least 80%, at least 90%, at least 95%). In one embodiment, the carboxy terminus of a CDRH1, CDRH2, CDRH3, CDRL1, CDRL2, and/or CDRL3 described herein may be shortened by one, two, three, four, five, or more amino acids compared to one or more of the CDRs described herein (e.g., SEQ ID NOs: 19-86) so long as specific binding to TREM2 (e.g., human TREM2) is maintained (e.g., substantially maintained, for example, at least 50%, at least 60%, at least 70%, at least 80%, at least 90%, at least 95%). Any method known in the art can be used to ascertain whether specific binding to TREM2 (e.g., human TREM2) is maintained, for example, the binding assays and conditions described in the "Examples" section provided herein.

In specific aspects, provided herein is an antibody comprising an antibody light chain and heavy chain, e.g., a separate light chain and heavy chain. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which specifically binds to a TREM2 polypeptide (e.g., human TREM2) comprises a light chain wherein the amino acid sequence of the VL domain comprises any amino acid sequence described herein (e.g., SEQ ID NOs: 110-125), and wherein the constant region of the light chain comprises the amino acid sequence of a human kappa light chain constant region. In another particular embodiment, an antibody described herein, which specifically binds a TREM2 polypeptide (e.g., human TREM2) comprises a light chain wherein the amino acid sequence of the VL domain can comprise any amino acid sequence described herein (e.g., SEQ ID NOs: 110-125), and wherein the constant region of the light chain comprises the amino acid sequence of a human lambda light chain constant region. Non-limiting examples of human constant region sequences have been described in the art, see, e.g., U.S. Pat. No. 5,693,780 and Kabat E A et al., (1991) supra.

In certain embodiments, the instant disclosure provides an antibody that specifically binds to TREM2 (e.g., human TREM2), the antibody comprising a light chain constant region comprising an amino acid sequence shown in Table 6. In some embodiments, the light chain constant region comprises the amino acid sequence of SEQ ID NO: 157 or 158. In some embodiments, the light chain constant region consists of the amino acid sequence of SEQ ID NO: 157 or 158.

TABLE 6

Light chain constant region amino acid sequences of exemplary anti-TREM2 antibodies

| Description | Amino Acid Sequence | SEQ ID |
|---|---|---|
| Kappa light chain constant region | RTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTK SFNRGEC | 157 |
| Lambda light chain constant region | GQPKANPTVTLFPPSSEELQANKATLVCLISDFYPGAVTVAWKADGSPVK AGVETTKPSKQSNNKYAASSYLSLTPEQWKSHRSYSCQVTHEGSTVEKTV APTECS | 158 |

In a particular embodiment, an antibody described herein, which specifically binds to TREM2 (e.g., human TREM2) comprises a light chain comprising or consisting of an amino acid sequence selected from the group consisting of SEQ ID NOs: 161-163.

TABLE 7

Light chain amino acid sequences of exemplary anti-TREM2 antibodies

| Antibody | Amino Acid Sequence | SEQ ID |
|---|---|---|
| EOS004281 | EIVLTQSPATLSLSPGERATLSCRASQSVSSYLAWFQQKPGQAPRLLIYD ASNRATGIPARFSGSGSGTDFTLTISSLEPEDFAVYYCQQDYHWPITFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 161 |
| EOS004282 | EIVLTQSPATLSLSPGERATLSCRASQSVSSYLAWFQQKPGQAPRLLIYD ASNRATGIPARFSGSGSGTDFTLTISSLEPEDFAVYYCQQDYHWPITFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 161 |
| EOS004283 | EIVLTQSPATLSLSPGERATLSCRASQSVSSYLAWFQQKPGQAPRLLIYD ASNRATGIPARFSGSGSGTDFTLTISSLEPEDFAVYYCQQDYEWPITFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 162 |
| EOS006233 | EIVLTQSPATLSLSPGERATLSCRASQSVSSYLAWFQQKPGQAPRLLIYD ASNRATGIPARFSGSGSGTDFTLTISSLEPEDFAVYYCQQDYEWPITFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 162 |
| EOS004284 | DIQMTQSPSSLSASVGDRVTITCQASQDITNYLNWYQQKPGKAPKLLIYD ASNLETGVPSRFSGSGSGTDFTFTISSLQPEDIATYYCQEYDSYITFGGG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSFNRGEC | 163 |
| EOS006215 | DIQMTQSPSSLSASVGDRVTITCQASQDITNYLNWYQQKPGKAPKLLIYD ASNLETGVPSRFSGSGSGTDFTFTISSLQPEDIATYYCQEYDSYITFGGG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSFNRGEC | 163 |

With respect to the heavy chain, in a specific embodiment, the heavy chain of an antibody described herein can be an alpha (α), delta (δ), epsilon (ε), gamma (0Y), or mu (μ) heavy chain. In another specific embodiment, the heavy chain of an antibody described can comprise a human alpha (α), delta (δ), epsilon (ε), gamma (γ), or mu (μ) heavy chain. In a particular embodiment, an antibody described herein, which specifically binds to TREM2 (e.g., human TREM2), comprises a heavy chain wherein the amino acid sequence of the VH domain can comprise any amino acid sequence described herein (e.g., any of SEQ ID NOs: 87-109), and wherein the constant region of the heavy chain comprises the amino acid sequence of a human gamma (γ) heavy chain constant region. In a specific embodiment, an antibody described herein, which specifically binds to TREM2 (e.g., human TREM2), comprises a heavy chain wherein the amino acid sequence of the VH domain comprises an amino acid sequence selected from the group consisting of SEQ ID NOs: 87-109, and wherein the constant region of the heavy chain comprises the amino acid of a human heavy chain described herein or known in the art. Non-limiting examples of human constant region sequences have been described in the art, see, e.g., U.S. Pat. No. 5,693,780 and Kabat E A et al., (1991) supra.

In certain embodiments, the instant disclosure provides an antibody that specifically binds to TREM2 (e.g., human TREM2), the antibody comprising a heavy chain constant region that is a variant of a wild-type heavy chain constant region, wherein the variant heavy chain constant region binds to an FcγR with lower affinity than the wild-type heavy chain constant region binds to the FcγR.

In certain embodiments, the instant disclosure provides an antibody that specifically binds to TREM2 (e.g., human TREM2), the antibody comprising a heavy chain constant region comprising an amino acid sequence shown in Table 8. In some embodiments, the heavy chain constant region comprises the amino acid sequence of SEQ ID NO: 159 or 160. In some embodiments, the heavy chain constant region consists of the amino acid sequence of SEQ ID NO: 159 or 160.

TABLE 8

Heavy chain constant region amino acid sequences of exemplary anti-TREM2 antibodies

| Description | Amino Acid Sequence | SEQ ID |
|---|---|---|
| WT IgG1 heavy chain constant region | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 159 |
| N297A IgG1 heavy chain constant region | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYASTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 160 |

In a particular embodiment, an antibody described herein, which specifically binds to TREM2 (e.g., human TREM2), comprises a heavy chain comprising or consisting of an amino acid sequence selected from the group consisting of SEQ ID NOs: 164-169.

TABLE 9

Heavy chain amino acid sequences of exemplary anti-TREM2 antibodies

| Antibody | Amino Acid Sequence | SEQ ID |
|---|---|---|
| EOS004281 | QVQLVQSGAEVKKPGSSVKVSCKASGGTFSSYAISWVRQAPGQGLEWMGG IIPISGTANYAQKFQGRVTITADESTSTAYMELSSLRSEDTAVYYCARTQ EYTLFDSWGQGTLVTVSSASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK | 164 |
| EOS004282 | QVQLVQSGAEVKKPGSSVKVSCKASGGTFSSYAISWVRQAPGQGLEWMGG IIPISGTANYAQKFQGRVTITADESTSTAYMELSSLRSEDTAVYYCARTQ EYTLFDSWGQGTLVTVSSASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYAST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK | 165 |
| EOS004283 | QVQLVQSGAEVKKPGSSVKVSCKASGGTFAQYAISWVRQAPGQGLEWMGV IIPDSGTANYAQKFQGRVTITADESTSTAYMELSSLRSEDTAVYYCARTQ ENTIFDIWGQGTLVTVSSASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK | 166 |

TABLE 9-continued

Heavy chain amino acid sequences of exemplary anti-TREM2 antibodies

| Antibody | Amino Acid Sequence | SEQ ID |
|---|---|---|
| EOS006233 | QVQLVQSGAEVKKPGSSVKVSCKASGGTFAQYAISWVRQAPGQGLEWMGV<br>IIPDSGTANYAQKFQGRVTITADESTSTAYMELSSLRSEDTAVYYCARTQ<br>ENTIFDIWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYAST<br>YRVVSVLTVLHQDWLNGKEYKCKVSNKALPAPIEKTISKAKGQPREPQVY<br>TLPPSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPGK | 167 |
| EOS004284 | EVQLVESGGGLVQPGRSLRLSCTASGFTFDDYTMSWFRQAPGKGLEWVGF<br>IGSKAYSATTEYTASVKGRFTISRDGSKSIAYLQMNSLKTEDTAVYYCAR<br>GKRYSYTYWTPAFDVWGQGTLVTVSSASTKGPSVFPLAPSSKSTSGGTAA<br>LGCLVKDYFPEPVTVSWNSGALTSGVHTFPAVLQSSGLYSLSSVVTVPSS<br>SLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSL<br>SLSPGK | 168 |
| EOS006215 | EVQLVESGGGLVQPGRSLRLSCTASGFTFDDYTMSWFRQAPGKGLEWVGF<br>IGSKAYSATTEYTASVKGRFTISRDGSKSIAYLQMNSLKTEDTAVYYCAR<br>GKRYSYTYWTPAFDVWGQGTLVTVSSASTKGPSVFPLAPSSKSTSGGTAA<br>LGCLVKDYFPEPVTVSWNSGALTSGVHTFPAVLQSSGLYSLSSVVTVPSS<br>SLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKP<br>REEQYASTYRVVSVLTVLHQDWLNGKEYKCKVSNKALPAPIEKTISKAKG<br>QPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSL<br>SLSPGK | 169 |

In a specific embodiment, an antibody described herein, which specifically binds to TREM2 (e.g., human TREM2) comprises a VH domain and a VL domain comprising any amino acid sequences described herein, and wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In another specific embodiment, an antibody described herein, which specifically binds to TREM2 (e.g., human TREM2) comprises a VH domain and a VL domain comprising any amino acid sequences described herein, and wherein the constant regions comprise the amino acid sequences of the constant regions of an IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule. In a particular embodiment, the constant regions comprise the amino acid sequences of the constant regions of a human IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule.

In another specific embodiment, an antibody described herein, which specifically binds to TREM2 (e.g., human TREM2), comprises a VH domain and a VL domain comprising any amino acid sequences described herein, and wherein the constant regions comprise the amino acid sequences of the constant regions of a human IgG1 (e.g., allotypes G1m3, G1m17,1 or G1m17,1,2) or human IgG4. In a particular embodiment, an antibody described herein, which specifically binds to TREM2 (e.g., human TREM2) comprises a VH domain and a VL domain comprising any amino acid sequences described herein, and wherein the constant regions comprise the amino acid sequences of the constant region of a human IgG1. Non-limiting examples of human constant regions are described in the art, see, e.g., Kabat E A et al., (1991) supra.

In another embodiment, an antibody described herein, which specifically binds to TREM2 (e.g., human TREM2) comprises a light chain comprising or consisting of an amino acid sequence selected from the group consisting of SEQ ID NOs: 161-163 and a heavy chain comprising or consisting of an amino acid sequence selected from the group consisting of SEQ ID NOs: 164-169. In certain embodiments, the instant disclosure provides an antibody that specifically binds to TREM2 (e.g., human TREM2), wherein the antibody comprises a light chain comprising or consisting of the amino acid sequence set forth in SEQ ID NO: 161 and a heavy chain comprising or consisting of the amino acid sequence set forth in SEQ ID NO: 164. In certain embodiments, the instant disclosure provides an antibody that specifically binds to TREM2 (e.g., human TREM2), wherein the antibody comprises a light chain comprising or consisting of the amino acid sequence set forth in SEQ ID NO: 161 and a heavy chain comprising or consisting of the amino acid sequence set forth in SEQ ID NO: 165. In certain embodiments, the instant disclosure provides an antibody that specifically binds to TREM2 (e.g., human TREM2), wherein the antibody comprises a light chain comprising or consisting of the amino acid sequence set forth in SEQ ID NO: 162 and a heavy chain comprising or consisting of the amino acid sequence set forth in SEQ ID NO: 166. In certain embodiments, the instant disclosure provides an antibody that specifically binds to TREM2 (e.g., human TREM2), wherein the antibody comprises a light chain comprising or consisting of the amino acid sequence set forth in SEQ ID NO: 162 and a heavy chain comprising or consisting of the amino acid sequence set forth in SEQ ID NO: 167. In certain embodiments, the instant disclosure provides an antibody that specifically binds to TREM2 (e.g., human TREM2), wherein the antibody comprises a light chain comprising or consisting of the amino acid sequence set forth in SEQ ID NO: 163 and a heavy chain comprising or consisting of the amino acid sequence set forth in SEQ ID NO: 168. In certain embodiments, the instant disclosure provides an antibody that specifically binds to TREM2 (e.g., human TREM2), wherein the antibody comprises a light chain comprising or consisting of the amino acid sequence set forth in SEQ ID NO: 163 and a heavy chain comprising or consisting of the amino acid sequence set forth in SEQ ID NO: 169.

In certain embodiments, one, two, or more mutations (e.g., amino acid substitutions) are introduced into the Fc region of an antibody described herein (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain may be altered to, e.g., facilitate assembly of the light and heavy chains, or to alter (e.g., increase or decrease) the stability of the antibody.

In some embodiments, one, two, or more mutations (e.g., amino acid substitutions) are introduced into the Fc region of an antibody described herein (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor are known to one of skill in the art. Examples of mutations in the Fc receptor of an antibody that can be made to alter the affinity of the antibody for an Fc receptor are described in, see, e.g., Smith P et al., (2012) PNAS 109:6181-6186, U.S. Pat. No. 6,737,056, and International Publication Nos. WO 02/060919; WO 98/23289; and WO 97/34631, which are incorporated herein by reference.

In a specific embodiment, one, two, or more amino acid mutations (i.e., substitutions, insertions, or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo. In some embodiments, one, two, or more amino acid mutations (i.e., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two, or more amino acid mutations (i.e., substitutions, insertions, or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In a specific embodiment, the constant region of the IgG1 of an antibody described herein comprises a methionine (M) to tyrosine (Y) substitution in position 252, a serine(S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display four-fold increased half-life as compared to wild-type versions of the same antibody (see Dall'Acqua W F et al., (2006) J Biol Chem 281:23514-24). In certain embodiments, an antibody comprises an IgG constant domain comprising one, two, three, or more amino acid substitutions of amino acid residues at positions 251-257, 285-290, 308-314, 385-389, and 428-436, numbered according to the EU index as in Kabat.

In a further embodiment, one, two, or more amino acid substitutions are introduced into an IgG constant domain Fc region to alter the effector function(s) of the antibody. For example, one or more amino acids selected from amino acid residues 234, 235, 236, 237, 297, 318, 320, and 322, numbered according to the EU index as in Kabat, can be replaced with a different amino acid residue such that the antibody has an altered affinity for an effector ligand but retains the antigen-binding ability of the parent antibody. The effector ligand to which affinity is altered can be, for example, an Fc receptor or the Cl component of complement. This approach is described in further detail in U.S. Pat. Nos. 5,624,821 and 5,648,260. In some embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In certain embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276:6591-604). In various embodiments, one or more of the following mutations in the constant region of an antibody described herein may be made: an N297A substitution; an N297Q substitution; an L235A substitution and an L237A substitution; an L234A substitution and an L235A substitution; an E233P substitution; an L234V substitution; an L235A substitution; a C236 deletion; a P238A substitution; a D265A substitution; an A327Q substitution; or a P329A substitution, numbered according to the EU index as in Kabat.

In a specific embodiment, an antibody described herein comprises the constant domain of an IgG1 with an N297A or N297Q amino acid substitution.

In certain embodiments, one or more amino acids selected from amino acid residues 329, 331, and 322 in the constant region of an antibody described herein, numbered according to the EU index as in Kabat, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues within amino acid positions 231 to 238 in the N-terminal region of the CH2 domain of an antibody described herein are altered to thereby alter the ability of the antibody to fix complement. This approach is described further in International Publication No. WO 94/29351. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438, or 439, numbered according to the EU index as in Kabat. This approach is described further in International Publication No. WO 00/42072.

In certain embodiments, an antibody described herein comprises the constant region of an IgG4 antibody and the serine at amino acid residue 228 of the heavy chain, numbered according to the EU index as in Kabat, is substituted for proline.

Antibodies with reduced fucose content have been reported to have an increased affinity for Fc receptors, such as, e.g., FcγRIIIa. Accordingly, in certain embodiments, the antibodies described herein have reduced fucose content or no fucose content. Such antibodies can be produced using techniques known to one skilled in the art. For example, the antibodies can be expressed in cells deficient or lacking the ability of fucosylation. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content. Alternatively, antibodies with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies which are not fucosylated. See, e.g., Longmore G D & Schachter H (1982) Carbohydr Res 100:365-92 and Imai-Nishiya H et al., (2007) BMC Biotechnol. 7:84, for methods for producing antibodies with no fucose content or reduced fucose content.

In certain embodiments, antibodies described herein have an increased affinity for CD32B (also known as FcγRIIB or FCGR2B), e.g., as compared to an antibody with a wild-type Fc region, e.g., an IgG1 Fc. In certain embodiments, antibodies described herein have a selectively increased affinity for CD32B (FcγRIIB) over both CD32A (FcγRIIA) and CD16 (FcγRIIIA). Sequence alterations that result in increased affinity for CD32B are provided, for example, in Mimoto et al., Protein Engineering, Design & Selection 10:589-598 (2013), Chu et al., Molecular Immunology 45:3926-3933 (2008), and Strohl, Current Opinion in Biology 20:685-691 (2009), each of which is herein incorporated by reference in its entirety. In some embodiments, the antibody with an increased affinity for CD32B comprises a heavy chain constant region, e.g., an IgG1 constant region comprising a mutation selected from the group consisting of: G236D, P238D, S239D, S267E, L328F, L328E, an arginine inserted after position 236, and combinations thereof, numbered according to EU index (Kabat et al., Sequences of Proteins of Immunological Interest, U.S. Department of Health and Human Services, Bethesda (1991)). In some embodiments, the antibody with an increased affinity for CD32B comprises a heavy chain constant region, e.g., an IgG1 constant region comprising S267E and L328F substitutions. In some embodiments, the antibody with an increased affinity for CD32B comprises a heavy chain constant region, e.g., an IgG1 constant region comprising P238D and L328E substitutions. In some embodiments, the antibody with an increased affinity for CD32B comprises a heavy chain constant region, e.g., an IgG1 constant region comprising a P238D substitution and substitution selected from the group consisting of E233D, G237D, H268D, P271G, A330R, and combinations thereof. In some embodiments, the antibody with an increased affinity for CD32B comprises a heavy chain constant region, e.g., an IgG1 constant region comprising P238D, E233D, G237D, H268D, P271G, and A330R substitutions. In some embodiments, the antibody with an increased affinity for CD32B comprises a heavy chain constant region, e.g., an IgG1 constant region comprising G236D and S267E. In some embodiments, the antibody with an increased affinity for CD32B comprises a heavy chain constant region, e.g., an IgG1 constant region comprising S239D and S267E. In some embodiments, the antibody with an increased affinity for CD32B comprises a heavy chain constant region, e.g., an IgG1 constant region comprising S267E and L328F. In some embodiments, the antibody with an increased affinity for CD32B comprises a heavy chain constant region, e.g., an IgG1 constant region comprising an arginine inserted after position 236 and L328R.

In another particular embodiment, an antibody described herein, which specifically binds to TREM2 (e.g., human TREM2), comprises a light chain and a heavy chain, wherein (i) the light chain comprises a VL domain comprising a VL CDR1, VL CDR2, and VL CDR3 having the amino acid sequences of any one of EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215 (e.g., those listed in Table 2); (ii) the heavy chain comprises a VH domain comprising a VH CDR1, VH CDR2, and VH CDR3 having the amino acid sequences of any one of EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215 (e.g., those listed in Table 1); (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 (optionally comprising an N297A mutation) heavy chain.

In another aspect, provided herein are antibodies that bind the same or an overlapping epitope of TREM2 (e.g., an epitope of human TREM2) as an antibody described herein (e.g., antibody EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215). In some embodiments, the antibody binds to an epitope overlapping the epitope of an antibody comprising 6 CDRs defined by any one of the Kabat, Chothia, IMGT, or combined Kabat/Chothia methods of any one of the antibodies described in Tables 1-5. In certain embodiments, the epitope is a TREM2 epitope described herein. In certain embodiments, the epitope of an antibody can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50 (Pt 4): 339-350; McPherson A (1990) Eur J Biochem 189:1-23; Chayen N E (1997) Structure 5:1269-1274; McPherson A (1976) J Biol Chem 251: 6300-6303). Antibody: antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds. Wyckoff H W et al.; U.S. Patent Application No. 2004/0014194), and BUSTER (Bricogne G (1993) Acta Crystallogr D Biol Crystallogr 49 (Pt 1): 37-60; Bricogne G (1997) Meth Enzymol 276A: 361-423, ed. Carter C W; Roversi P et al., (2000) Acta Crystallogr D Biol Crystallogr 56 (Pt 10): 1316-1323). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques.

In addition, antibodies that recognize and bind to the same or overlapping epitopes of TREM2 (e.g., human TREM2) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as TREM2. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9:242-253); solid phase direct biotin-avidin EIA (see Kirkland T N et al., (1986) J Immunol 137:3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (see Cheung R C et al., (1990) Virology 176:546-52); and direct labeled MA (see Moldenhauer G et al., (1990) Scand J Immunol 32:77-82). Typically, such an assay involves the use of purified antigen (e.g., TREM2 such as human TREM2) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually, the test immunoglobulin is present in excess. Usually, when a competing antibody is present in excess, it will inhibit specific binding of a reference antibody to a common antigen by at least 50-55%, 55-60%, 60-65%, 65-70% 70-75%, or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130:2308-2315; Wagener C et al., (1984) J Immunol Methods 68:269-274; Kuroki M et al., (1990) Cancer Res 50:4872-4879; Kuroki M et al., (1992) Immunol Invest 21:523-538; Kuroki M et al., (1992) Hybridoma 11:391-407, and Antibodies: A Laboratory Manual, Harlow E & Lane D eds. supra, pp. 386-389.

In one embodiment, a competition assay is performed using surface plasmon resonance (BIAcore®), e.g., by an "in tandem approach" such as that described by Abdiche Y N et al., (2009) Analytical Biochem 386:172-180, whereby TREM2 antigen is immobilized on the chip surface, for example, a CMS sensor chip and the anti-TREM2 antibodies are then run over the chip. To determine if an antibody competes with an anti-TREM2 antibody described herein, the anti-TREM2 antibody is first run over the chip surface to achieve saturation and then the potential, competing antibody is added. Binding of the competing antibody can then be determined and quantified relative to a non-competing control.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an antibody described herein (e.g., antibody EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215), or a chimeric or Fab antibody thereof, or an antibody comprising VH CDRs and VL CDRs of an antibody described herein (e.g., EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215).

In another aspect, provided herein are antibodies that compete (e.g., in a dose-dependent manner) for binding to TREM2 (e.g., human TREM2) with an antibody described herein (e.g., EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215), as determined using assays known to one of skill in the art or described herein (e.g., ELISA competitive assays or surface plasmon resonance). In some embodiments, the antibody competes for binding to TREM2 (e.g., human TREM2) with an antibody comprising 6 CDRs defined by any one of the Kabat, Chothia, IMGT, or combined Kabat/Chothia methods of any one of the antibodies described in Tables 1-5.

In another aspect, provided herein are antibodies that competitively inhibit (e.g., in a dose dependent manner) an antibody described herein (e.g., EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215) from binding to TREM2 (e.g., human TREM2), as determined using assays known to one of skill in the art or described herein (e.g., ELISA competitive assays, or suspension array or surface plasmon resonance assay). In particular embodiments, such competitively blocking antibody activates, induces or enhances one or more TREM2 activities. In some embodiments, the antibody competitively inhibits an antibody comprising 6 CDRs defined by any one of the Kabat, Chothia, IMGT, or combined Kabat/Chothia methods of any one of the antibodies described in Tables 1-5. In specific aspects, provided herein is an antibody which competes (e.g., in a dose dependent manner) for specific binding to TREM2 (e.g., human TREM2), with an antibody comprising the amino acid sequences described herein (e.g., VL and/or VH amino acid sequences of antibody EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215), as determined using assays known to one of skill in the art or described herein (e.g., ELISA competitive assays, or suspension array or surface plasmon resonance assay).

In specific aspects, provided herein is an antibody which competes (e.g., in a dose dependent manner) for specific binding to TREM2 (e.g., human TREM2), with an antibody comprising a VH domain having an amino acid sequence selected from the group consisting of SEQ ID NOs: 87-109, and a VL domain having an amino acid sequence selected from the group consisting of SEQ ID NOs: 110-125. In specific aspects, provided herein is an antibody which competes (e.g., in a dose dependent manner) for specific binding to TREM2 (e.g., human TREM2), with an antibody comprising a VH domain having an amino acid sequence selected from the group consisting of SEQ ID NOs: 87-109, and a VL domain having an amino acid sequence selected from the group consisting of SEQ ID NOs: 110-125.

In specific aspects, provided herein is an antibody which competes (e.g., in a dose dependent manner) for specific binding to TREM2 (e.g., human TREM2), with an antibody comprising (i) a VH domain comprising a CDRH1, CDRH2, and CDRH3 having the amino acid sequences of the VH CDRs of an antibody listed in Table 1; and (ii) a VL domain comprising a CDRL1, CDRL2, and CDRL3 having the amino acid sequences of the VL CDRs of an antibody listed in Table 2.

In a particular embodiment, provided herein is an antibody that competes (e.g., in a dose-dependent manner), for specific binding to TREM2 (e.g., human TREM2), with an antibody comprising the VH and VL CDRs of EOS004281 or EOS004282 (SEQ ID NOs: 19, 32, 55, 60, 66, and 71).

In a particular embodiment, provided herein is an antibody that competes (e.g., in a dose-dependent manner), for specific binding to TREM2 (e.g., human TREM2), with an antibody comprising the VH and VL CDRs of EOS004283 or EOS006233 (SEQ ID NOs: 20, 33, 43, 60, 66, and 72).

In a particular embodiment, provided herein is an antibody that competes (e.g., in a dose-dependent manner), for specific binding to TREM2 (e.g., human TREM2), with an antibody comprising the VH and VL CDRs of EOS004284 or EOS006215 (SEQ ID NOs: 29, 40, 53, 65, 70, and 82).

In a specific embodiment, an antibody described herein is one that is competitively blocked (e.g., in a dose dependent manner) by an antibody comprising a VH domain having an amino acid sequence selected from the group consisting of SEQ ID NOs: 87-109 and a VL domain having an amino acid sequence selected from the group consisting of SEQ ID NOs: 110-125, for specific binding to TREM2 (e.g., human TREM2). In a specific embodiment, an antibody described herein is one that is competitively blocked (e.g., in a dose dependent manner) by an antibody comprising a VH domain having an amino acid sequence selected from the group consisting of SEQ ID NOs: 87-109 and a VL domain having an amino acid sequence selected from the group consisting of SEQ ID NOs: 110-125, for specific binding to TREM2 (e.g., human TREM2).

In one embodiment, an antibody described herein is one that is competitively blocked by an antibody comprising a VH domain having the amino acid sequence of SEQ ID NO: 107 and a VL domain having the amino acid sequence of SEQ ID NO: 110 for specific binding to TREM2 (e.g., human TREM2).

In one embodiment, an antibody described herein is one that is competitively blocked by an antibody comprising a VH domain having the amino acid sequence of SEQ ID NO: 108 and a VL domain having the amino acid sequence of SEQ ID NO: 111 for specific binding to TREM2 (e.g., human TREM2).

In one embodiment, an antibody described herein is one that is competitively blocked by an antibody comprising a VH domain having the amino acid sequence of SEQ ID NO: 109 and a VL domain having the amino acid sequence of SEQ ID NO: 121 for specific binding to TREM2 (e.g., human TREM2).

In another specific embodiment, an antibody described herein is one that is competitively blocked (e.g., in a dose dependent manner) by an antibody comprising (i) a VH domain comprising a CDRH1, CDRH2, and CDRH3 having the amino acid sequences of the CDRs of antibody listed in Table 1 (e.g., the VH CDRs of a particular antibody referred by name in Table 1); and (ii) a VL domain comprising a CDRL1, CDRL2, and CDRL3 having the amino acid sequences of the CDRs of antibody listed in Table 2 (e.g., the VL CDRs of a particular antibody referred by name in Table 2).

In specific aspects, provided herein is an antibody which specifically binds to the same epitope as that of an antibody (e.g., any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215) comprising the amino acid sequences described herein (see, e.g., Tables 1-9). Assays known to one of skill in the art or described herein (e.g., X-ray crystallography, ELISA assays, etc.) can be used to determine if two antibodies bind to the same epitope.

In a specific embodiment, an antibody described herein specifically binds to the same epitope as that of an antibody (e.g., any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215) comprising a VH domain having an amino acid sequence selected from the group consisting of SEQ ID NOs: 87-109, and a VL domain having an amino acid sequence selected from the group consisting of SEQ ID NOs: 110-125.

In a specific embodiment, an antibody described herein specifically binds to the same epitope as that bound by an antibody comprising the VH domain and VL domain of antibody EOS004281 or EOS004282 (SEQ ID NOs: 107 and 110, respectively), or an epitope that overlaps the epitope of antibody comprising the VH domain and VL domain of antibody EOS004281 or EOS004282 (SEQ ID NOs: 107 and 110, respectively).

In a specific embodiment, an antibody described herein specifically binds to the same epitope as that bound by an antibody comprising the VH domain and VL domain of antibody EOS004283 or EOS006233 (SEQ ID NOs: 108 and 111, respectively), or an epitope that overlaps the epitope of antibody comprising the VH domain and VL domain of antibody EOS004283 or EOS006233 (SEQ ID NOs: 108 and 111, respectively).

In a specific embodiment, an antibody described herein specifically binds to the same epitope as that bound by an antibody comprising the VH domain and VL domain of antibody EOS004284 or EOS006215 (SEQ ID NOs: 109 and 121, respectively), or an epitope that overlaps the epitope of antibody comprising the VH domain and VL domain of antibody EOS004284 or EOS006215 (SEQ ID NOs: 109 and 121, respectively).

In another specific embodiment, an antibody described herein, specifically binds to the same epitope as that of an antibody comprising (i) a VH domain comprising a CDRH1, CDRH2, and CDRH3 having the amino acid sequences of the CDRs of antibody listed in Table 1 (e.g., the VH CDRs of a particular antibody referred to by name in Table 1) and (ii) a VL domain comprising a CDRL1, CDRL2, and CDRL3 having the amino acid sequences of the CDRs of antibody listed in Table 2 (e.g., the VL CDRs of a particular antibody referred to by name in Table 2).

In certain embodiments, the antibody disclosed herein is conjugated to a cytotoxic agent, cytostatic agent, toxin, radionuclide, or detectable label. In certain embodiments, the cytotoxic agent is able to induce death or destruction of a cell in contact therewith. In certain embodiments, the cytostatic agent is able to prevent or substantially reduce proliferation and/or inhibits the activity or function of a cell in contact therewith. In certain embodiments, the cytotoxic agent or cytostatic agent is a chemotherapeutic agent. In certain embodiments, the radionuclide is selected from the group consisting of the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$, and $^{186}Re$. In certain embodiments, the detectable label comprises a fluorescent moiety or a click chemistry handle.

Epitope

Exemplary anti-TREM2 antibodies described herein and having the sequences set forth in Tables 1-5 were derived from 7 parent antibody clones. Table 10 summarizes the lineage of the antibodies described herein.

TABLE 10

Antibody lineage

| Antibody | Parent | Optimization Method | VH CDR3 Lineage | VH Germline |
|---|---|---|---|---|
| EOS006165 | N/A | N/A | 19 | VH1-69 |
| EOS006163 | EOS006165 | H1H2 | 19 | VH1-69 |
| EOS006167 | N/A | N/A | 22 | VH3-23 |
| EOS006168 | N/A | N/A | 23 | VH3-23 |
| EOS006170 | N/A | N/A | 27 | VH4-4A |
| EOS006177 | EOS006170 | H1H2 | 27 | VH4-4A |
| EOS006169 | N/A | N/A | 51 | VH3-23 |
| EOS006178 | EOS006169 | H1H2 | 51 | VH3-23 |
| EOS006176 | EOS006169 | H1H2 | 51 | VH3-23 |
| EOS006166 | N/A | N/A | 64 | VH3-49 |
| EOS006174 | EOS006166 | H1H2 | 64 | VH3-49 |
| EOS006164 | EOS006166 | H1H2 | 64 | VH3-49 |
| EOS006181 | EOS006166 | H1H2 | 64 | VH3-49 |
| EOS006172 | EOS006165 | H3L3 | 19 | VH1-69 |
| EOS006162 | EOS006165 | H3L3 | 19 | VH1-69 |
| EOS006180 | EOS006168 | H3L3 | 23 | VH3-23 |
| EOS006175 | EOS006170 | H3L3 | 27 | VH4-4A |
| EOS006179 | EOS006169 | H3L3 | 51 | VH-3-23 |
| EOS006173 | EOS006166 | H3L3 | 64 | VH3-49 |
| EOS006171 | N/A | N/A | 48 | VH3-11 |

Parent antibody EOS006165, and its progeny (EOS006162, EOS006163, and EOS006172) bind to the same epitope as shown below in Table 11.

TABLE 11

Binding epitope for EOS006165 and progeny

| Antibody | TREM2 Epitope (19-157aa of SEQ ID NO: 1) |
|---|---|
| EOS006165 | HNTTVFQGVAGQSLQVSCPYDSMKHWGRRKAWCRQLGEKGPCQRVVSTHNLWLLSFLRRW NGSTAITDDTLGGTLTITLRNLQPHDAGLYQCQSLHGSEADTLRKVLVEVLADPLDHRDA GDLWFPGESESFEDAHVEH |
| EOS006162 | HNTTVFQGVAGQSLQVSCPYDSMKHWGRRKAWCRQLGEKGPCQRVVSTHNLWLLSELRRW NGSTAITDDTLGGTLTITLRNLQPHDAGLYQCQSLHGSEADTLRKVLVEVLADPLDHRDA GDLWFPGESESFEDAHVEH |

TABLE 11-continued

| Binding epitope for EOS006165 and progeny | |
|---|---|
| Antibody | TREM2 Epitope (19-157aa of SEQ ID NO: 1) |
| EOS006163 | HNTTVFQGVAGQSLQVSCPYDSMKHWGRRKAWCRQLGEKGPCQRVVSTHNLWLLSFLRRW<br>NGSTAITDDTLGGTLTITLRNLQPHDAGLYQCQSLHGSEADTLRKVLVEVLADPLDHRDA<br>GDLWFPGESESFEDAHVEH |
| EOS006172 | HNTTVFQGVAGQSLQVSCPYDSMKHWGRRKAWCRQLGEKGPCQRVVSTHNLWLLSFLRRW<br>NGSTAITDDTLGGTLTITLRNLQPHDAGLYQCQSLHGSEADTLRKVLVEVLADPLDHRDA<br>GDLWFPGESESFEDAHVEH |

Thus, in some embodiments, the present disclosure provides an antibody which binds to human TREM2 at an epitope comprising one or more of amino acid residues M41, K42, H43, W44, G45, R46, R47, H67, N68, L69, W70, L71, L72, F74, L75, R77, D87, T88, L89, L113, H114, G115, E117, and D119 of SEQ ID NO: 1. In some embodiments, the antibody binds to human TREM2 at an epitope comprising or consisting of amino acid residues 44, 46-47, 68-72, 74, 88-89, and 114-115 of SEQ ID NO: 1. In some embodiments, the antibody binds to human TREM2 at an epitope comprising or consisting of amino acid residues 41-42, 44-47, 68-72, 74, 88-89, 114-115, 117, and 119 of SEQ ID NO: 1. In some embodiments, the antibody binds to human TREM2 at an epitope comprising or consisting of amino acid residues 41-44, 46-47, 68-72, 74, 88-89, 114-115, 117, and 119 of SEQ ID NO: 1. In some embodiments, the antibody binds to human TREM2 at an epitope comprising or consisting of amino acid residues 44-47, 67-72, 74-75, 77, 87-89, and 114-115 of SEQ ID NO: 1. In some embodiments, the antibody bind to human TREM2 at an epitope comprising or consisting of amino acid residues 41-47, 67-72, 74, 88-89, 113-115, 117, and 119 of SEQ ID NO: 1.

Parent antibodies EOS006167, EOS006168, and EOS006169, and EOS006169 progeny (EOS006176, EOS006178, EOS006179, and EOS006180) bind to the same epitope as shown below in Table 12.

TABLE 12

| Binding epitope for EOS006167, EOS006168, and EOS006169 and EOS006169 progeny | |
|---|---|
| Antibody | TREM2 Epitope (19-157aa of SEQ ID NO: 1) |
| EOS006167 | HNTTVFQGVAGQSLQVSCPYDSMKHWGRRKAWCRQLGEKGPCQRVVSTHNLWLLSFLRRW<br>NGSTAITDDTLGGTLTITLRNLQPHDAGLYQCQSLHGSEADTLRKVLVEVLADPLDHRDA<br>GDLWFPGESESFEDAHVEH |
| EOS006168 | HNTTVFQGVAGQSLQVSCPYDSMKHWGRRKAWCRQLGEKGPCQRVVSTHNLWLLSFLRRW<br>NGSTAITDDTLGGTLTITLRNLQPHDAGLYQCQSLHGSEADTLRKVLVEVLADPLDHRDA<br>GDLWFPGESESFEDAHVEH |
| EOS006169 | HNTTVFQGVAGQSLQVSCPYDSMKHWGRRKAWCROLGEKGPCQRVVSTHNLWLLSFLRRW<br>NGSTAITDDTLGGTLTITLRNLQPHDAGLYQCQSLHGSEADTLRKVLVEVLADPLDHRDA<br>GDLWFPGESESFEDAHVEH |
| EOS006176 | HNTTVFQGVAGQSLQVSCPYDSMKHWGRRKAWCRQLGEKGPCQRVVSTHNLWLLSFLRRW<br>NGSTAITDDTLGGTLTITLRNLQPHDAGLYQCQSLHGSEADTLRKVLVEVLADPLDHRDA<br>GDLWFPGESESFEDAHVEH |
| EOS006178 | HNTTVFQGVAGQSLQVSCPYDSMKHWGRRKAWCROLGEKGPCQRVVSTHNLWLLSFLRRW<br>NGSTAITDDTLGGTLTITLRNLQPHDAGLYQCQSLHGSEADTLRKVLVEVLADPLDHRDA<br>GDLWFPGESESFEDAHVEH |
| EOS006179 | HNTTVFQGVAGQSLQVSCPYDSMKHWGRRKAWCRQLGEKGPCQRVVSTHNLWLLSFLRRW<br>NGSTAITDDTLGGTLTITLRNLQPHDAGLYQCQSLHGSEADTLRKVLVEVLADPLDHRDA<br>GDLWFPGESESFEDAHVEH |
| EOS006180 | HNTTVFQGVAGQSLQVSCPYDSMKHWGRRKAWCRQLGEKGPCQRVVSTHNLWLLSFLRRW<br>NGSTAITDDTLGGTLTITLRNLQPHDAGLYQCQSLHGSEADTLRKVLVEVLADPLDHRDA<br>GDLWFPGESESFEDAHVEH |

Thus, in some embodiments, the present disclosure provides an antibody which binds to human TREM2 at an epitope comprising one or more of amino acid residues L129, A130, D131, P132, L133, D134, H135, R136, D137, A138, G139, D140, L141, W142, F143, P144, G145, E146, S147, E148, S149, F150, A153, and H154 of SEQ ID NO: 1. In some embodiments, the antibody binds to human TREM2 at an epitope comprising or consisting of amino acid residues 133, 137-138, and 140-144 of SEQ ID NO: 1. In some embodiments, the antibody binds to human TREM2 at an epitope comprising or consisting of amino acid residues 133, 135-144, and 146 of SEQ ID NO: 1. In some embodiments, the antibody binds to human TREM2 at an epitope comprising or consisting of amino acid residues 132-134, 136-146, and 148 of SEQ ID NO: 1. In some embodiments, the antibody binds to human TREM2 at an epitope comprising or consisting of amino acid residues 132-133, and 136-148 of SEQ ID NO: 1. In some embodiments, the antibody binds to human TREM2 at an epitope comprising or consisting of amino acid residues 132-148 of SEQ ID NO: 1. In some embodiments, the antibody binds to human TREM2 at an epitope comprising or consisting of amino acid residues 129-133, 135-138, 140-144, 146, 149-150, and 153-154 of SEQ ID NO: 1. In some embodiments, the antibody binds to human TREM2 at an epitope comprising or consisting of amino acid residues 131-134 and 137-149 of SEQ ID NO: 1. In some embodiments, the antibody binds to human TREM2 at an epitope comprising or consisting of amino acid residues 132-133, 135-138, 140-144, and 150 of SEQ ID NO: 1.

Parent antibody EOS006166, and its progeny (EOS006164, EOS006173, EOS006174, and EOS006181) bind to the same epitope as shown below in Table 13.

TABLE 13

Binding epitope for EOS006166 and progeny

| Antibody | TREM2 Epitope (19-157aa of SEQ ID NO: 1) |
|---|---|
| EOS006166 | HNTTVFQGVAGQSLQVSCPYDSMKH**WG**RRKAWCRQLGEKGPCQRVVST**HNLWLL**S**FLRRW**<br>NGSTAITD**DTL**GGTLTITLRNLQPHDAGLYQCQSLHGSEADTLRKVLVEVLADPLDHRDA<br>GDLWFPGESESFEDAHVEH |
| EOS006164 | HNTTVFQGVAGQSLQVSCPYDSMKH**WG**RRKAWCROLGEKGPCQRVVST**HNLWLL**S**FLRRW**<br>NGSTAITD**DTL**GGTLTITLRNLQPHDAGLYQCQSLHGSEADTLRKVLVEVLADPLDHRDA<br>GDLWFPGESESFEDAHVEH |
| EOS006173 | HNTTVFQGVAGQSLQVSCPYDSMKH**WG**RRKAWCRQLGEKGPCQRVVST**HNLWLL**S**FLRRW**<br>NGSTAITD**DTL**GGTLTITLRNLQPHDAGLYQCQSLHGSEADTLRKVLVEVLADPLDHRDA<br>GDLWFPGESESFEDAHVEH |
| EOS006174 | HNTTVFQGVAGQSLQVSCPYDSMKH**WG**RRKAWCRQLGEKGPCQRVVST**HNLWLL**S**FLRRW**<br>NGSTAITDD**TL**GGTLTITLRNLQPHDAGLYQCQSLHGSEADTLRKVLVEVLADPLDHRDA<br>GDLWFPGESESFEDAHVEH |
| EOS006181 | HNTTVFQGVAGQSLQVSCPYDSMKH**WG**RRKAWCRQLGEKGPCQRVVST**HNLWLL**S**FLRRW**<br>NGSTAITD**DTL**GGTLTITLRNLQPHDAGLYQCQSLHGSEADTLRKVLVEVLADPLDHRDA<br>GDLWFPGESESFEDAHVEH |

Thus, in some embodiments, the present disclosure provides an antibody which binds to human TREM2 at an epitope comprising one or more of amino acid residues W44, G45, H67, N68, L69, W70, L71, L72, F74, L75, R76, R77, W78, D87, T88, and L89 of SEQ ID NO: 1. In some embodiments, the antibody binds to human TREM2 at an epitope comprising or consisting of amino acid residues 44-45, 67-72, 74-78, and 88-89 of SEQ ID NO: 1. In some embodiments, the antibody binds to human TREM2 at an epitope comprising or consisting of amino acid residues 44-45, 67-72, 74-78, and 87-89 of SEQ ID NO: 1.

Parent antibodies EOS006171 and EOS006170, and EOS006170 progeny (EOS006175 and EOS006177) bind to the same epitope as shown below in Table 14.

TABLE 14

Binding epitope for EOS006171 and EOS006170 and EOS006170 progeny

| Antibody | TREM2 Epitope (19-157aa of SEQ ID NO: 1) |
|---|---|
| EOS006171 | HNTTVF**Q**GVAGQSLQVSCPYDSMKHWGRRKAWC**RQLGE**KGPCQRVVSTHNLWLLSFLRRW<br>NGSTAITDDTLGGTLTITLRNL**QPH**D**AGL**YQCQSLHGSEADTLRKV**L**V**EVLAD**PL**DH**RDA<br>GDLWFPGESESFEDAHVEH |
| EOS006170 | HN**T**T**V**F**Q**GV**A**GQSLQVSCPYDSMKHWGRRKAWC**RQLGE**KGPCQRVVSTHNLWLLSFLRRW<br>NGSTAITDDTLGGTLTITLRNL**QPH**D**AGL**YQCQSLHGSEADTLRKV**LVEVLAD**PL**DH**RDA<br>GDLWFPGESESFEDAHVEH |
| EOS006175 | HN**T**T**V**F**Q**GVAGQSLQVSCPYDSMKHWGRRKAWC**RQLGE**KGPCQRVVSTHNLWLLSFLRRW<br>NGSTAITDDTLGGTLTITLRNL**QPH**D**AGL**YQCQSLHGSEADTLRKV**LVEVLA**D**P**L**DH**RDA<br>GDLWFPGESESFEDAHVEH |
| EOS006177 | HN**T**TVFQGVAGQSLQVSCPYDSMKHWGRRKAWC**RQLGEKGP**CQRVVSTHNLWLLSFLRRW<br>NGSTAITDDTLGGTLTITLRNL**QPH**D**AGL**YQCQSLHGSEADTLR**K**V**LVEV**LADPLDHRDA<br>GDLWFPGESESFEDAHVEH |

Thus, in some embodiments, the present disclosure provides an antibody which binds to human TREM2 at an epitope comprising one or more of amino acid residues T21, V23, Q25, A28, R52, Q53, L54, G55, E56, K57, G58, P59, Q101, P102, H103, A105, G106, L107, K123, L125, V126, E127, V128, L129, A130, D131, P132, D134, and H135 of SEQ ID NO: 1. In some embodiments, the antibody binds to human TREM2 at an epitope comprising or consisting of amino acid residues 52-56, 102-103, 105-107, 125, and 127-128 of SEQ ID NO: 1. In some embodiments, the antibody binds to human TREM2 at an epitope comprising or consisting of amino acid residues 25, 52-56, 102-103, 105-107, 125, 127-131, and 134-135 of SEQ ID NO: 1. In some embodiments, the antibody binds to human TREM2 at an epitope comprising or consisting of amino acid residues 21, 23, 25, 28, 52-57, 101-103, 105-107, 125-131, and 134-135 of SEQ ID NO: 1. In some embodiments, the antibody binds to human TREM2 at an epitope comprising or consisting of amino acid residues 21, 23, 25, 52-56, 102-103, 105-107, 125-130, 132, and 135 of SEQ ID NO: 1. In some embodiments, the antibody binds to human TREM2 at an epitope comprising or consisting of amino acid residues 21, 52-59, 102-103, 105-107, 123, and 125-128 of SEQ ID NO: 1.

In some embodiments, the antibody has antibody-dependent cellular cytotoxicity (ADCC) activity. ADCC can occur when antibodies bind to antigens on the surface of pathogenic or tumorigenic target-cells. Effector cells bearing Fc gamma receptors (FcγR or FCGR) on their cell surface, including cytotoxic T-cells, natural killer (NK) cells, macrophages, neutrophils, eosinophils, dendritic cells, or monocytes, recognize and bind the Fc region of antibodies bound to the target-cells. Such binding can trigger the activation of intracellular signaling pathways leading to cell death. In particular embodiments, the antibody's immunoglobulin Fc region subtypes (isotypes) include human IgG1 and IgG3. As used herein, ADCC refers to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII, and FcγRIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc. Natl. Acad. Sci. (USA) 95:652-656 (1998).

In some embodiments, the antibody has complement-dependent cytotoxicity (CDC) activity. Antibody-induced CDC is mediated through the proteins of the classical complement cascade and is triggered by binding of the complement protein C1q to the antibody. Antibody Fc region binding to C1q can induce activation of the complement cascade. In particular embodiments, the antibody's immunoglobulin Fc region subtypes (isotypes) include human IgG1 and IgG3. As used herein, CDC refers to the ability of a molecule to lyse a target in the presence of complement. The complement activation pathway is initiated by the binding of the first component of the complement system (C1q) to a molecule (e.g., polypeptide (e.g., an antibody)) complexed with a cognate antigen. To assess complement activation, a CDC assay, e.g., as described in Gazzano-Santoro et al., J. Immunol. Methods 202:163 (1996), may be performed.

In some embodiments, an antibody is an agonistic antibody. An agonistic antibody can induce (e.g., increase) one or more activities or functions of non-stimulatory myeloid cells (NSMs) after the antibody binds a TREM2 protein expressed on the cell. The agonistic antibody may bind to and activate NSMs, causing changes in proliferation of the cell or modifying antigen presentation capabilities. The agonistic antibody may bind to and activate NSMs, triggering intracellular signaling pathways that lead to modified cell growth or apoptosis.

In some embodiments, NSMs are tumor-associated macrophages (TAM), neutrophils, monocytes, or dendritic cells (DC). In some embodiments, the NSM is not a DC. In some embodiments, NSMs are neutrophils. In some embodiments, NSMs are TAMs. TAMs are macrophages present near or within cancerous tumors, and are derived from circulating monocytes or resident tissue macrophages.

In specific aspects, an antibody described herein, which specifically binds to TREM2 (e.g., human TREM2), exerts an antagonistic effect on TREM2-expressing cells.

In specific aspects, an antibody described herein, which specifically binds to TREM2 (e.g., human TREM2), exerts a reverse agonist effect on TREM2-expressing cells.

In specific aspects, an antibody described herein, which specifically binds to TREM2 (e.g., human TREM2), exerts an agonistic effect on TREM2-expressing cells.

In some embodiments, an antibody is an antagonistic antibody. An antagonistic antibody can block (e.g., decrease) one or more activities or functions of NSMs after the antibody binds a TREM2 protein expressed on the cell. For example, the antagonist antibody may bind to and block ligand binding to one or more NSM proteins, preventing differentiation and proliferation of the cell or modifying antigen presentation capabilities. The antagonist antibody may bind to and prevent activation of a TREM2 protein by its ligand, modifying intracellular signaling pathways that contribute to cell growth and survival.

In some embodiments, an antibody is a reverse agonist antibody. A reverse agonist antibody can bind to the same receptor-binding site on TREM2 as an agonist and not only antagonizes the effects of an agonist but, moreover, exerts the opposite effect by suppressing spontaneous receptor signaling (when present).

In some embodiments, an antibody is a stabilizing antibody. A stabilizing antibody can bind to and stabilize TREM2 at the cell surface (e.g., prevents shedding of TREM2 from the cell surface).

In some embodiments, an antibody is a depleting antibody. A depleting antibody is one that would kill a non-stimulatory myeloid cell upon contact through the antibody's interaction with other immune cells of molecules. For example, antibodies, when bound to cells bearing TREM2 proteins, could engage complement proteins and induce complement-dependent cell lysis. Antibodies, when bound to cells bearing TREM2 proteins, could also trigger neighboring cells bearing Fc receptors to kill them by ADCC.

In some embodiments, an antibody is a neutralizing antibody, and the antibody neutralizes one or more biological activities of NSMs. In some embodiments, TREM2 protein is expressed on the surface of NSMs, and the antibody recognizes the extracellular domain of TREM2 protein.

In some embodiments, an antibody is selective for NSMs (preferentially binds to TREM2). In certain embodiments, an antibody that selectively binds to NSMs has a dissociation constant (Kd) of range of 0.0001 nM to 1 μM. In certain embodiments, an antibody specifically binds to an epitope on a TREM2 protein that is conserved among the protein from different species. In another embodiment, selective binding includes, but does not require, exclusive binding.

In one embodiment, an anti-TREM2 antibody bound to its target is responsible for causing the in vivo depletion of NSMs to which it is bound. In some embodiments, effector proteins induced by clustered antibodies can trigger a variety of responses, including release of inflammatory cytokines, regulation of antigen production, endocytosis, or cell killing. In one embodiment, the antibody is capable of recruiting and activating complement or mediating ADCC in vivo, or mediating phagocytosis by binding Fc receptors in vivo. The antibody may also deplete non-stimulatory myeloid cells by inducing apoptosis or necrosis of the non-stimulatory myeloid cell upon binding.

In certain embodiments, an anti-TREM2 antibody reduces binding of a TREM2 ligand to TREM2. Examples of TREM2 ligands include, but are not limited to, bacteria, neuritic debris, apoptotic cells, nucleic acids, heat shock protein 60, anionic lipids, apolipoprotein E (APOE), APOE2, APOE3, APOE4, anionic APOE, anionic APOE2, anionic APOE3, anionic APOE4, lipidated APOE, lipidated APOE2, lipidated APOE3, lipidated APOE4, zwitterionic lipids, negatively charged phospholipids, lipopolysaccharides (LPS), phosphatidic acid (PA), phosphatidylserine (PS), sulfatides, phosphatidylcholine (PC), phosphatidylglycerol (PG), phosphatidylinositol (PI), cardiolipin, sphingomyelin, membrane phospholipids, lipidated proteins, proteolipids, low density lipoprotein (LDL), high density lipoprotein, lipidated peptides, and lipidated amyloid beta peptide. In some embodiments, the TREM2 ligand is low density lipoprotein (LDL).

In certain embodiments, an anti-TREM2 antibody interferes with multimerization of TREM2. TREM2 forms trimers of dimers. In some embodiments, an anti-TREM2 antibody interferes with dimerization of TREM2 monomers. In some embodiments, an anti-TREM2 antibody interferes with trimerization of TREM2 dimers.

In certain embodiments, an anti-TREM2 antibody reduces efferocytosis. As used herein, efferocytosis is defined as the clearance of apoptotic cell(s) by phagocytic cell(s). In some embodiments, the phagocytic cell(s) are macrophage(s). In some embodiments, the macrophage(s) are M2a-like macrophage(s). In some embodiments, an anti-TREM2 antibody reduces efferocytosis by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to efferocytosis in the absence of an anti-TREM2 antibody. In some embodiments, an anti-TREM2 antibody reduces efferocytosis by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% compared to efferocytosis in the absence of an anti-TREM2 antibody. In some embodiments, an anti-TREM2 antibody reduces efferocytosis by about 25-100%. In some embodiments, an anti-TREM2 antibody reduces efferocytosis by about 40-80%. In some embodiments, an anti-TREM2 antibody reduces efferocytosis by about 50-75%. In some embodiments, an anti-TREM2 antibody reduces efferocytosis by 25-100%. In some embodiments, an anti-TREM2 antibody reduces efferocytosis by 40-80%. In some embodiments, an anti-TREM2 antibody reduces efferocytosis by 50-75%.

In certain embodiments, an anti-TREM2 antibody reprograms macrophages. In some embodiments, an anti-TREM2 antibody reprograms macrophages (such as M2-like macrophages) towards a pro-inflammatory phenotype.

In certain embodiments, an anti-TREM2 antibody blocks pro-tumoral functions. In some embodiments, an anti-TREM2 antibody slows and/or reduces and/or inhibits tumor growth.

Polynucleotides, Vectors, and Methods of Production

The disclosure also provides polynucleotides encoding the anti-TREM2 antibodies disclosed herein or fragments thereof (e.g., a VL and/or a VH). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecules having less than about 15%, 10%, 5%, 2%, 1%, 0.5%, or 0.1% (in particular, less than about 10%) of other material, e.g., cellular material, culture medium, other nucleic acid molecules, chemical precursors and/or other chemicals. In an embodiment, a nucleic acid molecule(s) encoding a polypeptide described herein is isolated or purified.

In particular aspects, provided herein are polynucleotides comprising nucleotide sequences encoding antibodies, which specifically bind to a TREM2 polypeptide (e.g., human TREM2) and comprises an amino acid sequence as described herein, as well as antibodies which compete with such antibodies for binding to a TREM2 polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Tables 2 and 5). The polynucleotides can comprise nucleotide sequences encoding a heavy chain comprising the VH FRs and CDRs of antibodies described herein (see, e.g., Tables 1 and 4). In specific embodiments, a polynucleotide described herein encodes a VL domain described herein (see, e.g., Table 3). In some embodiments, a polynucleotide described herein encodes a VL domain comprising an amino acid sequence selected from the group consisting of SEQ ID NOs: 110-125. In specific embodiments, a polynucleotide described herein encodes a VL domain comprising the amino acid sequence of SEQ ID NO: 110, 111, or 121. In specific embodiments, a polynucleotide described herein encodes a VH domain described herein (see, e.g., Table 3). In some embodiments, a polynucleotide described herein encodes a VH domain comprising an amino acid sequence selected from the group consisting of SEQ ID NOs: 87-109. In specific embodiments, a polynucleotide described herein encodes a VH domain comprising the amino acid sequence of SEQ ID NO: 107, 108, or 109. In specific embodiments, a polynucleotide described herein encodes a VL and a VH comprising the amino acid sequence of any one of antibodies EOS004281/EOS004282, EOS004283/EOS006233, or EOS004284/EOS006215 (see, e.g., Table 3).

In particular embodiments, provided herein are polynucleotides comprising a nucleotide sequence encoding an anti-TREM2 antibody comprising three VL chain CDRs, e.g., containing VL CDR1, VL CDR2, and VL CDR3 of any one of antibodies described herein (e.g., see Table 2, for example, the VL CDRs in one row in Table 2). In specific embodiments, provided herein are polynucleotides comprising three VH chain CDRs, e.g., containing VH CDR1, VH CDR2, and VH CDR3 of any one of antibodies described herein (e.g., see Table 1, for example, the VH CDRs in one row in Table 1). In specific embodiments, provided herein are polynucleotides comprising a nucleotide sequence encoding an anti-TREM2 antibody comprising three VH chain CDRs, e.g., containing VL CDR1, VL CDR2, and VL CDR3 of any one of antibodies described herein (e.g., see Table 2, e.g., the VL CDRs in one row in Table 2) and three VH chain CDRs, e.g., containing VH CDR1, VH CDR2, and VH CDR3 of any one of antibodies described herein (e.g., see Table 1, e.g., the VH CDRs in one row in Table 1). In specific embodiments, a polynucleotide described herein encodes the VL CDRs of any one of antibodies EOS004281/EOS004282, EOS004283/EOS006233, and EOS004284/EOS006215 (e.g., SEQ ID NOs: 60, 66, and 71). In specific embodiments, a polynucleotide described herein encodes the VH CDRs of any one of antibodies EOS004281/EOS004282, EOS004283/EOS006233, and EOS004284/EOS006215 (e.g., SEQ ID NOs: 19, 32, and 55). In specific embodiments, a polynucleotide described herein encodes VL CDRs and VH CDRs of any one of antibodies EOS004281/EOS004282, EOS004283/EOS006233, and EOS004284/EOS006215 (e.g., SEQ ID NOs: 60, 66, 71, 19, 32, and 55).

In particular embodiments, provided herein are polynucleotides comprising a nucleotide sequence encoding an anti-TREM2 antibody comprising a VL domain, e.g., containing FR1-CDR1-FR2-CDR2-FR3-CDR3-FR4, comprising an amino acid sequence described herein (e.g., see Tables 2 and 5, e.g., the VL CDRs and VL FRs of a particular antibody identified by name in the tables). In specific embodiments, provided herein are polynucleotides comprising a nucleotide sequence encoding an anti-TREM2 antibody comprising a VH domain, e.g., containing FR1-CDR1-FR2-CDR2-FR3-CDR3-FR4, comprising an amino acid sequence described herein (e.g., see Tables 1 and 4, e.g., the VH CDRs and VH FRs of a particular antibody identified by name in the Tables).

In certain embodiments, a polynucleotide described herein comprises a nucleotide sequence encoding an antibody provided herein comprising a VL comprising an amino acid sequence described herein (see, e.g., Table 3), wherein the antibody specifically binds to TREM2. In some embodiments, a polynucleotide described herein comprises a nucleotide sequence encoding an antibody provided herein comprising a VL comprising an amino acid sequence of any one of SEQ ID NOs: 110-125, wherein the antibody specifically binds to TREM2 (e.g., human TREM2). In a certain embodiment, a polynucleotide described herein comprises a nucleotide sequence encoding antibodies EOS004281/EOS004282, EOS004283/EOS006233, or EOS004284/EOS006215 provided herein comprising a VL comprising an amino acid sequence described herein (e.g., SEQ ID NOs: 110, 111, or 121).

In certain embodiments, a polynucleotide described herein comprises a nucleotide sequence encoding an antibody provided herein comprising a VH comprising an amino acid sequence described herein (see, e.g., Table 3), wherein the antibody specifically binds to TREM2. In some embodiments, a polynucleotide described herein comprises a nucleotide sequence encoding an antibody provided herein comprising a VH comprising an amino acid sequence of any one of SEQ ID NOs: 87-109, wherein the antibody specifically binds to TREM2 (e.g., human TREM2). In a certain embodiment, a polynucleotide described herein comprises a nucleotide sequence encoding antibodies EOS004281/EOS004282, EOS004283/EOS006233, or EOS004284/EOS006215 provided herein comprising a VH comprising an amino acid sequence described herein (e.g., SEQ ID NOs: 107, 108, or 109).

In certain aspects, a polynucleotide comprises a nucleotide sequence encoding an antibody described herein comprising a VL domain comprising one or more VL FRs having the amino acid sequence described herein (e.g., see Table 5, e.g., the framework regions in one row of the table), wherein the antibody specifically binds to TREM2 (e.g., human TREM2). In certain aspects, a polynucleotide comprises a nucleotide sequence encoding an antibody described herein comprising a VH domain comprising one or more VH FRs having the amino acid sequence described herein (e.g., see Table 4, e.g., the framework regions in one row of the table), wherein the antibody specifically binds to TREM2 (e.g., human TREM2).

In specific embodiments, a polynucleotide provided herein comprises a nucleotide sequence encoding an antibody described herein comprising framework regions (e.g., framework regions of the VL domain and VH domain) that are human framework regions, wherein the antibody specifically binds TREM2 (e.g., human TREM2). In certain embodiments, a polynucleotide provided herein comprises a nucleotide sequence encoding an antibody or fragment thereof (e.g., CDRs or variable domain) described herein.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody described herein, which specifically binds to TREM2 (e.g., human TREM2), wherein the antibody comprises a light chain, and wherein the amino acid sequence of the VL domain can comprise any amino acid sequence described herein (e.g., SEQ ID NOs: 110-125), and wherein the constant region of the light chain comprises the amino acid sequence of a human kappa light chain constant region. In another particular embodiment, a polynucleotide provided herein comprises a nucleotide sequence encoding an antibody described herein, which specifically binds to TREM2 (e.g., human TREM2), and comprises a light chain, wherein the amino acid sequence of the VL domain can comprises any amino acid sequence described herein (e.g., SEQ ID NOs: 110-125), and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which specifically binds to TREM2 (e.g., human TREM2), wherein the antibody comprises a heavy chain, wherein the amino acid sequence of the VH domain can comprise any amino acid sequence described herein (e.g., SEQ ID NOs: 87-109), and wherein the constant region of the heavy chain comprises the amino acid sequence of a human gamma (γ) heavy chain constant region.

In a certain embodiment, a polynucleotide provided herein comprises a nucleotide sequence(s) encoding a VH domain and/or a VL domain of an antibody described herein (e.g., EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215, such as SEQ ID NOs: 87-109 for the VH domain or SEQ ID NOs: 110-125 for the VL domain), which specifically binds to TREM2 (e.g., human TREM2). In a certain embodiment, a polynucleotide provided herein comprises a nucleotide sequence(s) encoding a VH domain and/or a VL domain of antibody EOS004281/EOS004282, EOS004283/EOS006233, or EOS004284/EOS006215 (e.g., SEQ ID NOs: 107 and/or 110; 108 and/or 111; 109 and/or 121).

In yet another specific embodiment, a polynucleotide provided herein comprises a nucleotide sequence encoding an antibody described herein, which specifically binds TREM2 (e.g., human TREM2), wherein the antibody comprises a VL domain and a VH domain comprising any amino acid sequences described herein, and wherein the constant regions comprise the amino acid sequences of the constant regions of a human IgG1 or human IgG4.

In a specific embodiment, provided herein are polynucleotides comprising a nucleotide sequence encoding an anti-TREM2 antibody designated herein, see, e.g., Tables 1-5, for example antibody EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215.

Also provided herein are polynucleotides encoding a polypeptide as provided above that are optimized, e.g., by codon/RNA optimization, replacement with heterologous signal sequences, and elimination of mRNA instability elements. Methods to generate optimized nucleic acids for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In an embodiment, it can be desirable to alter one or more codons to encode a conservative mutation, e.g., a similar amino acid with similar chemical structure and properties and/or function as the original amino acid.

The polynucleotides can be obtained, and the nucleotide sequence of the polynucleotides determined, by any method known in the art. Nucleotide sequences encoding proteins described herein, and modified versions of these antibodies can be determined using methods well known in the art, i.e., nucleotide codons known to encode particular amino acids are assembled in such a way to generate a nucleic acid that encodes the protein. Such a polynucleotide encoding the protein can be assembled from chemically synthesized oligonucleotides (e.g., as described in Kutmeier G et al., (1994), BioTechniques 17:242-6, herein incorporated by reference in its entirety), which, briefly, involves the synthesis of overlapping oligonucleotides containing portions of the sequence encoding the antibody, annealing, and ligating of those oligonucleotides, and then amplification of the ligated oligonucleotides by PCR.

Alternatively, a polynucleotide encoding a protein described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the polypeptide of interest. Such PCR amplification methods can be used to obtain nucleic acids comprising the sequence encoding the polypeptide. The amplified nucleic acids can be cloned into vectors for expression in host cells and for further cloning.

If a clone containing a nucleic acid encoding a particular polypeptide is not available, but the sequence of the polypeptide is known, a nucleic acid encoding the polypeptide can be chemically synthesized or obtained from a suitable source (e.g., a cDNA library generated from, or nucleic acid, preferably poly A+ RNA, isolated from any tissue or cells expressing the polypeptide described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the polypeptide. Amplified nucleic acids generated by PCR can then be cloned into replicable cloning vectors using any method well known in the art.

DNA encoding proteins described herein can be readily isolated and sequenced using conventional procedures. Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce the proteins described herein.

Also provided are polynucleotides that hybridize under high stringency, intermediate or lower stringency hybridization conditions to polynucleotides that encode a protein described herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions is known to those of skill in the art and has been described, see, e.g., Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In an aspect, provided herein are cells (e.g., host cells) expressing (e.g., recombinantly) a protein described herein, and related polynucleotides and expression vectors. Provided herein are vectors (e.g., expression vectors) comprising polynucleotides comprising nucleotide sequences encoding a protein described herein for recombinant expression in host cells, preferably in mammalian cells (e.g., CHO cells). Also provided herein are host cells comprising such vectors for recombinantly expressing proteins described herein. In an aspect, provided herein are methods for producing a protein described herein, comprising expressing the polypeptide from a host cell.

Recombinant expression of a protein described herein generally involves construction of an expression vector containing a polynucleotide that encodes the polypeptide. Once a polynucleotide encoding a polypeptide described herein has been obtained, the vector for the production of the polypeptide can be produced by recombinant DNA technology using techniques well known in the art. Thus, methods for preparing a protein by expressing a polynucleotide containing a polypeptide encoding nucleotide sequence are described herein. Methods which are well known to those skilled in the art can be used to construct expression vectors containing polypeptide coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding containing a polypeptide described herein, operably linked to a promoter. Such vectors can, for example, include the nucleotide sequence encoding the constant region of the polypeptide (see, e.g., International Publication Nos. WO 86/05807 and WO 89/01036; and U.S. Pat. No. 5,122,464, which are herein incorporated by reference in their entireties), and variable regions of the polypeptide can be cloned into such a vector for expression of the entire heavy, the entire light chain, or both the entire heavy and light chains.

In an embodiment, a vector comprises a polynucleotide encoding an sdAb, Fab, scFv, VHH, VH, VL, heavy chain, and/or light chain of a polypeptide described herein. In another embodiment, a vector comprises a polynucleotide encoding the VH and the VL of a polypeptide described herein. In another embodiment, a vector comprises a polynucleotide encoding the heavy chain and the light chain of a polypeptide described herein.

An expression vector can be transferred to a cell (e.g., host cell) by conventional techniques and the resulting cells can then be cultured by conventional techniques to produce a polypeptide described herein or a fragment thereof. Thus, provided herein are host cells containing a polynucleotide encoding containing a polypeptide described herein or fragments thereof, or a heavy or light chain thereof, or fragment thereof, or a single chain antibody described herein, operably linked to a promoter for expression of such sequences in the host cell.

In an embodiment, a host cell containing a polynucleotide encoding an antibody described herein, or a heavy or light chain thereof, or fragment thereof, or a single chain antibody described herein (e.g., an antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215), operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein (e.g., an antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215), or a fragment thereof. In specific embodiments, a host cell contains two different vectors, a first vector comprising a polynucleotide encoding a heavy chain or a heavy chain variable region of an antibody described herein (e.g., an antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215) or a fragment thereof, and a second vector comprising a polynucleotide encoding a light chain or a light chain variable region of an antibody described herein (e.g., an antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215), or a fragment thereof. In other embodiments, a first host cell comprises a first vector comprising a polynucleotide encoding a heavy chain or a heavy chain variable region of an antibody described herein (e.g., an antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215), or a fragment thereof, and a second host cell comprises a second vector comprising a polynucleotide encoding a light chain or a light chain variable region of an antibody described herein (e.g., an antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215), or a fragment thereof. In specific embodiments, a heavy chain/heavy chain variable region expressed by a first cell associated with a light chain/light chain variable region of a second cell to form an anti-TREM2 antibody described herein (e.g., antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215). In certain embodiments, provided herein is a population of host cells comprising such first host cell and such second host cell.

In some embodiments, provided herein is a population of vectors comprising a first vector comprising a polynucleotide encoding a light chain/light chain variable region of an anti-TREM2 antibody described herein (e.g., antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215), and a second vector comprising a polynucleotide encoding a heavy chain/heavy chain variable region of an anti-TREM2 antibody described herein (e.g., antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215).

A variety of host-expression vector systems can be utilized to express polypeptides described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express a polypeptide described herein in situ. These include but are not limited to microorganisms such as bacteria (e.g., *E. coli* and *B. subtilis*) transformed with, e.g., recombinant bacteriophage DNA, plasmid DNA, or cosmid DNA expression vectors containing antibody coding sequences; yeast (e.g., *Saccharomyces* and *Pichia*) transformed with, e.g., recombinant yeast expression vectors containing antibody coding sequences; insect cell systems infected with, e.g., recombinant virus expression vectors (e.g., baculovirus) containing antibody coding sequences; plant cell systems (e.g., green algae such as *Chlamydomonas reinhardtii*) infected with, e.g., recombinant virus expression vectors (e.g., cauliflower mosaic virus, CaMV, tobacco mosaic virus, TMV) or transformed with, e.g., recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, NIH 3T3, HEK-293T, HepG2, SP210, R1.1, B-W, L-M, BSC1, BSC40, YB/20, and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In an embodiment, cells for expressing antibodies described herein are Chinese hamster ovary (CHO) cells, for example CHO cells from the CHO GS System™ (Lonza). In an embodiment, the heavy chain and/or light chain of an antibody produced by a CHO cell may have an N-terminal glutamine or glutamate residue replaced by pyroglutamate. In an embodiment, cells for expressing polypeptides described herein are human cells, e.g., human cell lines. In an embodiment, a mammalian expression vector is pOptiVEC™ or pcDNA3.3. In an embodiment, bacterial cells such as *Escherichia coli*, or eukaryotic cells (e.g., mammalian cells), are used for the expression of a recombinant polypeptide. For example, mammalian cells such as CHO cells, in conjunction with a vector such as the major intermediate early gene promoter element from human cytomegalovirus, are an effective expression system for antibodies (Foecking M K & Hofstetter H (1986) Gene 45:101-5; and Cockett M I et al., (1990) Biotechnology 8(7): 662-7, each of which is herein incorporated by reference in its entirety). In an embodiment, polypeptides described herein are produced by CHO cells or NS0 cells. In an embodiment, the expression of nucleotide sequences encoding polypeptides described herein is regulated by a constitutive promoter, inducible promoter, or tissue specific promoter.

In bacterial systems, a number of expression vectors can be advantageously selected depending upon the use intended for the antibody molecule being expressed. For example, when a large quantity of such a polypeptide is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2:1791-1794), in which the coding sequence can be ligated individually into the vector in frame with the lac Z coding region so that a fusion protein is produced; pIN vectors (Inouye S & Inouye M (1985) Nuc Acids Res 13:3101-3109; Van Heeke G & Schuster S M (1989) J Biol Chem 24:5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the molecule in infected hosts (see, e.g., Logan J & Shenk T (1984) PNAS 81 (12): 3655-9, which is herein incorporated by reference in its entirety). Specific initiation signals can also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153:516-544, which is herein incorporated by reference in its entirety).

In addition, a host cell strain can be chosen which modulates the expression of the inserted sequences or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include, but are not limited to, CHO, VERO, BHK, Hela, MDCK, HEK 293, NIH 3T3, W138, BT483, Hs578T, HTB2, BT20, and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10, and HsS78Bst cells. In an embodiment, proteins described herein are produced in mammalian cells, such as CHO cells.

In an embodiment, a polypeptide described herein comprises a portion of an antibody with reduced fucose content or no fucose content. Such proteins can be produced using techniques known to one skilled in the art. For example, the proteins can be expressed in cells deficient or lacking the ability to fucosylate. In an example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-TREM2 antibody described herein (e.g., an antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215) can be engineered. In specific embodiments, a cell provided herein stably expresses a light chain/light chain variable domain and a heavy chain/heavy chain variable domain which associate to form an antibody described herein (e.g., an antibody comprising the CDRs of any one of antibodies EOS006162, EOS006163, EOS006164, EOS006165, EOS006166, EOS006167, EOS006168, EOS006169, EOS006170, EOS006171, EOS006172, EOS006173, EOS006174, EOS006175, EOS006176, EOS006177, EOS006178, EOS006179, EOS006180, EOS006181, EOS004281, EOS004282, EOS004283, EOS006233, EOS004284, or EOS006215).

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for one to two days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method can advantageously be used to engineer cell lines which express an anti-TREM2 antibody. Such engineered cell lines can be particularly useful in the screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034), and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78:1527-31); gpt, which confers resistance to mycophenolic acid (Mulligan R C & Berg P (1981) PNAS 78 (4): 2072-6); neo, which confers resistance to the aminoglycoside G-418 (Wu G Y & Wu C H (1991) Biotherapy 3:87-95; Tolstoshev P (1993) Ann Rev Pharmacol Toxicol 32:573-596; Mulligan R C (1993) Science 260:926-932; and Morgan R A & Anderson W F (1993) Ann Rev Biochem 62:191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, NY (1993); Kriegler M, Gene Transfer and Expression, A Laboratory Manual, Stockton Press, NY (1990); and in Chapters 12 and 13, Dracopoli N C et al., (eds.), Current Protocols in Human Genetics, John Wiley & Sons, NY (1994); Colbère-Garapin F et al., (1981) J Mol Biol 150:1-14, all of which are herein incorporated by reference in their entireties.

The expression levels of a polypeptide can be increased by vector amplification (for a review, see, Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system is amplifiable, increase in the level of inhibitor present in culture of host cell will increase the number of copies of the marker gene. Since the amplified region is associated with the gene of interest, production of the polypeptide will also increase (Crouse G F et al., (1983) Mol Cell Biol 3:257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. The coding sequences can comprise cDNA or genomic DNA. The expression vector can be monocistronic or multicistronic. A multicistronic nucleic acid construct can encode 2, 3, 4, 5, 6, 7, 8, 9, 10, or more genes/nucleotide sequences, or in the range of 2-5, 5-10, or 10-20 genes/nucleotide sequences. For example, a bicistronic nucleic acid construct can comprise, in the following order, a promoter, a first gene and a second gene. In such an expression vector, the transcription of both genes can be driven by the promoter, whereas the translation of the mRNA from the first gene can be by a cap-dependent scanning mechanism, and the translation of the mRNA from the second gene can be by a cap-independent mechanism, e.g., by an IRES.

Once a polypeptide described herein has been produced by recombinant expression, it can be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins. Further, the polypeptides described herein can be fused to heterologous polypeptide sequences described herein or otherwise known in the art to facilitate purification.

In an embodiment, a polypeptide described herein is isolated or purified. In an embodiment, an isolated polypeptide is one that is substantially free of other polypeptides with different antigenic specificities than the isolated polypeptide. For example, in certain embodiments, a preparation of a protein described herein is substantially free of cellular material and/or chemical precursors. The language "substantially free of cellular material" includes preparations of a polypeptide in which the polypeptide is separated from cellular components of the cells from which it is isolated or recombinantly produced. Thus, a polypeptide that is substantially free of cellular material includes preparations of polypeptide having less than about 30%, 20%, 10%, 5%, 2%, 1%, 0.5%, or 0.1% (by dry weight) of heterologous protein (also referred to herein as a "contaminating protein") and/or variants of a polypeptide, for example, different post-translational modified forms of a polypeptide or other different versions of a polypeptide (e.g., polypeptide fragments). When the polypeptide is recombinantly produced, it is also generally substantially free of culture medium, i.e., culture medium represents less than about 20%, 10%, 2%, 1%, 0.5%, or 0.1% of the volume of the protein preparation. When the polypeptide is produced by chemical synthesis, it is generally substantially free of chemical precursors or other chemicals, i.e., it is separated from chemical precursors or other chemicals, which are involved in the synthesis of the protein. Accordingly, such preparations of the protein have less than about 30%, 20%, 10%, or 5% (by dry weight) of chemical precursors or compounds other than the antibody of interest. In an embodiment, polypeptides described herein are isolated or purified.

A polypeptide described herein can be produced by any method known in the art for the synthesis of proteins, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates); Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In an embodiment, a polypeptide described herein is prepared, expressed, created, or isolated by any means that involves creation, e.g., via synthesis, genetic engineering of DNA sequences. In an embodiment, such a polypeptide comprises sequences (e.g., DNA sequences or amino acid sequences) that do not naturally exist within the antibody germline repertoire of an animal or mammal (e.g., human) in vivo.

Pharmaceutical Compositions

Provided herein are compositions comprising an antibody described herein having the desired degree of purity in a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG). In a specific embodiment, pharmaceutical compositions comprise an antibody described herein, and optionally one or more additional prophylactic or therapeutic agents, in a pharmaceutically acceptable carrier. In a specific embodiment, pharmaceutical compositions comprise an effective amount of an antibody described herein, and optionally one or more additional prophylactic of therapeutic agents, in a pharmaceutically acceptable carrier. Examples of prophylactic or therapeutic agents are provided throughout the disclosure. In some embodiments, the antibody is the only active ingredient included in the pharmaceutical composition. Pharmaceutical compositions described herein can be useful in inhibiting, reducing, and/or blocking a TREM2 activity and treating a condition, such as cancer.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringer's Injection, Isotonic Dextrose Injection, Sterile Water Injection, Dextrose and Lactated Ringer's Injection. Nonaqueous parenteral vehicles include fixed oils of vegetable origin, cottonseed oil, corn oil, sesame oil, and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride, and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose, and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol, and propylene glycol for water miscible vehicles; and sodium hydroxide, hydrochloric acid, citric acid, or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular, or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol, or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions, or the like and can be formulated as creams, gels, ointments, emulsions, solutions, elixirs, lotions, suspensions, tinctures, pastes, foams, aerosols, irrigations, sprays, suppositories, bandages, dermal patches, or any other formulations suitable for topical administration.

An antibody described herein can be formulated as an aerosol for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An antibody described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

In certain embodiments, a pharmaceutical composition comprising an antibody described herein is a lyophilized powder, which can be reconstituted for administration as solutions, emulsions, and other mixtures. It may also be reconstituted and formulated as solids or gels. The lyophilized powder is prepared by dissolving an antibody described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose, or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The antibodies described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542, and 5,709,874. In a specific embodiment, an antibody described herein is targeted to a tumor.

The compositions to be used for in vivo administration can be sterile. This is readily accomplished by filtration through, e.g., sterile filtration membranes.

Methods of Treatment

In an aspect, methods for treating a disease or disorder in a subject are provided, comprising administering to the subject a therapeutically effective amount of an anti-TREM2 antibody according to the disclosure or a pharmaceutical composition comprising the same.

In some embodiments, the antibody binds to the extracellular domain of TREM2 on TREM2+ myeloid cells, optionally wherein the myeloid cells are intratumoral. In one embodiment, the antibody binds to the extracellular domain of TREM2 on myeloid cells, wherein the myeloid cells are NSMs that are CD45+, HLA-DR+, CD11c+, CD14+, and BDCA3−, wherein the antibody kills, disables, or depletes the NSMs via ADCC, CDC, and/or antibody-mediated cellular phagocytosis (ADCP) to a level that is less than the level of NSMs present in the cancer prior to the contacting of the NSMs with the antibody, wherein the NSMs are present in a population of immune cells comprising stimulatory myeloid cells that are CD45+, HLA-DR+, CD14−, CD11c+, BDCA1−, and BDCA3+ and the NSMs, and wherein the killing, disabling, or depleting of the NSMs treats the cancer.

In some embodiments, the antibody kills, disables, or depletes myeloid cells via ADCC, ADCP activity, or CDC. In some embodiments, the antibody has receptor-ligand blocking, agonism, or antagonism activity.

In some embodiments, the disease or disorder is cancer. In some embodiments, the cancer is a solid cancer. In some embodiments, the cancer is a liquid cancer. In some embodiments, the cancer is selected from the group consisting of lung cancer, liver cancer, ovarian cancer, kidney cancer, prostate cancer, testicular cancer, uterine cancer, gallbladder cancer, sarcoma, Ewing sarcoma, thyroid cancer, melanoma, skin cancer, pancreatic cancer; gastric cancer, gastrointestinal/stomach (GIST) cancer, lymphoma, head and neck cancer, glioma or brain cancer, colon cancer, rectal cancer, colorectal cancer, breast cancer, renal cell carcinoma, or kidney cancer. In some embodiments, the glioma or brain cancer is glioblastoma multiforme (GBM). In some embodiments, the liver cancer is hepatocellular carcinoma (HCC). In some embodiments, the uterine cancer is uterine corpus endometrial carcinoma (UCEC).

In another aspect, described herein are methods of killing, disabling, or depleting TREM2+ myeloid cells of a subject having cancer, comprising contacting the myeloid cells with an anti-TREM2 antibody described herein or the pharmaceutical composition described herein, optionally wherein the myeloid cells are intratumoral.

In some embodiments, the antibody binds to the extracellular domain of TREM2, wherein the TREM2+ myeloid cells are NSMs that are CD45+, HLA-DR+, CD11c+, CD14+, and BDCA3−, wherein the antibody kills, disables, or depletes the NSMs via ADCC, CDC, and/or ADCP to a level that is less than the level of NSMs present in the cancer prior to the contacting of the NSMs with the antibody, wherein the NSMs are present in a population of immune cells comprising stimulatory myeloid cells that are CD45+, HLA-DR+, CD14−, CD11c+, BDCA1+, and BDCA3+ and the NSMs, wherein the contacting does not substantially kill, disable, or deplete myeloid cells present outside of the cancer and/or stimulatory myeloid cells present in the cancer, and wherein the killing, disabling, or depleting of the NSMs treats the cancer by enhancing an immune response to the cancer.

In some embodiments, the antibody kills the myeloid cells by at least one of ADCC, CDC, and ADCP. In some embodiments, the antibody disables the myeloid cells by at least one of ADCC, CDC, and ADCP. In some embodiments, the antibody depletes the myeloid cells by at least one of ADCC, CDC, and ADCP. In some embodiments, the antibody has ADCC activity. In some embodiments, the antibody has CDC activity. In some embodiments, the antibody has ADCP activity. In some embodiments, the antibody has receptor-ligand blocking, agonism, reverse agonism, or antagonism activity.

In some embodiments, the myeloid cells are stimulatory myeloid cells. In some embodiments, the myeloid cells are NSMs. In some embodiments, the myeloid cells comprise at least one of dendritic cells, TAMs, neutrophils, or monocytes. In some embodiments, the myeloid cells are neutrophils. In some embodiments, the myeloid cells are TAMs. In some embodiments, the myeloid cells are intratumoral. In some embodiments, the myeloid cells are in a population of immune cells comprising stimulatory myeloid cells and NSMs.

In another aspect, the invention provides methods of treating an immune-related condition (e.g., cancer) in an individual comprising administering to the individual an effective amount of an anti-TREM2 antibody or a composition comprising an anti-TREM2 antibody. In another aspect, the invention provides methods of enhancing an immune response in an individual comprising administering to the individual an effective amount of an anti-TREM2 antibody or a composition comprising an anti-TREM2 antibody. In another aspect, the invention provides methods of reducing efferocytosis in an individual comprising administering to the individual an effective amount of an anti-TREM2 antibody or a composition comprising an anti-TREM2 antibody. In another aspect, the invention provides methods of reprogramming macrophages in an individual comprising administering to the individual an effective amount of an anti-TREM2 antibody or a composition comprising an anti-TREM2 antibody. In another aspect, the invention provides methods of blocking pro-tumoral functions in an individual comprising administering to the individual an effective amount of an anti-TREM2 antibody or a composition comprising an anti-TREM2 antibody. In another aspect, the invention provides methods of slowing and/or reducing and/or inhibiting tumor growth in an individual comprising administering to the individual an effective amount of an anti-TREM2 antibody or a composition comprising an anti-TREM2 antibody. In some embodiments, these methods are further provided in combination with other co-therapies such as a PDL blockade therapy, anti-PD-1 antibodies, anti-PD-L1 antibodies, anti-PD-L2 antibodies, a CTLA4 blockade therapy, anti-CTLA-4 antibodies, generalized checkpoint blockade therapy in which inhibitory molecules on T cells are blocked, adoptive T-cell therapy, CAR T-cell therapy, dendritic cell, or other cellular therapies, as well as conventional chemotherapies.

In an embodiment, the anti-TREM2 antibody is administered to the subject in combination with an additional therapeutic agent. As used herein, the term "in combination" refers to the use of more than one therapy (e.g., one or more prophylactic and/or therapeutic agents). The use of the term "in combination" does not restrict the order in which therapies are administered to a subject with a disease or disorder, or the route of administration. A first therapy (e.g., a prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disease or disorder or a symptom thereof. In certain embodiments, a therapy (e.g., an agent) administered in combination with an anti-TREM2 antibody to a subject is administered in the same composition (e.g., pharmaceutical composition). In other embodiments, a therapy (e.g., an agent) administered in combination with an anti-TREM2 antibody is administered to a subject in a different composition (e.g., two or more pharmaceutical compositions). The two compositions may be administered at the same or different times and/or by the same or different routes of administration.

In an embodiment, the additional therapeutic agent is a tissue damage enhancer. Non-limiting examples of tissue damage enhancers include chemotherapeutic agents, radiotherapy, and antibody drug conjugates (ADC). In some embodiments, the chemotherapeutic agent is a platinum drug, such as, for example, carboplatin, oxaliplatin, cisplatin, nedaplatin, triplatin tetranitrate, lobaplatin, phenanthriplatin, picoplatin, and satraplatin. In some embodiments, the ADC is gemtuzumab ozogamicin, brentuximab vedotin, trastuzumab emtansine, inotuzumab ozogamicin, polatuzumab vedotin, enfortumab vedotin, trastuzumab deruxtecan, sacituzumab govitecan, belantamab mafodotin, moxetumomab pasudotox, loncastuximab tesirine, tisotumab vedotin-tftv, ABBV-154, DS-8201, or any combination thereof.

In another embodiment, the additional therapeutic agent is an immune checkpoint inhibitor. In some embodiments, an immune checkpoint inhibitor may include a PD-1 inhibitor, a PD-L1 inhibitor, a CTLA-4 inhibitor, a TIM-3 inhibitor, a LAG3 inhibitor, a TIGIT inhibitor, a VISTA inhibitor, a KIR inhibitor, a 2B4 inhibitor, a CD160 inhibitor, a CGEN-15049 inhibitor, a CHK1 inhibitor, a CHK2 inhibitor, an A2aR inhibitor, or any combination thereof.

In some embodiments, a PD-1 inhibitor may include acrixolimab, adebrelimab, atezolizumab, avelumab, balstilimab, camrelizumab, cosibelimab, dostarlimab, durvalumab, enlonstobart, envafolimab, nivolumab, pembrolizumab, penpulimab, pidilizumab, pimivalimab, prolgolimab, pucotenlimab, retifanlimab, serplulimab, sintilimab, socazolimab, sugemalimab, tagitanlimab, tislelizumab, toripalimab, zimberelimab, AMP-224, AMP-514, AUNP-12, IBI-321, ZG005, cemiplimab (REGN2810), spartalizumab (PDR001), or any combination thereof.

In some embodiments, a PD-L1 inhibitor may include durvalumab, adebrelimab, atezolizumab, avelumab, balstilimab, camrelizumab, cemiplimab, cosibelimab, dostarlimab, durvalumab, enlonstobart, envafolimab, nivolumab, pembrolizumab, penpulimab, pidilizumab, prolgolimab, pucotenlimab, retifanlimab, serplulimab, sintilimab, socazolimab, sugemalimab, tagitanlimab, tislelizumab, toripalimab, zimberelimab, AUNP-12, CA-170, HLX-301, BMS-986189, or any combination thereof.

In some embodiments, a CTLA-4 inhibitor may include botensilimab, ipilimumab, tremelimumab, zalifrelimab (AGEN-1884), or any combination thereof.

In some embodiments, a TIM-3 inhibitor may include cobolimab, TSR-022, LY3321367, sabatolimab (MBG453), Sym023, INCAGN02390, or any combination thereof.

In some embodiments, a TIGIT inhibitor may include BMS-986207, AGEN1777, tiragolumab, vibostolimab (MK-7684), etigilimab (OMP-313M32), belrestotug (EOS-448), domvanalimab (AB154), ociperlimab, SEA-TGT, COM902, rilvegostomig, IBI-939 (tamgiblimab), IBI-321, BAT6005, JS-006, M6223, HB0030, BAT-6021, ZG005, AGEN1327, AK-127, HLX-301, $HLX_{53}$, ASP8374, or combinations thereof.

In some embodiments, a LAG-3 inhibitor may include relatlimab (BMS-986016), fianlimab (REGN3767), eftilagimod alpha (IMP321), ieramilimab (LAG525), miptenalimab (BI754111), favezelimab, INCAGN02385, TSR-033, or combinations thereof.

In some embodiments, a VISTA inhibitor may include CA-170, CI-8993, HMBD-002, KVA12123, SNS-101, W0180, a PSGL-1 antagonist as described in WO 2018/132476, or combinations thereof.

In another embodiment, the additional therapeutic agent is a "don't eat-me" signal inhibitor (such as, for example, a CD47 inhibitor, a PD-L1 inhibitor, an MHC class 1 inhibitor, or a CD24 inhibitor) or an ADCC/CP modulator. In some embodiments, the CD47 inhibitor may include ligufalimab, magrolimab, lemzoparlimab, letaplimab, CC-90002, IMM0306, TG-1801, TTI-621, TTI-622, evorpacept, IMM01, Hu5F9-G4, or any combination thereof. In some embodiments, a PD-L1 inhibitor may include durvalumab, adebrelimab, atezolizumab, avelumab, balstilimab, camrelizumab, cemiplimab, cosibelimab, dostarlimab, durvalumab, enlonstobart, envafolimab, nivolumab, pembrolizumab, penpulimab, pidilizumab, prolgolimab, pucotenlimab, retifanlimab, serplulimab, sintilimab, socazolimab, sugemalimab, tagitanlimab, tislelizumab, toripalimab, zimberelimab, AUNP-12, CA-170, HLX-301, BMS-986189, or any combination thereof. In some embodiments, an MHC class 1 inhibitor may include LILRBx. In some embodiments, the ADCC/CP modulator may include cetuximab, trastuzumab or any combination thereof. In some embodiments, the CD24 inhibitor may include ALB9, SWA11, SN3, G7mAb, rG7S-MICA, HN-01, or any combination thereof.

In another embodiment, the additional therapeutic agent is an angiogenesis inhibitor. In some embodiments, the angiogenesis inhibitor may include axitinib, bevacizumab, cabozantinib, everolimus, lenalidomide, lenvatinib mesylate, pazopanib, ramucirumab, regorafenib, sorafenib, sunitinib, thalidomide, vandetanib, ziv-aflibercept, or any combination thereof.

In some embodiments, the anti-TREM2 antibody is administered intravenously. In some embodiments, the anti-TREM2 antibody is administered intravenously once weekly, once every two weeks, once every three weeks, once every four weeks, once monthly, or once every six weeks.

In some embodiments, the anti-TREM2 antibody is administered subcutaneously. In some embodiments, the anti-TREM2 antibody is administered subcutaneously once weekly, once every two weeks, once every three weeks, once every four weeks, once monthly, or once every six weeks.

EXAMPLES

The following examples are offered by way of illustration, and not by way of limitation.

Example 1: Generation of Human Anti-TREM2 Antibodies

Anti-TREM2 antibodies were selected from a synthetic library of human antibodies expressed and presented on the surface of yeast cells in IgG format generally as described, (e.g., in WO2009036379; WO2010105256; WO2012009568; and Xu et al., Protein Eng Des Sel., Vol. 26(10), pp. 663-670 (2013)), and more specifically as provided below.

For naïve selections, eight naïve human synthetic yeast libraries (total library diversity >$10^{10}$) were propagated as (~$10^{10}$ cells/library) were incubated with different versions of biotinylated human TREM2 antigen (Table 15) fused to Fc: HuTREM2 ECD_19-174, HuTREM2 Stump_130-174 and HuTREM2 ECD_19-174_ΔL69-L75 (in-house production at Adimab). Sorting was performed using flow cytometry against the human TREM2 antigens fused to Fc to select for positive binders, followed by additional rounds selecting for binders to mouse or cyno TREM2_Fc (MoTREM2 ECD_19-171 or CyTREM2 ECD_19-174, respectively, each fused to Fc) to enrich in cross-reactive hits, and selecting against HuTREM1 ECD_21-200 fused to Fc to eliminate binders to human TREM1. Light-chain batch shuffle selection was also performed to identify the best clones in terms of affinity, broad epitopic coverage and developability. Developability and relevance to clinical antibody profiles were examined by flow cytometry with the use of Adimab's PolySpecificity Reagent (PSR) as a negative selection reagent. (Jain T et al., Proc Natl Acad Sci, 2017 Jan. 31; 114(5):944-949). Ultimately, sorting was performed using a FACS ARIA sorter (BD Biosciences) and sort gates were assigned to select for specific binders to human TREM2 relative to a background control. After the final round of sorting, yeast were plated and individual colonies were picked for sequencing. IgG were then produced and purified before characterization for nomination of clones for affinity maturation. 70 clones were screened for affinity, proximal and functional activity. From the screening, clones EOS006171, EOS006170, EOS006169, EOS006168, EOS006167, EOS006166, EOS006165 were selected for further sequence optimization.

TABLE 15

Antigen sequences

| Protein Name | AA Sequence |
|---|---|
| HuTREM2 ECD_19-174 | HNTTVFQGVAGQSLQVSCPYDSMKHWGRRKAWCRQLGEKGPCQRVVSTHNLWLLSFLRRWNGSTAITDDTLGGTLTITLRNLQPHDAGLYQCQSLHGSEADTLRKVLVEVLADPLDHRDAGDLWFPGESESFEDAHVEHSISRSLLEGEIPFPPTS (SEQ ID NO: 170) |
| HuTREM2 Stump_130-174 | ADPLDHRDAGDLWFPGESESFEDAHVEHSISRSLLEGEIPFPPTS (SEQ ID NO: 171) |
| HuTREM2 ECD_19-174_ΔL69-L75 | HNTTVFQGVAGQSLQVSCPYDSMKHWGRRKAWCRQLGEKGPCQRVVSTHNRRWNGSTAITDDTLGGTLTITLRNLQPHDAGLYQCQSLHGSEADTLRKVLVEVLADPLDHRDAGDLWFPGESESFEDAHVEHSISRSLLEGEIPFPPTS (SEQ ID NO: 172) |
| CyTREM2 ECD_19-174 | HNTTVFQGVEGQSLQVSCPYDSMKHWGRRKAWCRQLGEKGPCQRVVSTHNLWLLSFLRRRNGSTAITDDTLGGTLTITLRNLQPHDAGFYQCQSLHGSEADTLRKVLVEVLADPLDHRDAGDLWVPGESESFEDAHVEHSISRSLLEGEIPFPPTS (SEQ ID NO: 173) |
| MoTREM2 ECD_19-171 | LNTTVLQGMAGQSLRVSCTYDALKHWGRRKAWCRQLGEEGPCQRVVSTHGVWLLAFLKKRNGSTVIADDTLAGTVTITLKNLQAGDAGLYQCQSLRGREAEVLQKVLVEVLEDPLDDQDAGDLWVPEESSSFEGAQVEHSTSRNQETSFPPTS (SEQ ID NO: 174) |
| HuTREM1 ECD_21-200 | ATKLTEEKYELKEGQTLDVKCDYTLEKFASSQKAWQIIRDGEMPKTLACTERPSKNSHPVQVGRIILEDYHDHGLLRVRMVNLQVEDSGLYQCVIYQPPKEPHMLFDRIRLVVTKGFSGTPGSNENSTQNVYKIPPTTTKALCPLYTSPRTVTQAPPKSTADVSTPDSEINLTNVTDIIR (SEQ ID NO: 175) |

described previously (see, e.g., Xu et al., Protein Eng Des Sel., Vol. 26(10), pp. 663-670, 2013; WO2009036379; WO2010105256; and WO2012009568). For the first two rounds of selection, a magnetic bead sorting technique utilizing the Miltenyi MACS system was performed, as described (see, e.g., Siegel et al., 2004). Briefly, yeast cells Sequence optimization of the selected naïve clones was carried out utilizing different maturation strategies: diversification of CDRH3 and L3 and diversification of CDRH1 and CDRH2 within the selected CDRH3/L3 diversity pools. Selections were performed as during previous cycles using a combination of MACS and FACS sorting. For each FACS round, the libraries were assessed for PSR binding, species cross-reactivity, and affinity pressure, and sorting was performed to obtain populations with the desired characteristics.

In order to produce sufficient amounts of optimized and non-optimized selected antibodies for further characterization, selected antibodies were either produced in yeast and purified via a protein A column, or alternatively, produced in HEK293E-253 cells transduced with plasmid DNA coding for specific antibody clones, using the rPEx™ technology. Six days post transfection, the antibodies were purified on PrismA column, concentrated, and further purified by gel filtration.

Optimized antibodies were then characterized and screened for affinity, proximal, and functional activity as described in the following examples. Epitope binning for the different clones were determined via octet and Carterra (LodeStar Array technology) binning experiments against control bin representatives. See Table 16 for description of the optimized antibodies produced in yeast and Table 17 for the corresponding HEK293E-253-produced antibodies. Example 14 provides a description of the various benchmark antibodies used throughout the Examples.

TABLE 16

Yeast-produced anti-TREM2 antibodies

| Parent Clone | Bin | Optimized Antibody |
|---|---|---|
| EOS006165 | Ambiguous (likely 3.5) | EOS006163 |
| | | EOS006172 |
| | | EOS006162 |
| EOS006167 | 2 | None |
| EOS006168 | 2 | EOS006180 |
| EOS006170 | 3.5 | EOS006177 |
| | | EOS006175 |
| EOS006169 | 2 | EOS006178 |
| | | EOS006176 |
| | | EOS006179 |
| EOS006166 | 3.5 | EOS006164 |
| | | EOS006174 |
| | | EOS006181 |
| | | EOS006173 |
| EOS006171 | 1 | None |

TABLE 17

HEK293E-253-produced anti-TREM2 antibodies

| Yeast-produced antibody | WT IgG1 HEK293-produced antibody | N297A IgG1 HEK293-produced antibody |
|---|---|---|
| EOS006165 | EOS006335 | EOS006336 |
| EOS006166 | EOS006337 | EOS006338 |
| EOS006167 | EOS006339 | EOS006340 |
| EOS006168 | EOS006341 | EOS006342 |
| EOS006169 | EOS006343 | EOS006344 |
| EOS006171 | EOS006345 | EOS006346 |
| EOS006162 | EOS004281 | EOS004282 |
| EOS006163 | EOS004283 | EOS006233 |
| EOS006164 | EOS004284 | EOS006215 |

Example 2: Selection of TREM2-Specific Binding Antibodies

In order to test specificity of selected antibodies to TREM2, binding was tested by flow cytometry on THP-1 TREM2 KO (clone, produced using CRISPR technology in house) and on THP-1 WT. Cells were incubated with selected anti-TREM2 antibodies (final concentration of 10 μg/ml) for 30 min at 4° C. After washing, bound antibodies were detected with a secondary anti-human IgG Fc PE-labelled for 30 min at 4° C. Fluorescence intensity was measured by flow cytometry.

All antibodies showed a good specificity for TREM2 with fold over isotype control <2 on KO cells. Furthermore, MFI fold change (of THP-1 WT over THP-1 TREM2 KO) was ≥1.8 for 19 antibodies out of 20, which was much higher than benchmark antibody, PN37012 (1.4), which showed a poor specificity to TREM2 by binding 4.5 times more than the respective isotype control on TREM2 KO cells (Table 18).

TABLE 18

TREM2 binding specificity

| Antibody | Fold over isotype control THP1 WT | Fold over isotype control THP-1 TREM2 KO | MFI Fold change (THP-1 WT over THP-1 TREM2 KO) |
|---|---|---|---|
| EOS006162 | 9.9 | 1.3 | 11.0 |
| EOS006163 | 2.7 | 0.7 | 5.1 |
| EOS006164 | 3.7 | 1.0 | 4.3 |
| EOS006165 | 1.7 | 0.8 | 2.5 |
| EOS006166 | 7.3 | 1.1 | 1.8 |
| EOS006167 | 2.1 | 1.2 | 2.2 |
| EOS006168 | 3.0 | 1.6 | 2.3 |
| EOS006169 | 2.2 | 1.3 | 1.3 |
| EOS006170 | 2.3 | 0.9 | 3.2 |
| EOS006171 | 6.6 | 1.7 | 4.3 |
| EOS006172 | 8.7 | 1.4 | 8.9 |
| EOS006173 | 3.3 | 1.2 | 3.3 |
| EOS006174 | 4.0 | 0.9 | 5.1 |
| EOS006175 | 5.5 | 1.2 | 5.8 |
| EOS006176 | 2.7 | 0.9 | 3.4 |
| EOS006177 | 3.3 | 1.6 | 6.8 |
| EOS006178 | 2.1 | 1.0 | 2.4 |
| EOS006179 | 3.2 | 1.7 | 3.5 |
| EOS006180 | 4.4 | 2.0 | 4.5 |
| EOS006181 | 3.5 | 0.9 | 4.8 |
| PN-37012 | 5.2 | 4.5 | 1.4 |

Example 3: Epitope Mapping

TREM receptors are known to multimerize to activate downstream signaling events. For example, TREM1 multimerization is essential for its activation on monocytes and neutrophils (Carrasco et al., Cell Mol Immunol. 2019 May; 16(5): 460-472). In the case of TREM2, oligomerization of the extracellular domain has been shown to occur in the presence of phosphatidylserine (PS), one of its endogenous ligands (Sudom et al., J Biol Chem. 2018; 293:12634-12646). The three-dimensional X-ray structure of the complex of TREM2 with PS demonstrated that TREM2 forms trimers of dimers with a phospholipid-binding site at the interface of each dimer. Given the likelihood for a functional role of these structural self-arrangements, it was of interest to know if anti-TREM2 antibodies block these complexes (dimerization or trimerization). For this objective, an AlphaFold2-multimer algorithm was used to generate structural models of the antibody/TREM2 complexes for the selected sequences. The underlined, bolded residues in Tables 11-14 above represent TREM2 residues that are within a distance of 4 Å from the modeled antibody and are considered to be part of the structural epitope.

Antibodies EOS006162, EOS006163, and EOS006172 are related (EOS006165 is the parent antibody) and share the same epitope. Binding of these antibodies to TREM2 was shown to affect hexamer formation (as seen in the X-ray structure with PDB code 6B80), PS binding, and also to affect dimer or trimer formation.

Most of the tested antibodies (8) belong to bin 3/5. These antibodies were subdivided into two different binding models according to their parent antibody. For antibodies EOS006170 (parent), EOS006175, and EOS006177, no reliable structural models were obtained. Antibodies EOS006166 (parent), EOS006164, EOS006173, EOS006174, and EOS006181 bound to an epitope that has a crucial role in multimerization as well as PS binding. Although these five related antibodies bound to the same structural epitope, their orientation relative to TREM2 differed slightly. For EOS006173, TREM2 multimerization was not always hampered by binding, which was interesting because this antibody was shown to not antagonize PSYK. A superimposition of the antibody/TREM2 complex models illustrated a variety of antibody orientations relative to TREM2. Interestingly, the two non-antagonistic antibodies in this group (EOS006173 and EOS006181) interfaced with TREM2 at regions which flank those of the other antibodies in this group.

Of note, benchmark antibody PN-37012, as well as antibody EOS006171, which belongs to the same bin, did not appear to affect dimer, trimer, or hexamer formation, nor PS binding.

Antibodies EOS006167, EOS006168, EOS006169, EOS006176, EOS006178, EOS006179, and EOS006180 belong to the same bin and recognized a flexible region of the TREM2 ECD just C-terminal from the Ig-like domain. Since this region was not visible in the X-ray structure, these antibodies are not expected to directly affect oligomerization, nor PS binding.

Figure 1B:
Figure 1C:
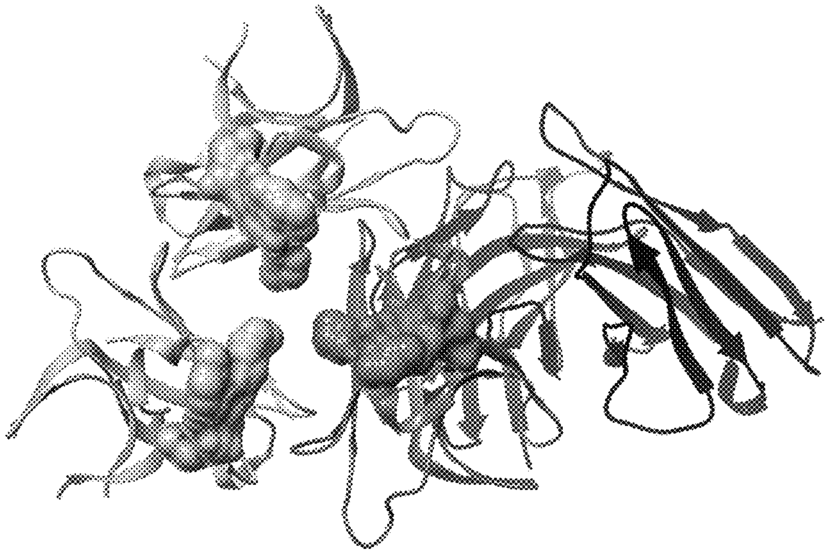
Figure 1D:

Models of exemplary antibodies that affect TREM2 oligomerization are represented in FIGS. 1A-1B.

TABLE 19

Binding epitope of exemplary antibodies Sequences whereby the residues within a distance of 4 Angstrom from the antibody are in bold and underlined.

| Clone | TREM2 epitope (19-157aa of SEQ ID NO: 1) |
|---|---|
| EOS006162 | HNTTVFQGVAGQSLQVSCPYDSMKHWGRRKAWCRQLGEKGPCQRVVSTH NLWLLSFLRRWNGSTAITDDTLGGTLTITLRNLQPHDAGLYQCQSLHGS EADTLRKVLVEVLADPLDHRDAGDLWFPGESESFEDAHVEH |
| EOS006163 | HNTTVFQGVAGQSLQVSCPYDSMKHWGRRKAWCRQLGEKGPCQRVVSTH NLWLLSFLRRWNGSTAITDDTLGGTLTITLRNLQPHDAGLYQCQSLHGS EADTLRKVLVEVLADPLDHRDAGDLWFPGESESFEDAHVEH |
| EOS006164 | HNTTVFQGVAGQSLQVSCPYDSMKHWGRRKAWCRQLGEKGPCQRVVSTH NLWLLSFLRRWNGSTAITDDTLGGTLTITLRNLQPHDAGLYQCQSLHGS EADTLRKVLVEVLADPLDHRDAGDLWFPGESESFEDAHVEH |
| EOS006181 | HNTTVFQGVAGQSLQVSCPYDSMKHWGRRKAWCRQLGEKGPCQRVVSTH NLWLLSFLRRWNGSTAITDDTLGGTLTITLRNLQPHDAGLYQCQSLHGS EADTLRKVLVEVLADPLDHRDAGDLWFPGESESFEDAHVEH |
| PN-37012 | HNTTVFQGVAGQSLQVSCPYDSMKHWGRRKAWCRQLGEKGPCQRVVSTH NLWLLSFLRRWNGSTAITDDTLGGTLTITLRNLQPHDAGLYQCQSLHGS EADTLRKVLVEVLADPLDHRDAGDLWFPGESESFEDAHVEH |

Example 4: Binding Affinity Determination of Anti-TREM2 Antibodies

M2a-like macrophages were produced in vitro from monocytes of healthy donors. Briefly, after PBMCs isolation from peripheral blood using Lymphoprep™ gradient, $CD14^+$ cells were purified and seeded in presence of MCSF 50 ng/ml for 6 days. Macrophages were then cultured with IL-13 and IL-4 at a concentration of 20 ng/ml for two additional days and then used for a cell-based binding assay.

M2a-like macrophages were incubated with anti-TREM2 antibodies (dose-response curve with 11 concentrations from 10 μg/ml to 0.0001 μg/ml) for 30 min at 4° C. After washing, bound antibodies were detected with a secondary anti-human IgG Fc PE-labelled for 30 min at 4° C. Fluorescence intensity was measured by flow cytometry. Equilibrium dissociation constant (kD) was then calculated for each antibody using median MFI normalized over isotype control.

Figure 2:
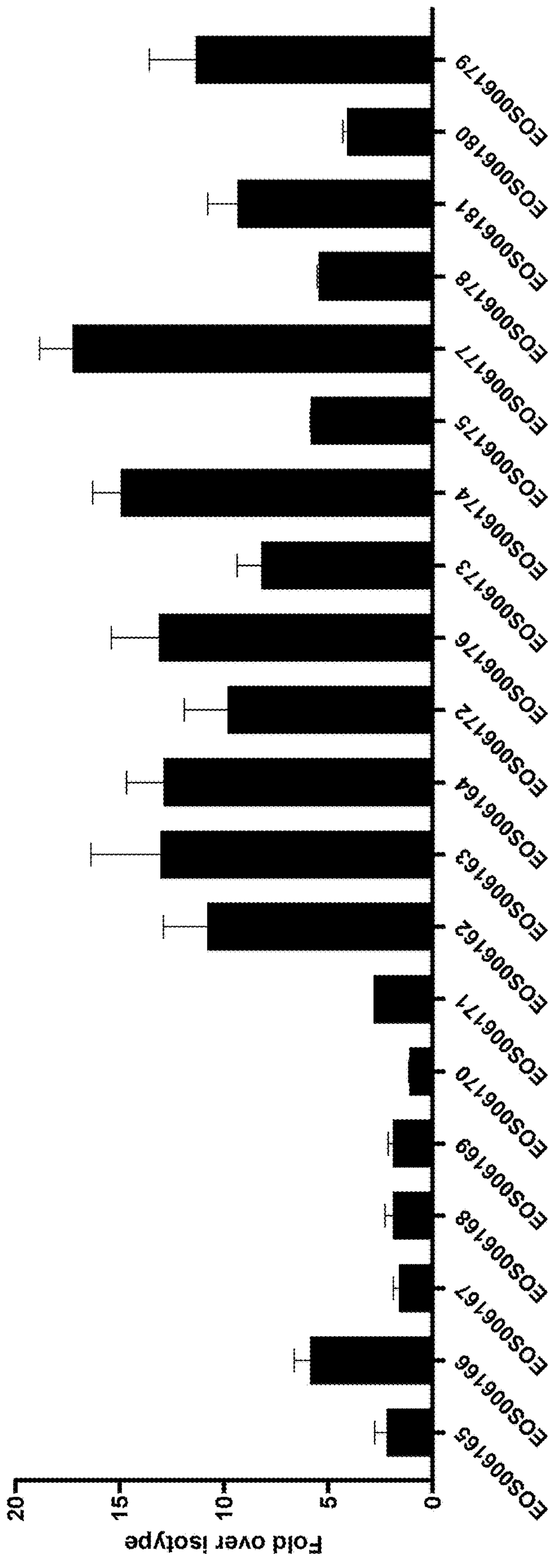
FIG. 2 shows binding of exemplary anti-TREM2 antibodies on target cells (in-vitro produced macrophages M2a-like; 2 different donors). All selected anti-TREM2 antibodies bind to target cells (at a concentration of 10 μg/ml), with a fold over isotype control ranging from 1.1 to 17.2.

Table 20 shows fold over isotype and binding affinity of selected antibodies to human TREM2, calculated by FACS on in vitro-produced macrophages (M2a). Out of sixteen antibodies tested, fourteen had stronger affinity for human TREM2 as compared to benchmark antibody, PN-37012, and reached a sub-nM kD affinity. Fold over isotype is also illustrated in FIG. 2.

TABLE 20

Binding affinity to human TREM2

| Antibody | kD (nM) | Fold over isotype |
|---|---|---|
| EOS006162 | 0.13 | 10.8 |
| EOS006163 | 0.15 | 13.0 |
| EOS006164 | 0.32 | 12.9 |
| EOS006165 | 0.41 | 2.2 |
| EOS006166 | 1.21 | 5.9 |
| EOS006167 | 10.2 | 1.6 |
| EOS006168 | 2.99 | 1.9 |
| EOS006169 | 3.45 | 1.9 |
| EOS006170 | 8.20 | 1.1 |
| EOS006171 | 2.8 | — |
| EOS006172 | 0.09 | 9.8 |
| EOS061730 | 0.30 | 8.2 |

TABLE 20-continued

| Binding affinity to human TREM2 | | |
|---|---|---|
| Antibody | kD (nM) | Fold over isotype |
| EOS006174 | 0.09 | 14.9 |
| EOS006175 | 1.06 | 5.8 |
| EOS006176 | ND | 13.1 |
| EOS006177 | 0.19 | 17.3 |
| EOS006178 | ND | 5.4 |
| EOS006179 | 3.13 | 11.4 |
| EOS006180 | ND | 4.1 |
| EOS006181 | ND | 9.3 |
| PN-37012 | 6.8 | — |

ND = not determined

Example 5: Stabilization of Membranal TREM2 by Anti-TREM2 Antibodies

In order to investigate the ability of anti-TREM2 antibodies to stabilize TREM2 at the cell surface and prevent its shedding, CHO OE hTREM2-hDAP12 cells were used for a flow cytometry-based stabilization assay. Benchmark antibody 14D3 was used as positive control.

Figure 3:
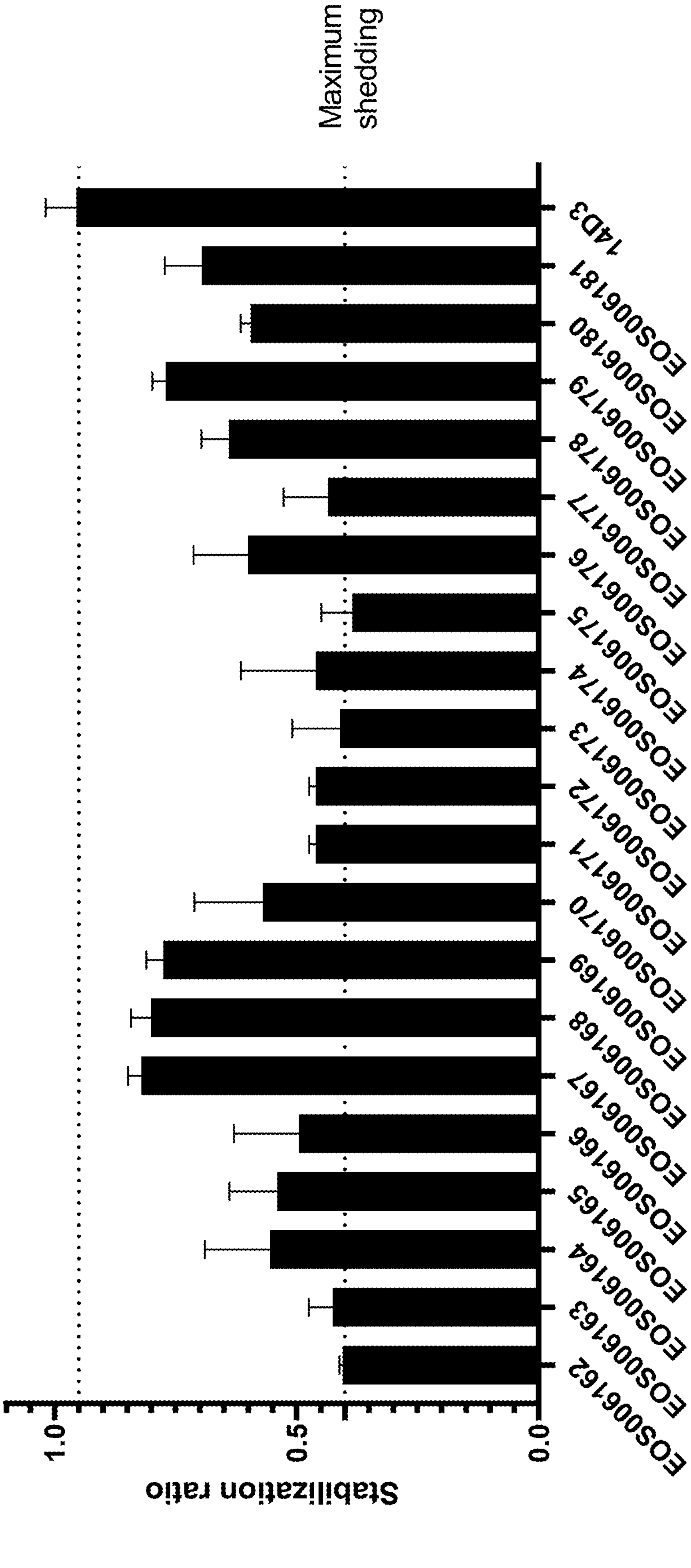
FIG. 3 shows stabilization of TREM2 at cell surface (CHO-K1 cells engineered to overexpress hTREM2-hDAP12) induced by exemplary anti-TREM2 antibodies. Data shown are from 2 independent replicates. A ratio closer to 1 indicates a good stabilization of membrane TREM2 at cell surface by the antibody was achieved. An antibody was considered as stabilizing when the stabilization ratio was >0.7. The dashed line labeled "Maximum shedding" indicates the stabilization ratio obtained without any primary antibody bound in presence of PMA. Benchmark antibody 14D3 was used as positive control.
Figure 4A:
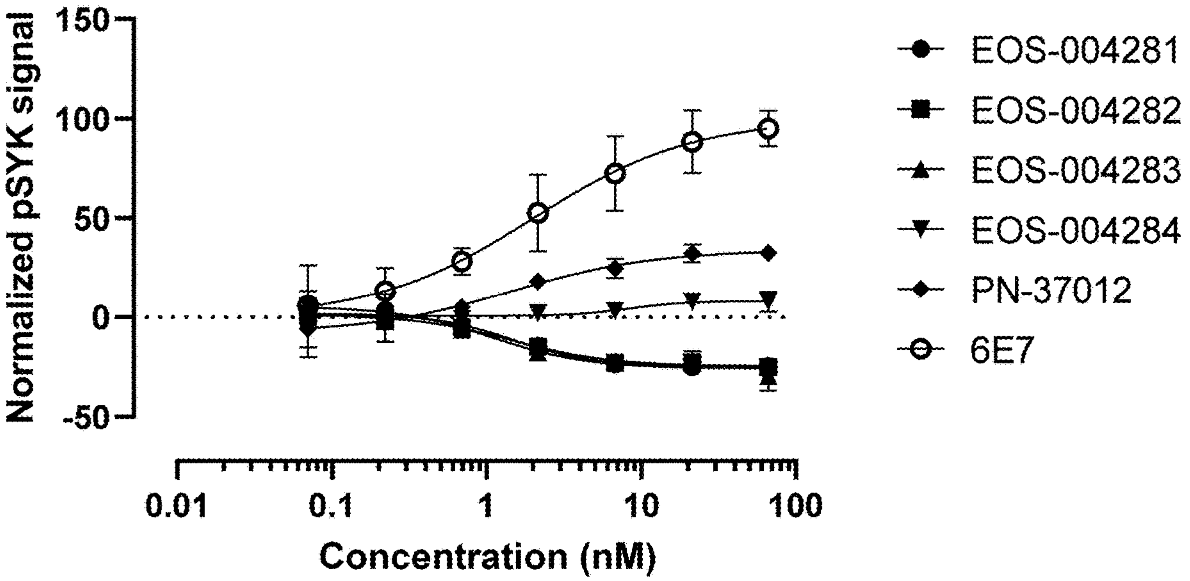
FIGS. 4A-4E show agonist activity of anti-TREM2 IgG1 antibodies on HEK293T overexpressing human TREM2/DAP12. Agonist effect has been assessed by pSYK and total SYK measurements with AlphaLISA technique.
Figure 4B:
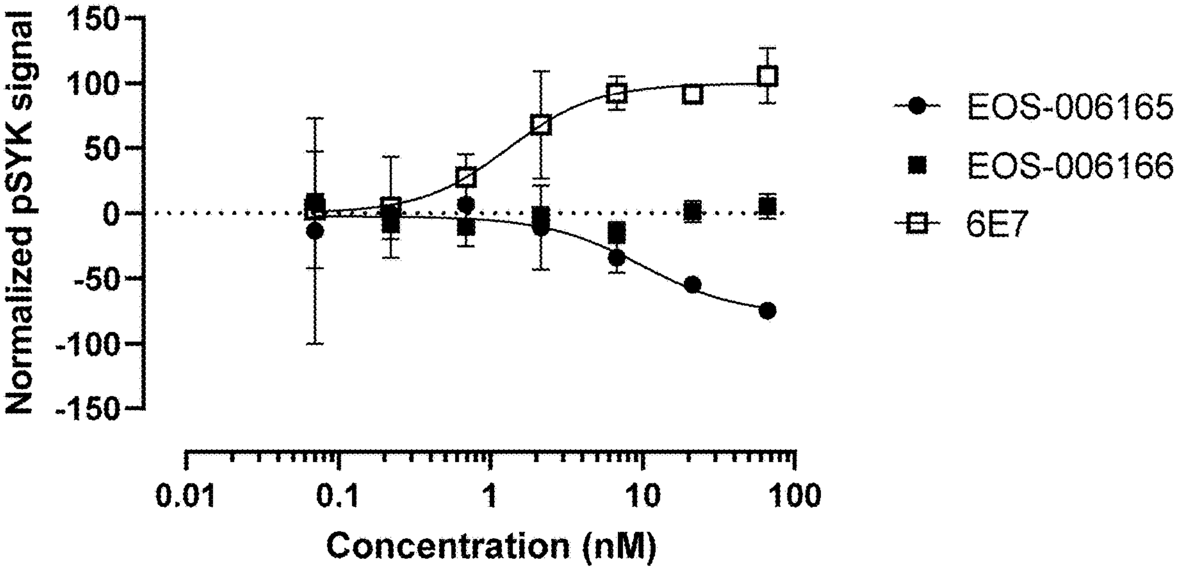
Figure 4C:
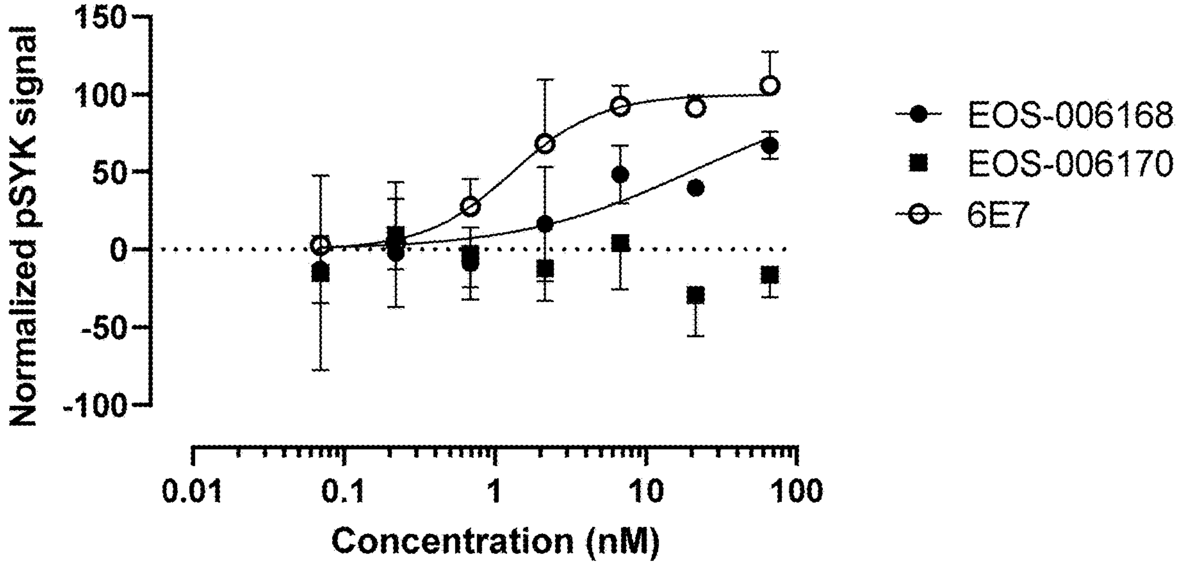
Figure 4D:
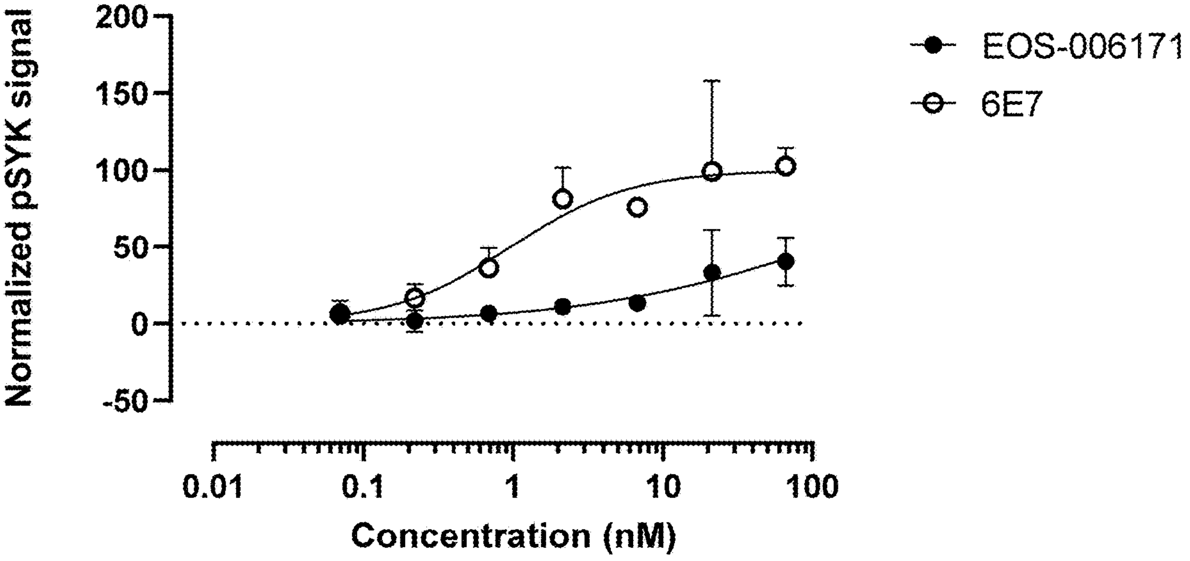
Figure 4E:
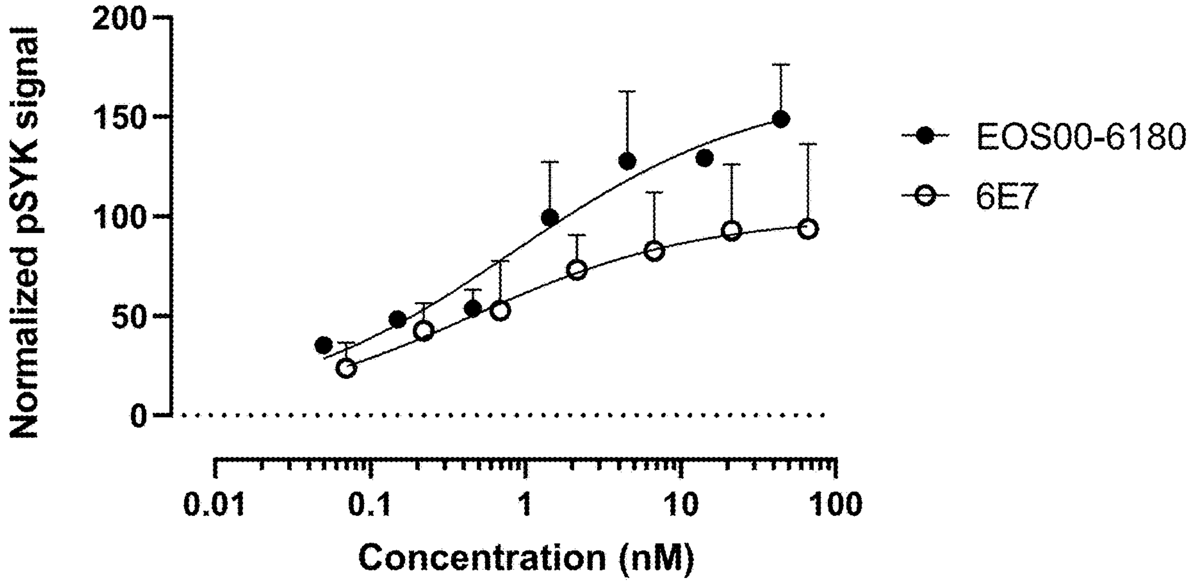
Figure 5A:
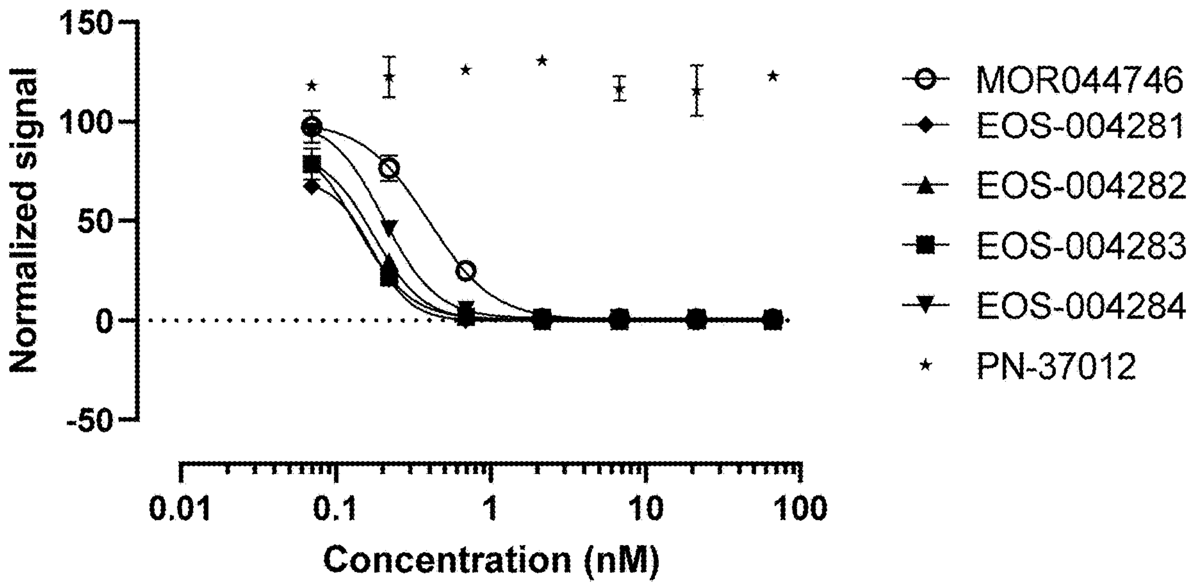
FIGS. 5A-5D show results from a competition assay for the occupancy of TREM2 between anti-TREM2 antibodies and ligand low-density lipoprotein (LDL). The competition between LDL and anti-TREM2 antibodies was assessed using LDL coupled with Alexafluor-488 and measured by flow cytometry.
Figure 5B:
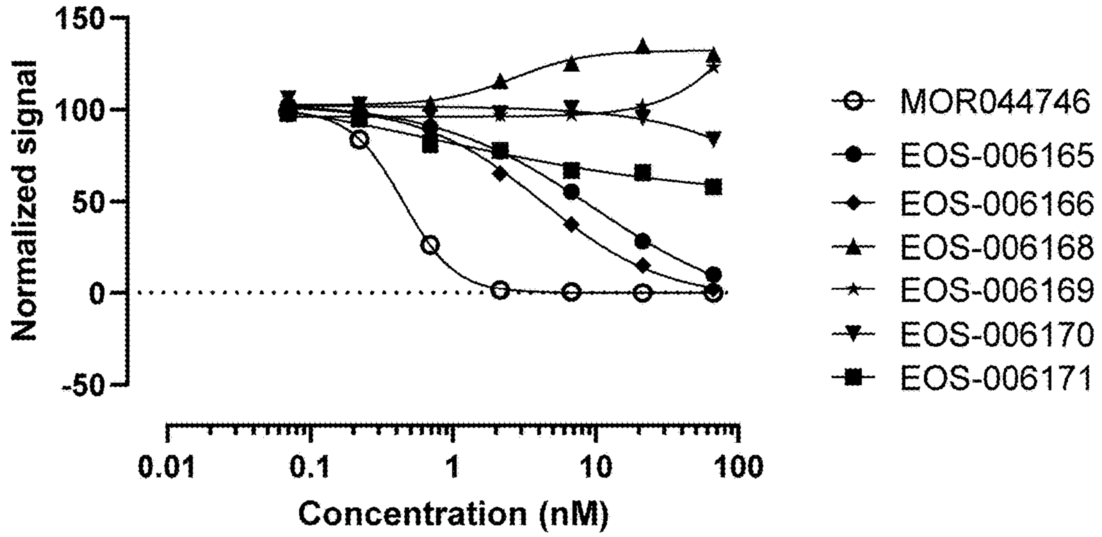
Figure 5C:
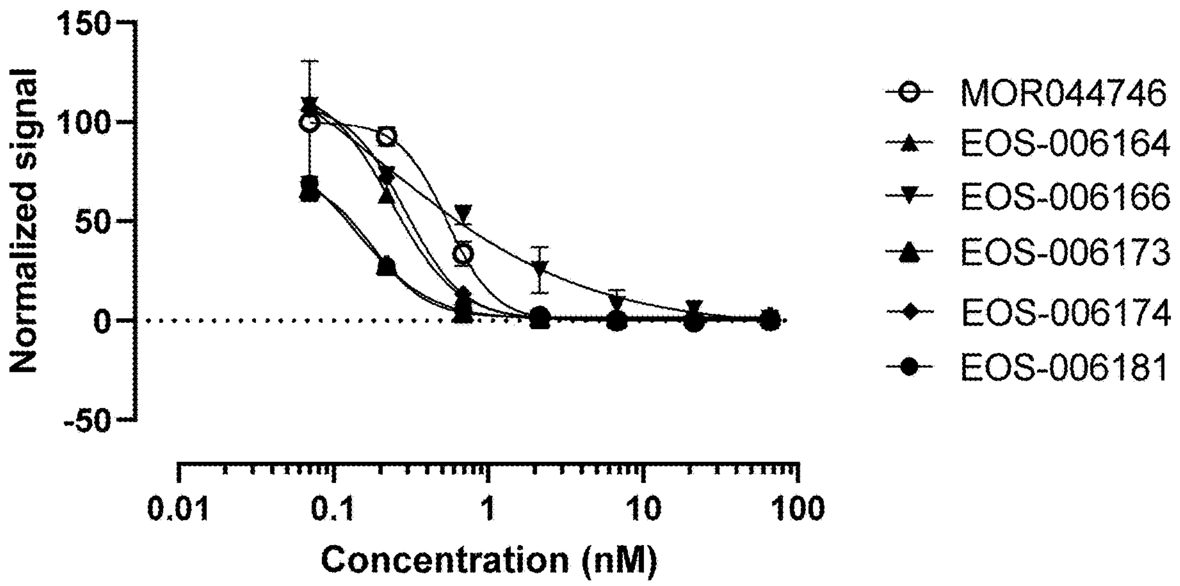
Figure 5D:
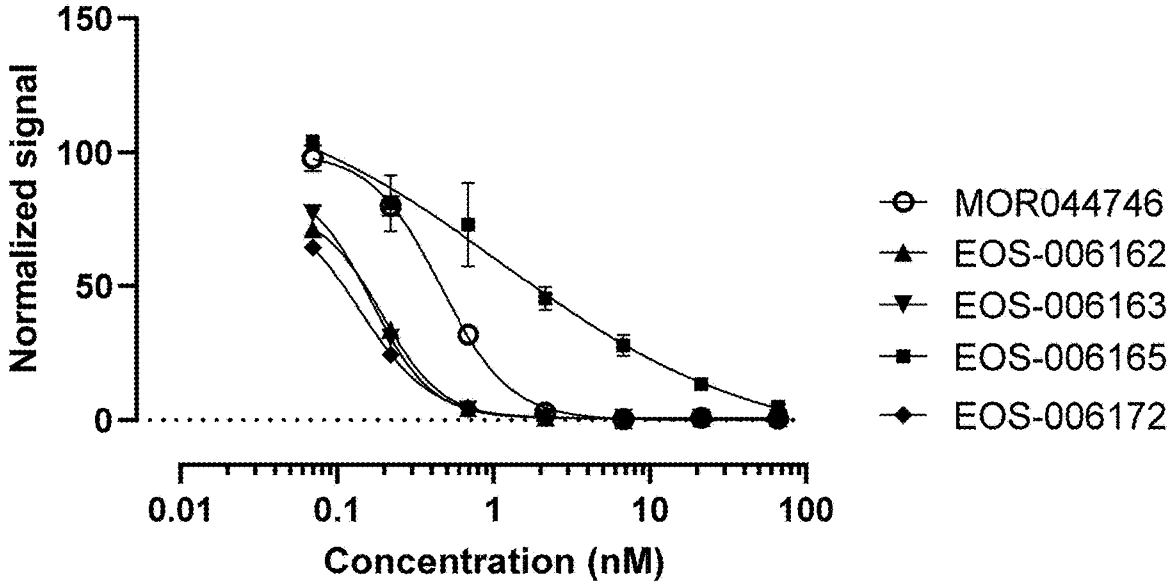
Figure 6B:
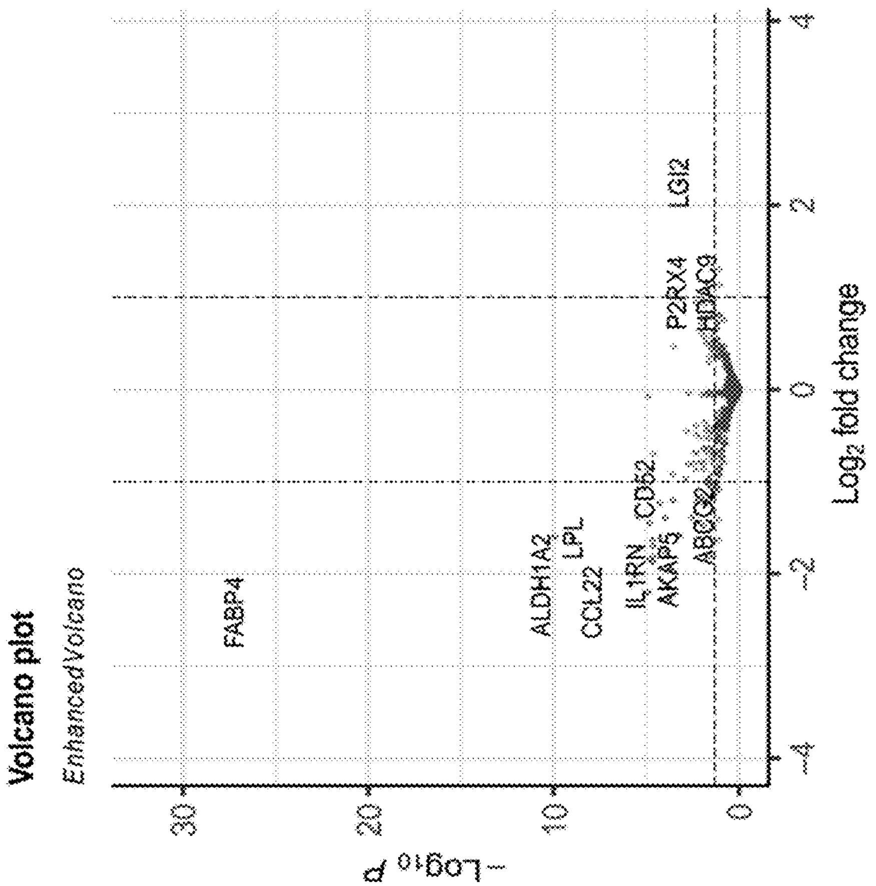
FIGS. 6A-6L show gene regulation by anti-TREM2 antibodies in a macrophage polarization assay. M2a-like macrophages were differentiated from monocytes in the presence of exemplary anti-TREM2 antibodies at 10 μg/ml. All antibodies were applied in 2 different isotypes WT hIgG1 and N297A hIgG1 and gene expression was measured by RNA sequencing with Lexogen. Volcano plots depict −log 10P that represents the level of significance of each gene as a function of log 2 fold change that represents the difference between the up- or down-regulation for each gene relative to its control isotype. Each dot represents one gene.
Figure 6A:
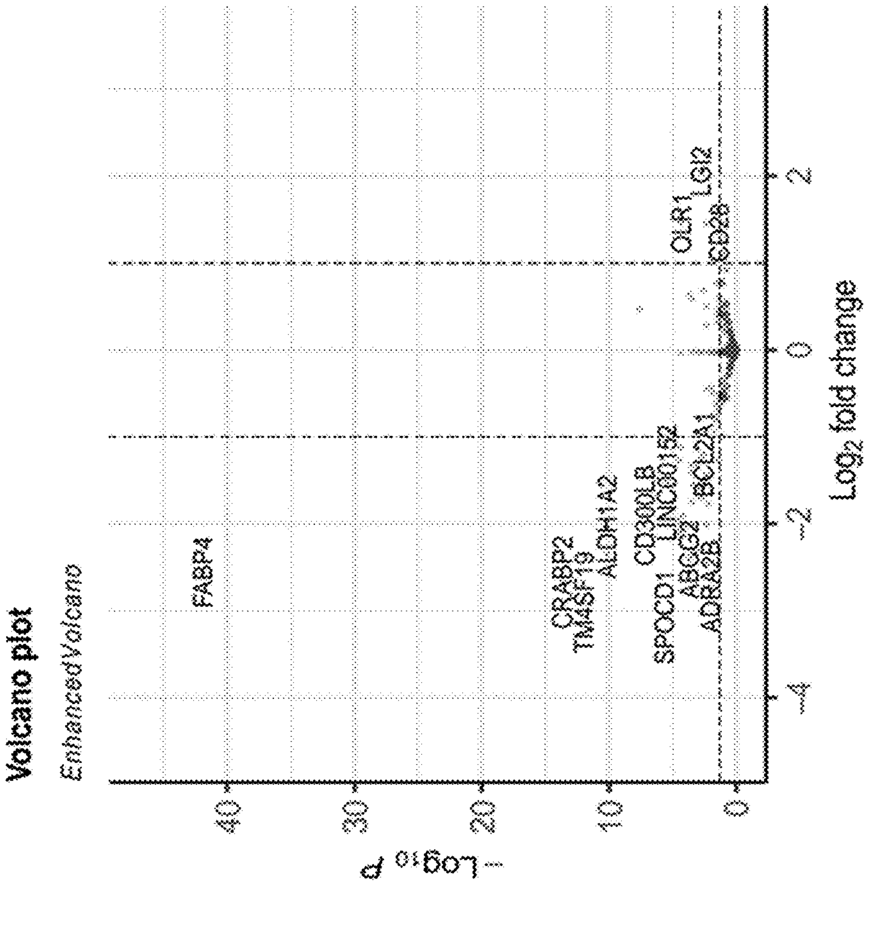
Figure 6C:
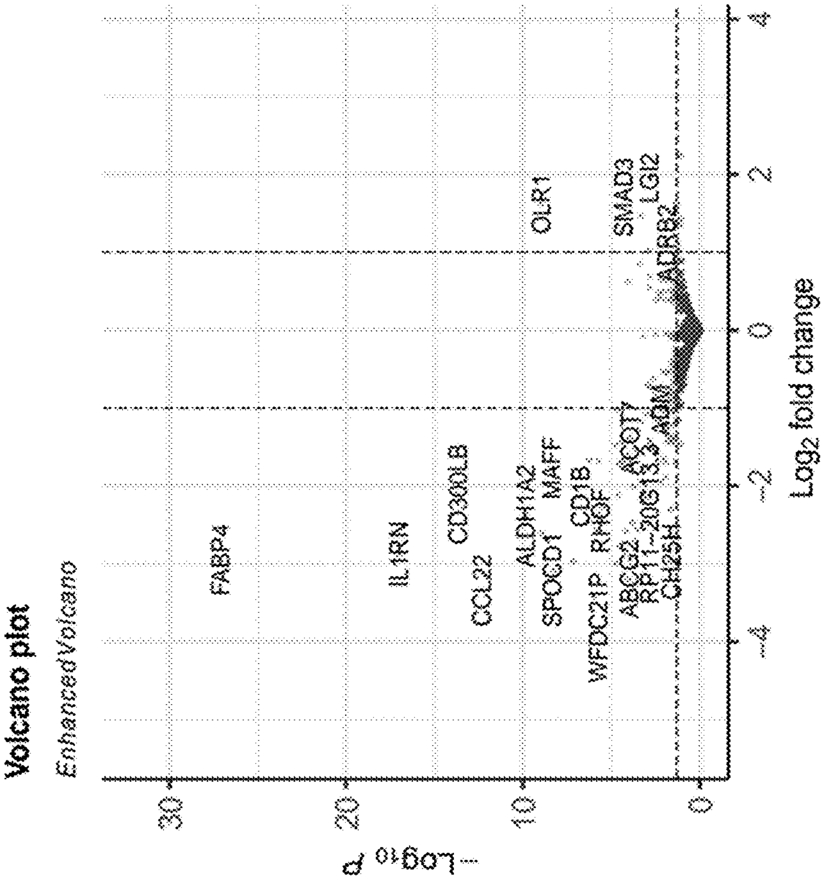
Figure 6D:
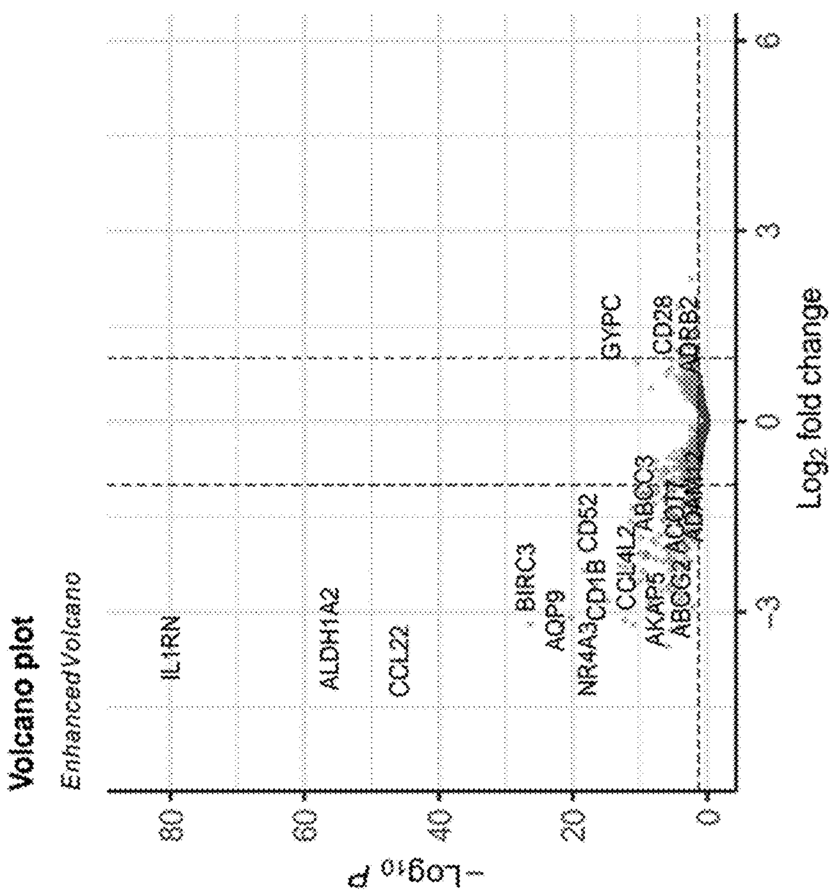
Figure 6E:
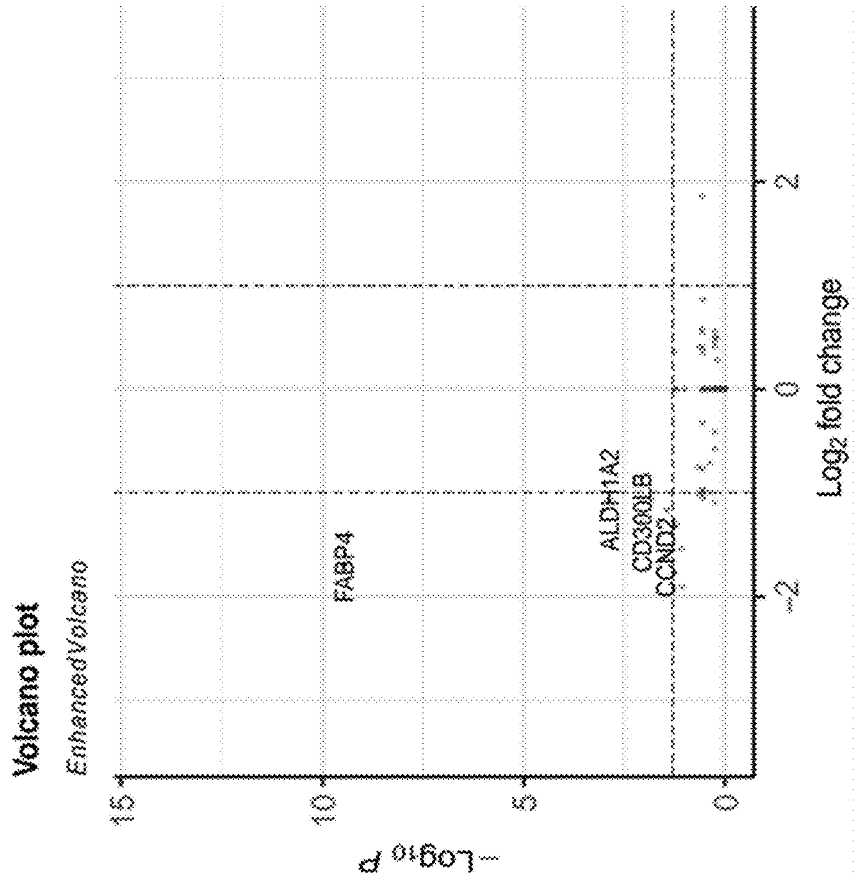
Figure 6F:
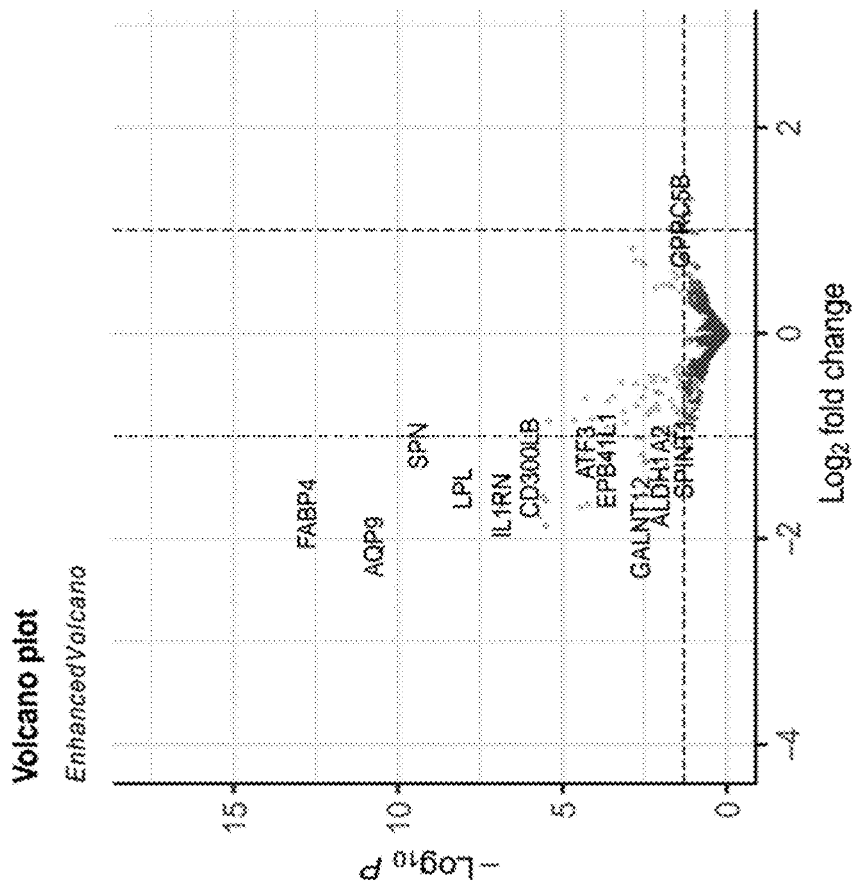
Figure 6H:
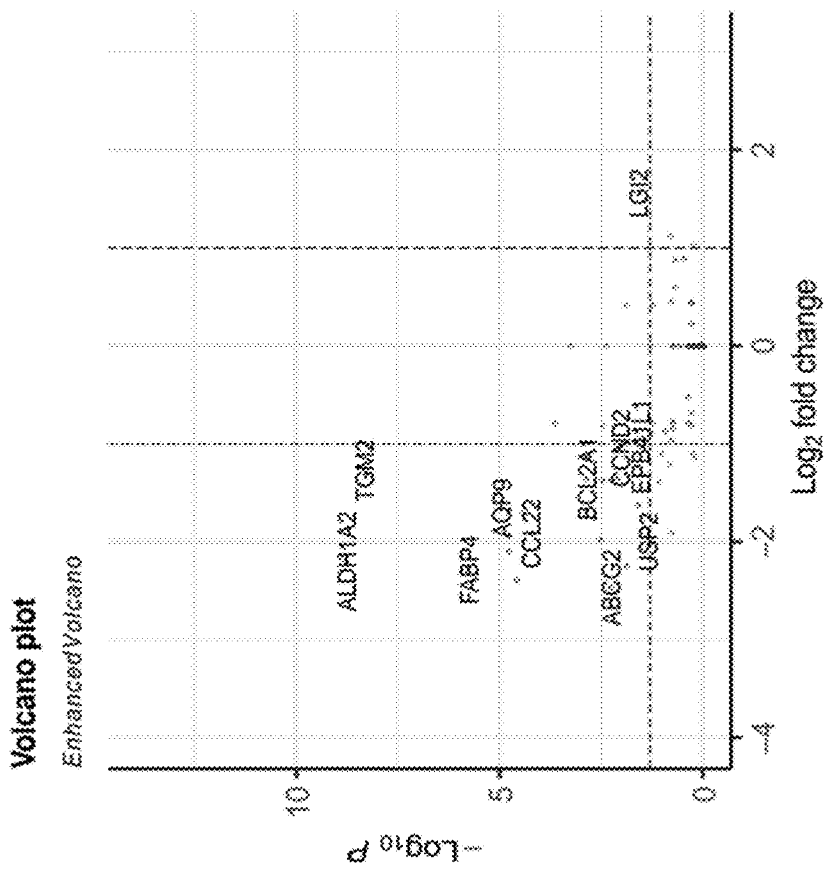
Figure 6G:
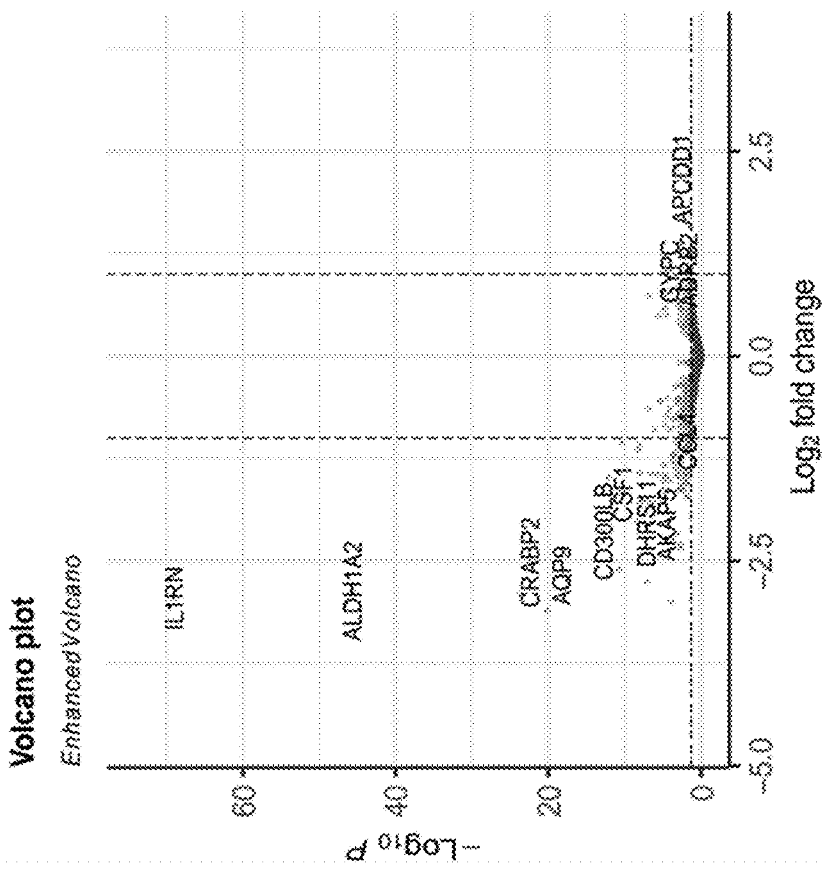
Figure 6I:
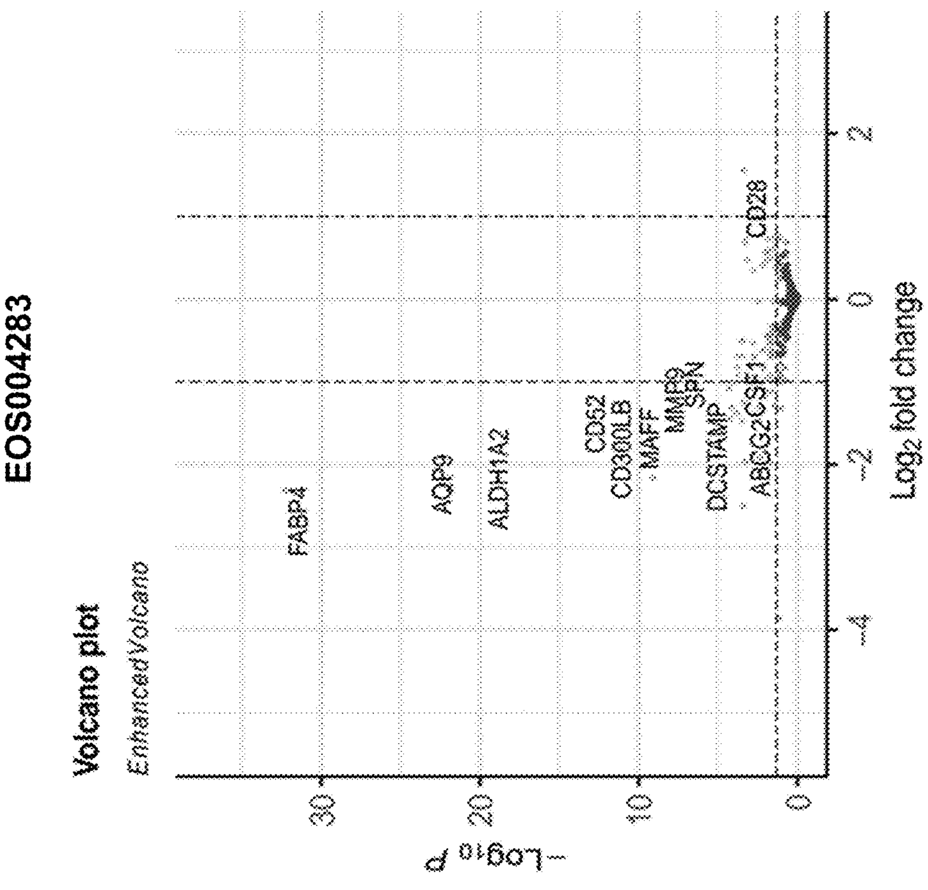
Figure 6J:
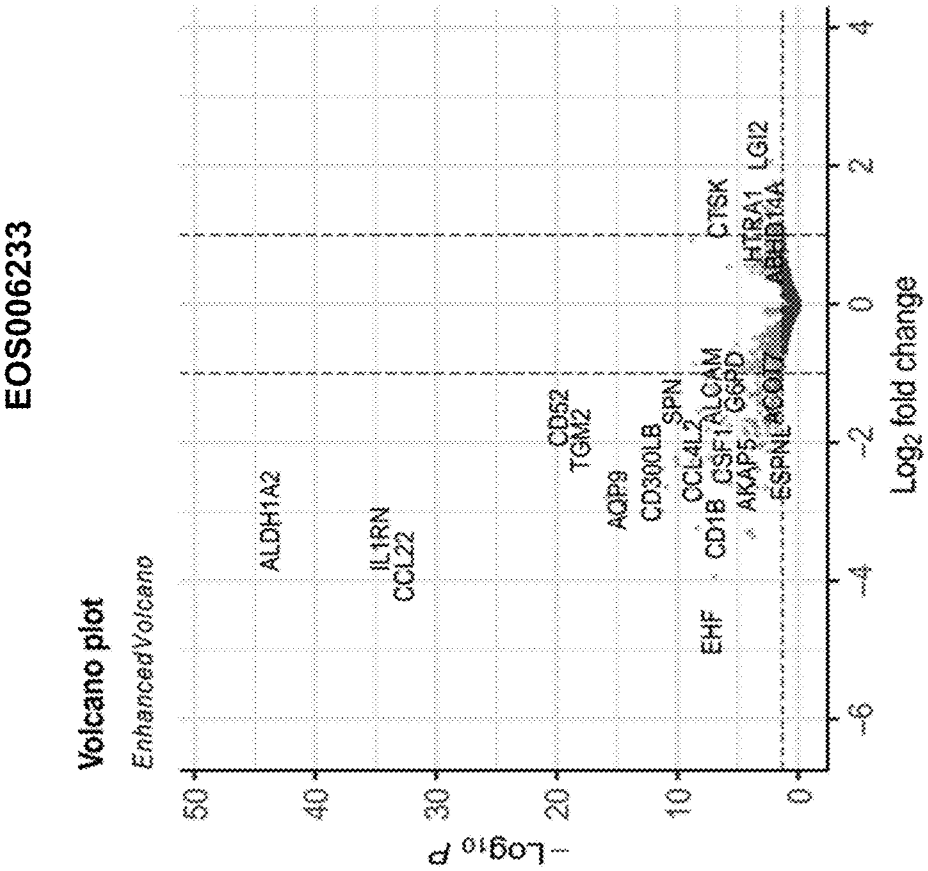
Figure 6L:
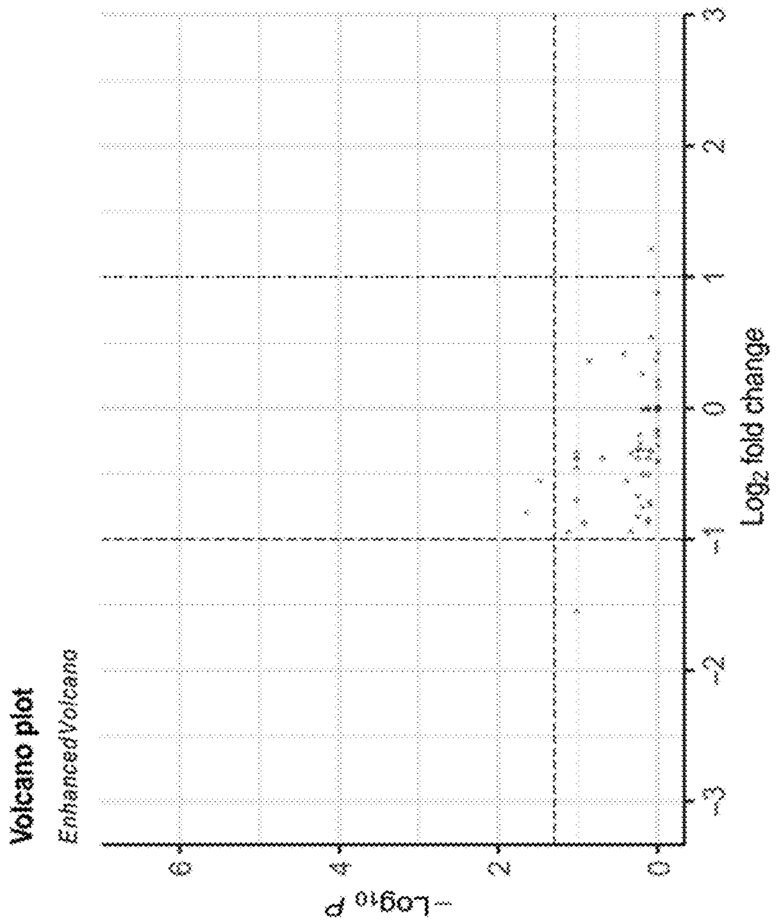
Figure 6K:
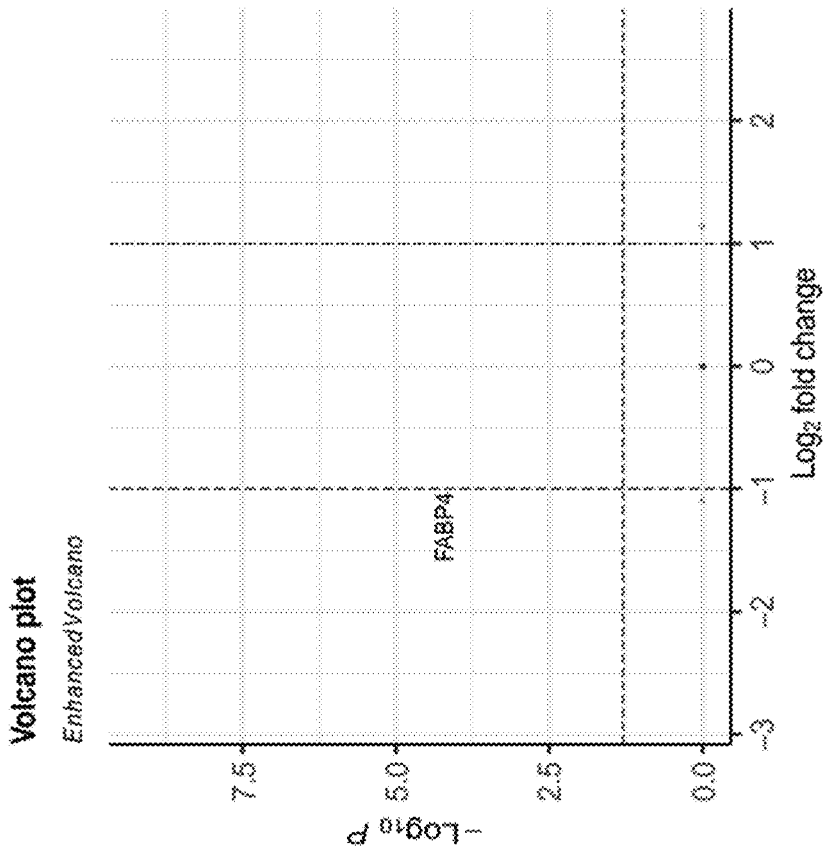

Cells were labelled with exemplary anti-TREM2 antibodies (final concentration of 10 μg/ml) before treatment with either TAPI-1 (5 μM) and GI254023X (5 μM) (ADAM inhibitors) or PMA (25 ng/ml) (inducing TREM2 shedding) for 1 hr at room temperature. After washing, primary antibodies bound to TREM2 were detected with a secondary anti-human Fc PE-labelled for 30 min at 4° C. The stabilization ratio was calculated as ratio of MFI from PMA-treated cells over MFI from cells treated with ADAM inhibitors. A ratio closer to 1 indicated a good stabilization of membranal TREM2 at cell surface by the antibody. An antibody was considered to be stabilizing if the ratio >0.7 (FIG. 3 and Table 21).

In order to assess minimal ratio that could be obtained, cells were incubated with either sheddase stimulator, PMA, or ADAM inhibitors, TAPI-1 and GI254023X, without pre-incubation with anti-TREM2 antibodies. After washing, TREM2 receptors left at cell surface were detected by an anti-TREM2 PE-labelled antibody and fluorescence intensity was measured by flow cytometry. In order to prove that reduction of TREM2 at cell surface was due to shedding and not internalization of the receptors, cells were also incubated with both PMA and ADAM inhibitors. Addition of ADAM inhibitors rescued TREM2 loss caused by incubation with PMA (data not shown). Maximum shedding is indicated by the ratio obtained without any primary antibody bound.

TABLE 21

| Stabilization of TREM2 by anti-TREM2 antibodies | | |
|---|---|---|
| Antibody | Stabilization ratio (Mean of 2 replicates) | Stabilizes TREM2 at cell surface |
| EOS006162 | 0.40 | No |
| EOS006163 | 0.42 | No |
| EOS006164 | 0.55 | No |
| EOS006165 | 0.54 | No |
| EOS006166 | 0.49 | No |
| EOS006167 | 0.82 | Yes |
| EOS006168 | 0.80 | Yes |
| EOS006169 | 0.78 | Yes |
| EOS006170 | 0.57 | No |
| EOS006171 | 0.46 | No |
| EOS006172 | 0.46 | No |
| EOS006173 | 0.41 | No |

TABLE 21-continued

| Stabilization of TREM2 by anti-TREM2 antibodies | | |
|---|---|---|
| Antibody | Stabilization ratio (Mean of 2 replicates) | Stabilizes TREM2 at cell surface |
| EOS006174 | 0.46 | No |
| EOS006175 | 0.39 | No |
| EOS006176 | 0.60 | No |
| EOS006177 | 0.44 | No |
| EOS006178 | 0.64 | No |
| EOS006179 | 0.77 | Yes |
| EOS006180 | 0.60 | No |
| EOS006181 | 0.69 | No |
| 14D3 | 0.96 | Yes |

Example 6: Cross-Reactivity of Anti-TREM2 Antibodies to Cynomolgus and Mouse TREM2

Cross-reactivity of anti-TREM2 antibodies to cynomolgus TREM2 (cynoTREM2) was assessed using CHO over-expressing cynoTREM2-DAP12 (Table 22). Benchmark antibodies, AB52 and PN-37012, were examined for comparison.

Seventeen anti-TREM2 antibodies and benchmark antibody Ab52 were considered cross-reactive to cynoTREM2 based on a fold change of CHO-cynoTREM2 over CHO empty vector of higher than 50. Two anti-TREM2 antibodies were considered to have low cross-reactivity to cynoTREM2 (fold change from 5 and 50). One anti-TREM2 antibody was considered to be not cross-reactive to cynoTREM2 (fold change less than 5). Benchmark antibody PN-37012 displayed a fold change of 5.7 and was thus considered to have low-to-no cross-reactivity to cynoTREM2.

TABLE 22

| Cross-reactivity to cynomolgus TREM2 | | | |
|---|---|---|---|
| Antibody | Binding to CHO-cTREM2 MFI | MFI Fold change (CHO-cTREM2 over CHO-EV) | Considered cross-reactive |
| EOS006162 | 17125 | 392.8 | Yes |
| EOS006163 | 17737 | 395.0 | Yes |
| EOS006164 | 14217 | 276.6 | Yes |
| EOS006165 | 8505 | 189.4 | Yes |
| EOS006166 | 25519 | 601.9 | Yes |
| EOS006167 | 7221 | 127.8 | Yes |
| EOS006168 | 194 | 3.3 | No |
| EOS006169 | 5136 | 125.0 | Yes |
| EOS006170 | 1646 | 42.8 | Low |
| EOS006171 | 13357 | 494.7 | Yes |
| EOS006172 | 17165 | 417.6 | Yes |
| EOS006173 | 13956 | 329.2 | Yes |
| EOS006174 | 15746 | 322.7 | Yes |
| EOS006175 | 10156 | 232.9 | Yes |
| EOS006176 | 20424 | 388.3 | Yes |
| EOS006177 | 19576 | 354.6 | Yes |
| EOS006178 | 19714 | 333.6 | Yes |
| EOS006179 | 21210 | 275.1 | Yes |
| EOS006180 | 2461 | 45.7 | Low |
| EOS006181 | 11908 | 250.7 | Yes |
| Ab52 | 25519 | 601.9 | Yes |
| PN-37012 | 490 | 5.7 | No-Low |

Cross-reactivity to mouse TREM2 was assessed using CT26 cells over-expressing mouse TREM2 and DAP12 (Table 23). Eight anti-TREM2 antibodies and both benchmark antibodies were considered cross-reactive to mouse TREM2 (MFI higher than isotype control and fold change of CT26-TREM2 over the CT26 Empty Vector higher than 5).

The remaining anti-TREM2 antibodies were considered as being low to not cross-reactive (fold change less than 5). EOS006171 was not tested due to clear non-cross-reactivity preliminary data by octet (data not shown).

TABLE 23

Cross-reactivity to mouse TREM2

| Antibody | Binding to CT26-TREM2 MFI | MFI Fold change (CT26-TREM2 over ) CT26-EV | Isotype control on CT26-TREM2 MFI | Considered cross-reactive |
|---|---|---|---|---|
| EOS006162 | 1998 | 6.4 | 2173 | No |
| EOS006163 | 1381 | 5.0 | 402 | No-low |
| EOS006164 | 6545 | 21.4 | 345 | Yes |
| EOS006165 | 649 | 2.3 | 2173 | No |
| EOS006166 | 644 | 2.2 | 295 | No-low |
| EOS006167 | 2060 | 4.7 | 2173 | No |
| EOS006168 | 655 | 1.6 | 2173 | No |
| EOS006169 | 649 | 1.8 | 679 | No |
| EOS006170 | 322 | 1.0 | 679 | No |
| EOS006171 | — | — | — | No |
| EOS006172 | 1658 | 4.9 | 2173 | No |
| EOS006173 | 3942 | 11.0 | 679 | Yes |
| EOS006174 | 10087 | 34.3 | 345 | Yes |
| EOS006175 | 1394 | 3.9 | 679 | No-Low |
| EOS006176 | 6335 | 15.0 | 345 | Yes |
| EOS006177 | 8677 | 21.4 | 345 | Yes |
| EOS006178 | 6792 | 15.8 | 345 | Yes |
| EOS006179 | 8697 | 7.3 | 679 | Yes |
| EOS006180 | 1892 | 1.8 | 2173 | No |
| EOS006181 | 4692 | 17.4 | 345 | Yes |
| Ab52 | 8814 | 33.6 | 402 | Yes |
| PN-37012 | 6754 | 21.0 | 302 | Yes |

Example 7: Agonist Activity of Anti-TREM2 Antibodies

Exemplary anti-TREM2 antibodies were tested in order to characterize their agonist effect on HEK293T cells overexpressing human TREM2/DAP12. Antibodies (dose response curves from 66.65 nM to 0.07 nM) were incubated for 30 min with cells in a soluble fashion and without any cross-linking method. Cells were then lysed to extract phosphorylated SYK (pSYK) and total SYK (TotSYK). Lysates were transferred in plate and mixed with acceptor and donor beads (per supplier protocol). After reaction step, plates were read in a multiplate reader allowing the measurement of AlphaLISA signal. Benchmark antibody 6E7 was used as positive control.

Different responses were observed (FIGS. 4A-4E). Indeed, some anti-TREM2 antibodies were able to induce SYK phosphorylation (agonist), whereas others did not agonize TREM2 as they did not induce SYK phosphorylation or even decreased it (possibly antagonist or reverse-agonist). (Table 24). Data are representative of 2 replicates (N=2).

TABLE 24

Agonist activity of anti-TREM2 antibodies

| Antibody | pSYK/TotSYK EC50 (nM) | Fold over isotype control at 66 nM |
|---|---|---|
| EOS-004281 | Not agonist | 0.335 |
| EOS-004282 | Not agonist | 0.367 |
| EOS-004283 | Not agonist | 0.267 |
| EOS-004284 | Not agonist | 0.928 |
| EOS-006165 | Not agonist | 1.03 |
| EOS-006166 | Not agonist | 1.75 |

TABLE 24-continued

Agonist activity of anti-TREM2 antibodies

| Antibody | pSYK/TotSYK EC50 (nM) | Fold over isotype control at 66 nM |
|---|---|---|
| EOS-006167 | 49.87 | 1.57 |
| EOS-006168 | 96 | 1.99 |
| EOS-006169 | 4267 | 2.43 |
| EOS-006170 | Not agonist | 1.31 |
| EOS-006171 | 9.7 | 2.40 |
| EOS-006172 | Not agonist | 0.590 |
| EOS-006162 | Not agonist | 0.785 |
| EOS-006180 | 1.51 | 2.436 |
| EOS-006175 | Not agonist | 0.757 |
| EOS-006179 | 14.5 | 2.521 |
| EOS-006173 | 1.08 | 1.336 |
| EOS-006163 | Not agonist | 0.701 |
| EOS-006177 | Not agonist | 0.950 |
| EOS-006178 | 3.89 | 2.506 |
| EOS-006176 | 4.05 | 2.645 |
| EOS-006174 | Not agonist | 0.897 |
| EOS-006164 | Not agonist | 1.155 |
| EOS-006181 | 1.088 | 2.84 |
| 6E7 | 1.289 | 1.925 |

Example 8: LDL Competition of Anti-TREM2 Antibodies

Exemplary anti-TREM2 antibodies were tested in order to characterize their ability to enter in competition with TREM2 ligand, LDL, on CHO overexpressing human TREM2/DAP12. Antibodies (dose response curves from 66.65 nM to 0.07 nM) were incubated for 30 min with cells in a soluble fashion, followed by an incubation with LDL coupled with Alexafluor-488 (at 1 μg/mL final) for 30 min. Finally, after 2 washes, cells were acquired on flow cytometer. The median MFI of Alexafluor-488 was used to plot the graphs. Benchmark antibody MOR044746 was used as positive control.

LDL (low-density lipoprotein), a cholesterol transporter, has been described as a ligand binding TREM2 on the hydrophobic region. It was observed that anti-TREM2 antibodies determined to bind to the hydrophobic region by octet were the only ones to compete with LDL. Among these antibodies competing in this hydrophobic region, the ones with a higher affinity were the strongest competitors. In contrast, one family of anti-TREM2 antibodies was shown to increase the binding of LDL-Alexafluor488 (EOS006168 family). Data are shown in FIGS. 5A-5D and in Table 25. Several exemplary antibodies, including EOS-006162, EOS-006163, EOS-006164, EOS-006172 and EOS-006173 showed enhanced competition compared to benchmark antibody MOR044746.

TABLE 25

LDL competition by anti-TREM2 antibodies (N = 2)

| Antibody | Competition IC50 (nM) |
|---|---|
| EOS-004281 | 0.171* |
| EOS-004282 | 0.175* |
| EOS-004283 | 0.138* |
| EOS-004284 | 0.203* |
| EOS-006165 | 5.29 |
| EOS-006166 | 0.865 |
| EOS-006167 | Not competing |
| EOS-006168 | Not competing |
| EOS-006169 | Not competing |
| EOS-006170 | Partial competition |

TABLE 25-continued

| LDL competition by anti-TREM2 antibodies (N = 2) | |
|---|---|
| Antibody | Competition IC50 (nM) |
| EOS-006171 | Partial competition |
| EOS-006172 | 0.115 |
| EOS-006162 | 0.116 |
| EOS-006180 | Not competing |
| EOS-006175 | 0.28* |
| EOS-006179 | Not competing |
| EOS-006173 | 0.145 |
| EOS-006163 | 0.169 |
| EOS-006177 | 0.195 |
| EOS-006178 | Not competing |
| EOS-006176 | Not competing |
| EOS-006174 | 0.3 |
| EOS-006164 | 0.265 |
| EOS-006181 | 0.280 |
| MOR044746 | 0.395 |

*Only 1 value generated

Example 9: Gene Regulation by Antagonist Anti-TREM2 Antibodies

M2a-like macrophages were differentiated from monocytes as described above in the presence of anti-TREM2 antibodies at 10 μg/mL. All antibodies were applied in 2 different isotypes, WT hIgG1 (EOS006337, EOS004284, EOS006335, EOS004281, EOS004283, EOS006341) and N297A hIgG1 (EOS006338, EOS006215, EOS006336, EOS004282, EOS006233 and EOS006342), to assess the impact of FcγR engagement on TREM2 biology. Gene expression was measured by RNA sequencing with Lexogen. Data are shown in FIGS. 6A-6L.

EOS006341 (WT IgG1) or EOS006342 (N297A IgG1) (agonist antibody) showed a very limited impact in this assay, while all the other anti-TREM2 antibodies strongly impacted the transcriptome of the monocyte-derived macrophages. Genes impacted by the anti-TREM2 antibodies mainly relate to immune responses (e.g., CCL22, IL1RN) and lipid metabolism (e.g., FABP4 and LPL), confirming a role for TREM2 in those processes and the ability of anti-TREM2 antibodies to modulate TREM2 biology. Moreover, multiples genes involved in extracellular matrix organization were significantly downregulated (e.g., MMP7, MMP9) by anti-TREM2 antibodies. The majority of the genes impacted by anti-TREM2 antibody treatment were downregulated.

Figure 7:
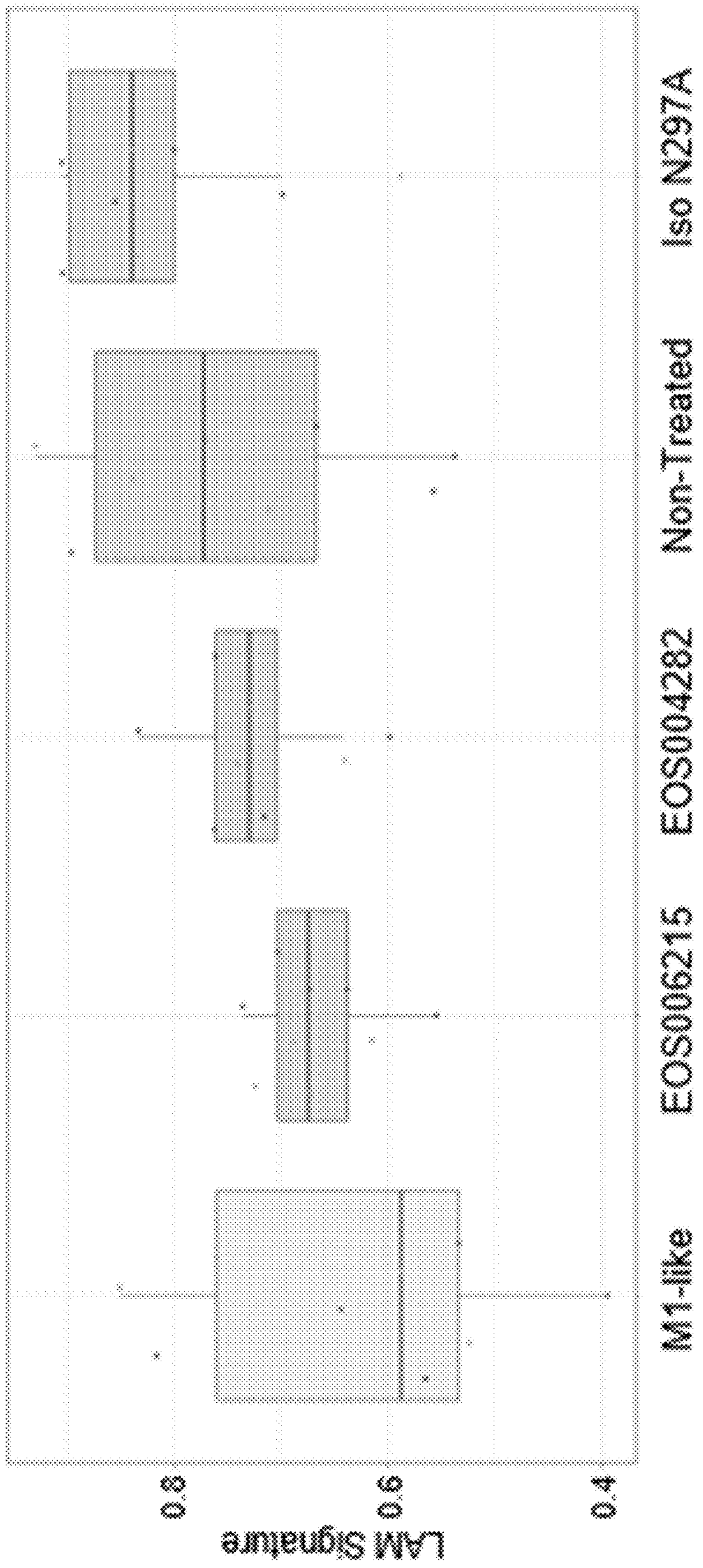
FIG. 7 shows lipid associated macrophage signature regulation by anti-TREM2 antibodies in a macrophage polarization assay. M2a-like macrophages were differentiated from monocytes in the presence of exemplary anti-TREM2 antibodies at 10 μg/mL. Cells treated with N297A hIgG1 isotype control (Iso N297A) and non-treated cells were included as negative controls. M1-like macrophages were included as a reference control. Gene expression was measured by RNA sequencing with Lexogen. The impact of gene signature described in Table 26 was measured. Each dot represents one healthy donor (n=9).

Both EOS006215 and EOS004282 downregulated the lipid-associated-tumor-associated macrophage (LA-TAM) gene signature described in Table 26 (Ma et al., Trends in Immunology, July 2022, 43(7): 546-63). Data are shown in FIG. 7.

TABLE 26

| LA-TAM gene signature | |
|---|---|
| Lipid associated signature genes | Transcription factors |
| ACP5, APOE, APOC1, ATF1, C1QA/B/C, CCL18, CD163, CD36, CD63, CHI3L1, CTSB/D/L, F13A1, FABP5, FOLR2, GPNMB, IRF3, LGALS3, LIPA, LPL, MARCO, MerTK, MMP7/9/12, MRC1, NR1H3, NRF1, NUPR1, PLA2G7, RNASE1, SPARC, SPP1, TFDP2, TREM2, ZEB1 | FOS/JUN, HIFIA, MAF/MAFB, NR1H3, TCF4, TFEC |

Example 10: Macrophage Reprogramming by Anti-TREM2 Antibodies

Exemplary anti-TREM2 antibodies were tested in order to characterize their ability to reprogram macrophages. CXCL10 was selected as a pro-inflammatory marker, while CCL17 is involved in the Treg chemoattraction in the tumor microenvironment and plays a role in the immunosuppressive properties of tumor associated macrophages.

Figure 8A:
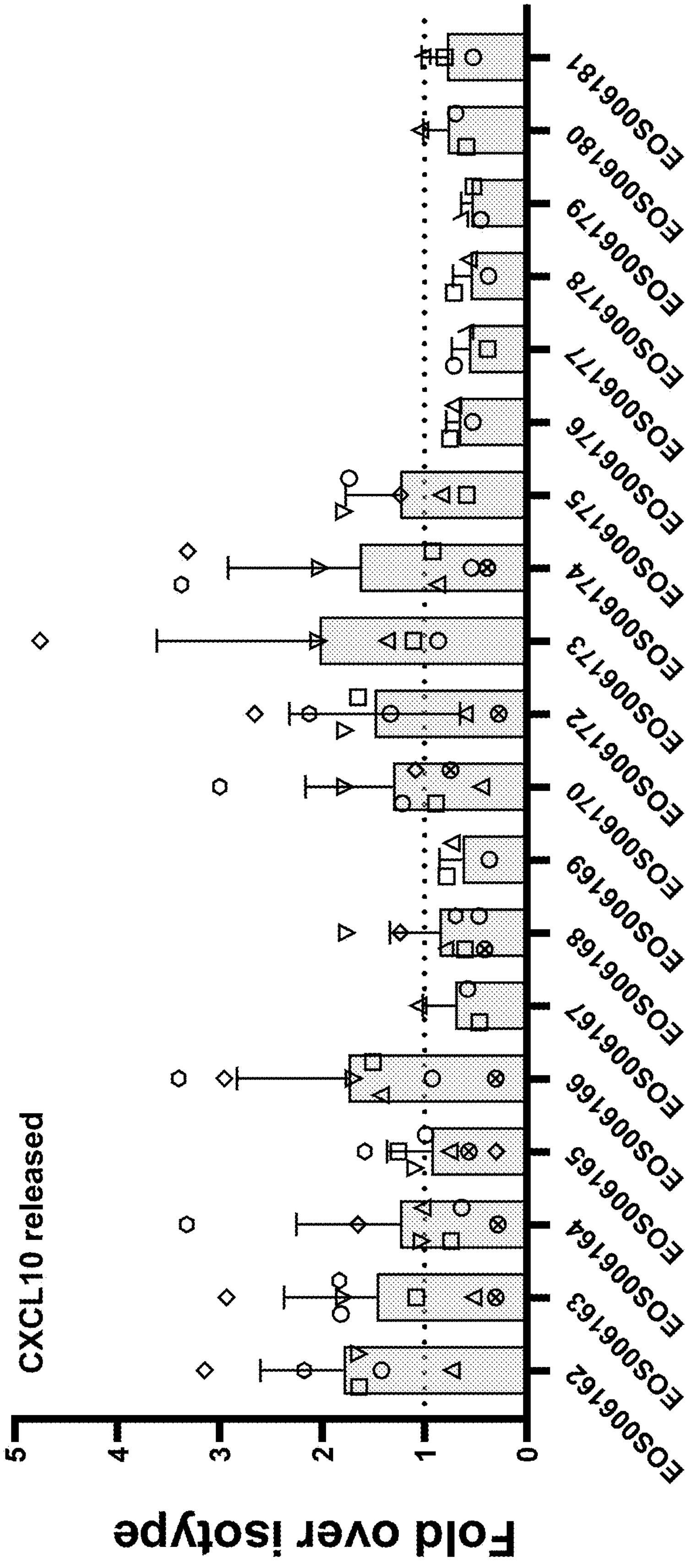
FIGS. 8A-8B show macrophage reprogramming by exemplary anti-TREM2 antibodies.
Figure 8B:
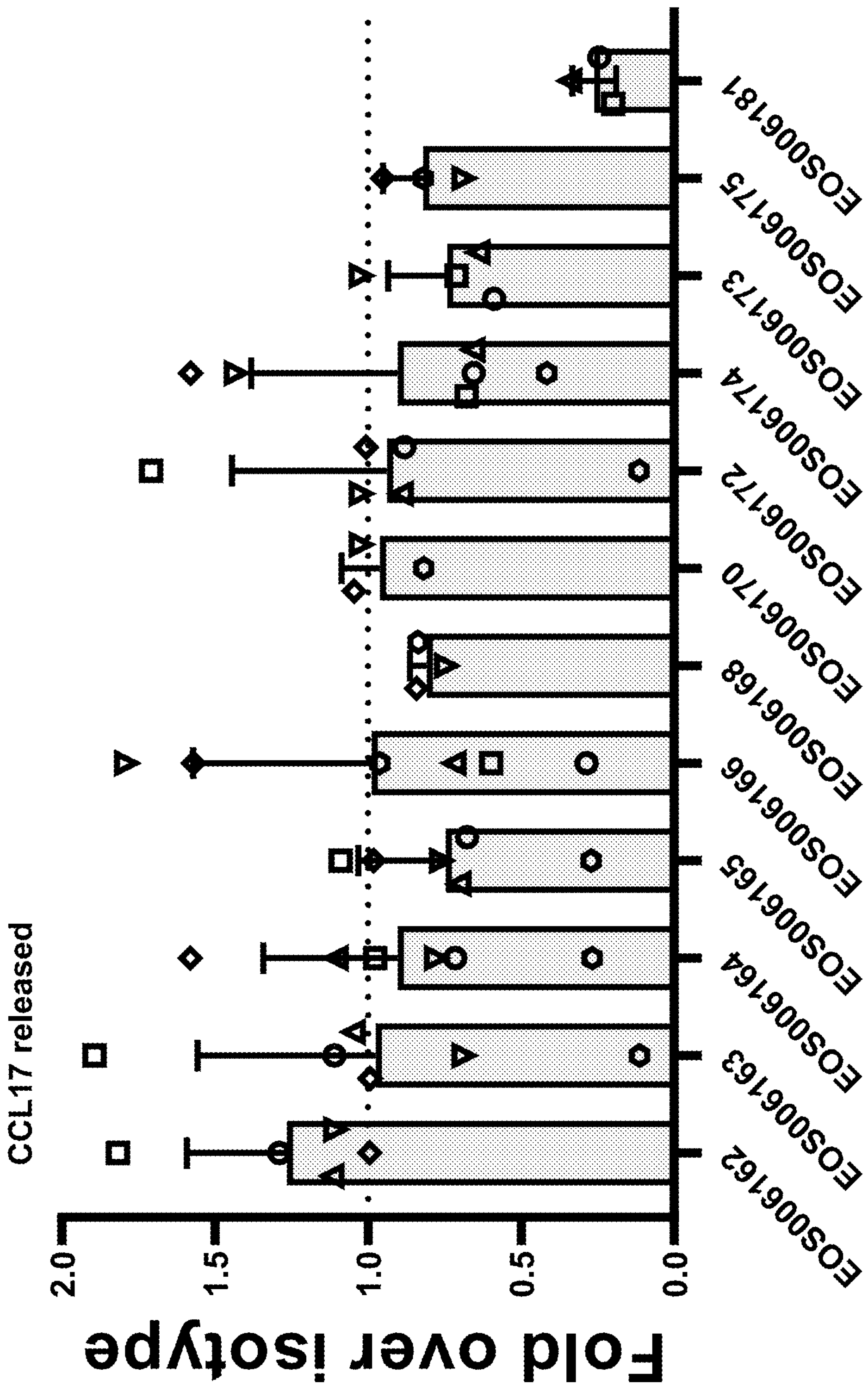

Monocytes isolated from healthy donors PBMCs were differentiated into M2a-like macrophages in the presence of the exemplary anti-TREM2 antibodies. The monocytes were treated for 6 days with M-CSF followed by 2 extra days of treatment with IL-4 and IL-13. Then the supernatant was harvested and CXCL10 and CCL17 concentrations were measured by LegendPlex and MSD. Effect of the anti-TREM2 antibodies on CXCL10 and CCL17 release by M2a-like macrophages is shown in FIGS. 8A-8B. Data are normalized against isotype control (yeast antibodies).

An increased secretion of CXCL10 was observed in response to incubation with the group of antibodies that compete with LDL and antagonize SYK phosphorylation when compared to the other exemplary anti-TREM2 antibodies and benchmark antibody PN-31702. Moreover, the impact on CCL17 production was limited, indicating that the overall function of the treated macrophages was shifted towards a more pro-inflammatory phenotype.

Example 11: Macrophage Reprogramming by EOS006215

Anti-TREM2 antibody EOS006215 was further tested in order to characterize its ability to reprogram macrophages by measuring its effect on CCL22, M-CSF and CXCL9 release.

Monocytes isolated from healthy donors PBMCs were differentiated into M2a-like macrophages in the presence of various concentrations of EOS006215, starting at 10 μg/mL (66.6 nM) followed by a 3-fold dilution series (9 points). The monocytes were treated for 6 days with M-CSF followed by 2 extra days of treatment with IL-4 and IL-13. Afterwards, the M2a-like macrophages were washed and restimulated overnight with LPS. Then, the supernatant was harvested and CCL22, M-CSF and CXCL9 concentrations were measured by MSD assay.

Figure 9A:
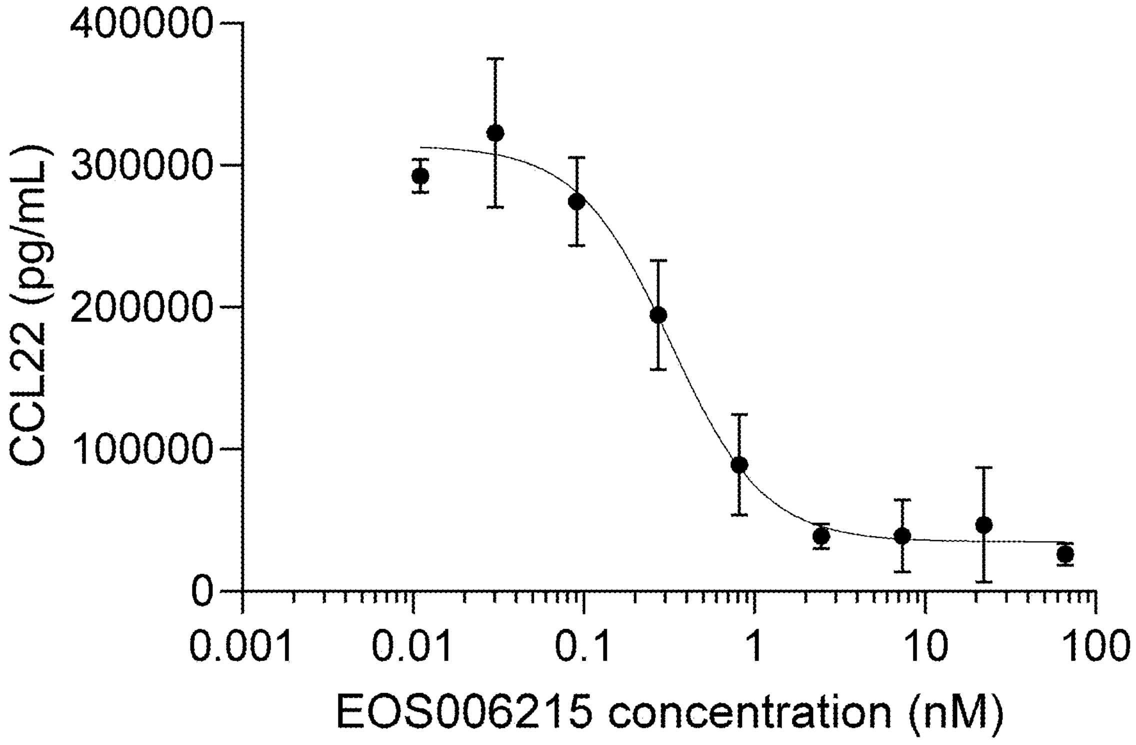
FIGS. 9A-9C show macrophage reprogramming potency of the EOS006215 anti-TREM2 antibody.
Figure 9B:
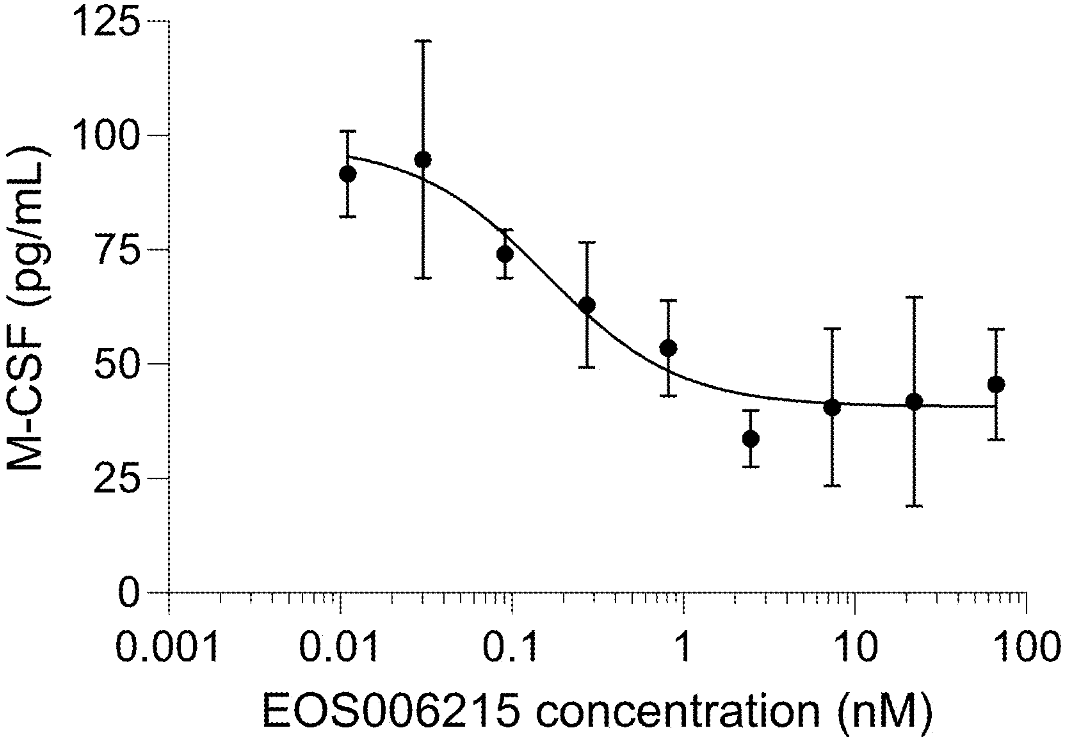
Figure 9C:
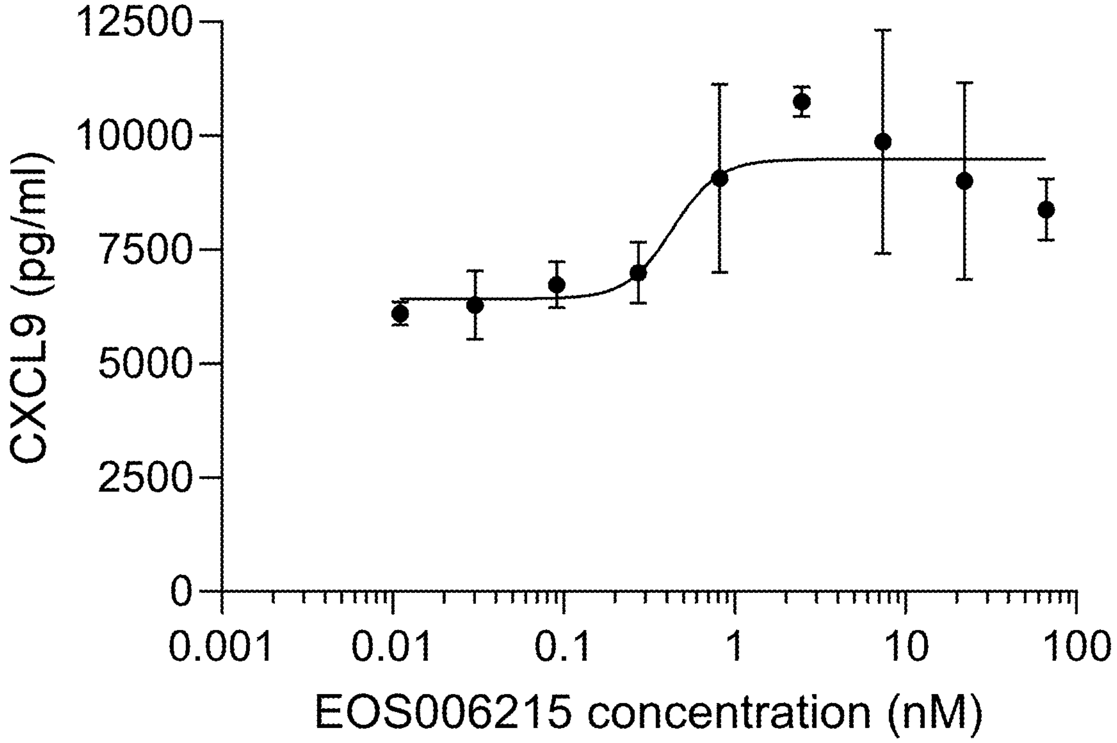

The effect of EOS006215 on M-CSF, CCL22 and CXCL9 release by M2a-like macrophages is shown in FIGS. 9A-9C. The measured IC50 for CCL22 and M-CSF are 0.32 nM and 0.16 nM, respectively, while the CXCL9 EC50 is 0.43 nM. These data demonstrate a reprograming of treated M2-like macrophages towards a pro-inflammatory phenotype.

Example 12: Rescue of T Cell Immunosuppression by Anti-TREM2 Antibodies

Figure 10:
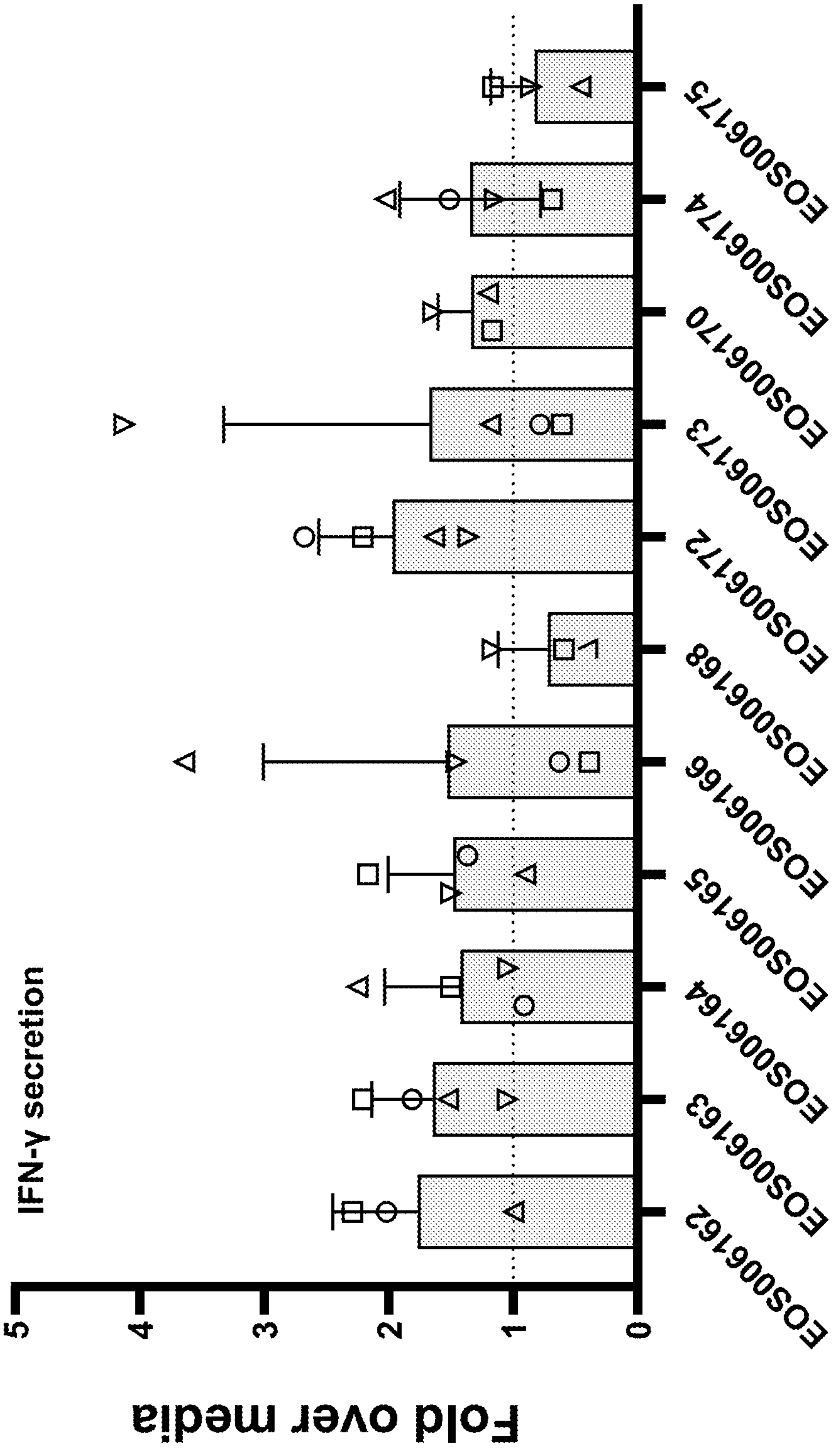
FIG. 10 shows IFN-γ secretion in co-culture of M2-like macrophages with autologous T cells in presence of anti-TREM2 antibodies. M2-like macrophages were differentiated from monocytes in the presence of the anti-TREM2 antibodies at 10 μg/mL, followed by a coculture with autologous CD3+ T cells and CD3/CD28 stimulation. After 5 days of coculture, the supernatant was harvested and IFN-γ concentration was measured by LegendPlex. Results are expressed as fold-increase over media. Each symbol represents a different donor (mean of quadruplicates).

Eleven exemplary anti-TREM2 antibodies were tested to characterize their ability to rescue T cell immunosuppression. Monocytes isolated from healthy donors PBMCs were differentiated into M2a-like macrophages in presence of exemplary anti-TREM2 antibodies as described above. On day 8, macrophages were washed and autologous $CD3^+$ T cells and anti-TREM2 antibodies were added to the macrophages for a co-culture experiment. During that time, T cells were stimulated with CD3/CD28 agonists in a soluble fashion. After 5 days of co-culture, the supernatant was harvested and IFN-γ concentration was measured by LegendPlex. The results are expressed in fold change over media as shown in FIG. 10 and Table 27.

The majority of exemplary anti-TREM2 antibodies induced an increase in IFN-γ secretion in comparison to both isotype and medium reference conditions. Only agonistic clone EOS006168 treatment led to a significant decrease in IFN-γ secretion and EOS006175 and PN-37012 (data not shown) had no effect.

TABLE 27

Median of fold-change in IFN-γ secretion over non-treated controls in an M2-like macrophages/T cells co-culture assay

| Antibody | Median Fold Change |
|---|---|
| Isotype yeast | 0.769 |
| EOS006165 | 1.444 |
| EOS006168 | 0.589 |
| EOS006170 | 1.340 |
| EOS006166 | 1.217 |
| EOS006174 | 1.436 |
| EOS006172 | 1.629 |
| EOS006162 | 1.903 |
| EOS006175 | 0.835 |
| EOS006173 | 1.102 |
| EOS006163 | 1.692 |
| EOS006164 | 1.202 |
| PN-37012 | 0.979 |

Example 13: Impairment of Efferocytosis by Anti-TREM2 Antibodies

Twelve exemplary anti-TREM2 antibodies were tested in order to evaluate their impact on efferocytosis. Efferocytosis is defined as the clearance of apoptotic cells by phagocytic cells such as macrophages and is known to be a strongly immunosuppressive process that could be, at least partly, mediated by TREM2 (Zhou et al., Cell Commun Signal. 2020 May 5, 18(1): 71; Wang et al., Immunity 2023 Jan. 10, 56(1): 58-77). The exemplary anti-TREM2 antibodies were compared with benchmark antibody PN-37012. Monocytes were isolated from healthy donor PBMCs using a positive selection ($CD14^+$). M2a-like macrophages were obtained as described above. On day 8, cells were washed and replated. On day 9, anti-TREM2 antibodies at 10 μg/mL were added to M2a-like macrophages. Then, apoptotic Jurkat cells were labelled with pHrodo and added to M2a-like macrophages at a 1:2 effector:target ratio. Coculture was analyzed by Incucyte technology. Results are expressed in total pHrodo area ($\mu m^2$/well) over time in FIGS. 11A and 11B and in fold over untreated after 3 hours of coculture in FIG. 11C.

Figure 11A:
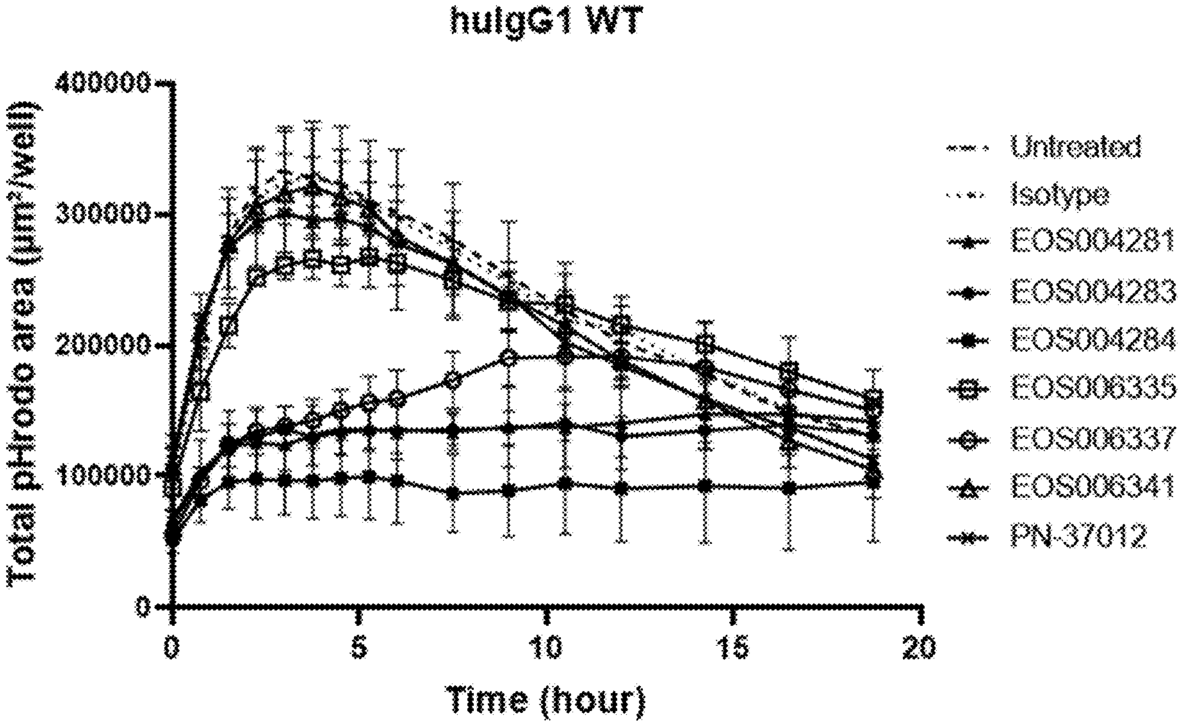
FIGS. 11A-11C show the impact of exemplary anti-TREM2 antibody on the efferocytosis of apoptotic Jurkat cells by M2a-like macrophages. M2a-like macrophages were treated in presence of anti-TREM2 antibodies at 10 μg/mL before being cultured with pHrodo-labelled apoptotic Jurkat cells. The level of pHrodo signal representing the apoptotic Jurkat phagocytosed by macrophages was measured over time by Incucyte technology. Results are expressed in total pHrodo area ($\mu m^2$/well) over time in FIGS. 11A and 11B and in fold over untreated in FIG. 11C.
Figure 11B:
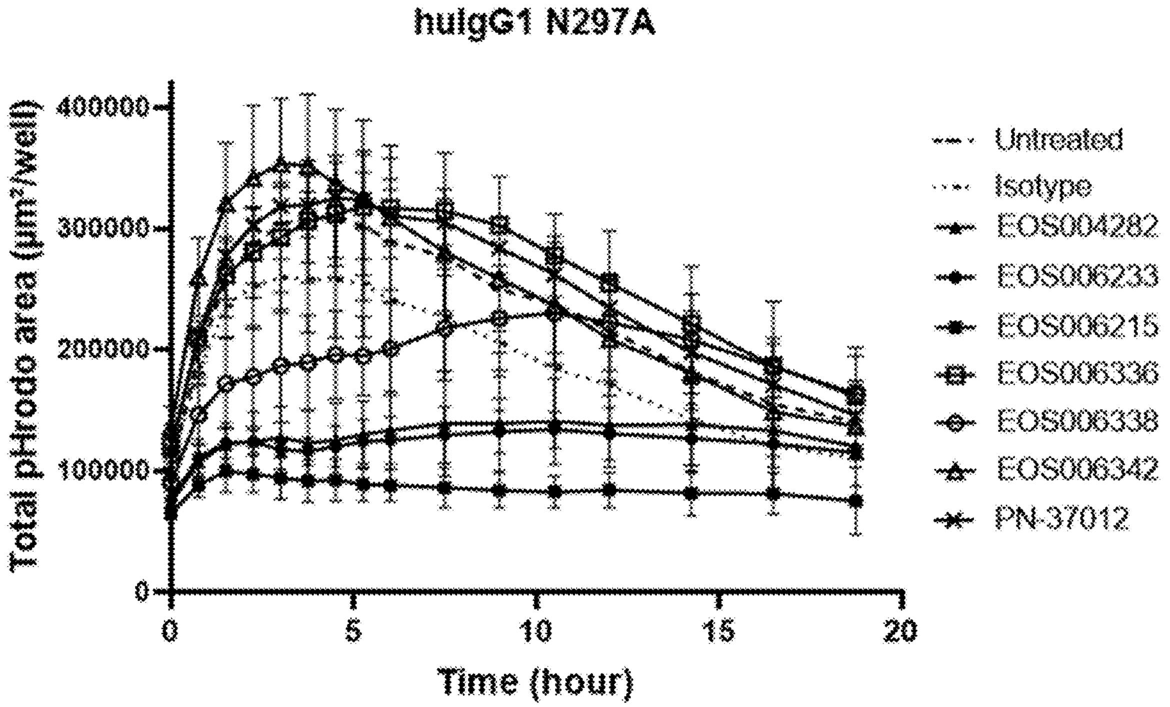

FIGS. 11A and 11B show that the total area of the pHrodo labelling increased over time in untreated and control isotype conditions. The treatment of M2a-like macrophages in the presence of EOS004281, EOS004282, EOS004283, EOS006233, EOS004284, EOS006215, EOS006337, and EOS006338 reduced levels of efferocytosis in comparison to their related control isotype. Some antibodies, such as EOS004281, EOS004283, and EOS004284, were very potent in decreasing efferocytosis in this assay. On the contrary, EOS006335, EOS006336, EOS006341, EOS006342, PN-37012 huIgG1 WT, and PN-37012 huIgG1 N297A did not reduce the level of efferocytosis.

Figure 11C:
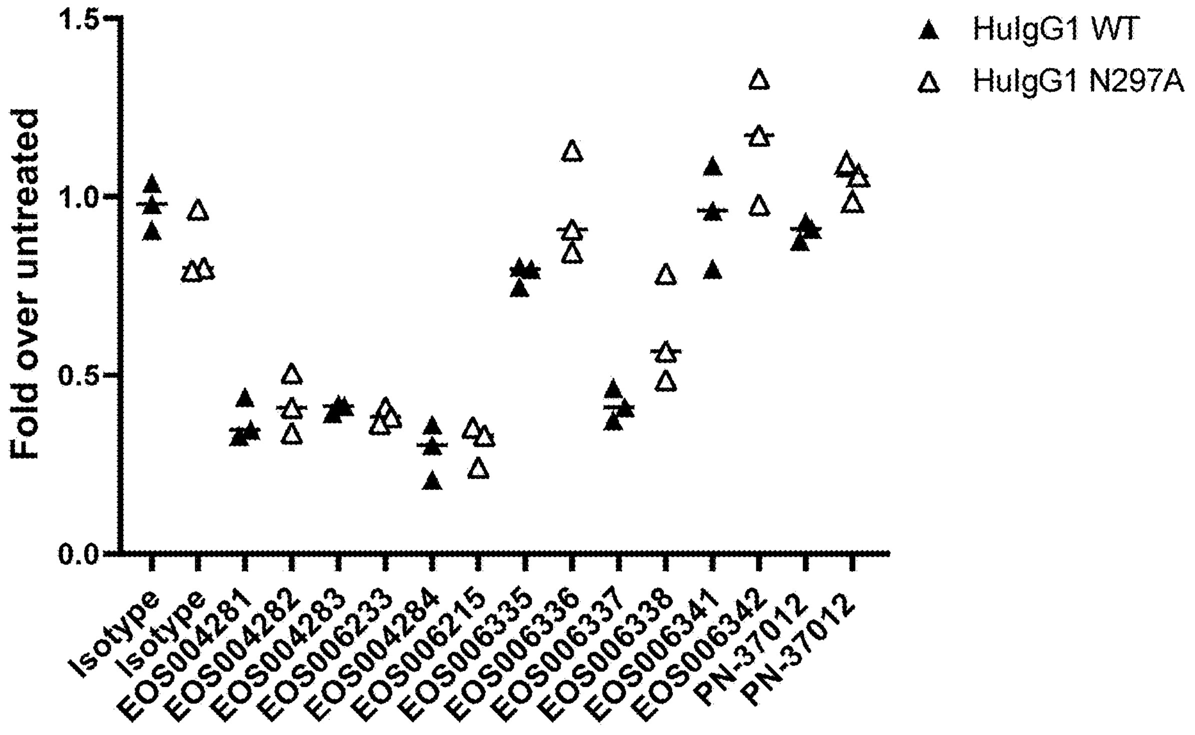

FIG. 11C compares the effect of the N297A mutation in antibodies to WT antibodies. Results showed that the N297A mutation did not influence the level of efferocytosis in most antibodies. However, EOS006336, EOS006338, EOS006342 and PN-37012 huIgG1 N297A presented an increased level of efferocytosis in comparison to their related WT antibodies.

Example 14: Impairment of Efferocytosis by Anti-TREM2 Antibody EOS006215

Figure 12:
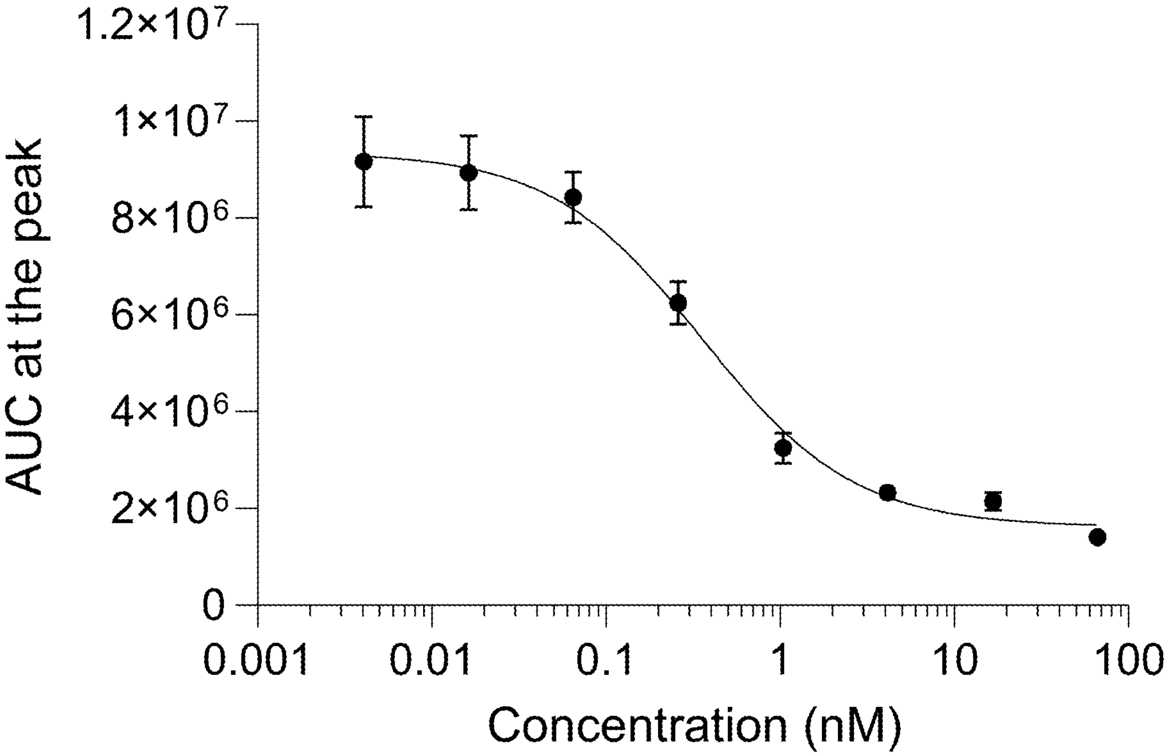
FIG. 12 shows the impact of the EOS006215 anti-TREM2 antibody on the efferocytosis of apoptotic Skov3 cells by M2a-like macrophages. EOS006215 was applied over a range of doses, starting at 10 μg/mL (66.6 nM) followed by a 4-fold dilution series (8 points) before being cultured with pHrodo-labelled apoptotic Skov3 cells. The level of pHrodo signal, representing the apoptotic Skov3 cells phagocytosed by macrophages, was measured over time by Incucyte technology. Results are expressed as area under the curve (AUC) at the peak of the pHrodo area ($\mu M^2$/well) measured under control conditions (non-treated). Each data point represents a triplicate (mean+−SD). Representative data from 1 healthy donor.

The potency of EOS006215 on efferocytosis was further evaluated. Monocytes were isolated from healthy donor PBMCs using a positive selection (CD14+). M2a-like macrophages were obtained as described above. On day 8, cells were harvested, washed and seeded in 96 well plate. On day 9, various concentrations of EOS006215 were applied to M2a-like macrophages, starting at 10 μg/mL (66.6 nM) followed by a 4-fold dilution series (8 points). Skov-3 cells were treated with palmitic acid at 400 μM for 48 h before the assay to induce cell death. Then, apoptotic Skov-3 cells were labelled with pHrodo and added to M2a-like macrophages at a 1:2 effector:target ratio. Coculture was analyzed by Incucyte technology. The results are presented in FIG. 12. Results are expressed as AUC at the peak of pHrodo area ($\mu m^2$/well) measured under control conditions (non-treated). The IC50 for EOS006215 was 0.36 nM in this assay.

Example 15: Anti-Tumor Activity of Anti-TREM2 Antibody in Monotherapy in Mouse Model In this experiment, C57BL/6 female mice of 9 weeks were inoculated with 500,000 MC38 cells subcutaneously. On day 3 after inoculation, mice were randomized in 2 treatment groups based on tumor volume. The anti-TREM2 group (n=8 mice) was treated with 200 μg of anti-TREM2 antibody EOS004284 by intraperitoneal injections on day 3, 6, 10, and 13. The vehicle group (n=7 mice) was treated on the same days with PBS. Tumor growth was monitored, and tumor volumes were measured with electronic calipers three times per week from day 3 until day 30.

Figure 13A:
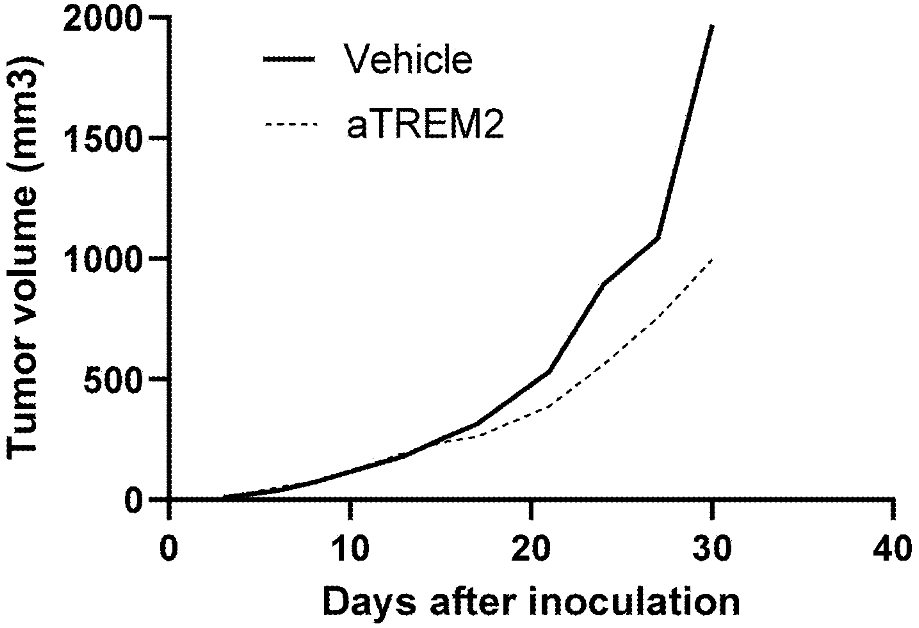
FIGS. 13A-13C shows anti-tumor efficacy of anti-TREM2 antibody in monotherapy in a MC38 model. Median tumor growth curves are shown in FIG. 13A. Individual tumor growth curves from mice treated with vehicle (FIG. 13B) and individual tumor growth curves from mice treated with anti-TREM2 antibody monotherapy (FIG. 13C) are also shown.
Figure 13B:
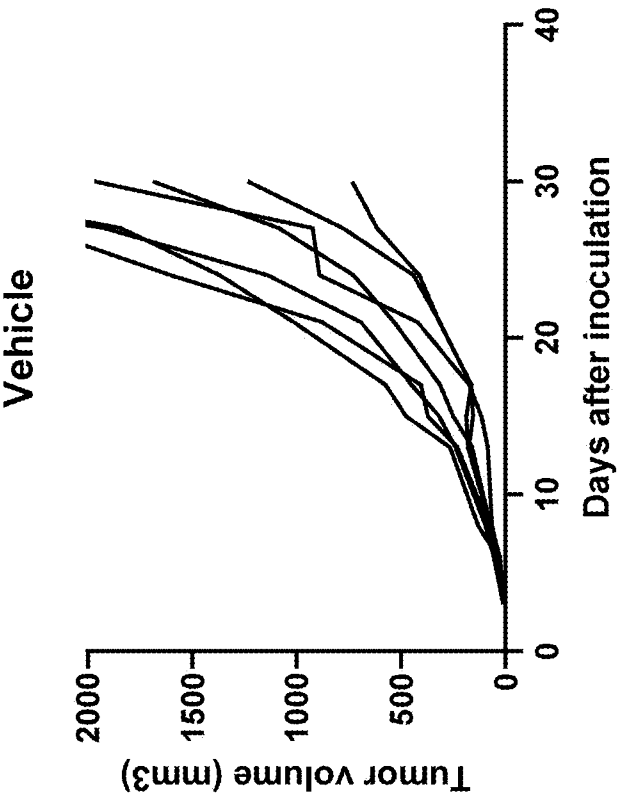
Figure 13C:
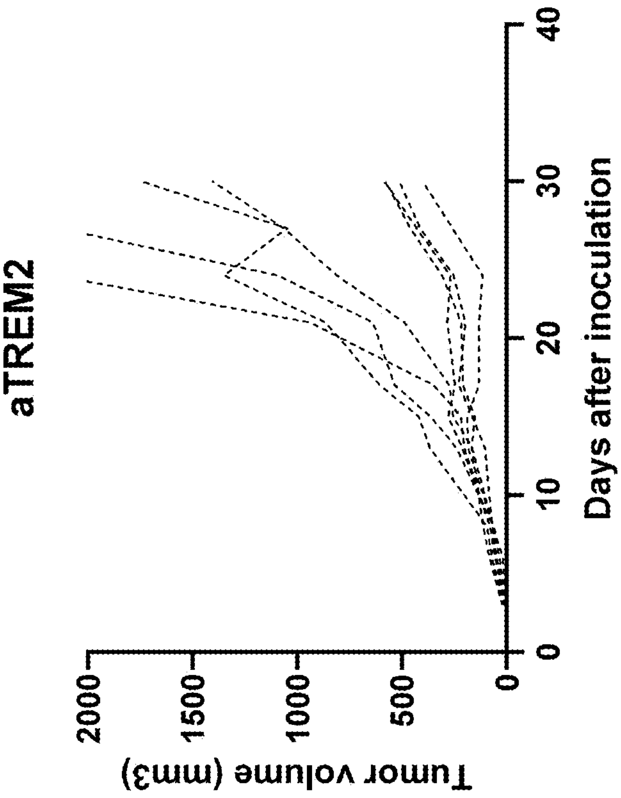
Figure 14A:
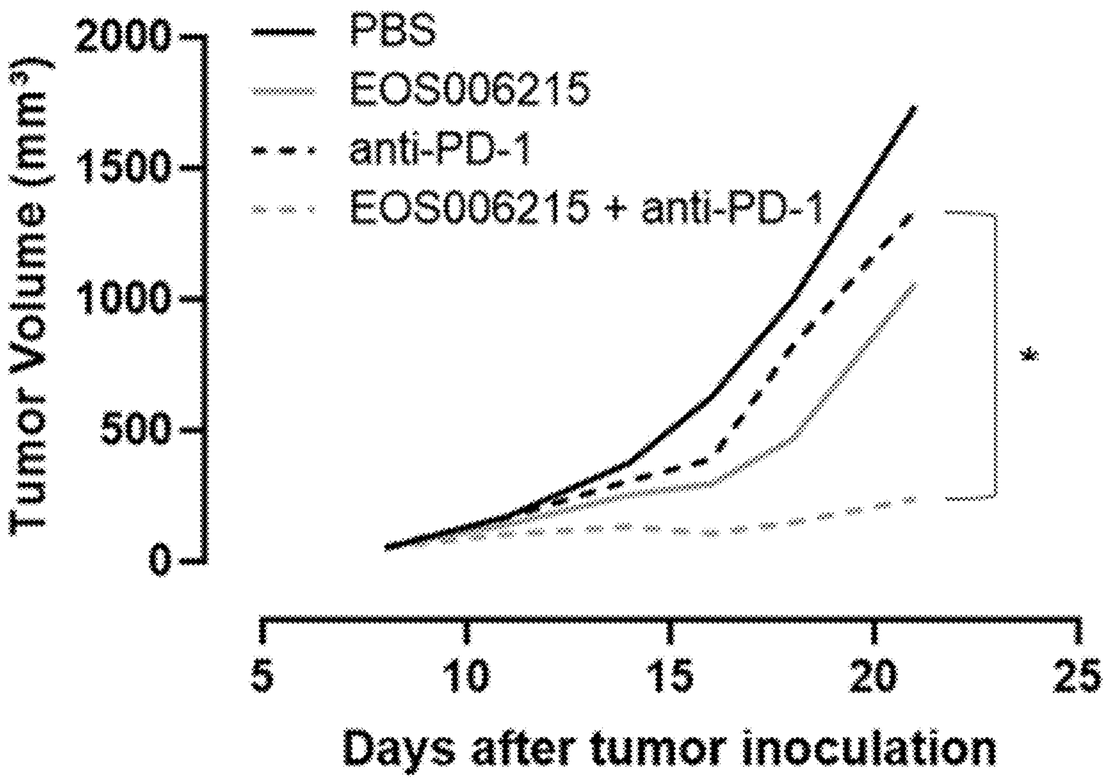
FIGS. 14A-14E shows tumor growth curves from CT26 tumor bearing mice under treatment. Median (FIG. 14A) and individual growth curves from mice treated with vehicle (FIG. 14B), anti-PD-1 antibody (FIG. 14C), EOS006215 (FIG. 14D) and the combination of EOS006215 and anti-PD-1 antibody (FIG. 14E) are shown. * represents a statistical significance of $p<0.05$.
Figure 14C:
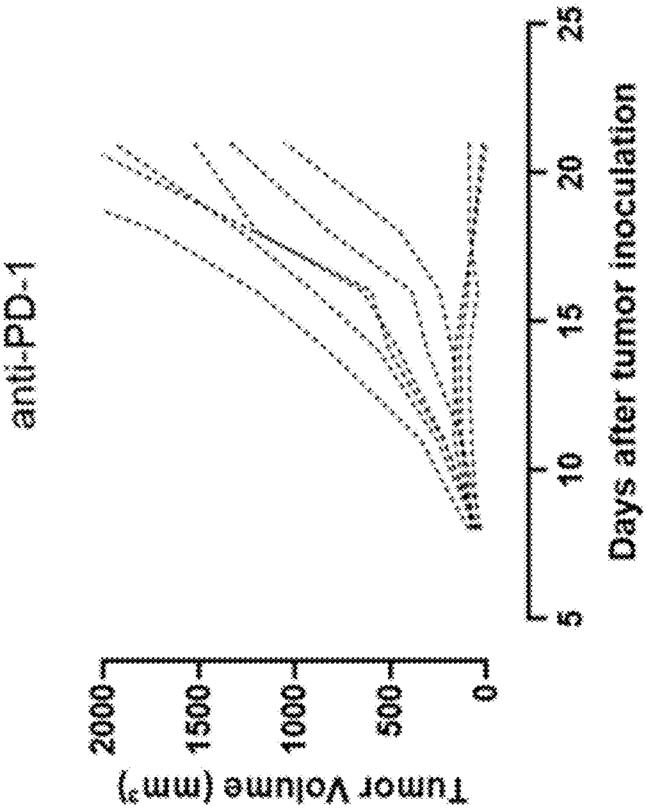
Figure 14B:
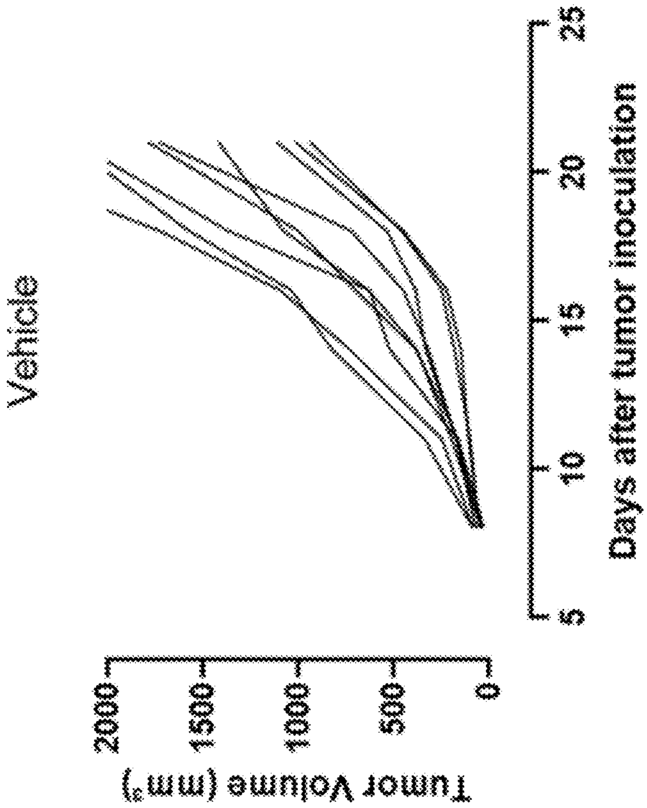
Figure 14E:
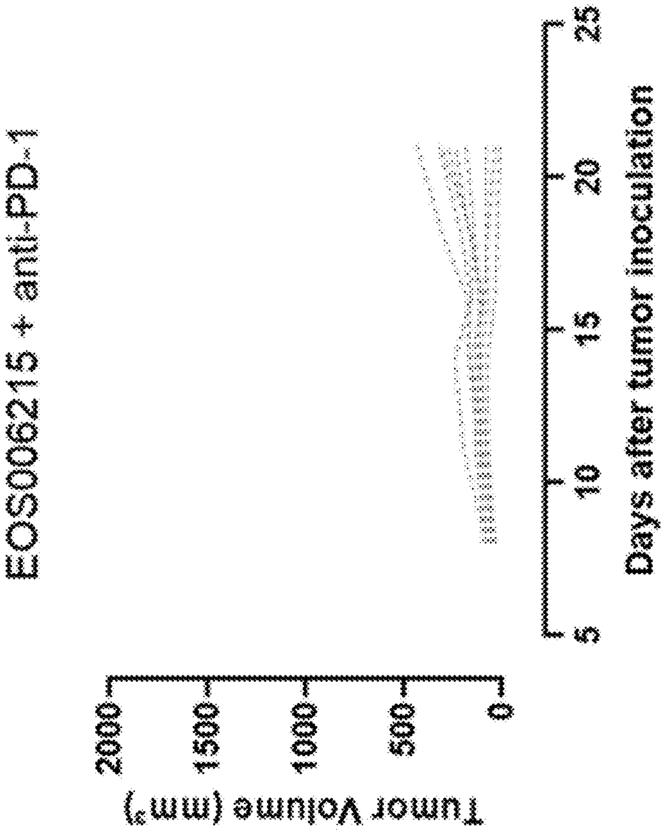
Figure 14D:
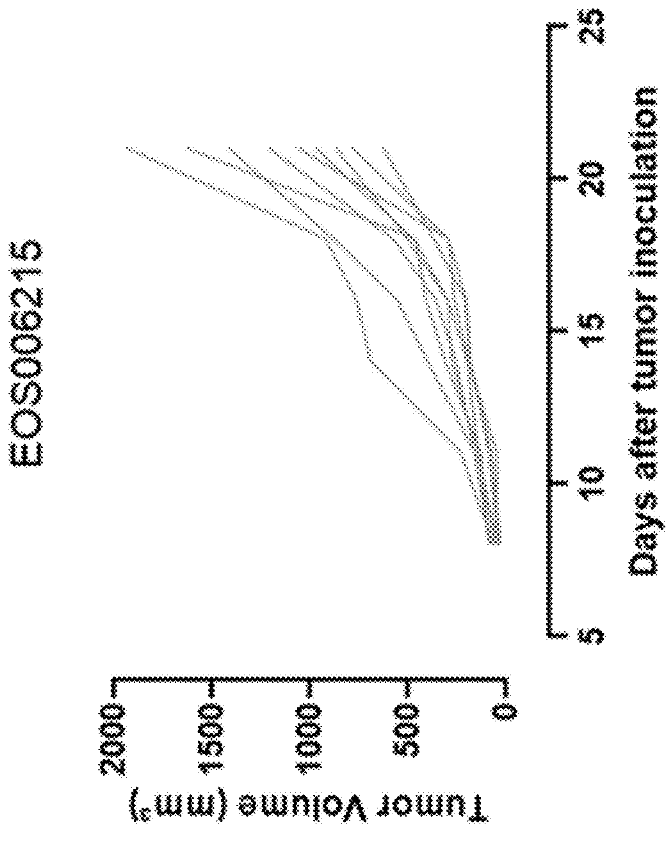
Figure 5D:
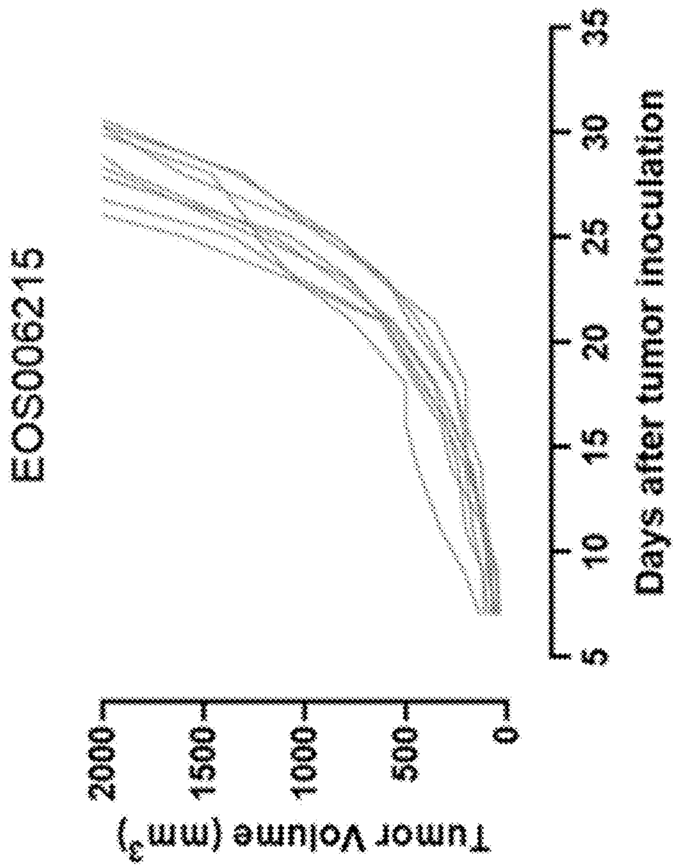

FIG. 13A shows the median tumor growth curve for the anti-TREM2 antibody monotherapy group compared to the vehicle group. Although non-significant (p=0.413), a trend towards anti-tumor efficacy was observed with anti-TREM2 antibody treatment. The individual curves shown in FIGS. 13B-13C highlight that the tumor delay trend comes from 4 responder mice in the anti-TREM2 group (50% of the mice in FIG. 13C). The tumor growth of the responder mice was significantly delayed compared to the tumor growth of the vehicle mice (p=0.014). These data demonstrate the significant anti-tumor efficacy of anti-TREM2 antibody treatment in a subset of the treated mice.

Example 16: Anti-Tumor Efficacy of Anti-TREM2 Antibody in Combination with Anti-PD-1 Antibody in a CT26 Mouse Model In this experiment, BALB/c female mice of 8 weeks were inoculated with 500,000 CT26 cells subcutaneously. On day 8 after inoculation, mice were randomized in 4 treatment groups (n=9 mice per group) based on tumor volume. Mice in the EOS006215 group were treated with 200 μg of anti-TREM2 antibody EOS006215 by intraperitoneal injections on day 8, 11, 14, 17, and 21. Mice in the vehicle group were treated by intraperitoneal injection on the same days with PBS. Mice in the anti-PD-1 group were treated with 200 μg of anti-PD-1 antibody by intraperitoneal injection on day 8, 11, and 14. Mice in the EOS006215+anti-PD-1 group were treated with 200 μg of EOS006215 by intraperitoneal injections on day 8, 11, 14, 17, and 21 and with 200 μg of anti-PD-1 antibody on day 8, 11, and 14. Tumor growth was monitored, and tumor volumes were measured with electronic calipers three times per week. Statistical anti-tumor difference (p-values) and percentage of Tumor Growth Inhibition (TGI) were calculated based on the AUC.

There was a non-significant trend towards tumor delay when the mice were treated with EOS006215 in monotherapy illustrated by a TGI of 30% (p=0.078). There was no overall anti-tumor efficacy of anti-PD-1 alone in the CT26 model (p=0.177). However, in the group of mice treated with anti-PD-1 alone, there were responders (33% of the mice) and non-responders to the treatment. When EOS006215 was given in combination with anti-PD-1, all mice showed a significant response (p=0.036) to the treatment, compared to anti-PD-1 alone (FIGS. 14A-14E).

Example 17: Anti-Tumor Efficacy of Anti-TREM2 Antibody in Combination with Anti-PD-1 Antibody in a MC38 Mouse Model In this experiment, C57BL/6 female mice of 11 weeks were inoculated with 500,000 MC38 cells subcutaneously. On day 7 after inoculation, mice were randomized in 5 treatment groups (n=9 mice per group) based on tumor volume. Mice in the EOS006215 group were treated with 200 μg of the anti-TREM2 antibody EOS006215 by intraperitoneal injections on day 7, 10, 14, 17, and 21. Mice in the vehicle group were treated by intraperitoneal injection on the same days with PBS. Mice in the anti-PD-1 group were treated with 200 μg anti-PD-1 antibody by intraperitoneal injection on day 7, 10, and 14. Mice in the EOS006215+anti-PD-1 group were treated with 200 μg of EOS006215 by intraperitoneal injections on day 8, 11, 14, 17, and 21 and with 200 μg of anti-PD-1 antibody on day 8, 11, and 14. A fifth group (anti-PD-1, then EOS006215) was included to investigate sequential treatment of anti-PD-1 followed by anti-TREM2. Mice in the anti-PD-1, then EOS006215 group received anti-PD-1 on the same days as the other groups (day 7, 10, and 14), but EOS006215 injections were performed later, on day 14, 17, 21, 24, and 28. Tumor growth was monitored, and tumor volumes were measured with electronic calipers three times per week. Statistical anti-tumor difference (p-values) and percentage of TGI were calculated based on the AUC. In addition, responses to treatment and disease progression on day 23 were categorized following the Response Evaluation Criteria In Solid Tumors (RECIST) guidelines.

Figure 15A:
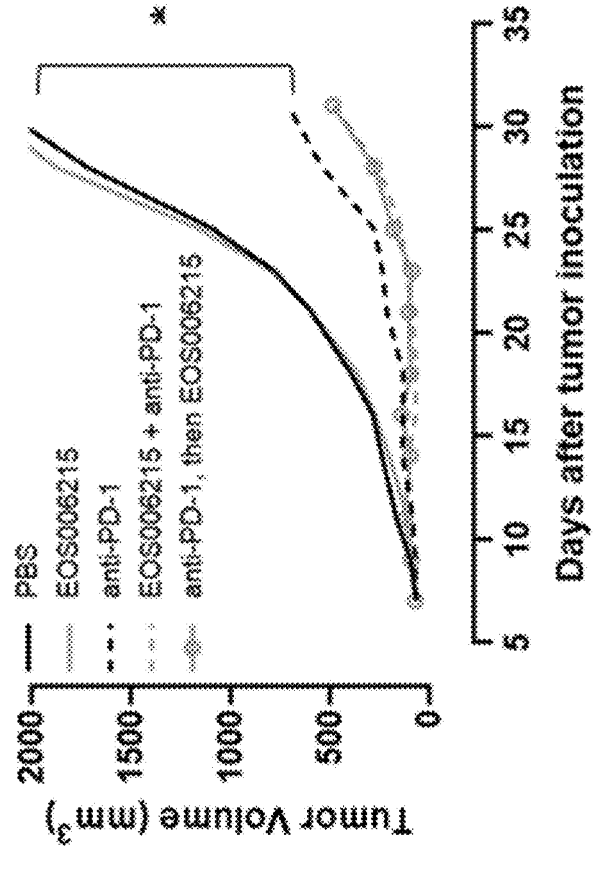
Figure 15B:
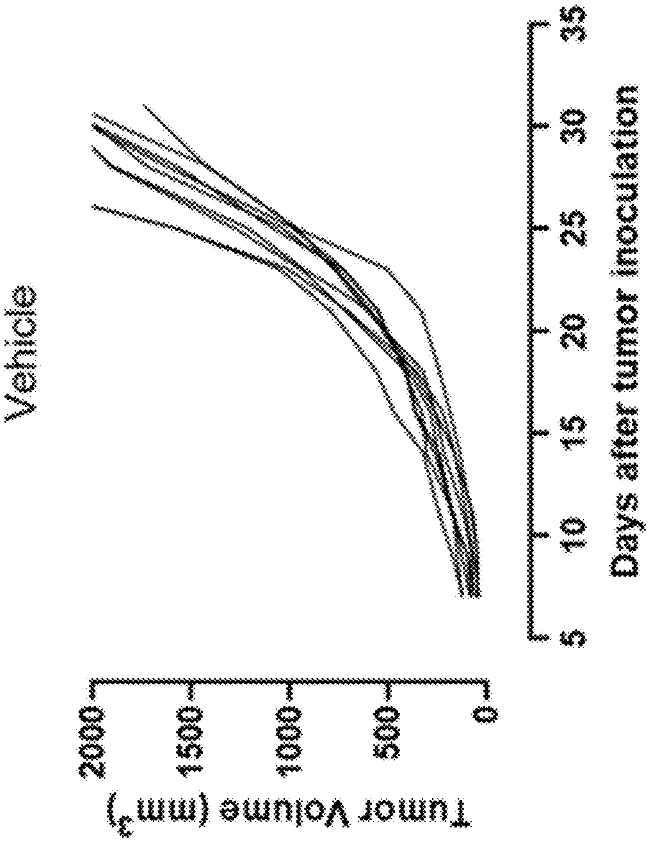
Figure 15C:
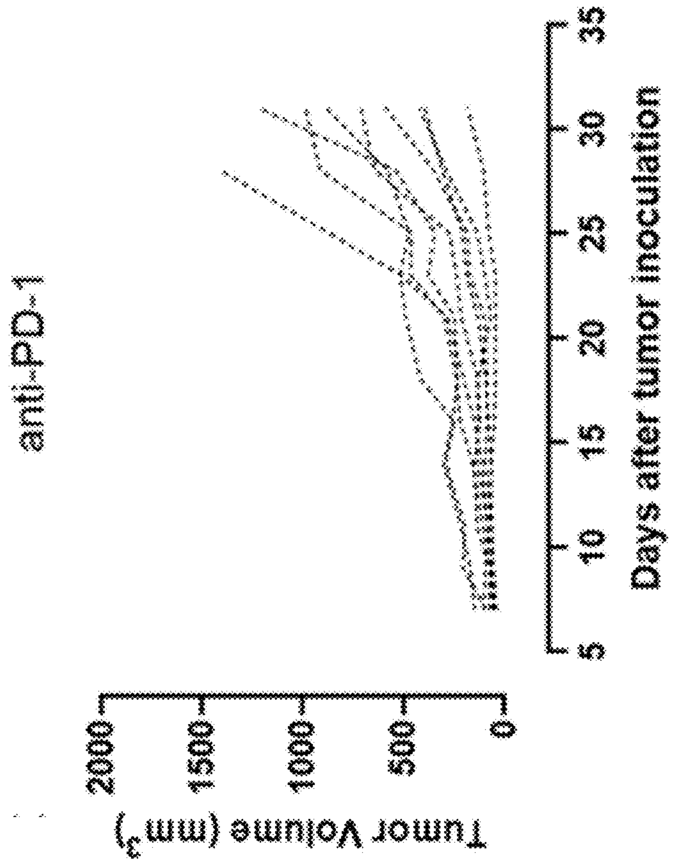
Figure 15E:
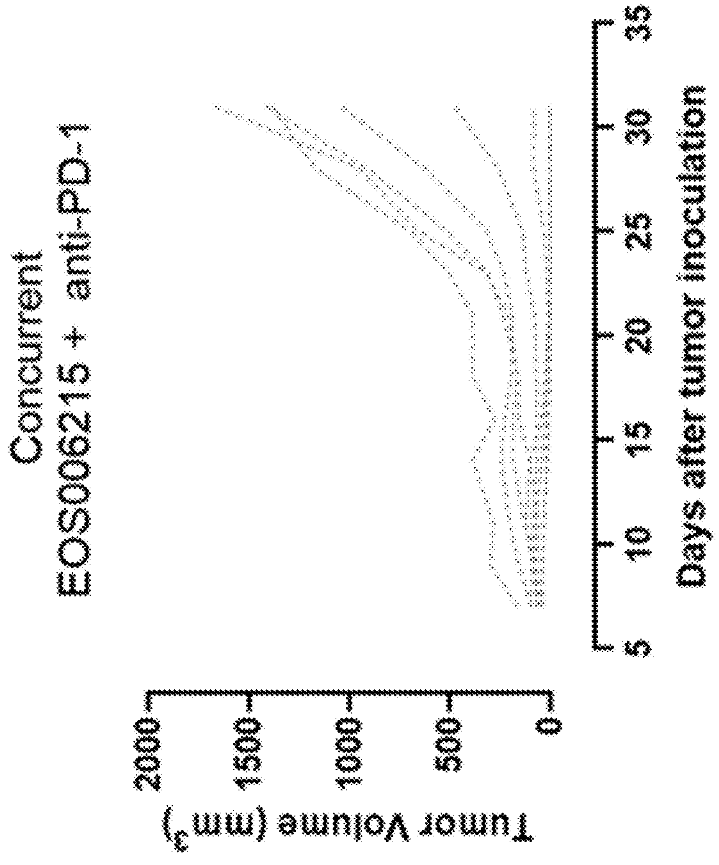
Figure 15F:
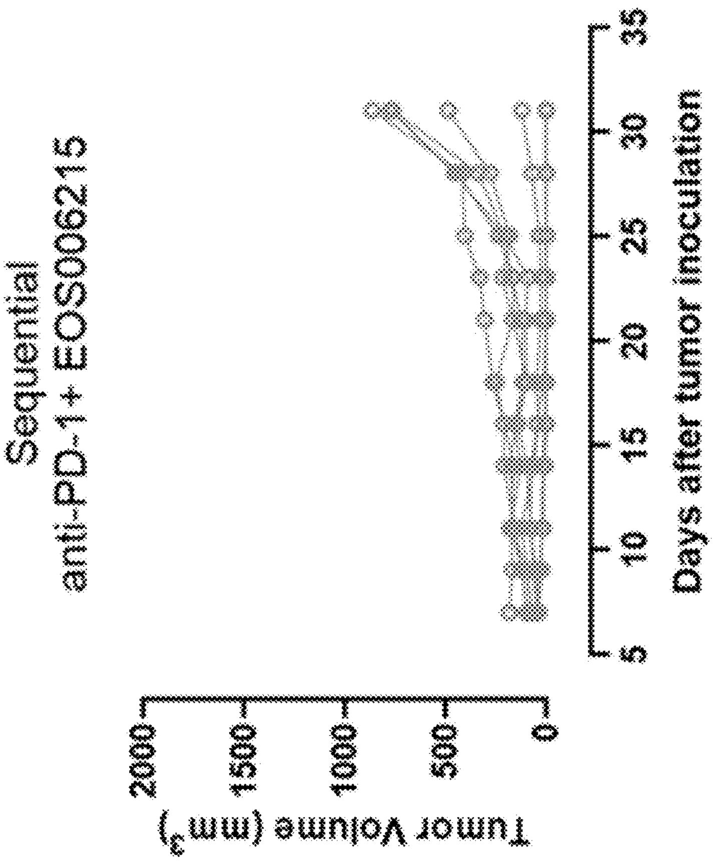

Treatment of MC38 tumor bearing mice with anti-PD-1 significantly delayed tumor growth compared to the vehicle (PBS) group (p=0.001, TGI of 57%). When mice received anti-PD-1 in concurrently with EOS006215, the anti-tumor response was moderately increased (FIG. 15E), but not significantly compared to anti-PD-1 alone (p=0.161, TGI of 46%). The sequential treatment of anti-PD-1 followed by EOS006215 tended to further increase the anti-tumor response, although the increase was still not significant compared with anti-PD-1 alone (p=0.072, TGI of 52%).

Figure 16:
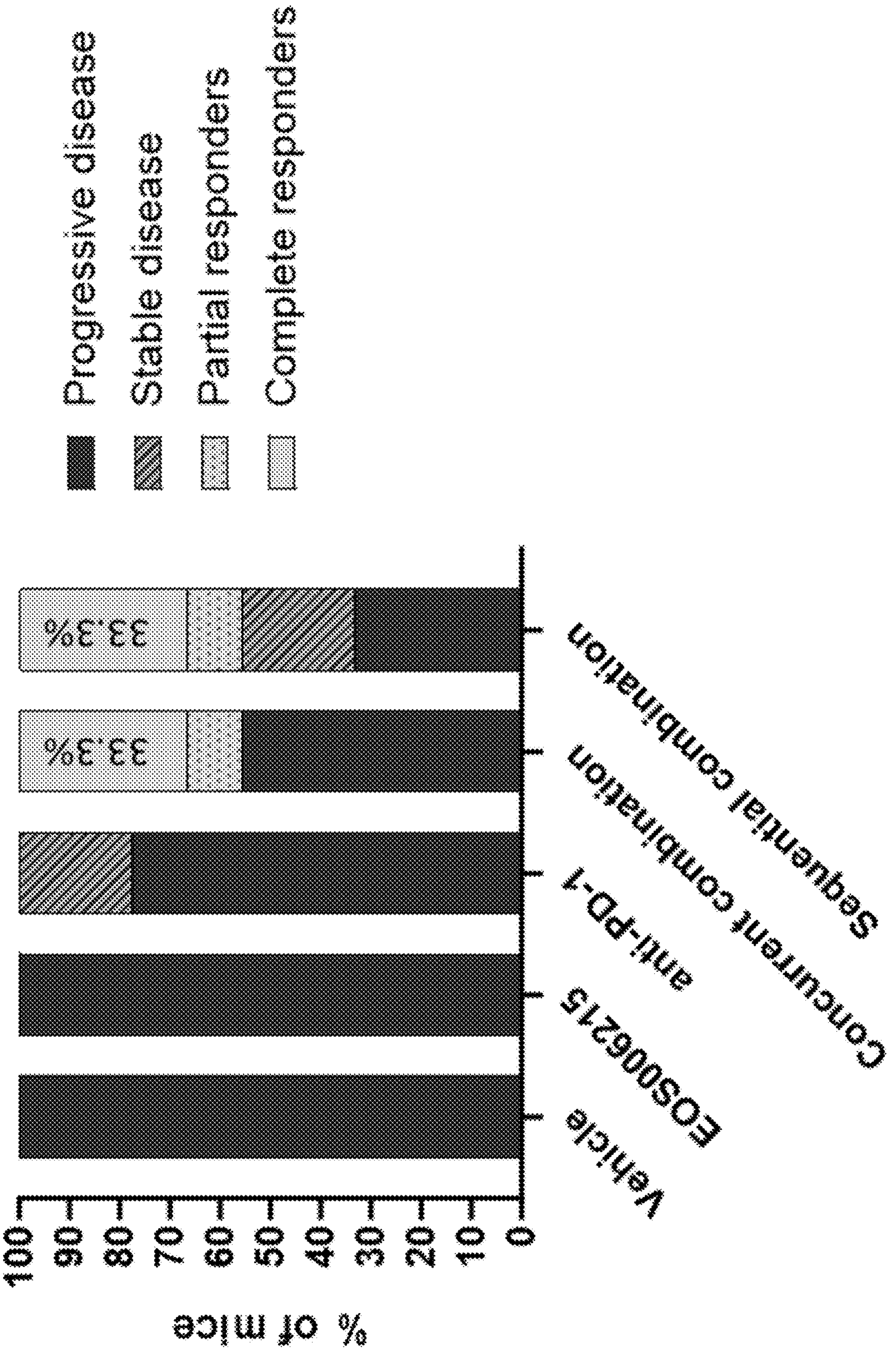
FIG. 16 shows the percentage of responding mice per treatment group, at 23 days post-inoculation with MC38.

In addition, analyzing individual responses to treatment on day 23 revealed more complete responses and partial responses in mice treated with the combination of anti-TREM2 and anti-PD-1 antibodies than in any other groups (FIG. 16). Administering the anti-TREM2+anti-PD-1 combination either concurrently or sequentially resulted in complete responses in 3/9 mice (33.3%) in both of these groups (versus 0% in every other group). Moreover, 1/9 mice (11.1%) showed a partial response in both anti-TREM2+anti-PD-1 groups (versus 0% in every other group). As mentioned above, sequential treatment seemed to delay tumor growth better than concurrent treatment. This was also reflected in the individual response analysis, since in addition to the complete and partial responses described above, 2/9 mice (22.2%) had stable disease in the sequential treatment group (versus 0% in the concurrent treatment group). Only 3/9 mice first receiving anti-PD-1, then EOS006215, had progressive disease 23 days post-inoculation. Significantly, all complete responders at day 23 remained tumor-free at the end of study (day 31).

Example 18: Efficacy of Anti-TREM2 Antibody Against Lung Metastasis in Monotherapy and in Combination with Anti-PD-1 Antibody in a Primary 4T1 Mouse Model In this experiment, BALB/c female mice of 8 weeks were inoculated orthotopically in the mammary fat pad with 100,000 4T1 cells overexpressing luciferase. On day 9 after inoculation, mice were randomized in 5 treatment groups (n=10 mice per group) based on tumor volume. Mice were treated Q3D with vehicle (PBS), isotype control, anti-PD-1, EOS006215, or the combination of anti-PD-1 and EOS006215 by intraperitoneal injections starting from the day of randomization. The mice received 3 injections of anti-PD-1 antibody and 4 injections of all the other treatments. On day 15 or 16, primary tumors were surgically removed. Four in vivo BioLuminescence Intensity (BLI) measurements of the thoracic region were performed to assess metastasis development in the lungs. Statistical anti-metastasis difference (p-values) and percentage of Metastasis Growth Inhibition (MGI) were calculated based on the AUC. At the end of the study (on days 42 and 43), lungs were collected, and metastasis development was confirmed by ex-vivo BLI measurements.

Figure 17B:
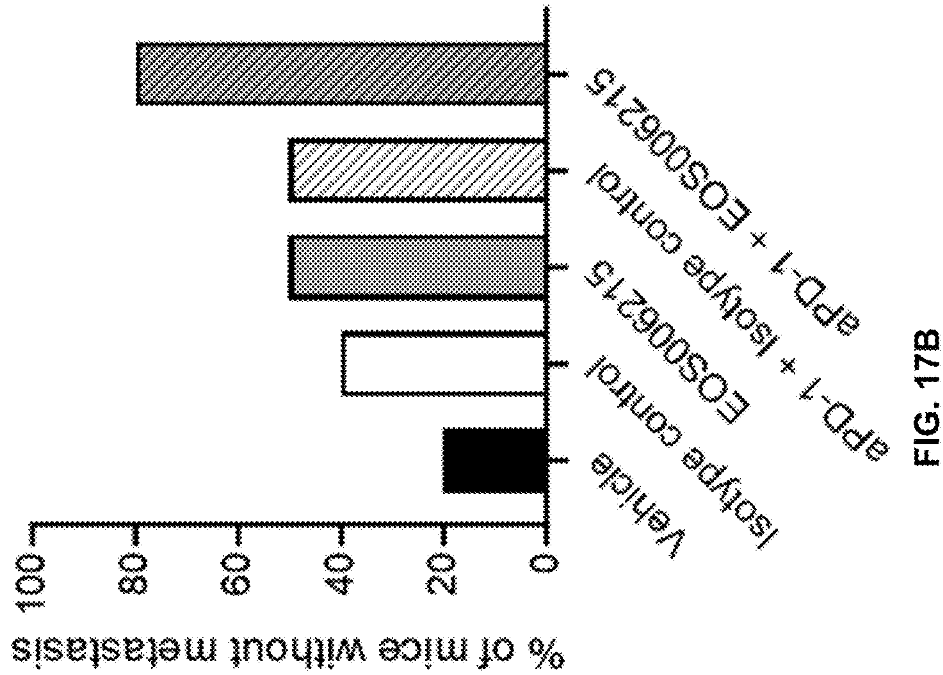
FIGS. 17A-17B shows the lung metastasis burden in a primary 4T1 mouse model after primary tumor removal and treatment with EOS006215 monotherapy or in combination with anti-PD-1 antibody.
Figure 17A:
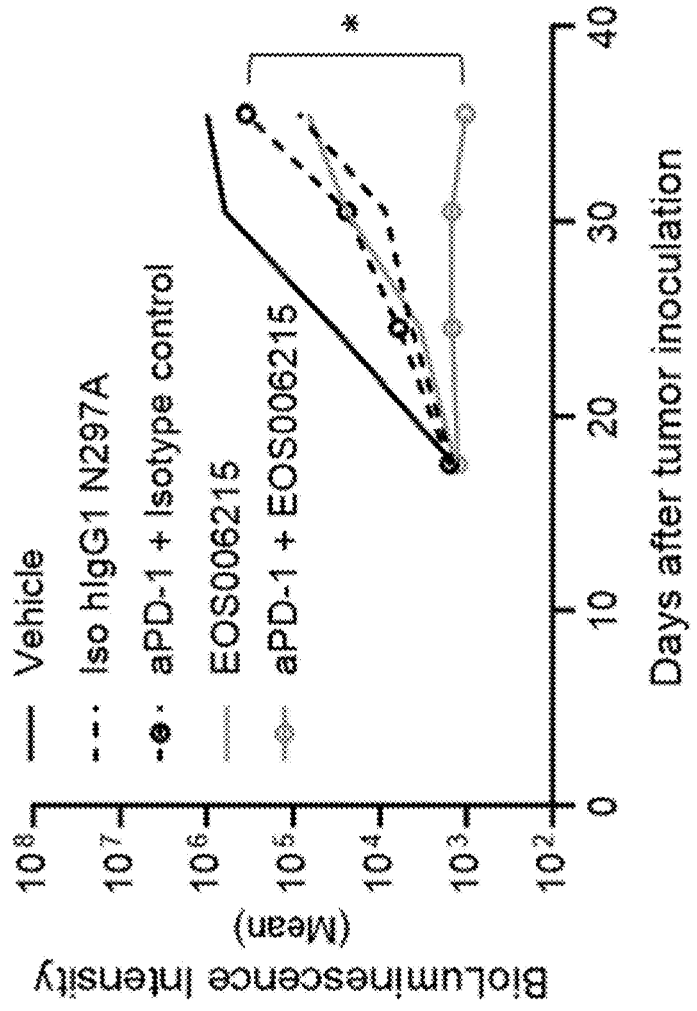
Figure 18A:
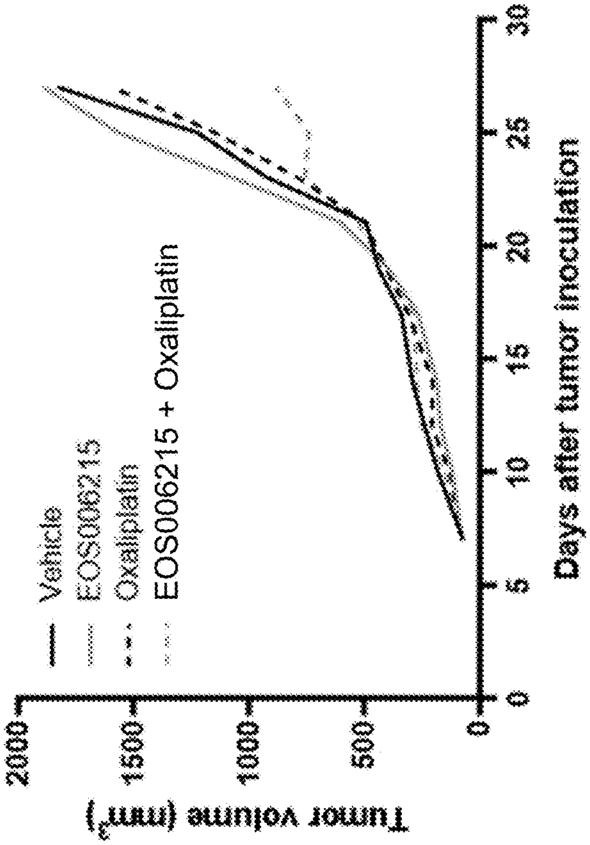
FIGS. 18A-18D shows tumor growth curves from the MC38 tumor bearing mice under treatment. Median (FIG. 18A) and individual growth curves from mice treated with oxaliplatin (FIG. 18B) and the combination of EOS006215 and oxaliplatin (FIG. 18C) are shown. Percentage survival curves representing time to reach 1200 $mm^3$ tumor volume are shown in FIG. 18D. ** represents a statistical significance of $p<0.01$.
Figure 18B:
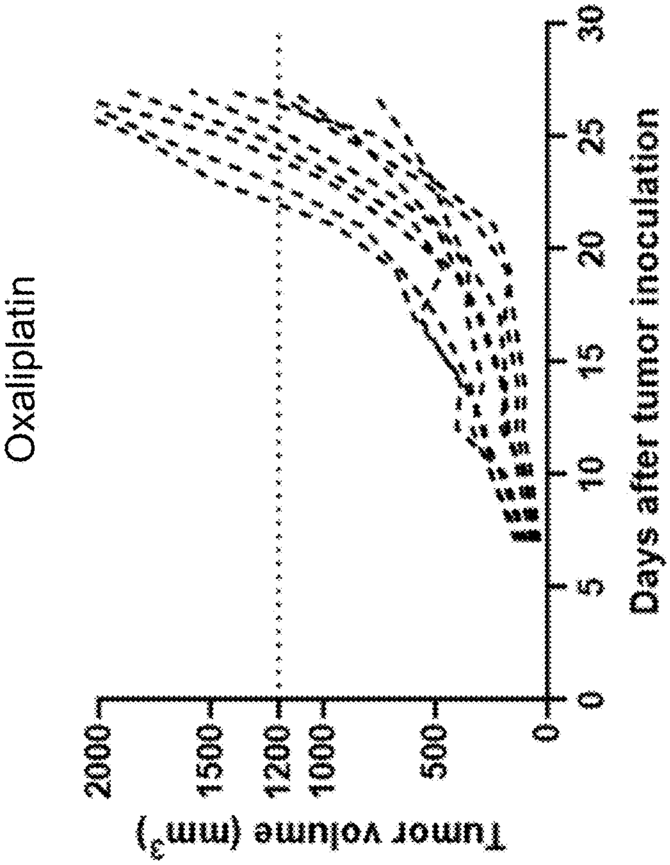
Figure 18D:
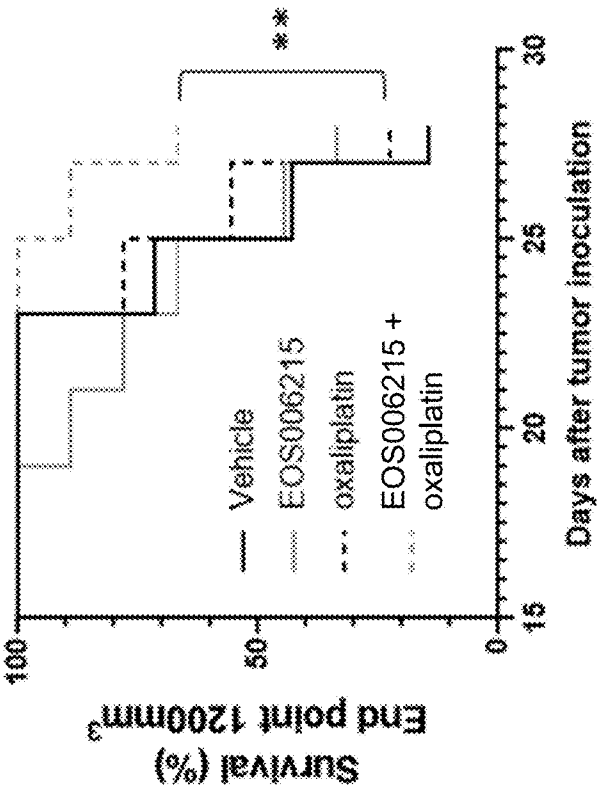
Figure 18C:
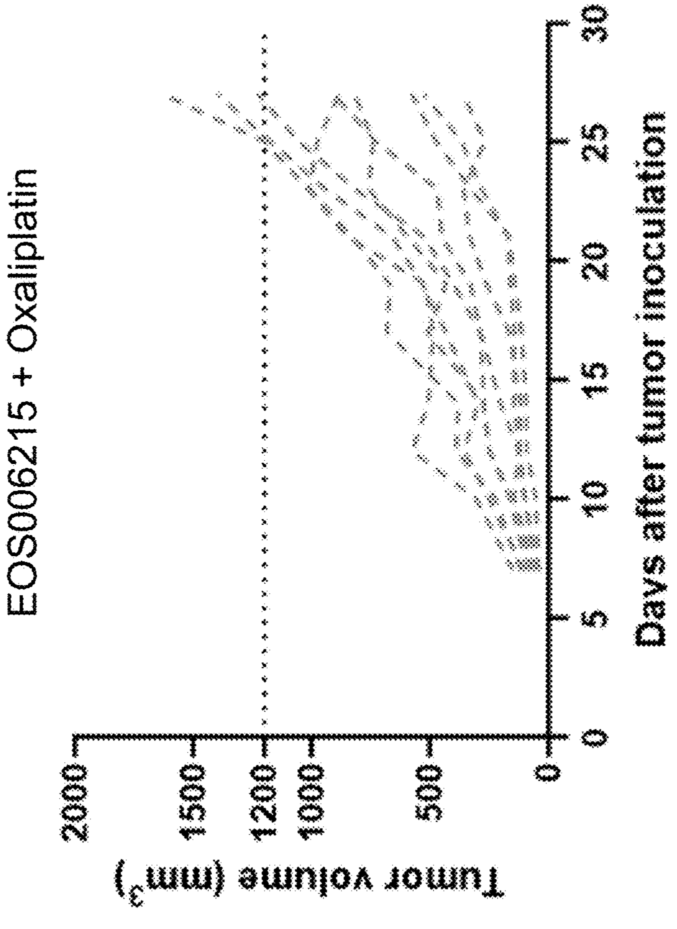

Although not statistically significant, BLI measurements over time show that treating mice with EOS006215 or anti-PD-1 in monotherapies induced an MGI of 63% and 48%, respectively, compared to vehicle. The data shown in FIG. 17A demonstrates that combining anti-PD-1 with EOS006215 significantly prevents metastasis development over time (p=0.022). The anti-metastasis efficacy was confirmed in FIG. 17B where no metastasis was measured by ex-vivo BLI in 50% of the mice treated with EOS006215 or anti-PD-1 monotherapies. The proportion of healthy lungs increased to 80% in the anti-PD-1+EOS006215 combination group.

Example 19: Anti-Tumor Efficacy of Anti-TREM2 Antibody in Combination with Oxaliplatin in a MC38 Mouse Model In this experiment, C57BL/6 female mice of 9 weeks were inoculated with 500,000 MC38 cells subcutaneously. On day 7 after inoculation, mice were randomized in 4 treatment groups (n=9 mice per group) based on tumor volume. Mice in the EOS006215 group were treated with 200 μg of the anti-TREM2 antibody EOS006215 by intraperitoneal injection on day 7, 10, 13, 17, and 20. Mice in the Oxaliplatin group were treated with 100 μg of oxaliplatin by intraperitoneal injection on day 7 and 14. Mice in the vehicle group were treated on the same days with PBS. Mice in the EOS006215+oxaliplatin group were treated with 200 μg EOS006215 by intraperitoneal injection on day 7, 10, 13, 17, and 20, and with 100 μg of oxaliplatin by intraperitoneal injection on day 7 and 14. Tumor growth was monitored, and tumor volumes were measured with electronic calipers three times per week. Statistical anti-tumor difference (p-values)

and percentage of TGI were calculated based on the AUC. Logrank test was performed as statistical analysis on survival curves.

FIGS. 18A-18D show the anti-tumor activity of combining anti-TREM2 treatment with chemotherapeutic agent oxaliplatin. There was no statistical difference in tumor growth comparing the growth curves in mice treated with oxaliplatin alone versus in combination with EOS006215 (p=0.439, TGI of 15%). However, the trend towards efficacy was confirmed by a significant percentage survival difference (time to reach 1200 $mm^3$ tumor volume) comparing the EOS006215+oxaliplatin group to the oxaliplatin group (p=0.0021).

Example 20: Benchmark Antibodies

Properties of exemplary anti-TREM2 antibodies shown in the above Examples were compared against anti-TREM2 antibody clones described in other patent applications. Specifically, exemplary anti-TREM2 antibodies were compared with: 6E7 (from WO2018195506); 14D3 (from WO2018015573); PN37012 (from US20190309064); MOR044746 (from WO2020079580) and Ab52 (from WO2016023019A2). The VH and VL sequences of the benchmark antibody clones are shown in Table 28 below:

TABLE 28

Sequences of VH and VL domains of comparative anti-TREM2 antibodies

| anti-TREM2 clone | Sequence | Bin |
|---|---|---|
| 6E7 | VH sequence: EVQLVQSGAEVKKPGESLKISCKGSGYSFTSYWIAWVRQMPGKGLEWMGIIYPGDSDTRYSPSFQGQVTISADKSISTAYLQWSSLKASDTAMYFCARQRTFYYDSSDYFDYWGQGTLVTVSS (SEQ ID NO: 176)<br><br>VL sequence: DIQMTQSPSSVSASVGDRVTITCRASQGISSWLAWYQQKPGKAPKLLIYAASSLQNGVPSRFSGSGSGTDFTLTISSLQPEDFATYFCQQADSFPRTFGQGTKLEIK (SEQ ID NO: 177) | 5 |
| 14D3 | VH sequence: EVKLLEFGGGLVQPGGSMRLSCAASGFTFTDFYMNWIRQPAGRAPEWLGLIRNKTKGYTTEYNRSVKGRFTISRDNTQNMLYLQMNSLRPEDTATYYCARIGVNNGGSLDYWGQGVMVTVSS (SEQ ID NO: 178)<br><br>VL sequence: DILIIQSPASLTVSAGARVTMSCKSSQSLLYSENNQDYLAWYQQKPGQFPKLLIYGASNRHTGVPDRFTGSGSGTDFTLTISSVQAEDLADYYCEQTYSYPYTFGAGTKLELK (SEQ ID NO: 179) | 4 |
| PN37012 | VH sequence: EVQLLESGGGLVQPGGSLRLSCAASGFTFSNYYMAWVRQAPGKGLEWVSSLTNSGGSTYYADSVKGRFTISRDNSKNTLYLQMNSLRAEDTAVYYCTREWAGSGYFDYWGQGTLVTVSS (SEQ ID NO: 180)<br><br>VL sequence: DIQMTQSPSSLSASVGDRVTITCKASQNVGNNLAWYQQKPGKAPKLLIYYTSNRFTGVPSRFSGSGSGTDFTLTISSLQPEDFATYYCQRIYNSPWTFGQGTKLEIK (SEQ ID NO: 181) | 1 |
| MOR044746 | VH sequence: QVQLQQSGPGLVKPSQTLSLTCAISGDSVSSSSAAWNWIRQSPSRGLEWLGHIGYRSKWYNEYAVSVKSRITINPDTSKNQFSLQLNSVTPEDTAVYYCARGMYGSVPYKEGYYFDIWGQGTLVTVSS (SEQ ID NO: 182)<br><br>VL sequence: DIQMTQSPSSLSASVGDRVTITCRASQGISSDLNWYQQKPGKAPKLLIYAASNLQSGVPSRFSGSGSGTDFTLTISSLQPEDFATYYCQQYTDESMTFGQGTKVEIK (SEQ ID NO: 183) | 3 |
| Ab52 | VH sequence: QVQLVQSGAEVKKPGASVKVSCKASGYTFTSYYIHWVRQAPGQGLEWMGIINPSGGSTSYAQKFQGRVTMTRDTSTSTVYMELSSLRSEDTAVYYCAREADDSSGYPLGLDVWGQGTMVTVSS (SEQ ID NO: 184) | 3, 5 |

TABLE 28-continued

| Sequences of VH and VL domains of comparative anti-TREM2 antibodies | | |
|---|---|---|
| anti-TREM2 clone | Sequence | Bin |
| | VL sequence:<br>EIVMTQSPATLSVSPGERATLSCRASQSVSSNLAWYQQKPGQA<br>PRLLIYGASTRATGIPARFSGSGSGTEFTLTISSLQSEDFAVY<br>YCQQVNSLPPTFGGGTKVEIK (SEQ ID NO: 185) | |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

The invention claimed is:

1. An antibody that specifically binds to TREM2, comprising a VH comprising CDRH1, CDRH2, and CDRH3, and a VL comprising CDRL1, CDRL2, and CDRL3, wherein the CDRH1, CDRH2, and CDRH3 comprise the CDRH1, CDRH2, and CDRH3 amino acid sequences of the VH amino acid sequence set forth in SEQ ID NO: 109; and the CDRL1, CDRL2, and CDRL3 comprise the CDRL1, CDRL2, and CDRL3 amino acid sequences of the VL amino acid sequence set forth in SEQ ID NO: 121; and wherein the amino acid sequences of the CDRH1, CDRH2, CDRH3, CDRL1, CDRL2, and CDRL3 of the antibody are determined according to Kabat, Chothia, MacCallum, or IMGT numbering.

2. The antibody of claim 1, wherein the CDRH1, CDRH2, CDRH3, CDRL1, CDRL2, and CDRL3 each comprise the CDRH1 sequence set forth in SEQ ID NO: 29, the CDRH2 sequence set forth in SEQ ID NO: 40, the CDRH3 sequence set forth in SEQ ID NO: 53, the CDRL1 sequence set forth in SEQ ID NO: 65, the CDRL2 sequence set forth in SEQ ID NO: 70, and the CDRL3 sequence set forth in SEQ ID NO: 82.

3. The antibody of claim 1, wherein the VH comprises the amino acid sequence set forth in SEQ ID NO: 109.

4. The antibody of claim 1, wherein the VL comprises the amino acid sequence set forth in SEQ ID NO: 121.

5. The antibody of claim 1, wherein the VH comprises the amino acid sequence set forth in SEQ ID NO: 109 and the VL comprises the amino acid sequence set forth in SEQ ID NO: 121.

6. The antibody of claim 1, further comprising heavy and/or light chain constant regions.

7. The antibody of claim 6, wherein the heavy chain constant region comprises an amino acid sequence set forth in SEQ ID NO: 159 or SEQ ID NO: 160.

8. The antibody of claim 6, wherein the light chain constant region comprises an amino acid sequence set forth in SEQ ID NO: 157 or SEQ ID NO: 158.

9. The antibody of claim 6, wherein the heavy chain constant region comprises an amino acid sequence set forth in SEQ ID NO: 159 or SEQ ID NO: 160 and the light chain constant region comprises an amino acid sequence set forth in SEQ ID NO: 157 or SEQ ID NO: 158.

10. The antibody of claim 5, further comprising heavy and/or light chain constant regions.

11. The antibody of claim 10, wherein the heavy chain constant region comprises an amino acid sequence set forth in SEQ ID NO: 159 or SEQ ID NO: 160.

12. The antibody of claim 10, wherein the light chain constant region comprises an amino acid sequence set forth in SEQ ID NO: 157 or SEQ ID NO: 158.

13. The antibody of claim 10, wherein the heavy chain constant region comprises an amino acid sequence set forth in SEQ ID NO: 159 or SEQ ID NO: 160, and the light chain constant region comprises an amino acid sequence set forth in SEQ ID NO: 157 or SEQ ID NO: 158.

14. The antibody of claim 6, wherein the antibody comprises a heavy chain comprising an amino acid sequence set forth in SEQ ID NO: 168 or SEQ ID NO: 169, and a light chain comprising an amino acid sequence set forth in SEQ ID NO: 163.

15. The antibody of claim 1, wherein the antibody is conjugated to a cytotoxic agent, cytostatic agent, toxin, radionuclide, or detectable label.

16. A polynucleotide or polynucleotides encoding a VH and/or a VL, or a heavy chain and/or a light chain of the antibody of claim 1.

17. An expression vector comprising the polynucleotide or polynucleotides of claim 16.

18. A host cell comprising the polynucleotide or polynucleotides of claim 16.

19. A method for producing an antibody that binds to human TREM2, comprising culturing the host cell of claim 18 under conditions which permit expression of the antibody.

20. A composition comprising the antibody of claim 1, and at least one pharmaceutically acceptable carrier.

21. A method of reducing binding of low-density lipoprotein (LDL) to TREM2 in a subject, wherein the method comprises administering to the subject an effective amount of the antibody of claim 1.

22. A method of reducing efferocytosis in a subject, wherein the method comprises administering to the subject an effective amount of the antibody of claim 1.

23. A method of reprogramming macrophages in a subject, wherein the method comprises administering to the subject an effective amount of the antibody of claim 1.

24. A method of slowing, reducing, or inhibiting tumor growth in a subject, wherein the method comprises administering to the subject an effective amount of the antibody of claim 1.

25. A method of treating cancer in a subject, wherein the method comprises administering to the subject an effective amount of the antibody of claim 1.

* * * * *

SEQUENCE LISTING

```
Sequence total quantity: 185
SEQ ID NO: 1           moltype = AA  length = 230
FEATURE                Location/Qualifiers
source                 1..230
                       mol_type = protein
                       organism = Homo sapiens
SEQUENCE: 1
MEPLRLLILL FVTELSGAHN TTVFQGVAGQ SLQVSCPYDS MKHWGRRKAW CRQLGEKGPC  60
QRVVSTHNLW LLSFLRRWNG STAITDDTLG GTLTITLRNL QPHDAGLYQC QSLHGSEADT  120
LRKVLVEVLA DPLDHRDAGD LWFPGESESF EDAHVEHSIS RSLLEGEIPF PPTSILLLLA  180
CIFLIKILAA SALWAAAWHG QKPGTHPPSE LDCGHDPGYQ LQTLPGLRDT             230

SEQ ID NO: 2           moltype = AA  length = 219
FEATURE                Location/Qualifiers
source                 1..219
                       mol_type = protein
                       organism = Homo sapiens
SEQUENCE: 2
MEPLRLLILL FVTELSGAHN TTVFQGVAGQ SLQVSCPYDS MKHWGRRKAW CRQLGEKGPC  60
QRVVSTHNLW LLSFLRRWNG STAITDDTLG GTLTITLRNL QPHDAGLYQC QSLHGSEADT  120
LRKVLVEVLA DPLDHRDAGD LWFPGESESF EDAHVEHSIS RAERHVKEDD GRKSPGEVPP  180
GTSPACILAT WPPGLLVLLW QETTLPEHCF SWTLEAGTG                        219

SEQ ID NO: 3           moltype = AA  length = 222
FEATURE                Location/Qualifiers
source                 1..222
                       mol_type = protein
                       organism = Homo sapiens
SEQUENCE: 3
MEPLRLLILL FVTELSGAHN TTVFQGVAGQ SLQVSCPYDS MKHWGRRKAW CRQLGEKGPC  60
QRVVSTHNLW LLSFLRRWNG STAITDDTLG GTLTITLRNL QPHDAGLYQC QSLHGSEADT  120
LRKVLVEVLA DPLDHRDAGD LWFPGESESF EDAHVEHSIS RPSQGSHLPS CLSKEPLGRR  180
NPLPTHFHPS PPGLHLSHQD SSSQRPLGCS LAWTEARDTS TQ                     222

SEQ ID NO: 4           moltype = RNA  length = 983
FEATURE                Location/Qualifiers
source                 1..983
                       mol_type = mRNA
                       organism = Homo sapiens
SEQUENCE: 4
actctgcttc tgcccttggc tggggaaggg tggcatggag cctctccggc tgctcatctt  60
actctttgtc acagagctgt ccggagccca caacaccaca gtgttccagg gcgtggcggg  120
ccagtccctg caggtgtctt gcccctatga ctccatgaag cactggggga ggcgcaaggc  180
ctggtgccgc cagctgggag agaagggccc atgccagcgt gtggtcagca cgcacaactt  240
gtggctgctg tccttcctga ggaggtggaa tgggagcaca gccatcacag acgataccct  300
gggtggcact ctcaccatta cgctgcggaa tctacaaccc catgatgcgg gtctctacca  360
gtgccagagc ctccatggca gtgaggctga caccctcagg aaggtcctgg tggaggtgct  420
ggcagacccc ctggatcacc gggatgctgg agatctctgg ttccccgggg agtctgagag  480
cttcgaggat gcccatgtgg agcacagcat ctccaggagc ctcttggaag gagaaatccc  540
cttcccaccc acttccatcc ttctcctcct ggcctgcatc tttctcatca agattctagc  600
agccagcgcc ctctgggctg cagcctggca tggacagaag ccagggacac atccacccag  660
tgaactggac tgtggccatg acccagggta tcagctccaa actctgccag ggctgagaga  720
```

```
cacgtgaagg aagatgatgg gaggaaaagc ccaggagaag tcccaccagg gaccagccca  780
gcctgcatac ttgccacttg gccaccagga ctccttgttc tgctctggca agagactact  840
ctgcctgaac actgcttctc ctggaccctg gaagcaggga ctggttgagg gagtggggag  900
gtggtaagaa cacctgacaa cttctgaata ttggacattt taaacactta caaataaatc  960
caagactgtc atatttagct gga                                          983

SEQ ID NO: 5            moltype =   length =
SEQUENCE: 5
000

SEQ ID NO: 6            moltype =   length =
SEQUENCE: 6
000

SEQ ID NO: 7            moltype =   length =
SEQUENCE: 7
000

SEQ ID NO: 8            moltype = AA  length = 9
FEATURE                 Location/Qualifiers
source                  1..9
                        mol_type = protein
                        organism = synthetic construct
VARIANT                 4
                        note = S or A
VARIANT                 5
                        note = S or Q
SEQUENCE: 8
GTFXXYAIS                                                          9

SEQ ID NO: 9            moltype = AA  length = 17
FEATURE                 Location/Qualifiers
source                  1..17
                        mol_type = protein
                        organism = synthetic construct
VARIANT                 1
                        note = G or V
VARIANT                 5
                        note = I or D
SEQUENCE: 9
XIIPXSGTAN YAQKFQG                                                 17

SEQ ID NO: 10           moltype = AA  length = 11
FEATURE                 Location/Qualifiers
source                  1..11
                        mol_type = protein
                        organism = synthetic construct
VARIANT                 6
                        note = Y or N
VARIANT                 8
                        note = A, I, or L
VARIANT                 11
                        note = I or S
SEQUENCE: 10
ARTQEXTXFD X                                                       11

SEQ ID NO: 11           moltype = AA  length = 9
FEATURE                 Location/Qualifiers
source                  1..9
                        mol_type = protein
                        organism = synthetic construct
VARIANT                 4
                        note = G or D
VARIANT                 5
                        note = D or E
VARIANT                 6
                        note = Y or H
VARIANT                 7
                        note = A or T
SEQUENCE: 11
FTFXXXXMS                                                          9

SEQ ID NO: 12           moltype = AA  length = 19
FEATURE                 Location/Qualifiers
source                  1..19
                        mol_type = protein
                        organism = synthetic construct
VARIANT                 8
                        note = G or V
```

```
VARIANT                 9
                        note = I or D
SEQUENCE: 12
FIGSKAYXXT TEYTASVKG                                                    19

SEQ ID NO: 13           moltype = AA  length = 17
FEATURE                 Location/Qualifiers
source                  1..17
                        mol_type = protein
                        organism = synthetic construct
VARIANT                 6
                        note = Y or R
VARIANT                 7
                        note = S or D
VARIANT                 9
                        note = G or T
VARIANT                 10
                        note = Y or G
VARIANT                 12
                        note = H, T, or V
SEQUENCE: 13
ARGKRXXYXX WXPAFDV                                                      17

SEQ ID NO: 14           moltype =   length =
SEQUENCE: 14
000

SEQ ID NO: 15           moltype =   length =
SEQUENCE: 15
000

SEQ ID NO: 16           moltype =   length =
SEQUENCE: 16
000

SEQ ID NO: 17           moltype = AA  length = 9
FEATURE                 Location/Qualifiers
source                  1..9
                        mol_type = protein
                        organism = synthetic construct
VARIANT                 4
                        note = Y or F
VARIANT                 5
                        note = H or E
SEQUENCE: 17
QQDXXWPIT                                                               9

SEQ ID NO: 18           moltype = AA  length = 8
FEATURE                 Location/Qualifiers
source                  1..8
                        mol_type = protein
                        organism = synthetic construct
VARIANT                 2
                        note = Q or E
VARIANT                 5
                        note = S or Q
VARIANT                 7
                        note = L or I
VARIANT                 8
                        note = T or A
SEQUENCE: 18
QXYDXYXX                                                                8

SEQ ID NO: 19           moltype = AA  length = 9
FEATURE                 Location/Qualifiers
source                  1..9
                        mol_type = protein
                        organism = synthetic construct
SEQUENCE: 19
GTFSSYAIS                                                               9

SEQ ID NO: 20           moltype = AA  length = 9
FEATURE                 Location/Qualifiers
source                  1..9
                        mol_type = protein
                        organism = synthetic construct
SEQUENCE: 20
GTFAQYAIS                                                               9
```

```
SEQ ID NO: 21            moltype = AA  length = 9
FEATURE                  Location/Qualifiers
source                   1..9
                         mol_type = protein
                         organism = synthetic construct
SEQUENCE: 21
FTFSNYAMS                                                             9

SEQ ID NO: 22            moltype = AA  length = 9
FEATURE                  Location/Qualifiers
source                   1..9
                         mol_type = protein
                         organism = synthetic construct
SEQUENCE: 22
FTFSSYAMS                                                             9

SEQ ID NO: 23            moltype = AA  length = 10
FEATURE                  Location/Qualifiers
source                   1..10
                         mol_type = protein
                         organism = synthetic construct
SEQUENCE: 23
GSISSSNWWS                                                            10

SEQ ID NO: 24            moltype = AA  length = 10
FEATURE                  Location/Qualifiers
source                   1..10
                         mol_type = protein
                         organism = synthetic construct
SEQUENCE: 24
GSISDSAWWS                                                            10

SEQ ID NO: 25            moltype = AA  length = 9
FEATURE                  Location/Qualifiers
source                   1..9
                         mol_type = protein
                         organism = synthetic construct
SEQUENCE: 25
FTFSNYGMG                                                             9

SEQ ID NO: 26            moltype = AA  length = 9
FEATURE                  Location/Qualifiers
source                   1..9
                         mol_type = protein
                         organism = synthetic construct
SEQUENCE: 26
FTFSTHAMT                                                             9

SEQ ID NO: 27            moltype = AA  length = 9
FEATURE                  Location/Qualifiers
source                   1..9
                         mol_type = protein
                         organism = synthetic construct
SEQUENCE: 27
FTFGDYAMS                                                             9

SEQ ID NO: 28            moltype = AA  length = 9
FEATURE                  Location/Qualifiers
source                   1..9
                         mol_type = protein
                         organism = synthetic construct
SEQUENCE: 28
FTFGEYTMS                                                             9

SEQ ID NO: 29            moltype = AA  length = 9
FEATURE                  Location/Qualifiers
source                   1..9
                         mol_type = protein
                         organism = synthetic construct
SEQUENCE: 29
FTFDDYTMS                                                             9

SEQ ID NO: 30            moltype = AA  length = 9
FEATURE                  Location/Qualifiers
source                   1..9
                         mol_type = protein
                         organism = synthetic construct
SEQUENCE: 30
FTFDDHAMS                                                             9
```

```
SEQ ID NO: 31          moltype = AA  length = 9
FEATURE                Location/Qualifiers
source                 1..9
                       mol_type = protein
                       organism = synthetic construct
SEQUENCE: 31
FTFSDYYMS                                                              9

SEQ ID NO: 32          moltype = AA  length = 17
FEATURE                Location/Qualifiers
source                 1..17
                       mol_type = protein
                       organism = synthetic construct
SEQUENCE: 32
GIIPISGTAN YAQKFQG                                                     17

SEQ ID NO: 33          moltype = AA  length = 17
FEATURE                Location/Qualifiers
source                 1..17
                       mol_type = protein
                       organism = synthetic construct
SEQUENCE: 33
VIIPDSGTAN YAQKFQG                                                     17

SEQ ID NO: 34          moltype = AA  length = 17
FEATURE                Location/Qualifiers
source                 1..17
                       mol_type = protein
                       organism = synthetic construct
SEQUENCE: 34
AISGSGGSTY YADSVKG                                                     17

SEQ ID NO: 35          moltype = AA  length = 16
FEATURE                Location/Qualifiers
source                 1..16
                       mol_type = protein
                       organism = synthetic construct
SEQUENCE: 35
EIYHSGSTNY NPSLKS                                                      16

SEQ ID NO: 36          moltype = AA  length = 16
FEATURE                Location/Qualifiers
source                 1..16
                       mol_type = protein
                       organism = synthetic construct
SEQUENCE: 36
EIYHDADTNY NPSLKS                                                      16

SEQ ID NO: 37          moltype = AA  length = 17
FEATURE                Location/Qualifiers
source                 1..17
                       mol_type = protein
                       organism = synthetic construct
SEQUENCE: 37
AISANAGKTY YADSVKG                                                     17

SEQ ID NO: 38          moltype = AA  length = 19
FEATURE                Location/Qualifiers
source                 1..19
                       mol_type = protein
                       organism = synthetic construct
SEQUENCE: 38
FIGSKAYGGT TEYTASVKG                                                   19

SEQ ID NO: 39          moltype = AA  length = 19
FEATURE                Location/Qualifiers
source                 1..19
                       mol_type = protein
                       organism = synthetic construct
SEQUENCE: 39
FIGSKAYAGT TEYTASVKG                                                   19

SEQ ID NO: 40          moltype = AA  length = 19
FEATURE                Location/Qualifiers
source                 1..19
                       mol_type = protein
                       organism = synthetic construct
SEQUENCE: 40
```

```
FIGSKAYSAT TEYTASVKG                                                19

SEQ ID NO: 41          moltype = AA  length = 17
FEATURE                Location/Qualifiers
source                 1..17
                       mol_type = protein
                       organism = synthetic construct
SEQUENCE: 41
YISSSGSTIY YADSVKG                                                  17

SEQ ID NO: 42          moltype = AA  length = 11
FEATURE                Location/Qualifiers
source                 1..11
                       mol_type = protein
                       organism = synthetic construct
SEQUENCE: 42
ARTQEYTAFD I                                                        11

SEQ ID NO: 43          moltype = AA  length = 11
FEATURE                Location/Qualifiers
source                 1..11
                       mol_type = protein
                       organism = synthetic construct
SEQUENCE: 43
ARTQENTIFD I                                                        11

SEQ ID NO: 44          moltype = AA  length = 12
FEATURE                Location/Qualifiers
source                 1..12
                       mol_type = protein
                       organism = synthetic construct
SEQUENCE: 44
AKHYDRGRAF DI                                                       12

SEQ ID NO: 45          moltype = AA  length = 12
FEATURE                Location/Qualifiers
source                 1..12
                       mol_type = protein
                       organism = synthetic construct
SEQUENCE: 45
AKSPAYFGYG ET                                                       12

SEQ ID NO: 46          moltype = AA  length = 12
FEATURE                Location/Qualifiers
source                 1..12
                       mol_type = protein
                       organism = synthetic construct
SEQUENCE: 46
ARDTKYQAGM DV                                                       12

SEQ ID NO: 47          moltype = AA  length = 12
FEATURE                Location/Qualifiers
source                 1..12
                       mol_type = protein
                       organism = synthetic construct
SEQUENCE: 47
ARDTKYWGGM DV                                                       12

SEQ ID NO: 48          moltype = AA  length = 15
FEATURE                Location/Qualifiers
source                 1..15
                       mol_type = protein
                       organism = synthetic construct
SEQUENCE: 48
AKDRGGYEVG PTFDP                                                    15

SEQ ID NO: 49          moltype = AA  length = 15
FEATURE                Location/Qualifiers
source                 1..15
                       mol_type = protein
                       organism = synthetic construct
SEQUENCE: 49
ASLRGGYEVG PTFDP                                                    15

SEQ ID NO: 50          moltype = AA  length = 15
FEATURE                Location/Qualifiers
source                 1..15
                       mol_type = protein
                       organism = synthetic construct
```

```
SEQUENCE: 50
ASLRGGYEVG PTFDS                                              15

SEQ ID NO: 51          moltype = AA  length = 17
FEATURE                Location/Qualifiers
source                 1..17
                       mol_type = protein
                       organism = synthetic construct
SEQUENCE: 51
ARGKRYSYGY WHPAFDV                                            17

SEQ ID NO: 52          moltype = AA  length = 17
FEATURE                Location/Qualifiers
source                 1..17
                       mol_type = protein
                       organism = synthetic construct
SEQUENCE: 52
ARGKRYSYGG WVPAFDV                                            17

SEQ ID NO: 53          moltype = AA  length = 17
FEATURE                Location/Qualifiers
source                 1..17
                       mol_type = protein
                       organism = synthetic construct
SEQUENCE: 53
ARGKRYSYTY WTPAFDV                                            17

SEQ ID NO: 54          moltype = AA  length = 11
FEATURE                Location/Qualifiers
source                 1..11
                       mol_type = protein
                       organism = synthetic construct
SEQUENCE: 54
ARTQEYTLFD I                                                  11

SEQ ID NO: 55          moltype = AA  length = 11
FEATURE                Location/Qualifiers
source                 1..11
                       mol_type = protein
                       organism = synthetic construct
SEQUENCE: 55
ARTQEYTLFD S                                                  11

SEQ ID NO: 56          moltype = AA  length = 12
FEATURE                Location/Qualifiers
source                 1..12
                       mol_type = protein
                       organism = synthetic construct
SEQUENCE: 56
AKHPAVFGYG ET                                                 12

SEQ ID NO: 57          moltype = AA  length = 15
FEATURE                Location/Qualifiers
source                 1..15
                       mol_type = protein
                       organism = synthetic construct
SEQUENCE: 57
AKLRGGYEVG PTFDP                                              15

SEQ ID NO: 58          moltype = AA  length = 17
FEATURE                Location/Qualifiers
source                 1..17
                       mol_type = protein
                       organism = synthetic construct
SEQUENCE: 58
ARGKRRDYGY WHPAFDV                                            17

SEQ ID NO: 59          moltype = AA  length = 14
FEATURE                Location/Qualifiers
source                 1..14
                       mol_type = protein
                       organism = synthetic construct
SEQUENCE: 59
ARLGGYYSLG PMDV                                               14

SEQ ID NO: 60          moltype = AA  length = 11
FEATURE                Location/Qualifiers
source                 1..11
                       mol_type = protein
```

```
                        organism = synthetic construct
SEQUENCE: 60
RASQSVSSYL A                                                      11

SEQ ID NO: 61           moltype = AA  length = 12
FEATURE                 Location/Qualifiers
source                  1..12
                        mol_type = protein
                        organism = synthetic construct
SEQUENCE: 61
RASQSVSSSY LA                                                     12

SEQ ID NO: 62           moltype = AA  length = 12
FEATURE                 Location/Qualifiers
source                  1..12
                        mol_type = protein
                        organism = synthetic construct
SEQUENCE: 62
RASQSVSSSF LA                                                     12

SEQ ID NO: 63           moltype = AA  length = 11
FEATURE                 Location/Qualifiers
source                  1..11
                        mol_type = protein
                        organism = synthetic construct
SEQUENCE: 63
QASQDISNYL N                                                      11

SEQ ID NO: 64           moltype = AA  length = 17
FEATURE                 Location/Qualifiers
source                  1..17
                        mol_type = protein
                        organism = synthetic construct
SEQUENCE: 64
KSSQSVLYSS NNKNYLA                                                17

SEQ ID NO: 65           moltype = AA  length = 11
FEATURE                 Location/Qualifiers
source                  1..11
                        mol_type = protein
                        organism = synthetic construct
SEQUENCE: 65
QASQDITNYL N                                                      11

SEQ ID NO: 66           moltype = AA  length = 7
FEATURE                 Location/Qualifiers
source                  1..7
                        mol_type = protein
                        organism = synthetic construct
SEQUENCE: 66
DASNRAT                                                           7

SEQ ID NO: 67           moltype = AA  length = 7
FEATURE                 Location/Qualifiers
source                  1..7
                        mol_type = protein
                        organism = synthetic construct
SEQUENCE: 67
GASSRAT                                                           7

SEQ ID NO: 68           moltype = AA  length = 7
FEATURE                 Location/Qualifiers
source                  1..7
                        mol_type = protein
                        organism = synthetic construct
SEQUENCE: 68
DASNLAT                                                           7

SEQ ID NO: 69           moltype = AA  length = 7
FEATURE                 Location/Qualifiers
source                  1..7
                        mol_type = protein
                        organism = synthetic construct
SEQUENCE: 69
WASTRES                                                           7

SEQ ID NO: 70           moltype = AA  length = 7
FEATURE                 Location/Qualifiers
source                  1..7
```

```
                        mol_type = protein
                        organism = synthetic construct
SEQUENCE: 70
DASNLET                                                         7

SEQ ID NO: 71           moltype = AA  length = 9
FEATURE                 Location/Qualifiers
source                  1..9
                        mol_type = protein
                        organism = synthetic construct
SEQUENCE: 71
QQDYHWPIT                                                       9

SEQ ID NO: 72           moltype = AA  length = 9
FEATURE                 Location/Qualifiers
source                  1..9
                        mol_type = protein
                        organism = synthetic construct
SEQUENCE: 72
QQDYEWPIT                                                       9

SEQ ID NO: 73           moltype = AA  length = 9
FEATURE                 Location/Qualifiers
source                  1..9
                        mol_type = protein
                        organism = synthetic construct
SEQUENCE: 73
QQYDDVPYT                                                       9

SEQ ID NO: 74           moltype = AA  length = 9
FEATURE                 Location/Qualifiers
source                  1..9
                        mol_type = protein
                        organism = synthetic construct
SEQUENCE: 74
QQYYSPPIT                                                       9

SEQ ID NO: 75           moltype = AA  length = 8
FEATURE                 Location/Qualifiers
source                  1..8
                        mol_type = protein
                        organism = synthetic construct
SEQUENCE: 75
QQYVVFPT                                                        8

SEQ ID NO: 76           moltype = AA  length = 8
FEATURE                 Location/Qualifiers
source                  1..8
                        mol_type = protein
                        organism = synthetic construct
SEQUENCE: 76
QQYVEAPT                                                        8

SEQ ID NO: 77           moltype = AA  length = 9
FEATURE                 Location/Qualifiers
source                  1..9
                        mol_type = protein
                        organism = synthetic construct
SEQUENCE: 77
QQHYLTPIT                                                       9

SEQ ID NO: 78           moltype = AA  length = 9
FEATURE                 Location/Qualifiers
source                  1..9
                        mol_type = protein
                        organism = synthetic construct
SEQUENCE: 78
QQHYLWPIS                                                       9

SEQ ID NO: 79           moltype = AA  length = 9
FEATURE                 Location/Qualifiers
source                  1..9
                        mol_type = protein
                        organism = synthetic construct
SEQUENCE: 79
QQHYIWPIT                                                       9

SEQ ID NO: 80           moltype = AA  length = 8
FEATURE                 Location/Qualifiers
```

```
source                  1..8
                        mol_type = protein
                        organism = synthetic construct
SEQUENCE: 80
QQYDSYLT                                                                  8

SEQ ID NO: 81           moltype = AA  length = 8
FEATURE                 Location/Qualifiers
source                  1..8
                        mol_type = protein
                        organism = synthetic construct
SEQUENCE: 81
QEYDSYLA                                                                  8

SEQ ID NO: 82           moltype = AA  length = 8
FEATURE                 Location/Qualifiers
source                  1..8
                        mol_type = protein
                        organism = synthetic construct
SEQUENCE: 82
QEYDSYIT                                                                  8

SEQ ID NO: 83           moltype = AA  length = 9
FEATURE                 Location/Qualifiers
source                  1..9
                        mol_type = protein
                        organism = synthetic construct
SEQUENCE: 83
QQDFHWPIT                                                                 9

SEQ ID NO: 84           moltype = AA  length = 9
FEATURE                 Location/Qualifiers
source                  1..9
                        mol_type = protein
                        organism = synthetic construct
SEQUENCE: 84
QQYYGLPIT                                                                 9

SEQ ID NO: 85           moltype = AA  length = 8
FEATURE                 Location/Qualifiers
source                  1..8
                        mol_type = protein
                        organism = synthetic construct
SEQUENCE: 85
QEYDQYLT                                                                  8

SEQ ID NO: 86           moltype = AA  length = 9
FEATURE                 Location/Qualifiers
source                  1..9
                        mol_type = protein
                        organism = synthetic construct
SEQUENCE: 86
QQDSAFPFT                                                                 9

SEQ ID NO: 87           moltype = AA  length = 118
FEATURE                 Location/Qualifiers
source                  1..118
                        mol_type = protein
                        organism = synthetic construct
SEQUENCE: 87
QVQLVQSGAE VKKPGSSVKV SCKASGGTFS SYAISWVRQA PGQGLEWMGG IIPISGTANY  60
AQKFQGRVTI TADESTSTAY MELSSLRSED TAVYYCARTQ EYTAFDIWGQ GTMVTVSS    118

SEQ ID NO: 88           moltype = AA  length = 118
FEATURE                 Location/Qualifiers
source                  1..118
                        mol_type = protein
                        organism = synthetic construct
SEQUENCE: 88
QVQLVQSGAE VKKPGSSVKV SCKASGGTFA QYAISWVRQA PGQGLEWMGV IIPDSGTANY  60
AQKFQGRVTI TADESTSTAY MELSSLRSED TAVYYCARTQ ENTIFDIWGQ GTMVTVSS    118

SEQ ID NO: 89           moltype = AA  length = 119
FEATURE                 Location/Qualifiers
source                  1..119
                        mol_type = protein
                        organism = synthetic construct
SEQUENCE: 89
EVQLLESGGG LVQPGGSLRL SCAASGFTFS NYAMSWVRQA PGKGLEWVSA ISGSGGSTYY  60
```

```
ADSVKGRFTI SRDNSKNTLY LQMNSLRAED TAVYYCAKHY DRGRAFDIWG QGTMVTVSS   119

SEQ ID NO: 90          moltype = AA  length = 119
FEATURE                Location/Qualifiers
source                 1..119
                       mol_type = protein
                       organism = synthetic construct
SEQUENCE: 90
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKSP AYFGYGETWG QGTLVTVSS   119

SEQ ID NO: 91          moltype = AA  length = 119
FEATURE                Location/Qualifiers
source                 1..119
                       mol_type = protein
                       organism = synthetic construct
SEQUENCE: 91
QVQLQESGPG LVKPSGTLSL TCAVSGGSIS SSNWWSWVRQ PPGKGLEWIG EIYHSGSTNY  60
NPSLKSRVTI SVDKSKNQFS LKLSSVTAAD TAVYYCARDT KYQAGMDVWG QGTTVTVSS   119

SEQ ID NO: 92          moltype = AA  length = 119
FEATURE                Location/Qualifiers
source                 1..119
                       mol_type = protein
                       organism = synthetic construct
SEQUENCE: 92
QVQLQESGPG LVKPSGTLSL TCAVSGGSIS DSAWWSWVRQ PPGKGLEWIG EIYHDADTNY  60
NPSLKSRVTI SVDKSKNQFS LKLSSVTAAD TAVYYCARDT KYWGGMDVWG QGTTVTVSS   119

SEQ ID NO: 93          moltype = AA  length = 122
FEATURE                Location/Qualifiers
source                 1..122
                       mol_type = protein
                       organism = synthetic construct
SEQUENCE: 93
EVQLLESGGG LVQPGGSLRL SCAASGFTFS NYAMSWVRQA PGKGLEWVSA ISGSGGSTYY  60
ADSVKGRFTI SRDNSKNTLY LQMNSLRAED TAVYYCAKDR GGYEVGPTFD PWGQGTLVTV  120
SS                                                                122

SEQ ID NO: 94          moltype = AA  length = 122
FEATURE                Location/Qualifiers
source                 1..122
                       mol_type = protein
                       organism = synthetic construct
SEQUENCE: 94
EVQLLESGGG LVQPGGSLRL SCAASGFTFS NYGMGWVRQA PGKGLEWVSA ISANAGKTYY  60
ADSVKGRFTI SRDNSKNTLY LQMNSLRAED TAVYYCASLR GGYEVGPTFD PWGQGTLVTV  120
SS                                                                122

SEQ ID NO: 95          moltype = AA  length = 122
FEATURE                Location/Qualifiers
source                 1..122
                       mol_type = protein
                       organism = synthetic construct
SEQUENCE: 95
EVQLLESGGG LVQPGGSLRL SCAASGFTFS THAMTWVRQA PGKGLEWVSA ISANAGKTYY  60
ADSVKGRFTI SRDNSKNTLY LQMNSLRAED TAVYYCASLR GGYEVGPTFD SWGQGTLVTV  120
SS                                                                122

SEQ ID NO: 96          moltype = AA  length = 126
FEATURE                Location/Qualifiers
source                 1..126
                       mol_type = protein
                       organism = synthetic construct
SEQUENCE: 96
EVQLVESGGG LVQPGRSLRL SCTASGFTFG DYAMSWFRQA PGKGLEWVGF IGSKAYGGTT  60
EYTASVKGRF TISRDGSKSI AYLQMNSLKT EDTAVYYCAR GKRYSYGYWH PAFDVWGQGT  120
MVTVSS                                                            126

SEQ ID NO: 97          moltype = AA  length = 126
FEATURE                Location/Qualifiers
source                 1..126
                       mol_type = protein
                       organism = synthetic construct
SEQUENCE: 97
EVQLVESGGG LVQPGRSLRL SCTASGFTFG EYTMSWFRQA PGKGLEWVGF IGSKAYAGTT  60
EYTASVKGRF TISRDGSKSI AYLQMNSLKT EDTAVYYCAR GKRYSYGGWV PAFDVWGQGT  120
MVTVSS                                                            126
```

```
SEQ ID NO: 98          moltype = AA  length = 126
FEATURE                Location/Qualifiers
source                 1..126
                       mol_type = protein
                       organism = synthetic construct
SEQUENCE: 98
EVQLVESGGG LVQPGRSLRL SCTASGFTFD DYTMSWFRQA PGKGLEWVGF IGSKAYSATT  60
EYTASVKGRF TISRDGSKSI AYLQMNSLKT EDTAVYYCAR GKRYSYTYWT PAFDVWGQGT  120
MVTVSS                                                            126

SEQ ID NO: 99          moltype = AA  length = 126
FEATURE                Location/Qualifiers
source                 1..126
                       mol_type = protein
                       organism = synthetic construct
SEQUENCE: 99
EVQLVESGGG LVQPGRSLRL SCTASGFTFD DHAMSWFRQA PGKGLEWVGF IGSKAYGGTT  60
EYTASVKGRF TISRDGSKSI AYLQMNSLKT EDTAVYYCAR GKRYSYTYWT PAFDVWGQGT  120
MVTVSS                                                            126

SEQ ID NO: 100         moltype = AA  length = 118
FEATURE                Location/Qualifiers
source                 1..118
                       mol_type = protein
                       organism = synthetic construct
SEQUENCE: 100
QVQLVQSGAE VKKPGSSVKV SCKASGGTFS SYAISWVRQA PGQGLEWMGG IIPISGTANY  60
AQKFQGRVTI TADESTSTAY MELSSLRSED TAVYYCARTQ EYTLFDIWGQ GTMVTVSS    118

SEQ ID NO: 101         moltype = AA  length = 118
FEATURE                Location/Qualifiers
source                 1..118
                       mol_type = protein
                       organism = synthetic construct
SEQUENCE: 101
QVQLVQSGAE VKKPGSSVKV SCKASGGTFS SYAISWVRQA PGQGLEWMGG IIPISGTANY  60
AQKFQGRVTI TADESTSTAY MELSSLRSED TAVYYCARTQ EYTLFDSWGQ GTMVTVSS    118

SEQ ID NO: 102         moltype = AA  length = 119
FEATURE                Location/Qualifiers
source                 1..119
                       mol_type = protein
                       organism = synthetic construct
SEQUENCE: 102
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKHP AVFGYGETWG QGTLVTVSS   119

SEQ ID NO: 103         moltype = AA  length = 119
FEATURE                Location/Qualifiers
source                 1..119
                       mol_type = protein
                       organism = synthetic construct
SEQUENCE: 103
QVQLQESGPG LVKPSGTLSL TCAVSGGSIS SSNWWSWVRQ PPGKGLEWIG EIYHSGSTNY  60
NPSLKSRVTI SVDKSKNQFS LKLSSVTAAD TAVYYCARDT KYWGGMDVWG QGTTVTVSS   119

SEQ ID NO: 104         moltype = AA  length = 122
FEATURE                Location/Qualifiers
source                 1..122
                       mol_type = protein
                       organism = synthetic construct
SEQUENCE: 104
EVQLLESGGG LVQPGGSLRL SCAASGFTFS NYAMSWVRQA PGKGLEWVSA ISGSGGSTYY  60
ADSVKGRFTI SRDNSKNTLY LQMNSLRAED TAVYYCAKLR GGYEVGPTFD PWGQGTLVTV  120
SS                                                                122

SEQ ID NO: 105         moltype = AA  length = 126
FEATURE                Location/Qualifiers
source                 1..126
                       mol_type = protein
                       organism = synthetic construct
SEQUENCE: 105
EVQLVESGGG LVQPGRSLRL SCTASGFTFG DYAMSWFRQA PGKGLEWVGF IGSKAYGGTT  60
EYTASVKGRF TISRDGSKSI AYLQMNSLKT EDTAVYYCAR GKRRDYGYWH PAFDVWGQGT  120
MVTVSS                                                            126

SEQ ID NO: 106         moltype = AA  length = 121
FEATURE                Location/Qualifiers
source                 1..121
```

```
                        mol_type = protein
                        organism = synthetic construct
SEQUENCE: 106
QVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARLG GYYSLGPMDV WGQGTTVTVS  120
S                                                                  121

SEQ ID NO: 107          moltype = AA  length = 118
FEATURE                 Location/Qualifiers
source                  1..118
                        mol_type = protein
                        organism = synthetic construct
SEQUENCE: 107
QVQLVQSGAE VKKPGSSVKV SCKASGGTFS SYAISWVRQA PGQGLEWMGG IIPISGTANY  60
AQKFQGRVTI TADESTSTAY MELSSLRSED TAVYYCARTQ EYTLFDSWGQ GTLVTVSS    118

SEQ ID NO: 108          moltype = AA  length = 118
FEATURE                 Location/Qualifiers
source                  1..118
                        mol_type = protein
                        organism = synthetic construct
SEQUENCE: 108
QVQLVQSGAE VKKPGSSVKV SCKASGGTFA QYAISWVRQA PGQGLEWMGV IIPDSGTANY  60
AQKFQGRVTI TADESTSTAY MELSSLRSED TAVYYCARTQ ENTIFDIWGQ GTLVTVSS    118

SEQ ID NO: 109          moltype = AA  length = 126
FEATURE                 Location/Qualifiers
source                  1..126
                        mol_type = protein
                        organism = synthetic construct
SEQUENCE: 109
EVQLVESGGG LVQPGRSLRL SCTASGFTFD DYTMSWFRQA PGKGLEWVGF IGSKAYSATT  60
EYTASVKGRF TISRDGSKSI AYLQMNSLKT EDTAVYYCAR GKRYSYTYWT PAFDVWGQGT  120
LVTVSS                                                             126

SEQ ID NO: 110          moltype = AA  length = 107
FEATURE                 Location/Qualifiers
source                  1..107
                        mol_type = protein
                        organism = synthetic construct
SEQUENCE: 110
EIVLTQSPAT LSLSPGERAT LSCRASQSVS SYLAWFQQKP GQAPRLLIYD ASNRATGIPA  60
RFSGSGSGTD FTLTISSLEP EDFAVYYCQQ DYHWPITFGG GTKVEIK                107

SEQ ID NO: 111          moltype = AA  length = 107
FEATURE                 Location/Qualifiers
source                  1..107
                        mol_type = protein
                        organism = synthetic construct
SEQUENCE: 111
EIVLTQSPAT LSLSPGERAT LSCRASQSVS SYLAWFQQKP GQAPRLLIYD ASNRATGIPA  60
RFSGSGSGTD FTLTISSLEP EDFAVYYCQQ DYEWPITFGG GTKVEIK                107

SEQ ID NO: 112          moltype = AA  length = 108
FEATURE                 Location/Qualifiers
source                  1..108
                        mol_type = protein
                        organism = synthetic construct
SEQUENCE: 112
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYDDVPYTFG GGTKVEIK               108

SEQ ID NO: 113          moltype = AA  length = 108
FEATURE                 Location/Qualifiers
source                  1..108
                        mol_type = protein
                        organism = synthetic construct
SEQUENCE: 113
EIVLTQSPGT LSLSPGERAT LSCRASQSVS SSFLAWYQQK PGQAPRLLIY GASSRATGIP  60
DRFSGSGSGT DFTLTISRLE PEDFAVYYCQ QYYSPPITFG GGTKVEIK               108

SEQ ID NO: 114          moltype = AA  length = 106
FEATURE                 Location/Qualifiers
source                  1..106
                        mol_type = protein
                        organism = synthetic construct
SEQUENCE: 114
DIQMTQSPSS LSASVGDRVT ITCQASQDIS NYLNWYQQKP GKAPKLLIYD ASNLATGVPS  60
RFSGSGSGTD FTFTISSLQP EDIATYYCQQ YVVFPTFGGG TKVEIK                 106
```

```
SEQ ID NO: 115          moltype = AA  length = 106
FEATURE                 Location/Qualifiers
source                  1..106
                        mol_type = protein
                        organism = synthetic construct
SEQUENCE: 115
DIQMTQSPSS LSASVGDRVT ITCQASQDIS NYLNWYQQKP GKAPKLLIYD ASNLATGVPS  60
RFSGSGSGTD FTFTISSLQP EDIATYYCQQ YVEAPTFGGG TKVEIK                106

SEQ ID NO: 116          moltype = AA  length = 113
FEATURE                 Location/Qualifiers
source                  1..113
                        mol_type = protein
                        organism = synthetic construct
SEQUENCE: 116
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQHYLT PITFGGGTKV EIK        113

SEQ ID NO: 117          moltype = AA  length = 113
FEATURE                 Location/Qualifiers
source                  1..113
                        mol_type = protein
                        organism = synthetic construct
SEQUENCE: 117
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQHYLW PISFGGGTKV EIK        113

SEQ ID NO: 118          moltype = AA  length = 113
FEATURE                 Location/Qualifiers
source                  1..113
                        mol_type = protein
                        organism = synthetic construct
SEQUENCE: 118
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQHYIW PITFGGGTKV EIK        113

SEQ ID NO: 119          moltype = AA  length = 106
FEATURE                 Location/Qualifiers
source                  1..106
                        mol_type = protein
                        organism = synthetic construct
SEQUENCE: 119
DIQMTQSPSS LSASVGDRVT ITCQASQDIT NYLNWYQQKP GKAPKLLIYD ASNLETGVPS  60
RFSGSGSGTD FTFTISSLQP EDIATYYCQQ YDSYLTFGGG TKVEIK                106

SEQ ID NO: 120          moltype = AA  length = 106
FEATURE                 Location/Qualifiers
source                  1..106
                        mol_type = protein
                        organism = synthetic construct
SEQUENCE: 120
DIQMTQSPSS LSASVGDRVT ITCQASQDIT NYLNWYQQKP GKAPKLLIYD ASNLETGVPS  60
RFSGSGSGTD FTFTISSLQP EDIATYYCQE YDSYLAFGGG TKVEIK                106

SEQ ID NO: 121          moltype = AA  length = 106
FEATURE                 Location/Qualifiers
source                  1..106
                        mol_type = protein
                        organism = synthetic construct
SEQUENCE: 121
DIQMTQSPSS LSASVGDRVT ITCQASQDIT NYLNWYQQKP GKAPKLLIYD ASNLETGVPS  60
RFSGSGSGTD FTFTISSLQP EDIATYYCQE YDSYITFGGG TKVEIK                106

SEQ ID NO: 122          moltype = AA  length = 107
FEATURE                 Location/Qualifiers
source                  1..107
                        mol_type = protein
                        organism = synthetic construct
SEQUENCE: 122
EIVLTQSPAT LSLSPGERAT LSCRASQSVS SYLAWFQQKP GQAPRLLIYD ASNRATGIPA  60
RFSGSGSGTD FTLTISSLEP EDFAVYYCQQ DFHWPITFGG GTKVEIK               107

SEQ ID NO: 123          moltype = AA  length = 108
FEATURE                 Location/Qualifiers
source                  1..108
                        mol_type = protein
                        organism = synthetic construct
SEQUENCE: 123
```

```
EIVLTQSPGT LSLSPGERAT LSCRASQSVS SSFLAWYQQK PGQAPRLLIY GASSRATGIP  60
DRFSGSGSGT DFTLTISRLE PEDFAVYYCQ QYYGLPITFG GGTKVEIK              108

SEQ ID NO: 124         moltype = AA  length = 106
FEATURE                Location/Qualifiers
source                 1..106
                       mol_type = protein
                       organism = synthetic construct
SEQUENCE: 124
DIQMTQSPSS LSASVGDRVT ITCQASQDIT NYLNWYQQKP GKAPKLLIYD ASNLETGVPS  60
RFSGSGSGTD FTFTISSLQP EDIATYYCQE YDQYLTFGGG TKVEIK                106

SEQ ID NO: 125         moltype = AA  length = 107
FEATURE                Location/Qualifiers
source                 1..107
                       mol_type = protein
                       organism = synthetic construct
SEQUENCE: 125
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ DSAFPFTFGG GTKVEIK               107

SEQ ID NO: 126         moltype = AA  length = 26
FEATURE                Location/Qualifiers
source                 1..26
                       mol_type = protein
                       organism = synthetic construct
SEQUENCE: 126
QVQLVQSGAE VKKPGSSVKV SCKASG                                      26

SEQ ID NO: 127         moltype = AA  length = 26
FEATURE                Location/Qualifiers
source                 1..26
                       mol_type = protein
                       organism = synthetic construct
SEQUENCE: 127
EVQLLESGGG LVQPGGSLRL SCAASG                                      26

SEQ ID NO: 128         moltype = AA  length = 26
FEATURE                Location/Qualifiers
source                 1..26
                       mol_type = protein
                       organism = synthetic construct
SEQUENCE: 128
QVQLQESGPG LVKPSGTLSL TCAVSG                                      26

SEQ ID NO: 129         moltype = AA  length = 26
FEATURE                Location/Qualifiers
source                 1..26
                       mol_type = protein
                       organism = synthetic construct
SEQUENCE: 129
EVQLVESGGG LVQPGRSLRL SCTASG                                      26

SEQ ID NO: 130         moltype = AA  length = 26
FEATURE                Location/Qualifiers
source                 1..26
                       mol_type = protein
                       organism = synthetic construct
SEQUENCE: 130
QVQLVESGGG LVKPGGSLRL SCAASG                                      26

SEQ ID NO: 131         moltype = AA  length = 14
FEATURE                Location/Qualifiers
source                 1..14
                       mol_type = protein
                       organism = synthetic construct
SEQUENCE: 131
WVRQAPGQGL EWMG                                                   14

SEQ ID NO: 132         moltype = AA  length = 14
FEATURE                Location/Qualifiers
source                 1..14
                       mol_type = protein
                       organism = synthetic construct
SEQUENCE: 132
WVRQAPGKGL EWVS                                                   14

SEQ ID NO: 133         moltype = AA  length = 14
FEATURE                Location/Qualifiers
```

```
source                  1..14
                        mol_type = protein
                        organism = synthetic construct
SEQUENCE: 133
WVRQPPGKGL EWIG                                                   14

SEQ ID NO: 134          moltype = AA  length = 14
FEATURE                 Location/Qualifiers
source                  1..14
                        mol_type = protein
                        organism = synthetic construct
SEQUENCE: 134
WFRQAPGKGL EWVG                                                   14

SEQ ID NO: 135          moltype = AA  length = 14
FEATURE                 Location/Qualifiers
source                  1..14
                        mol_type = protein
                        organism = synthetic construct
SEQUENCE: 135
WIRQAPGKGL EWVS                                                   14

SEQ ID NO: 136          moltype = AA  length = 30
FEATURE                 Location/Qualifiers
source                  1..30
                        mol_type = protein
                        organism = synthetic construct
SEQUENCE: 136
RVTITADEST STAYMELSSL RSEDTAVYYC                                  30

SEQ ID NO: 137          moltype = AA  length = 30
FEATURE                 Location/Qualifiers
source                  1..30
                        mol_type = protein
                        organism = synthetic construct
SEQUENCE: 137
RFTISRDNSK NTLYLQMNSL RAEDTAVYYC                                  30

SEQ ID NO: 138          moltype = AA  length = 30
FEATURE                 Location/Qualifiers
source                  1..30
                        mol_type = protein
                        organism = synthetic construct
SEQUENCE: 138
RVTISVDKSK NQFSLKLSSV TAADTAVYYC                                  30

SEQ ID NO: 139          moltype = AA  length = 30
FEATURE                 Location/Qualifiers
source                  1..30
                        mol_type = protein
                        organism = synthetic construct
SEQUENCE: 139
RFTISRDGSK SIAYLQMNSL KTEDTAVYYC                                  30

SEQ ID NO: 140          moltype = AA  length = 30
FEATURE                 Location/Qualifiers
source                  1..30
                        mol_type = protein
                        organism = synthetic construct
SEQUENCE: 140
RFTISRDNAK NSLYLQMNSL RAEDTAVYYC                                  30

SEQ ID NO: 141          moltype = AA  length = 11
FEATURE                 Location/Qualifiers
source                  1..11
                        mol_type = protein
                        organism = synthetic construct
SEQUENCE: 141
WGQGTMVTVS S                                                      11

SEQ ID NO: 142          moltype = AA  length = 11
FEATURE                 Location/Qualifiers
source                  1..11
                        mol_type = protein
                        organism = synthetic construct
SEQUENCE: 142
WGQGTLVTVS S                                                      11

SEQ ID NO: 143          moltype = AA  length = 11
```

```
FEATURE                Location/Qualifiers
source                 1..11
                       mol_type = protein
                       organism = synthetic construct
SEQUENCE: 143
WGQGTTVTVS S                                                      11

SEQ ID NO: 144         moltype = AA  length = 23
FEATURE                Location/Qualifiers
source                 1..23
                       mol_type = protein
                       organism = synthetic construct
SEQUENCE: 144
EIVLTQSPAT LSLSPGERAT LSC                                         23

SEQ ID NO: 145         moltype = AA  length = 23
FEATURE                Location/Qualifiers
source                 1..23
                       mol_type = protein
                       organism = synthetic construct
SEQUENCE: 145
EIVLTQSPGT LSLSPGERAT LSC                                         23

SEQ ID NO: 146         moltype = AA  length = 23
FEATURE                Location/Qualifiers
source                 1..23
                       mol_type = protein
                       organism = synthetic construct
SEQUENCE: 146
DIQMTQSPSS LSASVGDRVT ITC                                         23

SEQ ID NO: 147         moltype = AA  length = 23
FEATURE                Location/Qualifiers
source                 1..23
                       mol_type = protein
                       organism = synthetic construct
SEQUENCE: 147
DIVMTQSPDS LAVSLGERAT INC                                         23

SEQ ID NO: 148         moltype = AA  length = 15
FEATURE                Location/Qualifiers
source                 1..15
                       mol_type = protein
                       organism = synthetic construct
SEQUENCE: 148
WFQQKPGQAP RLLIY                                                  15

SEQ ID NO: 149         moltype = AA  length = 15
FEATURE                Location/Qualifiers
source                 1..15
                       mol_type = protein
                       organism = synthetic construct
SEQUENCE: 149
WYQQKPGQAP RLLIY                                                  15

SEQ ID NO: 150         moltype = AA  length = 15
FEATURE                Location/Qualifiers
source                 1..15
                       mol_type = protein
                       organism = synthetic construct
SEQUENCE: 150
WYQQKPGKAP KLLIY                                                  15

SEQ ID NO: 151         moltype = AA  length = 15
FEATURE                Location/Qualifiers
source                 1..15
                       mol_type = protein
                       organism = synthetic construct
SEQUENCE: 151
WYQQKPGQPP KLLIY                                                  15

SEQ ID NO: 152         moltype = AA  length = 32
FEATURE                Location/Qualifiers
source                 1..32
                       mol_type = protein
                       organism = synthetic construct
SEQUENCE: 152
GIPARFSGSG SGTDFTLTIS SLEPEDFAVY YC                               32
```

```
SEQ ID NO: 153         moltype = AA  length = 32
FEATURE                Location/Qualifiers
source                 1..32
                       mol_type = protein
                       organism = synthetic construct
SEQUENCE: 153
GIPDRFSGSG SGTDFTLTIS RLEPEDFAVY YC                                32

SEQ ID NO: 154         moltype = AA  length = 32
FEATURE                Location/Qualifiers
source                 1..32
                       mol_type = protein
                       organism = synthetic construct
SEQUENCE: 154
GVPSRFSGSG SGTDFTFTIS SLQPEDIATY YC                                32

SEQ ID NO: 155         moltype = AA  length = 32
FEATURE                Location/Qualifiers
source                 1..32
                       mol_type = protein
                       organism = synthetic construct
SEQUENCE: 155
GVPDRFSGSG SGTDFTLTIS SLQAEDVAVY YC                                32

SEQ ID NO: 156         moltype = AA  length = 10
FEATURE                Location/Qualifiers
source                 1..10
                       mol_type = protein
                       organism = synthetic construct
SEQUENCE: 156
FGGGTKVEIK                                                         10

SEQ ID NO: 157         moltype = AA  length = 107
FEATURE                Location/Qualifiers
source                 1..107
                       mol_type = protein
                       organism = Homo sapiens
SEQUENCE: 157
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 158         moltype = AA  length = 106
FEATURE                Location/Qualifiers
source                 1..106
                       mol_type = protein
                       organism = Homo sapiens
SEQUENCE: 158
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                 106

SEQ ID NO: 159         moltype = AA  length = 330
FEATURE                Location/Qualifiers
source                 1..330
                       mol_type = protein
                       organism = Homo sapiens
SEQUENCE: 159
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 160         moltype = AA  length = 330
FEATURE                Location/Qualifiers
source                 1..330
                       mol_type = protein
                       organism = synthetic construct
SEQUENCE: 160
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 161         moltype = AA  length = 214
FEATURE                Location/Qualifiers
source                 1..214
```

```
                        mol_type = protein
                        organism = synthetic construct
SEQUENCE: 161
EIVLTQSPAT LSLSPGERAT LSCRASQSVS SYLAWFQQKP GQAPRLLIYD ASNRATGIPA  60
RFSGSGSGTD FTLTISSLEP EDFAVYYCQQ DYHWPITFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 162          moltype = AA  length = 214
FEATURE                 Location/Qualifiers
source                  1..214
                        mol_type = protein
                        organism = synthetic construct
SEQUENCE: 162
EIVLTQSPAT LSLSPGERAT LSCRASQSVS SYLAWFQQKP GQAPRLLIYD ASNRATGIPA  60
RFSGSGSGTD FTLTISSLEP EDFAVYYCQQ DYEWPITFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 163          moltype = AA  length = 213
FEATURE                 Location/Qualifiers
source                  1..213
                        mol_type = protein
                        organism = synthetic construct
SEQUENCE: 163
DIQMTQSPSS LSASVGDRVT ITCQASQDIT NYLNWYQQKP GKAPKLLIYD ASNLETGVPS  60
RFSGSGSGTD FTFTISSLQP EDIATYYCQE YDSYITFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 164          moltype = AA  length = 448
FEATURE                 Location/Qualifiers
source                  1..448
                        mol_type = protein
                        organism = synthetic construct
SEQUENCE: 164
QVQLVQSGAE VKKPGSSVKV SCKASGGTFS SYAISWVRQA PGQGLEWMGG IIPISGTANY  60
AQKFQGRVTI TADESTSTAY MELSSLRSED TAVYYCARTQ EYTLFDSWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 165          moltype = AA  length = 448
FEATURE                 Location/Qualifiers
source                  1..448
                        mol_type = protein
                        organism = synthetic construct
SEQUENCE: 165
QVQLVQSGAE VKKPGSSVKV SCKASGGTFS SYAISWVRQA PGQGLEWMGG IIPISGTANY  60
AQKFQGRVTI TADESTSTAY MELSSLRSED TAVYYCARTQ EYTLFDSWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 166          moltype = AA  length = 448
FEATURE                 Location/Qualifiers
source                  1..448
                        mol_type = protein
                        organism = synthetic construct
SEQUENCE: 166
QVQLVQSGAE VKKPGSSVKV SCKASGGTFA QYAISWVRQA PGQGLEWMGV IIPDSGTANY  60
AQKFQGRVTI TADESTSTAY MELSSLRSED TAVYYCARTQ ENTIFDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 167          moltype = AA  length = 448
FEATURE                 Location/Qualifiers
source                  1..448
                        mol_type = protein
```

```
                         organism = synthetic construct
SEQUENCE: 167
QVQLVQSGAE VKKPGSSVKV SCKASGGTFA QYAISWVRQA PGQGLEWMGV IIPDSGTANY  60
AQKFQGRVTI TADESTSTAY MELSSLRSED TAVYYCARTQ ENTIFDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 168           moltype = AA  length = 456
FEATURE                  Location/Qualifiers
source                   1..456
                         mol_type = protein
                         organism = synthetic construct
SEQUENCE: 168
EVQLVESGGG LVQPGRSLRL SCTASGFTFD DYTMSWFRQA PGKGLEWVGF IGSKAYSATT  60
EYTASVKGRF TISRDGSKSI AYLQMNSLKT EDTAVYYCAR GKRYSYTYWT PAFDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PELLGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSRDELTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                             456

SEQ ID NO: 169           moltype = AA  length = 456
FEATURE                  Location/Qualifiers
source                   1..456
                         mol_type = protein
                         organism = synthetic construct
SEQUENCE: 169
EVQLVESGGG LVQPGRSLRL SCTASGFTFD DYTMSWFRQA PGKGLEWVGF IGSKAYSATT  60
EYTASVKGRF TISRDGSKSI AYLQMNSLKT EDTAVYYCAR GKRYSYTYWT PAFDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PELLGGPSVF LFPPKPKDTL MISRTPEVTC VVVDVSHEDP EVKFNWYVDG VEVHNAKTKP  300
REEQYASTYR VVSVLTVLHQ DWLNGKEYKC KVSNKALPAP IEKTISKAKG QPREPQVYTL  360
PPSRDELTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                             456

SEQ ID NO: 170           moltype = AA  length = 156
FEATURE                  Location/Qualifiers
source                   1..156
                         mol_type = protein
                         organism = Homo sapiens
SEQUENCE: 170
HNTTVFQGVA GQSLQVSCPY DSMKHWGRRK AWCRQLGEKG PCQRVVSTHN LWLLSFLRRW  60
NGSTAITDDT LGGTLTITLR NLQPHDAGLY QCQSLHGSEA DTLRKVLVEV LADPLDHRDA  120
GDLWFPGESE SFEDAHVEHS ISRSLLEGEI PFPPTS                             156

SEQ ID NO: 171           moltype = AA  length = 45
FEATURE                  Location/Qualifiers
source                   1..45
                         mol_type = protein
                         organism = Homo sapiens
SEQUENCE: 171
ADPLDHRDAG DLWFPGESES FEDAHVEHSI SRSLLEGEIP FPPTS                   45

SEQ ID NO: 172           moltype = AA  length = 149
FEATURE                  Location/Qualifiers
source                   1..149
                         mol_type = protein
                         organism = synthetic construct
SEQUENCE: 172
HNTTVFQGVA GQSLQVSCPY DSMKHWGRRK AWCRQLGEKG PCQRVVSTHN RRWNGSTAIT  60
DDTLGGTLTI TLRNLQPHDA GLYQCQSLHG SEADTLRKVL VEVLADPLDH RDAGDLWFPG  120
ESESFEDAHV EHSISRSLLE GEIPFPPTS                                    149

SEQ ID NO: 173           moltype = AA  length = 156
FEATURE                  Location/Qualifiers
source                   1..156
                         mol_type = protein
                         organism = Macaca fascicularis
SEQUENCE: 173
HNTTVFQGVE GQSLQVSCPY DSMKHWGRRK AWCRQLGEKG PCQRVVSTHN LWLLSFLRRR  60
NGSTAITDDT LGGTLTITLR NLQPHDAGFY QCQSLHGSEA DTLRKVLVEV LADPLDHRDA  120
GDLWVPGESE SFEDAHVEHS ISRSLLEGEI PFPPTS                             156
```

-continued

```
SEQ ID NO: 174         moltype = AA  length = 153
FEATURE                Location/Qualifiers
source                 1..153
                       mol_type = protein
                       organism = Mus musculus
SEQUENCE: 174
LNTTVLQGMA GQSLRVSCTY DALKHWGRRK AWCRQLGEEG PCQRVVSTHG VWLLAFLKKR  60
NGSTVIADDT LAGTVTITLK NLQAGDAGLY QCQSLRGREA EVLQKVLVEV LEDPLDDQDA  120
GDLWVPEESS SFEGAQVEHS TSRNQETSFP PTS                               153

SEQ ID NO: 175         moltype = AA  length = 180
FEATURE                Location/Qualifiers
source                 1..180
                       mol_type = protein
                       organism = Homo sapiens
SEQUENCE: 175
ATKLTEEKYE LKEGQTLDVK CDYTLEKFAS SQKAWQIIRD GEMPKTLACT ERPSKNSHPV  60
QVGRIILEDY HDHGLLRVRM VNLQVEDSGL YQCVIYQPPK EPHMLFDRIR LVVTKGFSGT  120
PGSNENSTQN VYKIPPTTTK ALCPLYTSPR TVTQAPPKST ADVSTPDSEI NLTNVTDIIR  180

SEQ ID NO: 176         moltype = AA  length = 123
FEATURE                Location/Qualifiers
source                 1..123
                       mol_type = protein
                       organism = synthetic construct
SEQUENCE: 176
EVQLVQSGAE VKKPGESLKI SCKGSGYSFT SYWIAWVRQM PGKGLEWMGI IYPGDSDTRY  60
SPSFQGQVTI SADKSISTAY LQWSSLKASD TAMYFCARQR TFYYDSSDYF DYWGQGTLVT  120
VSS                                                                123

SEQ ID NO: 177         moltype = AA  length = 107
FEATURE                Location/Qualifiers
source                 1..107
                       mol_type = protein
                       organism = synthetic construct
SEQUENCE: 177
DIQMTQSPSS VSASVGDRVT ITCRASQGIS SWLAWYQQKP GKAPKLLIYA ASSLQNGVPS  60
RFSGSGSGTD FTLTISSLQP EDFATYFCQQ ADSFPRTFGQ GTKLEIK                107

SEQ ID NO: 178         moltype = AA  length = 122
FEATURE                Location/Qualifiers
source                 1..122
                       mol_type = protein
                       organism = synthetic construct
SEQUENCE: 178
EVKLLEFGGG LVQPGGSMRL SCAASGFTFT DFYMNWIRQP AGRAPEWLGL IRNKTKGYTT  60
EYNRSVKGRF TISRDNTQNM LYLQMNSLRP EDTATYYCAR IGVNNGGSLD YWGQGVMVTV  120
SS                                                                 122

SEQ ID NO: 179         moltype = AA  length = 113
FEATURE                Location/Qualifiers
source                 1..113
                       mol_type = protein
                       organism = synthetic construct
SEQUENCE: 179
DILIIQSPAS LTVSAGARVT MSCKSSQSLL YSENNQDYLA WYQQKPGQFP KLLIYGASNR  60
HTGVPDRFTG SGSGTDFTLT ISSVQAEDLA DYYCEQTYSY PYTFGAGTKL ELK          113

SEQ ID NO: 180         moltype = AA  length = 119
FEATURE                Location/Qualifiers
source                 1..119
                       mol_type = protein
                       organism = synthetic construct
SEQUENCE: 180
EVQLLESGGG LVQPGGSLRL SCAASGFTFS NYYMAWVRQA PGKGLEWVSS LTNSGGSTYY  60
ADSVKGRFTI SRDNSKNTLY LQMNSLRAED TAVYYCTREW AGSGYFDYWG QGTLVTVSS   119

SEQ ID NO: 181         moltype = AA  length = 107
FEATURE                Location/Qualifiers
source                 1..107
                       mol_type = protein
                       organism = synthetic construct
SEQUENCE: 181
DIQMTQSPSS LSASVGDRVT ITCKASQNVG NNLAWYQQKP GKAPKLLIYY TSNRFTGVPS  60
RFSGSGSGTD FTLTISSLQP EDFATYYCQR IYNSPWTFGQ GTKLEIK                107

SEQ ID NO: 182         moltype = AA  length = 128
FEATURE                Location/Qualifiers
source                 1..128
```

-continued

```
                         mol_type = protein
                         organism = synthetic construct
SEQUENCE: 182
QVQLQQSGPG LVKPSQTLSL TCAISGDSVS SSSAAWNWIR QSPSRGLEWL GHIGYRSKWY  60
NEYAVSVKSR ITINPDTSKN QFSLQLNSVT PEDTAVYYCA RGMYGSVPYK EGYYFDIWGQ  120
GTLVTVSS                                                           128

SEQ ID NO: 183           moltype = AA  length = 107
FEATURE                  Location/Qualifiers
source                   1..107
                         mol_type = protein
                         organism = synthetic construct
SEQUENCE: 183
DIQMTQSPSS LSASVGDRVT ITCRASQGIS SDLNWYQQKP GKAPKLLIYA ASNLQSGVPS  60
RFSGSGSGTD FTLTISSLQP EDFATYYCQQ YTDESMTFGQ GTKVEIK                107

SEQ ID NO: 184           moltype = AA  length = 123
FEATURE                  Location/Qualifiers
source                   1..123
                         mol_type = protein
                         organism = synthetic construct
SEQUENCE: 184
QVQLVQSGAE VKKPGASVKV SCKASGYTFT SYYIHWVRQA PGQGLEWMGI INPSGGSTSY  60
AQKFQGRVTM TRDTSTSTVY MELSSLRSED TAVYYCAREA DDSSGYPLGL DVWGQGTMVT  120
VSS                                                                123

SEQ ID NO: 185           moltype = AA  length = 107
FEATURE                  Location/Qualifiers
source                   1..107
                         mol_type = protein
                         organism = synthetic construct
SEQUENCE: 185
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ VNSLPPTFGG GTKVEIK                107
```